United States Patent
Galetto et al.

(10) Patent No.: US 11,274,316 B2
(45) Date of Patent: *Mar. 15, 2022

(54) USE OF PRE T ALPHA OR FUNCTIONAL VARIANT THEREOF FOR EXPANDING TCR ALPHA DEFICIENT T CELLS

(71) Applicant: Cellectis, Paris (FR)

(72) Inventors: Roman Galetto, Paris (FR); Agnes Gouble, Paris (FR); Stephanie Grosse, Saint-cyr sur Morin (FR); Cecile Mannioui, Villiers sur Marne (FR); Laurent Poirot, Paris (FR); Andrew Scharenberg, Seattle, WA (US); Julianne Smith, Le Plessis-Robinson (FR)

(73) Assignee: CELLECTIS, Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 17/198,505

(22) Filed: Mar. 11, 2021

(65) Prior Publication Data

US 2021/0220405 A1 Jul. 22, 2021

Related U.S. Application Data

(60) Continuation of application No. 16/361,438, filed on Mar. 22, 2019, which is a continuation of application No. 15/659,792, filed on Jul. 26, 2017, now Pat. No. 10,286,007, which is a division of application No. 14/403,937, filed as application No. PCT/US2013/040766 on May 13, 2013, now Pat. No. 10,426,795.

(60) Provisional application No. 61/696,612, filed on Sep. 4, 2012, provisional application No. 61/651,933, filed on May 25, 2012.

(51) Int. Cl.
| | |
|---|---|
| *C12N 15/85* | (2006.01) |
| *A61K 35/17* | (2015.01) |
| *C07K 14/705* | (2006.01) |
| *C12N 5/0783* | (2010.01) |
| *C07K 14/725* | (2006.01) |
| *C07K 16/28* | (2006.01) |
| *A61K 39/00* | (2006.01) |
| *A61K 38/00* | (2006.01) |

(52) U.S. Cl.
CPC ............ *C12N 15/85* (2013.01); *A61K 35/17* (2013.01); *C07K 14/7051* (2013.01); *C07K 14/70517* (2013.01); *C07K 14/70521* (2013.01); *C07K 14/70578* (2013.01); *C07K 16/28* (2013.01); *C07K 16/2803* (2013.01); *C12N 5/0636* (2013.01); *A61K 38/00* (2013.01); *A61K 39/00* (2013.01); *C07K 2317/14* (2013.01); *C07K 2317/24* (2013.01); *C07K 2317/569* (2013.01); *C07K 2317/622* (2013.01); *C07K 2319/00* (2013.01); *C07K 2319/03* (2013.01); *C07K 2319/74* (2013.01); *C12N 2501/39* (2013.01); *C12N 2501/51* (2013.01); *C12N 2501/515* (2013.01); *C12N 2501/599* (2013.01); *C12N 2502/99* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 10,268,007 B2 | 5/2019 | Galetto et al. | |
| 10,363,270 B2 | 7/2019 | Galetto et al. | |
| 10,426,795 B2 | 10/2019 | Galetto et al. | |
| 10,472,611 B2 | 11/2019 | Angel et al. | |
| 10,662,410 B1 | 5/2020 | Angel et al. | |
| 10,829,738 B2 | 11/2020 | Angel et al. | |
| 2007/0286857 A1 | 12/2007 | Arthaud et al. | |
| 2011/0301073 A1 | 12/2011 | Gregory et al. | |
| 2012/0060230 A1 | 3/2012 | Collingwood et al. | |
| 2012/0222143 A1* | 8/2012 | Fahrenkrug | C12N 15/85 800/15 |
| 2013/0196373 A1 | 8/2013 | Gregory et al. | |
| 2013/0315884 A1 | 11/2013 | Galetto et al. | |

(Continued)

FOREIGN PATENT DOCUMENTS

| | | |
|---|---|---|
| WO | 2007/043200 A2 | 4/2007 |
| WO | 2010/027423 A2 | 3/2010 |

OTHER PUBLICATIONS

Tesson et al Nature Biotechnology 29(8) Supplemental Information dio:10.1038/nbt.1940. Aug. 2011.pp. 1-13 (Year: 2011).*

(Continued)

*Primary Examiner* — Marcia S Noble
(74) *Attorney, Agent, or Firm* — Arrigo, Lee, Guttman & Mouta-Bellum LLP

(57) ABSTRACT

A method of expanding TCRalpha deficient T-cells by expressing pTalpha or functional variants thereof into said cells, thereby restoring a functional CD3 complex. This method is particularly useful to enhance the efficiency of immunotherapy using primary T-cells from donors. This method involves the use of pTalpha or functional variants thereof and polynucleotides encoding such polypeptides to expand TCRalpha deficient T-cells. Such engineered cells can be obtained by using specific rare-cutting endonuclease, preferably TALE-nucleases. The use of Chimeric Antigen Receptor (CAR), especially multi-chain CAR, in such engineered cells to target malignant or infected cells. The invention opens the way to standard and affordable adoptive immunotherapy strategies for treating cancer and viral infections.

Figure 1:
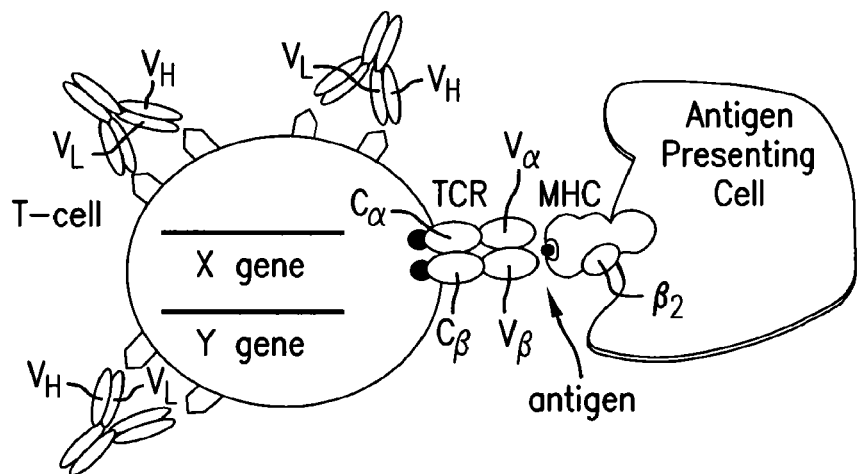

5 Claims, 27 Drawing Sheets
Specification includes a Sequence Listing.

(56) References Cited

U.S. PATENT DOCUMENTS

2014/0349402 A1    11/2014   Cooper et al.
2015/0203817 A1    7/2015   Galetto et al.

OTHER PUBLICATIONS

Liu et al. Journal of Genetics and Genomics=Yi chuan xue bao (2012) 39(5):209-215 (abstract provided). (Year: 2012).*

Singh et al. Curr Hematol Malig Rep 12:522-529,2017 (Year: 2017).*

Tesson et al., Knockout rats generated by embryo microinjection of TALENs, Nature Biotechnology, vol. 29, No. 8, Aug. 2011, 695-696.

Ramiro et al., Differential Developmental Regulation and Functional Effects of Pre-TCR Surface Expression of Human pTaa and pTab Spliced Isoforms, J. Immunol. (2001) vol. 167, pp. 5106-5114.

Carrasco et al., An Endoplasmic Reticulum Retention Function for the Cytoplasmic Tail of the Human Pre-T Cell Receptor (TCR) a Chain: Potential Role in the Regulation of Cell Surface pre-TCR Expression Levels, J. Exp. Med. (2001) vol. 193, No. 9, pp. 1045-1057.

Trop et al., "Competitive displacement of pT alpha by TCR-alpha during TCR assembly prevents surface coexpression of pre-TCR and alpha beta TCR.", The Journal of Immunology, vol. 165, No. 10, Nov. 1, 2000 (Nov. 1, 2000), pp. 5566-5572.

H. Torikai et al., "A foundation for universal T-cell based immunotherapy: T cells engineered to express a CD19-specific chimeric-antigen-receptor and eliminate expression of endogenous TCR", Blood, Published Online Apr. 24, 2012, vol. 119, No. 24, Apr. 24, 2012 (Apr. 24, 2012), pp. 5697-5705.

Mizoguchi E et al.,: "Pathogenic role of IL-4, but not IFN-gamma in colitis of TCRalpha knockout mice", Gastroenterology, Elsevier, Philadelphia, PA,, Abstract G4261, vol. 114, Apr. 15, 1998 (Apr. 15, 1998), p. A1041.

M. M. Mahfouz et al., "De novo-engineered transcription activator-like effector (TALE) hybrid nuclease with novel DNA binding specificity creates double-strand breaks", Proceedings of the National Academy of Sciences, vol. 108, No. 6, Feb. 8, 2011 (Feb. 8, 2011), pp. 2623-2628.

Osterborg et al., Clonal CD8'and CD52. T Cells are Induced in Responding B Cell Lymphoma Patients Treated with Campath-1H (anti-CD52), European Journal of Haematology, vol. 58, No. 1, XP-008067708, Jan. 1, 1997, pp. 5-13.

Cermak et al., Efficient design and assembly of custom TALEN and other TAL effector-based constructs for DNA targeting, Nucleic Acids Research, 2011, vol. 39, No. 12, 1-11.

Mockery et al., mRNA transfection of dendritic cells: Synergistic effect of ARCA mRNA capping with Poly(A) chains in cis and in trans for a high protein expression level, Biochemical and Biophysical Research Communications 340 (2006) 1062-1068.

Kariko et al., Incorporation of Pseudouridine Into mRNA Yields Superior Nonimmunogenic Vector With Increased Translational Capacity and Biological Stability, Mol Ther. Nov. 2008; 16(11): 1833-1840.

Rodgers et al., Regulated a-globin mRNA decay is a cytoplasmic event proceeding through 3'-to-5' exosome-dependent decapping, RNA(2002), 8:1526-1537.

Verado et al., Regulatory sequences in the 3' Untranslated region of the human cGMP-Phosphodiesterase β-Subunit gene, Invest Ophthalmol Vis Sci. Jun. 2009 ; 50(6): 2591-2598.

Tanguay et al., Translational Efficiency is Regulated by the Length of the 3' Untranslated Region, Molecular and Cellular Biology, Jan. 1996, 16(1), p. 146-156.

Quasim et al., Molecular remission of infant B-ALL after infusion of universal TALEN gene-edited CAR T cells, Sci. Transl. Med. 9, eaaj2013 (2017) Jan. 25, 2017, 1-8.

Poirot et al., Multiplex Genome-Edited T-cell Manufacturing Platform for 'Off-the-Shelf' Adoptive T-cell Immunotherapies. Cancer Res; 75(18); 3853-64. (2015).

Wood et al. Targeted genome editing across species using ZFNs and TALENs. Science 333:307, 2011.

* cited by examiner

|  | LEFT HALF TARGET | Spacer size (bp) | RIGHT HALF TARGET | |
|---|---|---|---|---|
| TRAC | TTGTCCCACAGATATCC (SEQ ID NO:140) | 15 | CCGTGTACCCAGCTGAGA (SEQ ID NO:141) | |
| CD52 | TTCCTCCTACTCACCAT (SEQ ID NO:142) | 15 | GGTACAGGTAAGAGCAA (SEQ ID NO:143) | |
| Potential offsite targets | Left matched sequence | Spacer size (bp) | Right matched sequence | Mis matc hes |
| 1 | ttgctctCaccAgtaTA (SEQ ID NO:144) | 25 | TTtTcaggtaagTgcaa (SEQ ID NO:159) | 8 |
| 2 | tCActcttacctgGacc (SEQ ID NO:145) | 19 | CCtacaggttaagGgcCa (SEQ ID NO:160) | 7 |
| 3 | tctcagAtgAtacacCC (SEQ ID NO:146) | 24 | AgtacaggCaTgagcCa (SEQ ID NO:161) | 8 |
| 4 | tGAtcccacagaAatAc (SEQ ID NO:147) | 18 | gCatTtctgtgggaTCa (SEQ ID NO:162) | 8 |
| 5 | ttCctctAacctgtaTT (SEQ ID NO:148) | 25 | gAtCcaggtaagGTcaa (SEQ ID NO:163) | 8 |
| 6 | tAgtcccCcagatatGA (SEQ ID NO:149) | 19 | aAggtgTgGaTgaggaa (SEQ ID NO:164) | 8 |
| 7 | ttgtcAcacaTataCcG (SEQ ID NO:150) | 21 | TgGtatTtgtggacaa (SEQ ID NO:165) | 8 |
| 8 | tAActcttacctgtaGT (SEQ ID NO:151) | 16 | AgatTtcTCtgggGcaa (SEQ ID NO:166) | 8 |
| 9 | ttActccAactAacTat (SEQ ID NO:152) | 16 | ccgtTtaccGgctTaga (SEQ ID NO:167) | 7 |
| 10 | tGgctcAtacctgtaGT (SEQ ID NO:153) | 14 | aGgAtgagGTggaggaa (SEQ ID NO:168) | 8 |
| 11 | ttgctcAtacAtgtGcA (SEQ ID NO:154) | 21 | atgCtgtgtaggTggTa (SEQ ID NO:169) | 8 |
| 12 | ttgtcccacagaCatTc (SEQ ID NO:155) | 18 | ccACgtaGcagctgGga (SEQ ID NO:170) | 6 |
| 13 | tcAcaCctggtacaTAg (SEQ ID NO:156) | 27 | GtgTtTagtaggGggaa (SEQ ID NO:171) | 8 |
| 14 | ttgtcccacagCtaCcc (SEQ ID NO:157) | 29 | gAgtCtTtgtAggacaa (SEQ ID NO:172) | 6 |
| 15 | tctcaActgAAacaAgg (SEQ ID NO:158) | 23 | TgtaAtgTCaagagcaa (SEQ ID NO:173) | 8 |

*Fig. 9A*

|  | Control transfection (no RNA) | | | CD52-TALEN+TRAC+TALEN transfection | | |
| --- | --- | --- | --- | --- | --- | --- |
|  | Nb seq analyzed | Nb indels | Frequency indels (less than) | Nb seq analyzed | Nb indels | Frequency indels (less than) |
|  | 3965 | 0 | 2.52E-04 | 7560 | 3371 | 0.44 |
|  | 1046 | 0 | 9.56E-04 | 2266 | 1056 | 0.47 |
| Matched sequence |  |  |  |  |  |  |
| CD52-R_TRAC-R | 7132 | 0 | 1.4E-04 | 7644 | 1 | 1.3E-04 |
| CD52-R_TRAC-R | 6431 | 0 | 1.6E-04 | 7377 | 2 | 2.7E-04 |
| CD52-R_TRAC-R | 2771 | 0 | 3.6E-04 | 2704 | 80 | 3.7E-04 |
| TRAC-L_CD52-L | 5525 | 0 | 1.8E-04 | 4739 | 0 | 2.1E-04 |
| CD52-R_TRAC-R | 27958 | 0 | 3.6E-05 | 16646 | 0 | 6.0E-05 |
| TRAC-L_CD52-L | 22456 | 0 | 4.5E-05 | 32912 | 10 | 3.0E-04 |
| TRAC-L_CD52-L | 8275 | 0 | 1.2E-04 | 5629 | 0 | 1.8E-04 |
| TRAC-L_CD52-R | 23253 | 0 | 4.3E-05 | 22054 | 16 | 7.3E-04 |
| CD52-L_TRAC-R | 13371 | 0 | 7.5E-05 | 13688 | 1 | 7.3E-05 |
| CD52 | 22856 | 0 | 4.4E-05 | 31292 | 0 | 3.2E-05 |
| CD52 | 3238 | 1 | 3.1E-04 | 3064 | 0 | 3.3E-04 |
| TRAC | 4530 | 0 | 2.2E-04 | 4652 | 0 | 2.1E-04 |
| CD52-L_TRAC-R | 17361 | 0 | 5.8E-05 | 14454 | 0 | 6.9E-05 |
| TRAC-L_CD52-L | 32823 | 0 | 3.0E-05 | 33911 | 1 | 2.9E-05 |
| CD52-R_TRAC-R | 6479 | 0 | 1.5E-04 | 6088 | 0 | 1.6E-04 |

*Fig. 9B*

USE OF PRE T ALPHA OR FUNCTIONAL VARIANT THEREOF FOR EXPANDING TCR ALPHA DEFICIENT T CELLS

CROSS-REFERENCE TO RELATED APPLICATIONS

This application is a continuation of U.S. patent application Ser. No. 16/361,438, filed Mar. 22, 2019, which is a continuation of U.S. patent application Ser. No. 15/659,792, filed Jul. 26, 2017, which is a division of U.S. patent application Ser. No. 14/403,937, filed Nov. 25, 2014, which is a National Stage entry of International Application No. PCT/US2013/040766, filed May 13, 2013, which claims priority to U.S. Provisional Application No. 61/696,612, filed Sep. 4, 2012, and to U.S. Provisional Application No. 61/651,933, filed May 25, 2012. The disclosures of the prior applications are hereby incorporated by reference in their entireties.

SEQUENCE LISTING

The instant application contains a Sequence Listing which has been submitted electronically in ASCII format and is hereby incorporated by reference in its entirety. Said ASCII copy, created on Jul. 7, 2021, is named 17198505_ST25.txt and is 326,320 bytes in size.

FIELD OF THE INVENTION

The present invention concerns cell therapy and more specifically relates to a method of expanding TCRalpha deficient T-cells by expressing pTalpha or functional variants thereof into said cells, thereby restoring a functional CD3 complex. This method is particularly useful to enhance the efficiency of immunotherapy using primary T-cells from donors. This method involves the use of pTalpha or functional variants thereof and polynucleotides encoding such polypeptides to expand TCRalpha deficient T-cells. Such engineered cells can be obtained by using specific rare-cutting endonuclease, preferably TALE-nucleases. The invention further relates to the use of Chimeric Antigen Receptor (CAR), especially multi-chain CAR, in such engineered cells to target malignant or infected cells. The invention opens the way to standard and affordable adoptive immunotherapy strategies for treating cancer and viral infections.

BACKGROUND OF THE INVENTION

Adoptive immunotherapy, which involves the transfer of autologous antigen-specific T cells generated ex vivo, is a promising strategy to treat viral infections and cancer. The T cells used for adoptive immunotherapy can be generated either by expansion of antigen-specific T cells or redirection of T cells through genetic engineering (Park, Rosenberg et al. 2011). Transfer of viral antigen specific T cells is a well-established procedure used for the treatment of transplant associated viral infections and rare viral-related malignancies. Similarly, isolation and transfer of tumor specific T cells has been shown to be successful in treating melanoma.

Novel specificities in T cells have been successfully generated through the genetic transfer of transgenic T cell receptors or chimeric antigen receptors (CARs) (Jena, Dotti et al. 2010). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. First generation CARs have been shown to successfully redirect T cell cytotoxicity, however, they failed to provide prolonged expansion and anti-tumor activity in vivo. Signaling domains from co-stimulatory molecules including CD28, OX-40 (CD134), and 4-1BB (CD137) have been added alone (second generation) or in combination (third generation) to enhance survival and increase proliferation of CAR modified T cells. CARs have successfully allowed T cells to be redirected against antigens expressed at the surface of tumor cells from various malignancies including lymphomas and solid tumors (Jena, Dotti et al. 2010).

Present CAR architectures are built on a design in which all relevant domains are contained within a single polypeptide. This design necessitates serial appending of signaling domains, thus necessitating moving some domains from their natural juxtamembrane positions. Thus, architectures in which ligands and signaling domains are separate may allow for improved function of costimulatory domains placed on different chains in their normal juxtamembrane positions, rather than appended together with some domains positioned distal from the plasma membrane. A natural receptor, the high affinity receptor for IgE (FcεRI) would afford such architecture. FcεRI present on mast cells and basophils binds IgE with high affinity. FcεRI is a tetrameric receptor complex consisting of ligand binding alpha subunit, a beta subunit and a homodimer of two signal-transducing gamma subunits (Metzger, Alcaraz et al. 1986). FcεRI alpha domain consists of an extracellular domain containing two Ig-like domains that bind IgE, a transmembrane domain and a short cytoplasmic tail. Beta subunit contains four transmembrane segments separating amino and carboxy terminal cytoplasmic tails. The gamma chain consists essentially of a transmembrane region and cytoplasmic tail containing one immunoreceptor tyrosine-based activation motif (ITAM) (Cambier 1995). The zeta chain of the TCR complex is closely related to the gamma chain and can substitute for the gamma chain of FcεRI (Howard, Rodewald et al. 1990).

The current protocol for treatment of patients using adoptive immunotherapy is based on autologous cell transfer. In this approach, T lymphocytes are recovered from patients, genetically modified or selected ex vivo, cultivated in vitro in order to amplify the number of cells if necessary and finally infused into the patient. In addition to lymphocyte infusion, the host may be manipulated in other ways that support the engraftment of the T cells or their participation in an immune response, for example pre-conditioning (with radiation or chemotherapy) and administration of lymphocyte growth factors (such as IL-2). Each patient receives an individually fabricated treatment, using the patient's own lymphocytes (i.e. an autologous therapy). Autologous therapies face substantial technical and logistic hurdles to practical application, their generation requires expensive dedicated facilities and expert personnel, they must be generated in a short time following a patient's diagnosis, and in many cases, pretreatment of the patient has resulted in degraded immune function, such that the patient's lymphocytes may be poorly functional and present in very low numbers. Because of these hurdles, each patient's autologous cell preparation is effectively a new product, resulting in substantial variations in efficacy and safety. Ideally, one would like to use a standardized therapy in which allogeneic therapeutic cells could be pre-manufactured, characterized in detail, and available for immediate administration to patients. By allogeneic it is meant that the cells are obtained from individuals belonging to the same species but are genetically dissimilar. However, the use of allogeneic cells presently has many drawbacks. In immune-competent hosts allogeneic cells are rapidly rejected, a process termed host versus graft rejection (HvG), and this substantially limits the efficacy of the transferred cells. In immune-incompetent hosts, allogeneic cells are able to engraft, but their endogenous TCR specificities recognize the host tissue as foreign, resulting in graft versus host disease (GvHD), which can lead to serious tissue damage and death. In order to effectively use allogeneic cells, both of these problems must be overcome.

In immunocompetent hosts, allogeneic cells are rapidly rejected by the host immune system. It has been demonstrated that, allogeneic leukocytes present in non-irradiated blood products will persist for no more than 5 to 6 days. (Boni, Muranski et al. 2008). Thus, to prevent rejection of allogeneic cells, the host's immune system must be effectively suppressed. Glucocorticoidsteroids are widely used therapeutically for immunosuppression (Coutinho and Chapman 2011). This class of steroid hormones binds to the glucocorticoid receptor (GR) present in the cytosol of T cells resulting in the translocation into the nucleus and the binding of specific DNA motifs that regulate the expression of a number of genes involved in the immunologic process. Treatment of T cells with glucocorticoid steroids results in reduced levels of cytokine production leading to T cell anergy and interfering in T cell activation. Alemtuzumab, also known as CAMPATH1-H, is a humanized monoclonal antibody targeting CD52, a 12 amino acid glycosylphosphatidyl-inositol-(GPI) linked glycoprotein (Waldmann and Hale 2005). CD52 is expressed at high levels on T and B lymphocytes and lower levels on monocytes while being absent on granulocytes and bone marrow precursors. Treatment with Alemtuzumab, a humanized monoclonal antibody directed against CD52, has been shown to induce a rapid depletion of circulating lymphocytes and monocytes. It is frequently used in the treatment of T cell lymphomas and in certain cases as part of a conditioning regimen for transplantation. However, in the case of adoptive immunotherapy the use of immunosuppressive drugs will also have a detrimental effect on the introduced therapeutic T cells. Therefore, to effectively use an adoptive immunotherapy approach in these conditions, the introduced cells would need to be resistant to the immunosuppressive treatment.

On the other hand, T cell receptors (TCR) are cell surface receptors that participate in the activation of T cells in response to the presentation of antigen. The TCR is generally made from two chains, alpha and beta, which assemble to form a heterodimer and associates with the CD3-transducing subunits to form the T-cell receptor complex present on the cell surface. Each alpha and beta chain of the TCR consists of an immunoglobulin-like N-terminal variable (V) and constant (C) region, a hydrophobic transmembrane domain, and a short cytoplasmic region. As for immunoglobulin molecules, the variable region of the alpha and beta chains are generated by V(D)J recombination, creating a large diversity of antigen specificities within the population of T cells. However, in contrast to immunoglobulins that recognize intact antigen, T cells are activated by processed peptide fragments in association with an MHC molecule, introducing an extra dimension to antigen recognition by T cells, known as MHC restriction. Recognition of MHC disparities between the donor and recipient through the T cell receptor leads to T cell proliferation and the potential development of GVHD. It has been shown that normal surface expression of the TCR depends on the coordinated synthesis and assembly of all seven components of the complex (Ashwell and Klusner 1990). The inactivation of TCRalpha or TCRbeta can result in the elimination of the TCR from the surface of T cells preventing recognition of alloantigen and thus GVHD. However, TCR disruption results in the elimination of the CD3 signaling component and alters the means of further T cell expansion.

In normal T-cells, T cell receptors emanate from the pre-T cell receptors (pTCR) which are expressed by immature thymocytes and are crucial for T cell development from the double negative (CD4– CD8–) to the double-positive (CD4+ CD8+) stages. Pre-T cells that succeed in productive rearrangements of the TCRbeta locus express a functional TCRbeta chain which pairs with an invariant preTalpha chain and CD3 signaling components to form the pre-TCR complex.

The expression of the preTCR at the cell surface is necessary for triggering beta-selection, a process that induces the expansion of developing T cells, enforces allelic exclusion of the TCRbeta locus and results in the induction of rearrangements at the TCRalpha locus (von Boehmer 2005). After productive TCRalpha rearrangements and substitution of pTalpha by TCRalpha to form a mature TCR, thymocytes undergo a second step of selection, referred to as positive or TCRalpha/beta selection upon binding of self peptide MHC complexes expressed on thymic epithelial cells. Thus, mature T cells recognize and respond to the antigen/MHC complex through their TCR. The most immediate consequence of TCR activation is the initiation of signaling pathways via the associated CD3 subunits that result in multiple events including clonal expansion of T cells, upregulation of activation markers on the cell surface and induction of cytotoxicity or cytokine secretion.

Because of the nature of selection of TCRbeta chains through pairing with preTalpha during thymic development, in T cells in which TCRalpha has been inactivated, the heterologous introduction of the pTalpha transgene can result in the formation of a preTCR. This pTCR can serve as a means of T cell activation or stimulation in a manner that is non-MHC dependent, thus for example allowing continued expansion of alpha/beta T-cells following TCRalpha inactivation. Importantly, the pTCR complex displays a similar biochemical composition as the TCR in terms of associated CD3 subunits (Carrasco, Ramiro et al. 2001). In addition, in contrast to the TCR, pre-TCR signaling may occur in part by a ligand independent event. The crystal structure of the pTCR extracellular domain has provided a structural basis for the possible ligand-independence of pTCR signaling. The pTCR has been shown to form a head to tail dimer where two pTalpha-TCRbeta heterodimers associate (Pang, Berry et al. 2010).

In the present invention, the inventors have achieved the production of genetically modified T-cells, which overcome the limitations of present immunotherapy strategies, allowing them to be both non-alloreactive and resistant to immunosuppressive agents. This was made possible by gene inactivation using specific TALE-nucleases directed against TCRalpha or TCRbeta, coupled with inactivation of genes encoding targets for different immunosuppressive agents, in particular CD52 and GR.

In particular, the inactivation of TCRalpha or TCRbeta coupled with inactivation of CD52 or the glucocorticoid receptor in T lymphocytes derived from an allogeneic donor significantly reduces the risk of GVHD, by eliminating the TCR, responsible for recognition of MHC disparities, while permitting proliferation and activity of the introduced lymphocytes in the presence of immunosuppressive drugs, such as Alemtuzumab or glucocorticoid steroids, that prevent rejection of these cells. Thus, these modified allogeneic T cells are expected to more efficiently expand in patient's blood, where they can target tumor cells or infected cells.

In addition to the above conception of genetically modified T cells, which can be both non alloreactive and immunosuppressive resistant, the inventors, by the use and design of specific TALE-nucleases, have concomitantly inactivated these different genes in T-cells, thereby obtaining double mutants. As a matter of fact, double gene targeting by DSB has been so far unachieved in T cells due to the difficulty of yielding and maintaining T-cells in culture over time, to their low transformation rates, and loss during selection procedures. These difficulties result in a low probability of success for obtaining such cells.

Thus, one significant part of the invention is to have designed specific TALE-nucleases, allowing higher rates of DSB events within the T-cells, which are well tolerated by the cells, (especially upon co-transfection), able to target the selection of genes according to the invention. By using rare cutting endonucleases, such as the TALE-nucleases described therein, the probability of obtaining double inactivation of the genes in the transfected T-cells was significantly increased, so that it now appears possible to produce engineered T cells available from donors on a regular basis, using standard procedures.

In addition, the present invention proposes an embodiment where T-cells are engineered to allow proliferation when TCRalpha is inactivated. A significant problem with T-cells that have undergone TCR subunit inactivation is that the cells can no longer be expanded through the CD3 complex. To overcome this problem, the inventors indeed provide means to expand T-cells in which TCRalpha has been inactivated through the CD3 complex, by expression of preTalpha in the cells, thus restoring a functional CD3 complex in the absence of a functional alpha/beta TCR.

Finally, T cells are further transformed with CAR to redirect allogeneic cells specificity towards tumor associated antigens independent of MHC. In particular, the invention relates to a multi-chain CAR, in which costimulatory domains are placed in their normal juxtamembrane positions to improve their functions and so enhance survival and increase proliferation of engineered T-cells. As a result, the invention provides methods, polypeptides and polynucleotides that allow the effective transformation of allogeneic T cells for adoptive immunotherapy, and their facile expansion through the CD3 complex.

SUMMARY OF THE INVENTION

In one aspect, the present invention discloses methods to engineer T cells, in particular allogeneic T cells obtainable from donors, to make them suitable for immunotherapy purposes. The methods of the present invention more particularly allow the precise modification of the genome of cells relevant for immunotherapy by inactivating or replacing genes involved in MHC recognition and or targets of immunosuppressive drugs for the treatment of cancer and/or viral infections. In certain embodiments, the modified cells relevant for immunotherapy further comprise exogenous recombinant polynucleotides encoding CARs for specific cell recognition. Present CARs are single fusion molecules that necessitate serial appending of signaling domains. Moving signaling domains from their natural juxtamembrane position may interfere with their function. Thus, to overcome this drawback, the inventors design a multi-chain CAR derived from FcεRI to allow normal juxtamembrane position of all relevant signaling domains. The high affinity IgE binding domain of FcεRI alpha chain is replaced by an extracellular ligand-binding domain such as scFv to redirect T-cell specificity to cell targets and the N and/or C-termini tails of FcεRI beta chain is used to place costimulatory signals in normal juxtamembrane positions.

In another aspect, in order to promote activation or stimulation of T cells in which TCRalpha has been inactivated, pTalpha or functional variant thereof are introduced into the engineered T-cells. The pTalpha or functional variant thereof used can be either full-length pTalpha, a splice variant (Saint-Ruf, Lechner et al. 1998), a C-terminal truncated version that has been shown to increase preTCR cell surface expression (Carrasco, Ramiro et al. 2001). Other additional truncations either smaller or larger than that described could be used. Different preTalpha versions may further comprise signaling moieties from other molecules (CD28, CD137, CD8, TCRalpha, etc.) to promote proliferation and survival or comprise mutations that affect its ability to dimerize, such as the D22A, R24A, R102A or R117A mutations previously described in mice (Yamasaki, Ishikawa et al. 2006) or the W46R mutation described in humans (Pang, Berry et al. 2010) to decrease the proliferation potential. The scFv portion of the CAR may also be fused to the extracellular domain of a pTalpha or a functional variant thereof, thus coupling the specificity towards target antigens directly with the proliferative activity of the preTCR.

In another aspect, the present invention relates to the polypeptides and the polynucleotides, which encode the rare-cutting endonucleases, to precisely target the above genes of interest, in particular TCRalpha, TCRbeta, GR and CD52, thereby enabling the genetic modification of the T-cells for immunotherapy. The present invention provides more particularly specific target sequences within these genes and TALE-nucleases designed to respectively target those genes.

The present invention also relates to the isolated cells or cell lines comprising any of the proteins, polypeptides or vectors described herein. In certain embodiments, the T cells of the present invention comprise inactivated TCRalpha, TCRbeta, GR or CD52 genes for their use in immunotherapy. The isolated cells of the present invention or cell lines can further comprise exogenous recombinant polynucleotides, in particular polynucleotides encoding pTalpha or functional variant thereof, CARs or multi-chain CARs.

In a preferred embodiment, the modified T cells are used as a therapeutic product, ideally as an "off the shelf" product.

In another aspect, the present invention concerns the method for treating or preventing cancer or infections in the patient by administrating an engineered T-cell obtainable by the above methods.

BRIEF DESCRIPTION OF THE FIGURES AND TABLES

In addition to the preceding features, the invention further comprises other features which will emerge from the description which follows, as well as to the appended drawings. A more complete appreciation of the invention and many of the attendant advantages thereof will be readily obtained as the same becomes better understood by reference to the following Figures in conjunction with the detailed description below.

FIG. 1: Schematic representation of the normal relationship between T-cells and antigen presenting cell.

Figure 2:
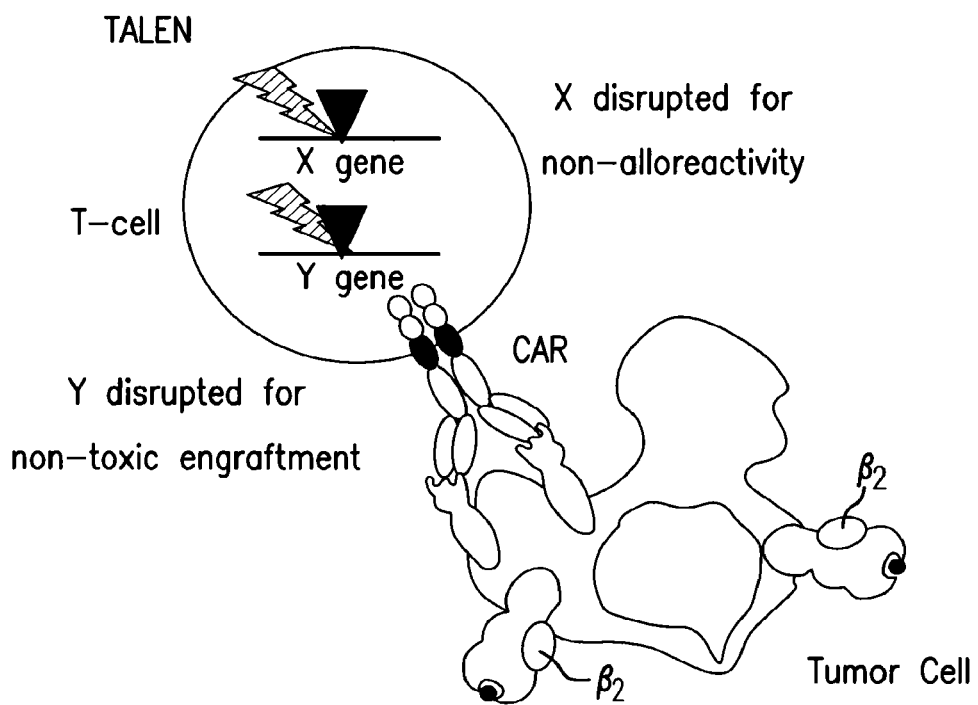

FIG. 2: Schematic representation of the genetically modified therapeutic T-cells according to the invention and the patient's tumor cells.

Figure 3:
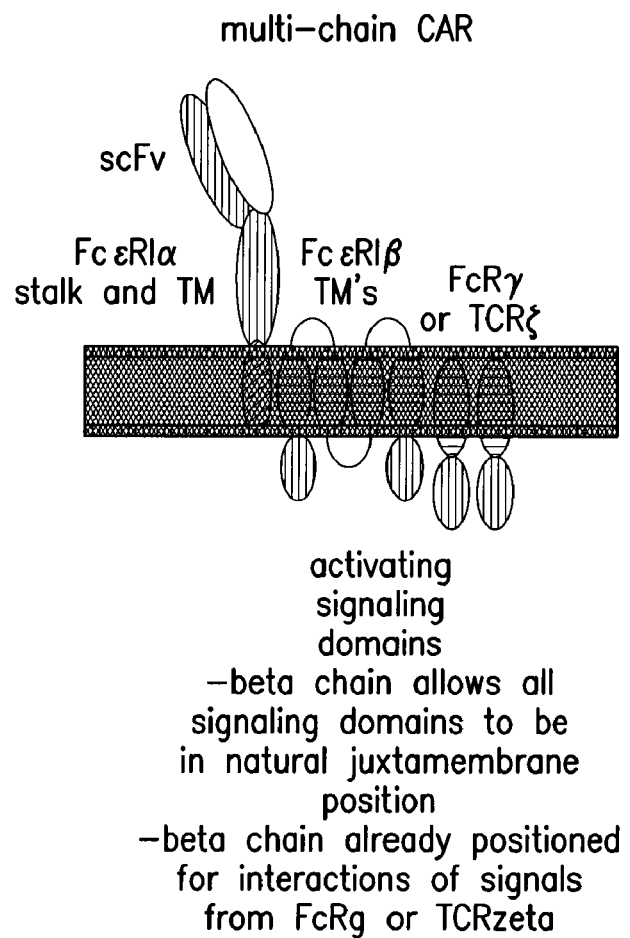

FIG. 3: Schematic representation of multi-chain CAR.

Figure 4A:
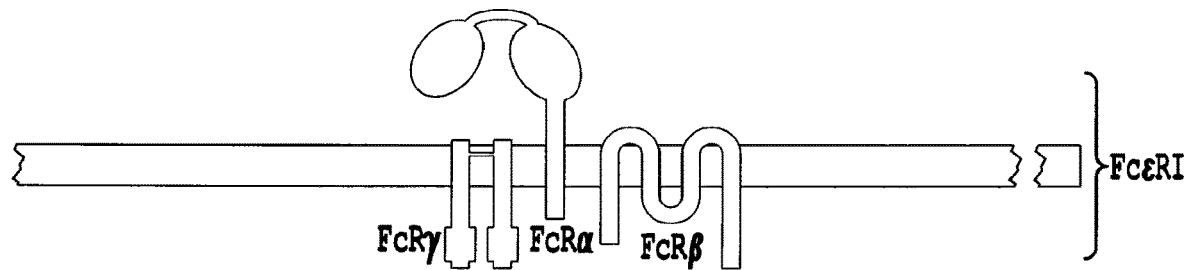
Figure 4B:
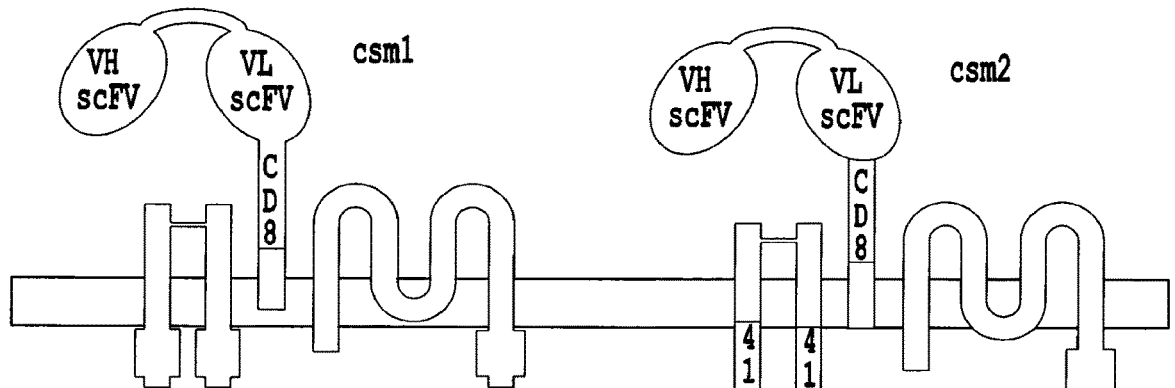
Figure 4B:
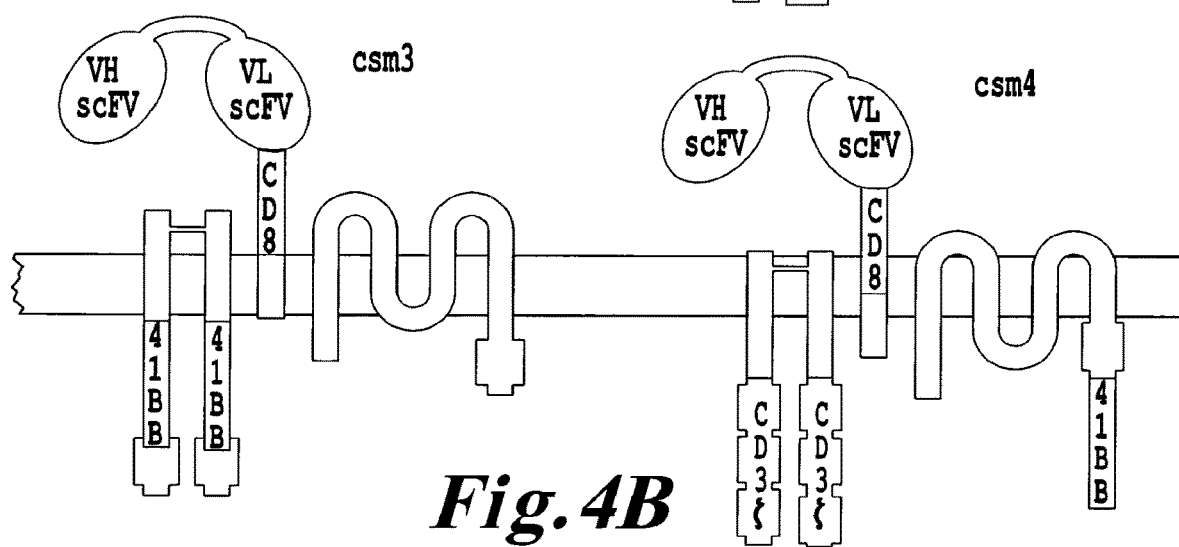
Figure 4C:
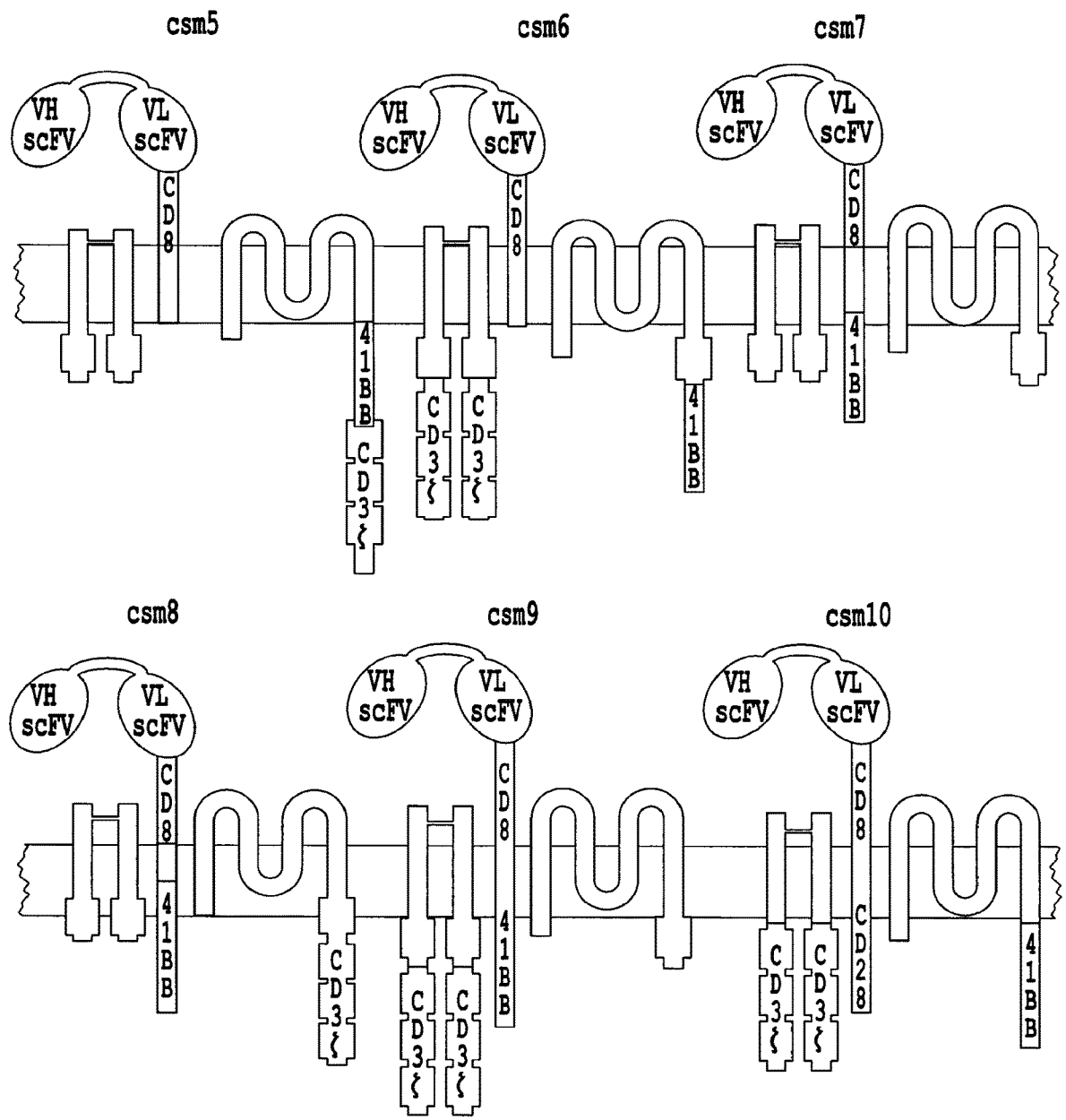

FIG. 4A-C: Schematic of different versions of multi-chain CARs. A. Schematic of the FcεRI receptor. B-C Different versions of multi-chain CARs (csm1 to csm10) comprising a scFv and a CD8 stalk region fused to the transmembrane domain of FcεRI alpha chain. At least one 41BB, CD28 and/or CD3 zeta domains can be fused to a FcεRI alpha, beta and/or gamma chain.

Figure 5:
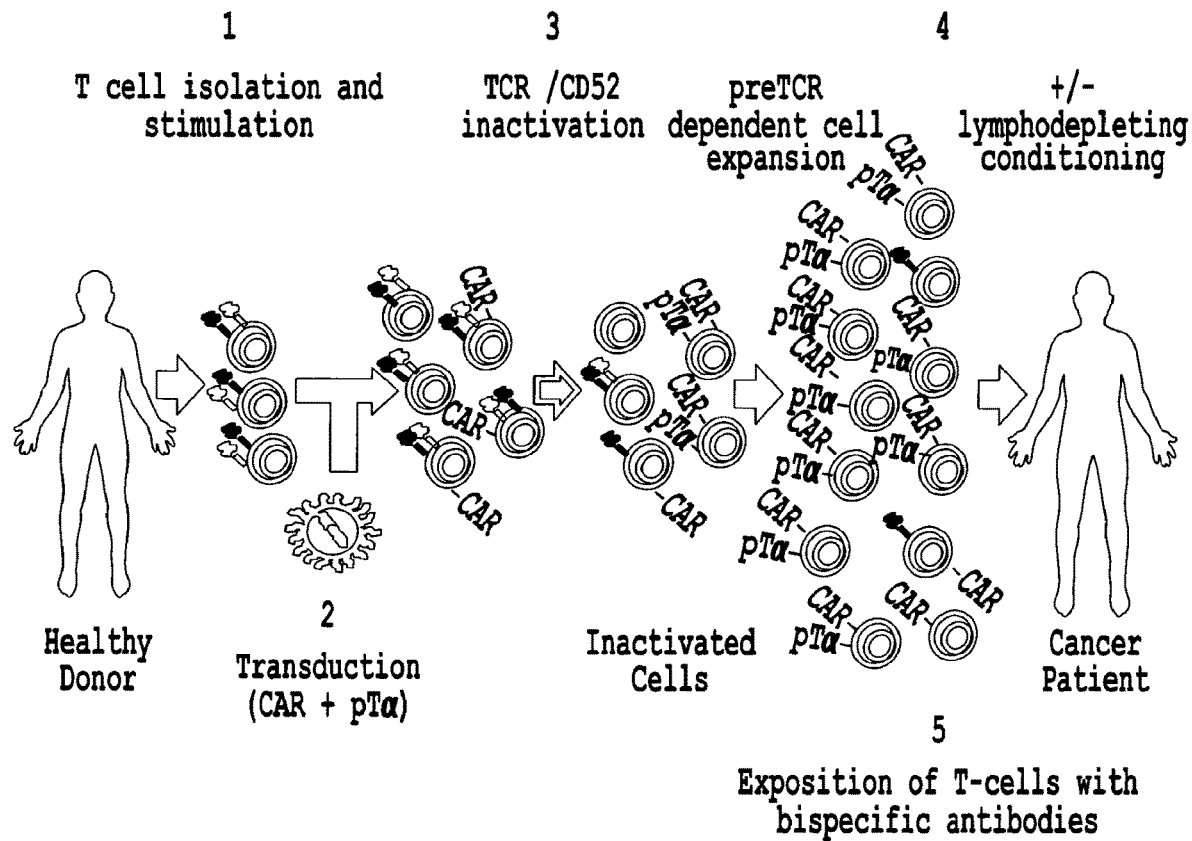

FIG. 5: Schematic representation of one example of the method of engineering human allogenic cells for immunotherapy FIG. 6: Concentration in cells per milliliter of live CD52-positive or CD52-negative cells after treatment with anti-CD52 antibody (CAMPATH1-H) with complement or controls.

Figure 7:
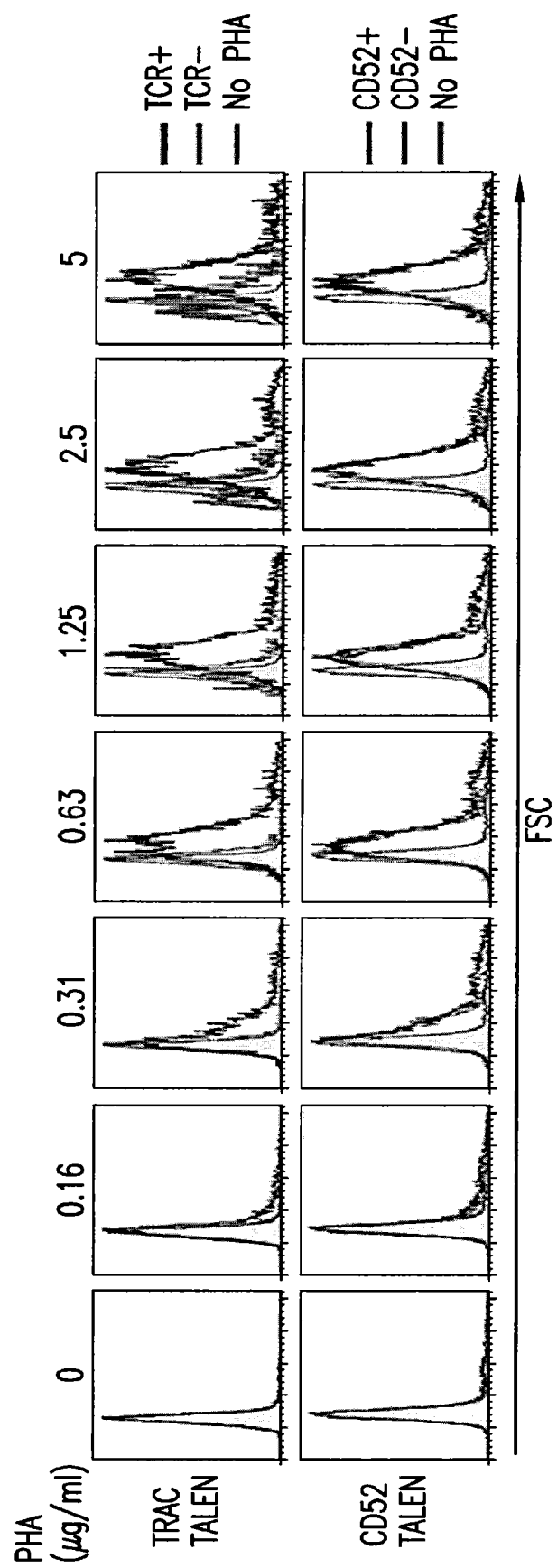
Figure 8A:
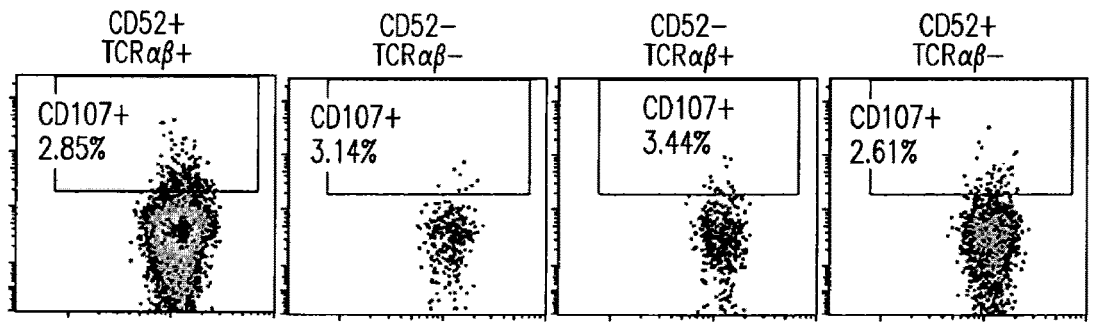
Figure 8B:
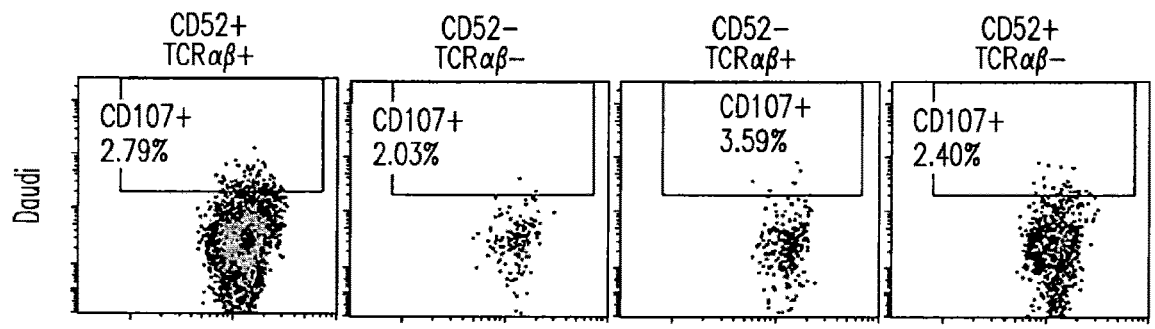
Figure 8C:
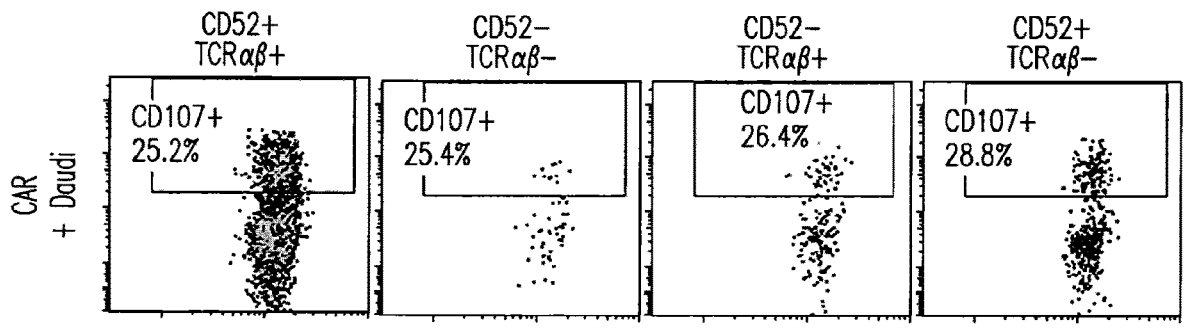
Figure 8D:
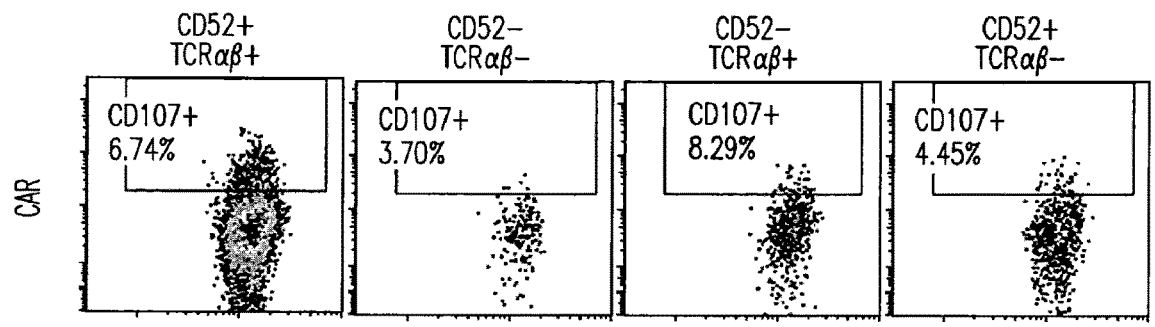
Figure 8E:
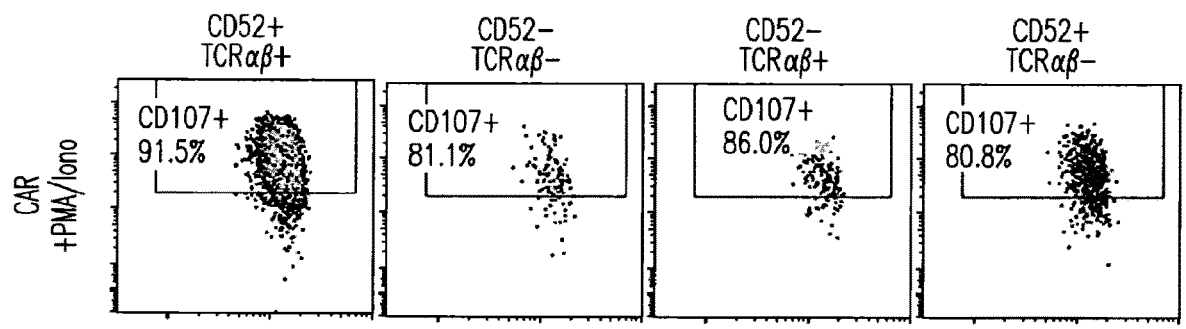

FIG. 7: Comparison of the forward side scatter (FSC) distribution, an indicator of cell size, between TCR-positive and TCR-negative cells, or between CD52-positive and CD52-negative cells, and non activated cells as control.

FIG. 8A-E: Flow cytometry analysis of CD107a expression (marker of degranulation) on targeted CD52 and TCRalpha inactivated T cells. CD107 expression is analyzed on CD52+TCRαβ+ cells (first column), CD52-TCRαβ– cells (second column), CD52-TCRαβ+ cells (third column) and CD52+TCRαβ– cells (fourth column) before (A) and after incubation with Daudi cells (B); C) represents flow cytometry analysis of T cells further transfected with a CAR and incubated with Daudi cells; D) represents flow cytometry analysis of T cells transfected with a CAR but not incubated with Daudi cells and E) represents flow cytometry analysis of T cells transfected with a CAR and treated to PMA/ionomycin (positive control).

FIG. 9A-B: Deep sequencing analysis of CD52 and TRAC TALE-nucleases potential off-site targets.

Figure 10:
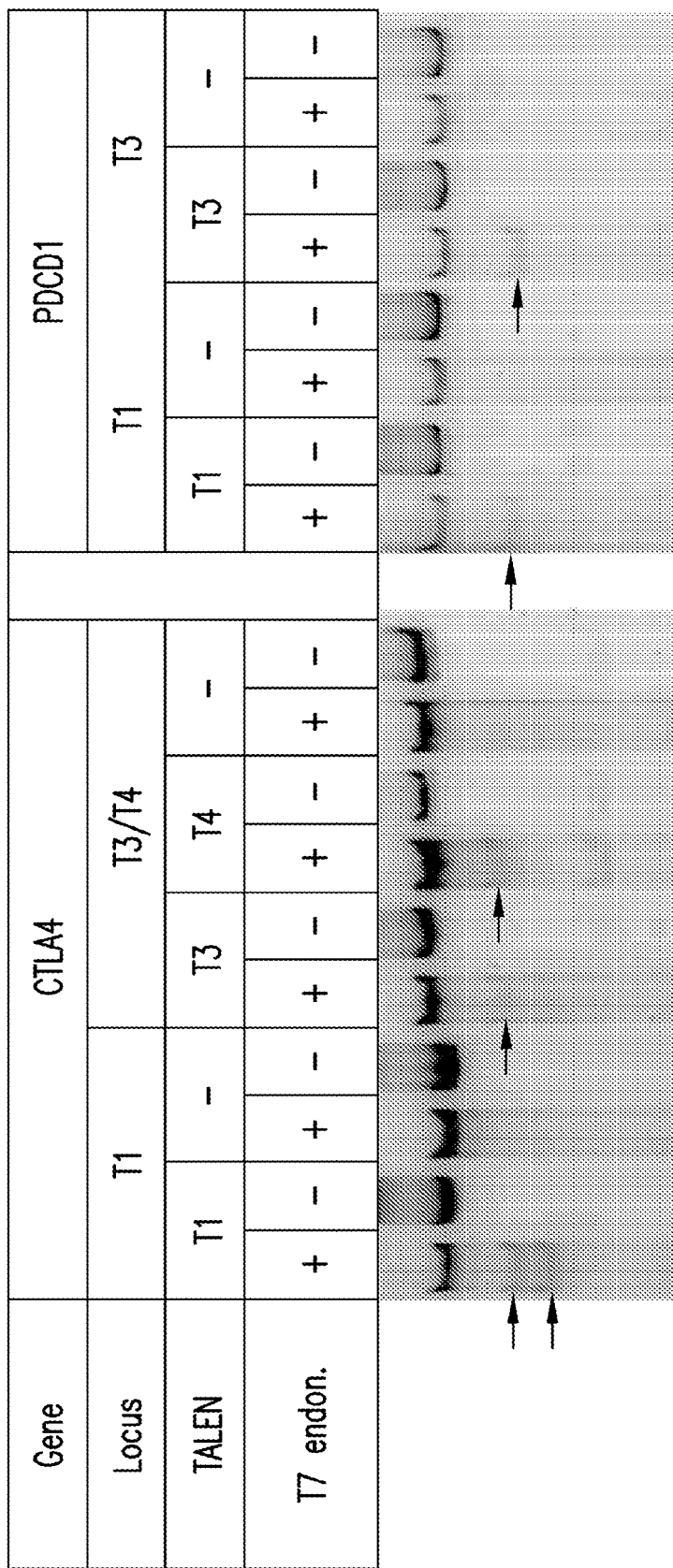

FIG. 10: Analysis of PDCD1 and CTLA-4 genomic locus by T7-endonuclease assay. Arrows point to digested PCR products.

Figure 11:
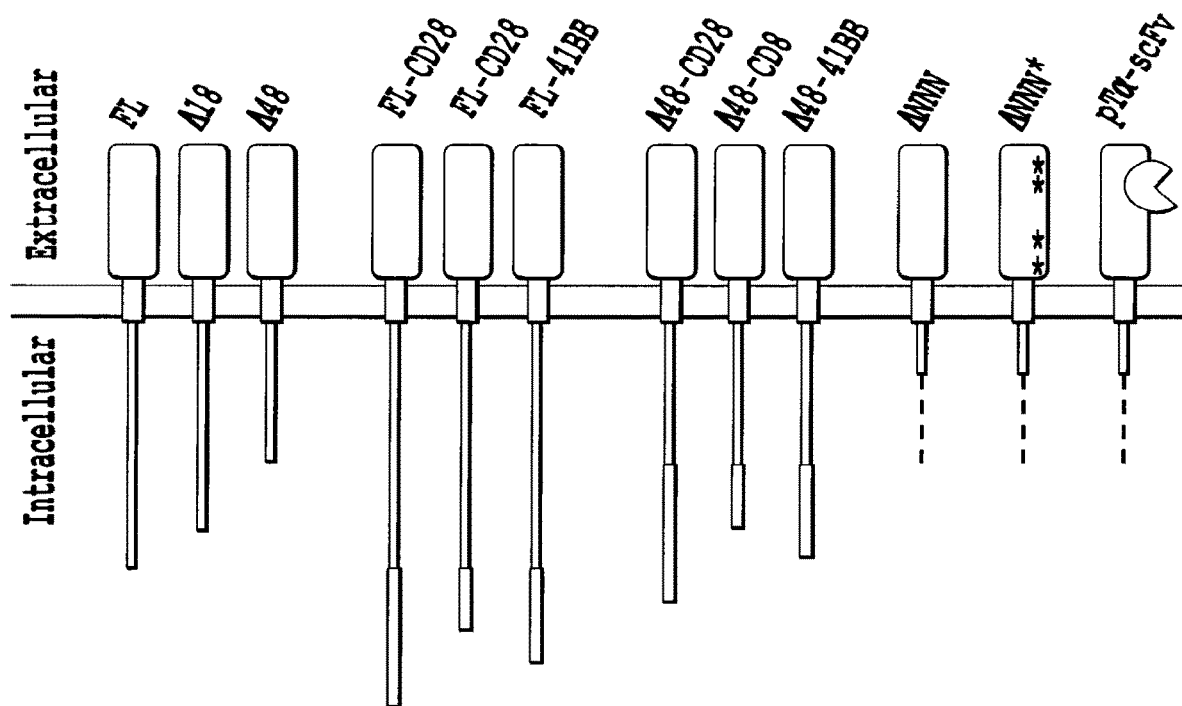

FIG. 11: Schematic representation of some examples of preTalpha constructs.

Figure 12:
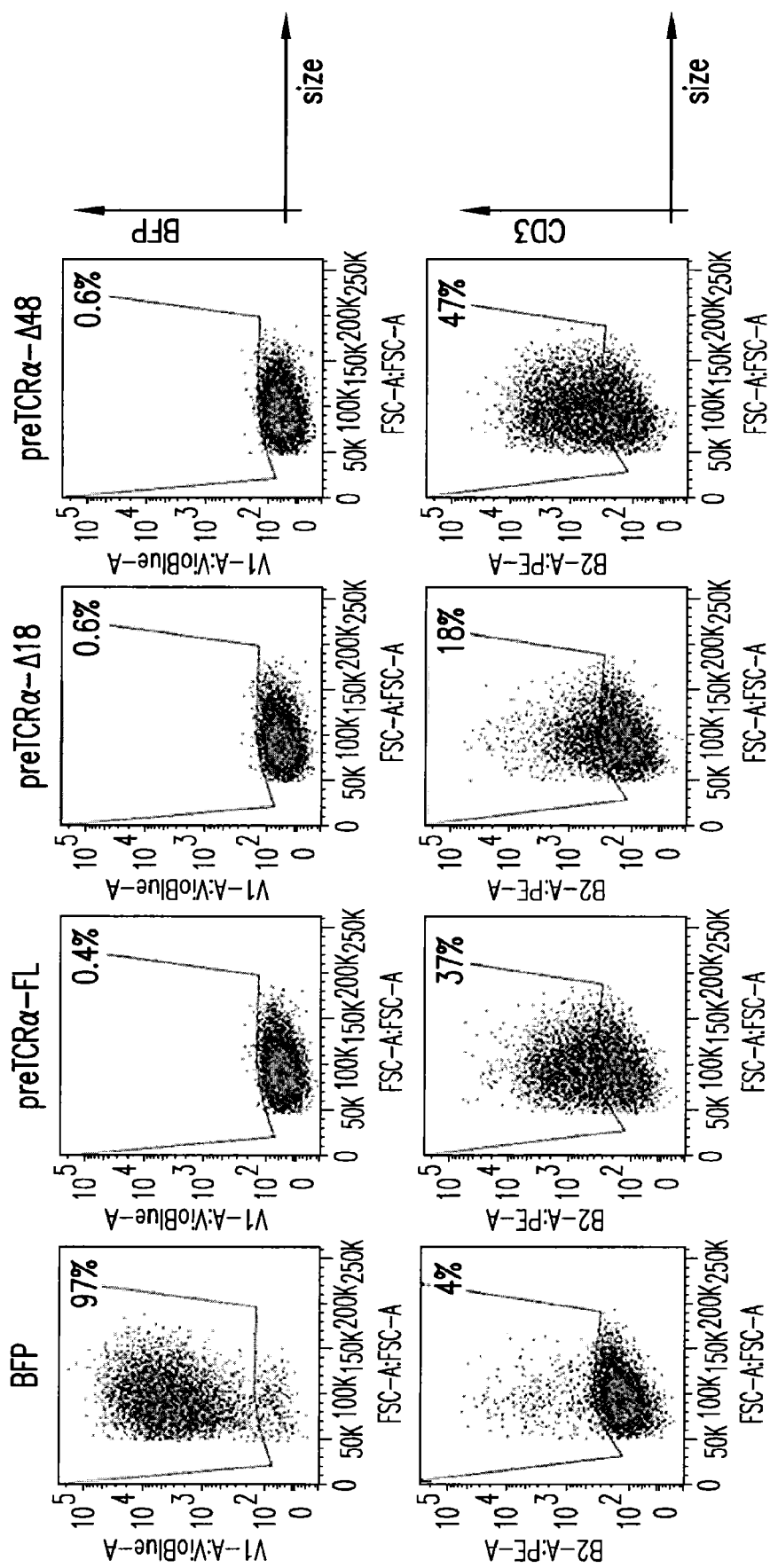

FIG. 12: Flow cytometry analysis of transduction efficiency (% BFP+ cells) and activity of the FL, Δ18, Δ48 pTalpha constructs (% CD3 surface expression) in TCR alpha inactivated Jurkat cells.

Figure 13:

FIG. 13: Schematic representation of a lentiviral construct coding for pTalpha protein (preTCRα).

Figure 14A:
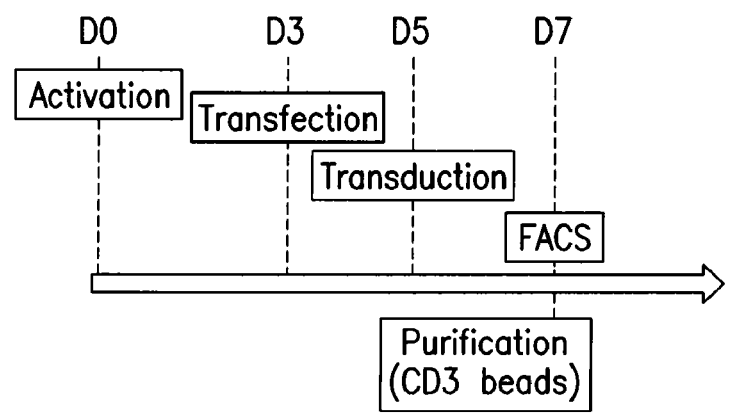
Figure 14B:
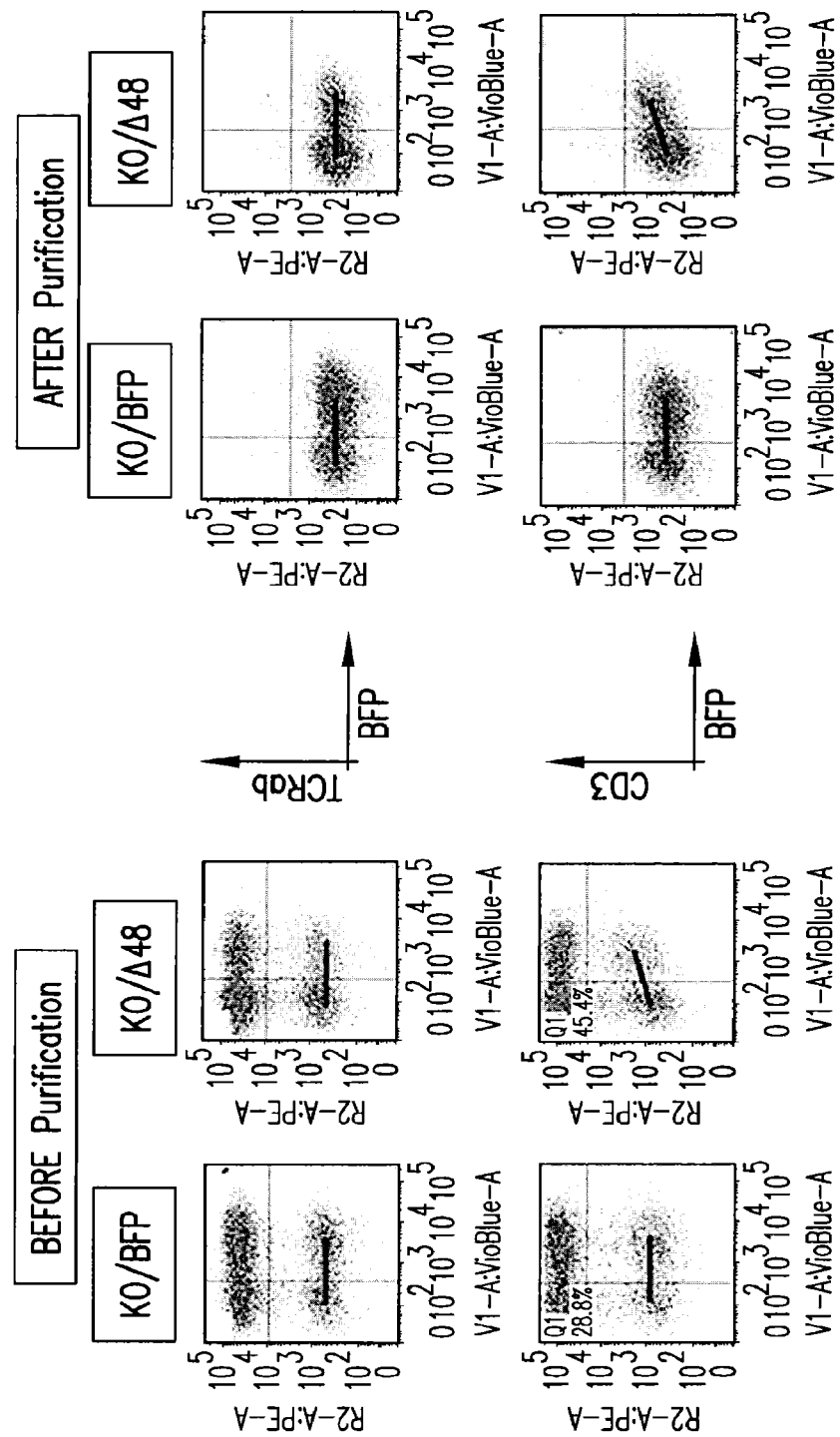
Figure 14C:
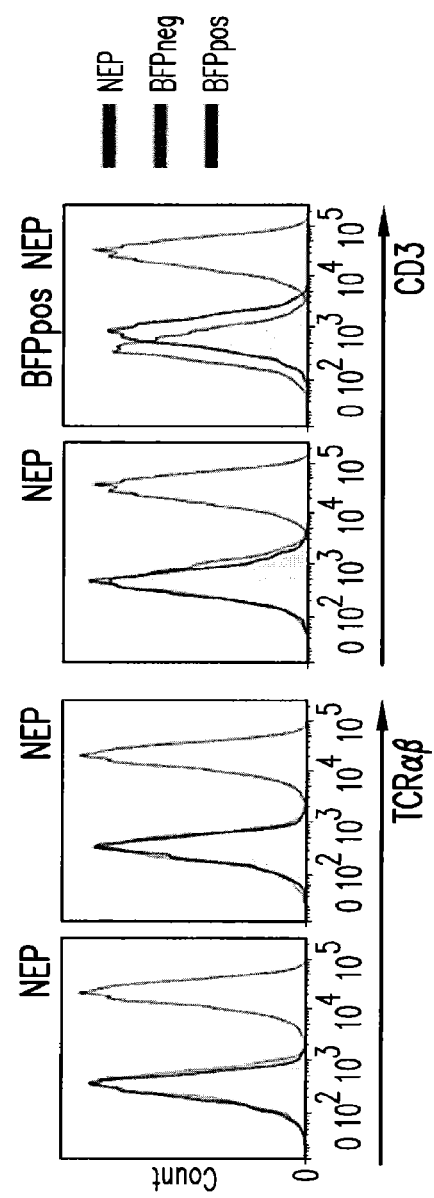

FIG. 14A-C: A. Representation of the experimental protocol. B. Flow cytometry analysis of TCR alpha/beta, CD3 expression and BFP expression on TCRalpha inactivated T cells (KO) transduced with either BFP-2A-pTalphaΔ48 (KO/Δ48) or control BFP lentiviral vector (KO/BFP) before and after purification. C. Flow cytometry analysis of TCR alpha/beta and CD3 expression on purified TCR alpha inactivated cells transduced (BFPpos) or not (BFPneg) with BFP-2A-pTalphaΔ48 lentiviral vector. NEP represents non electroporated cells with TRAC TALE-nucleases.

Figure 15A:
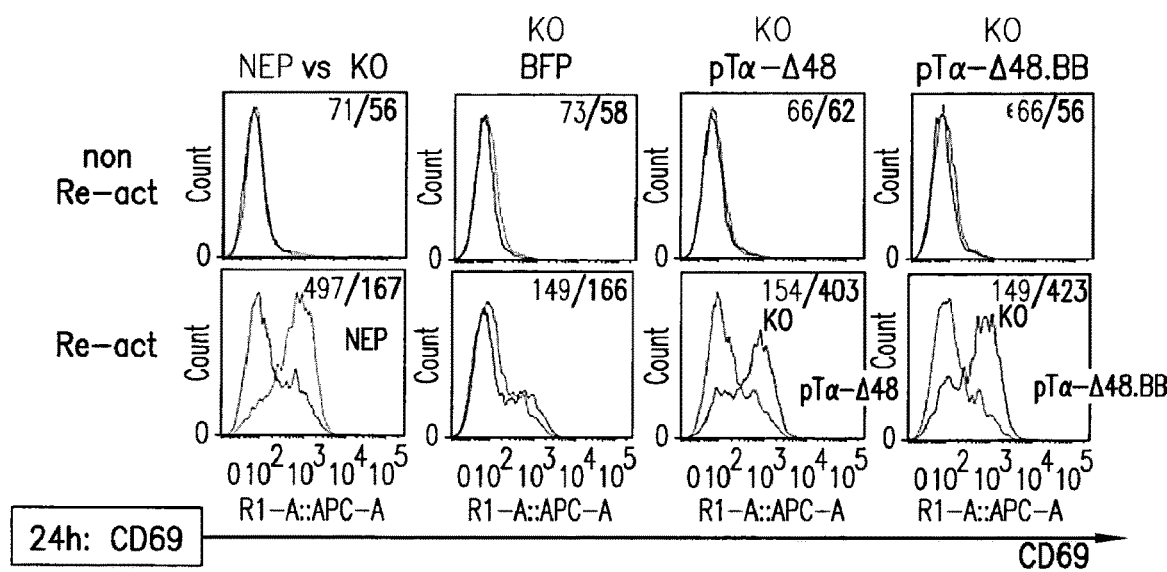
Figure 15B:
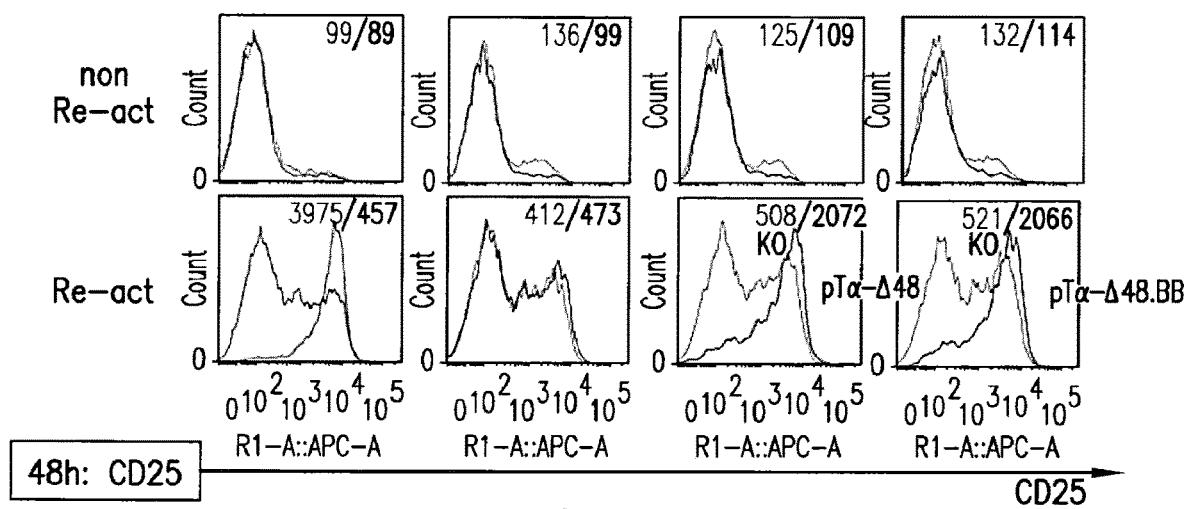
Figure 15C:
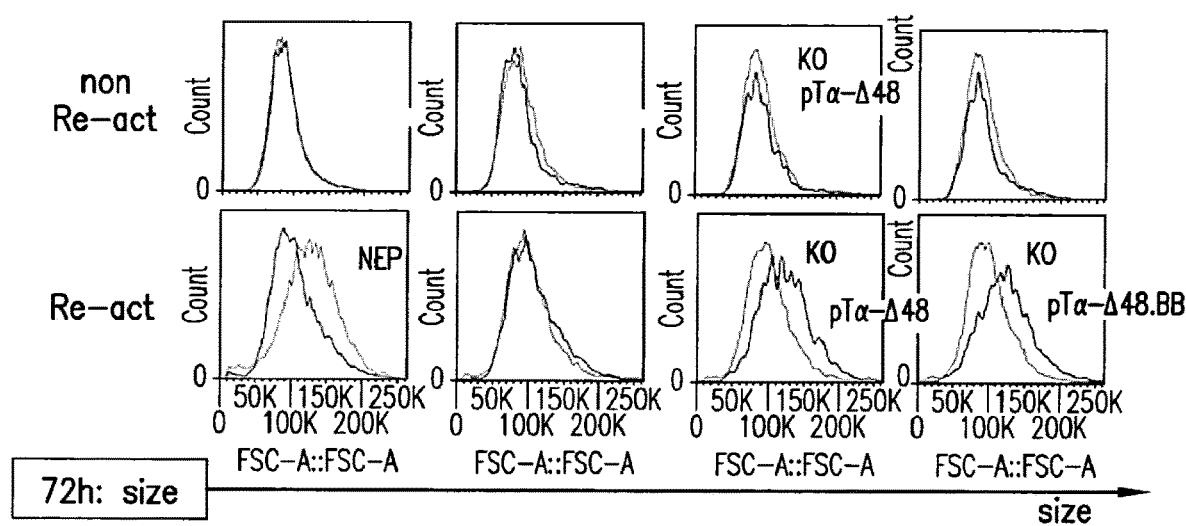

FIG. 15A-C: A-B. Flow cytometry analysis of early activation marker CD69 (A), late activation marker CD25 (B) expression 24 and 48 hours after re-activation with anti-CD3/CD28 beads respectively on non electroporated cells (NEP) and TCRalpha inactivated cells (KO) transduced with BFP-2A-pTα-Δ48 lentiviral vector (pTα-Δ48), BFP-2A-pTα-Δ48.41BB lentiviral vector (pTα-Δ48.BB) or control BFP vector (BFP). pTα-Δ48 histograms correspond to the signal detected in TCR inactivated cells expressing pTα-Δ48 (BFP+ cells) while the KO histograms correspond to TCRalpha inactivated cells which do not express pTα-Δ48 (BFP– cells) pTα-Δ48.BB histograms correspond to the signal detected in TCR inactivated cells expressing pTα-Δ48.41BB (BFP+ cells) while the KO histograms correspond to TCRalpha inactivated cells which do not express pTα-Δ48.41BB (BFP– cells). NEP (non electroporated) histograms correspond to signal detected in non engineered cells. C. Flow cytometry analysis of the size of cells 72 hours after re-activation with anti-CD3/CD28 beads on non electroporated cells (NEP) and TCRalpha inactivated cells (KO) transduced with BFP-2A-pTα-Δ48 lentiviral vector (pTα-Δ48), BFP-2A-pTα-Δ48.41BB lentiviral vector (pTα-Δ48.BB) or control BFP vector (BFP). The values indicated in the upper part of each graph correspond to the geometrical mean of the fluorescence of each population.

Figure 16A:
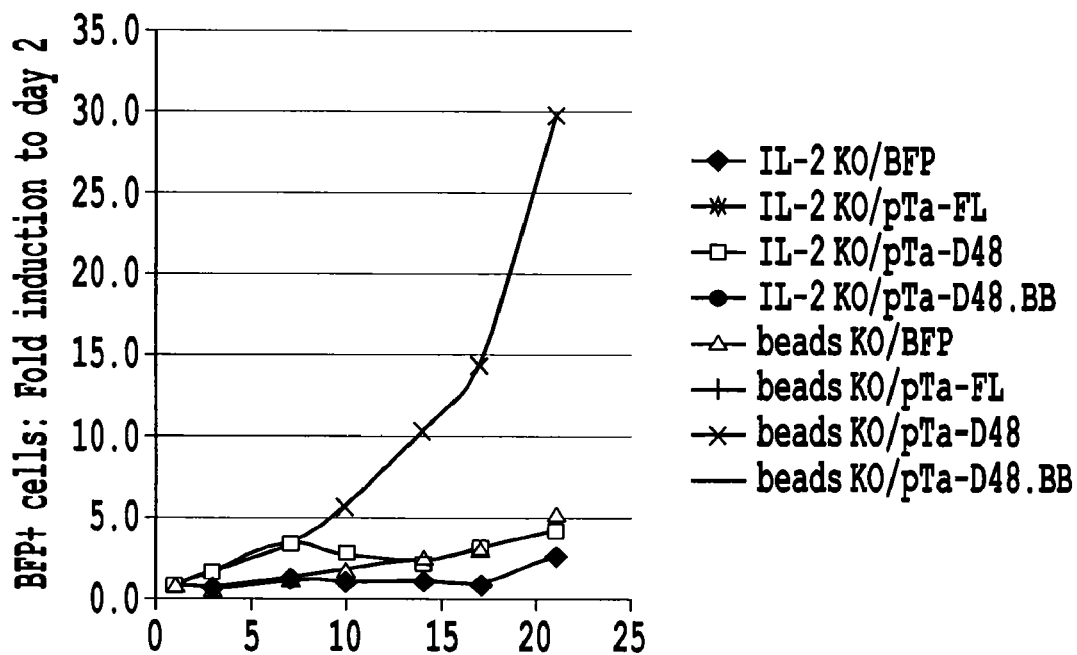
Figure 16B:
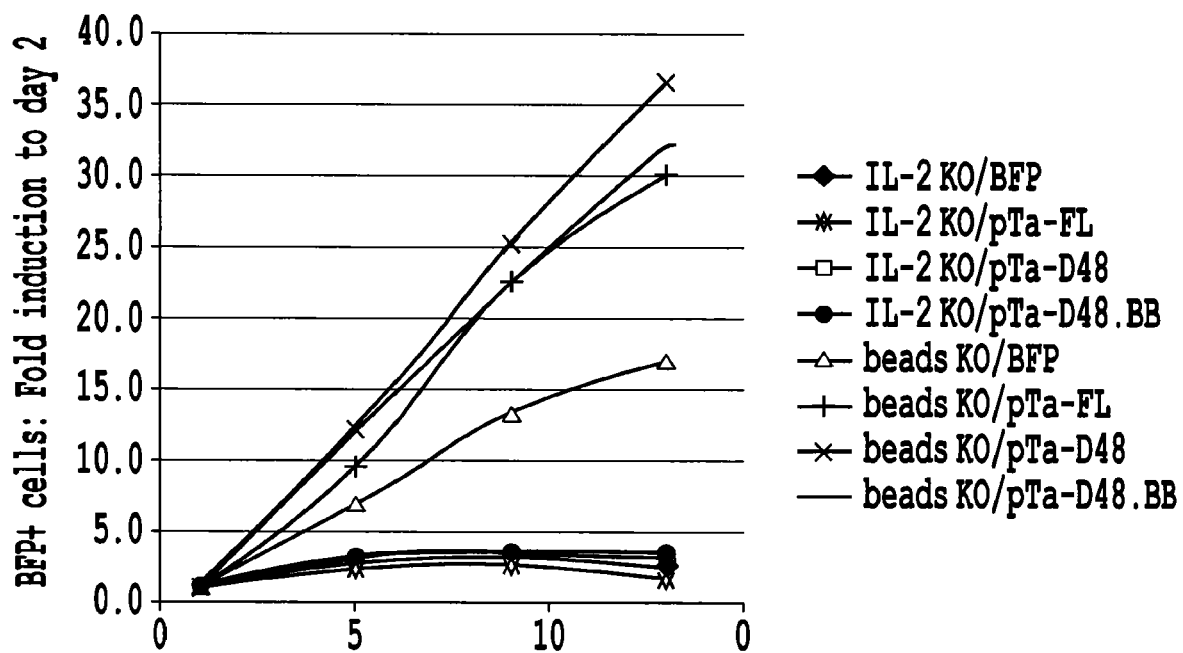

FIG. 16A-B: Cell growth analysis of TCR alpha inactivated cells (KO) transduced with pTalpha-Δ48 (pTaΔ48) or control BFP vector (BFP) maintained in IL2 or in IL2 with anti-CD3/CD28 beads at different time points (x-axis). The BFP+ cells number is estimated at different time points for each condition and the fold induction of these cells (y-axis) was estimated with respect to the value obtained at day 2 post re-activation. The results are obtained from two independent donors. For the second donor, cell growth was also determined for cells transduced with pTalpha-Δ48.41BB (pTα-Δ48.BB) and full-length pTalpha- (pTα-FL).

Figure 17A:
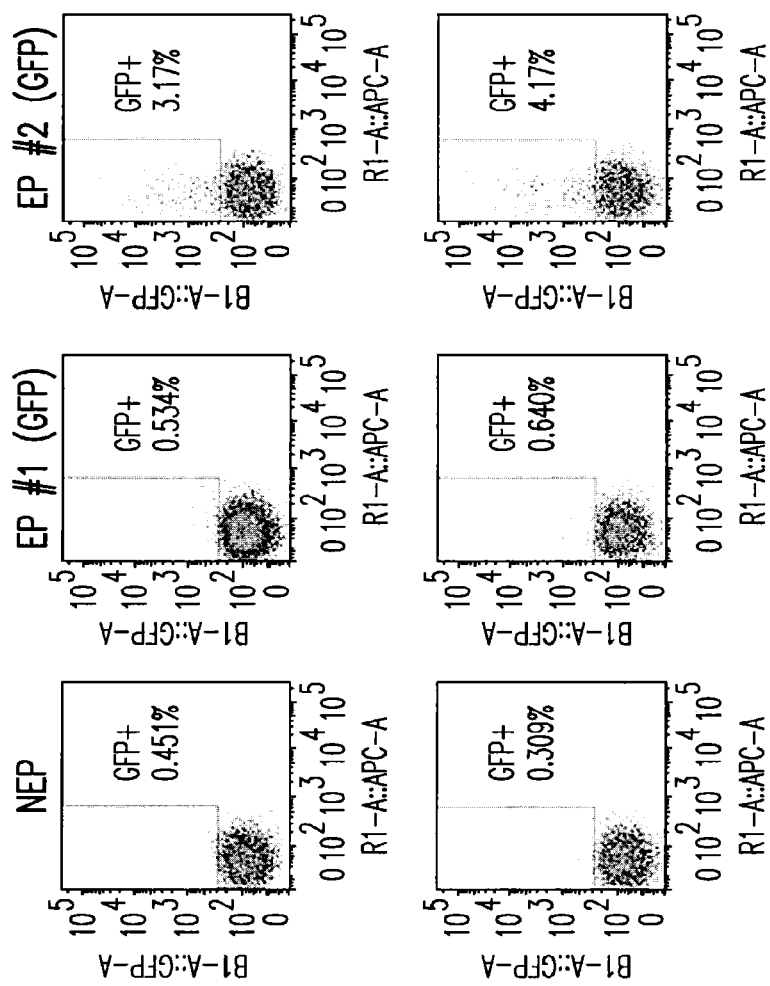
Figure 17B:
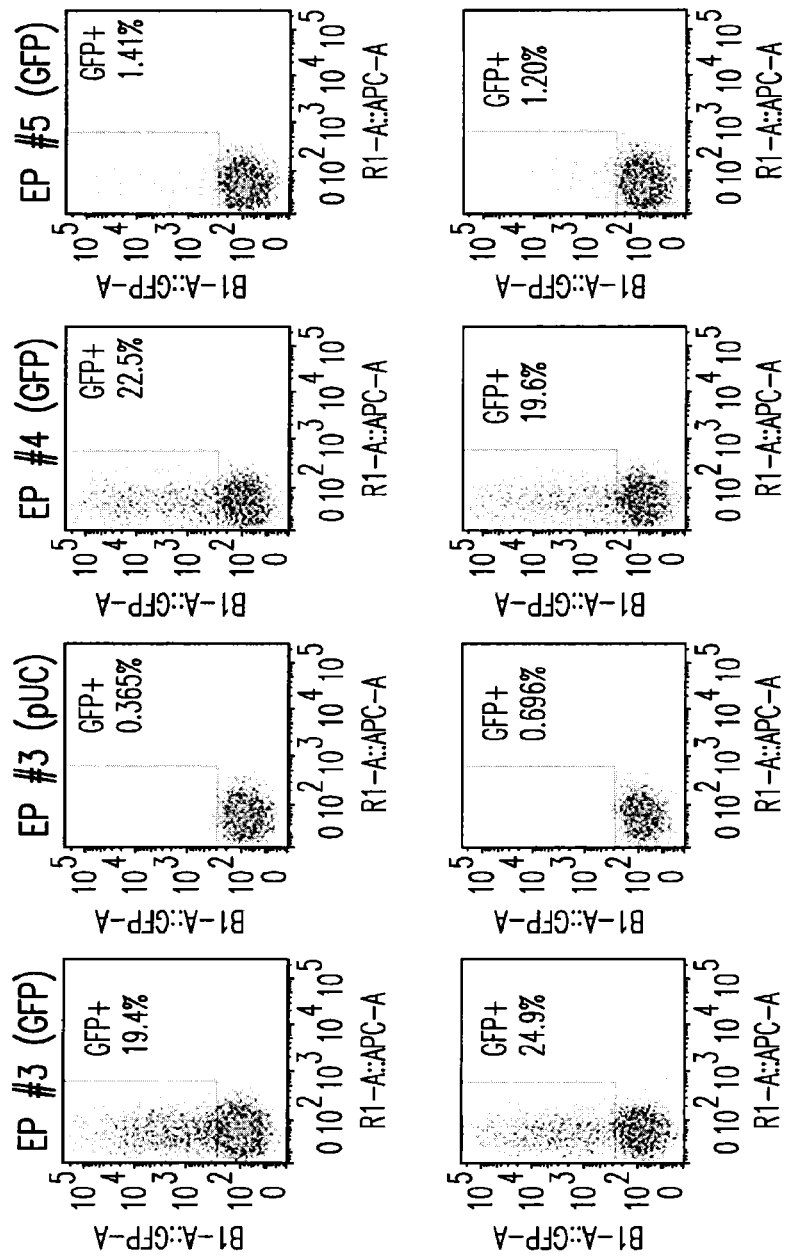

FIG. 17A-B: Flow cytometry analysis of GFP positive cells on PBMCs electroporated with the five different Cytopulse programs. The upper line corresponds to transfection of 6×10⁶ cells per cuvette, while the lower line corresponds to transfection of 3×10⁶ cells per cuvette.

Figure 18A:
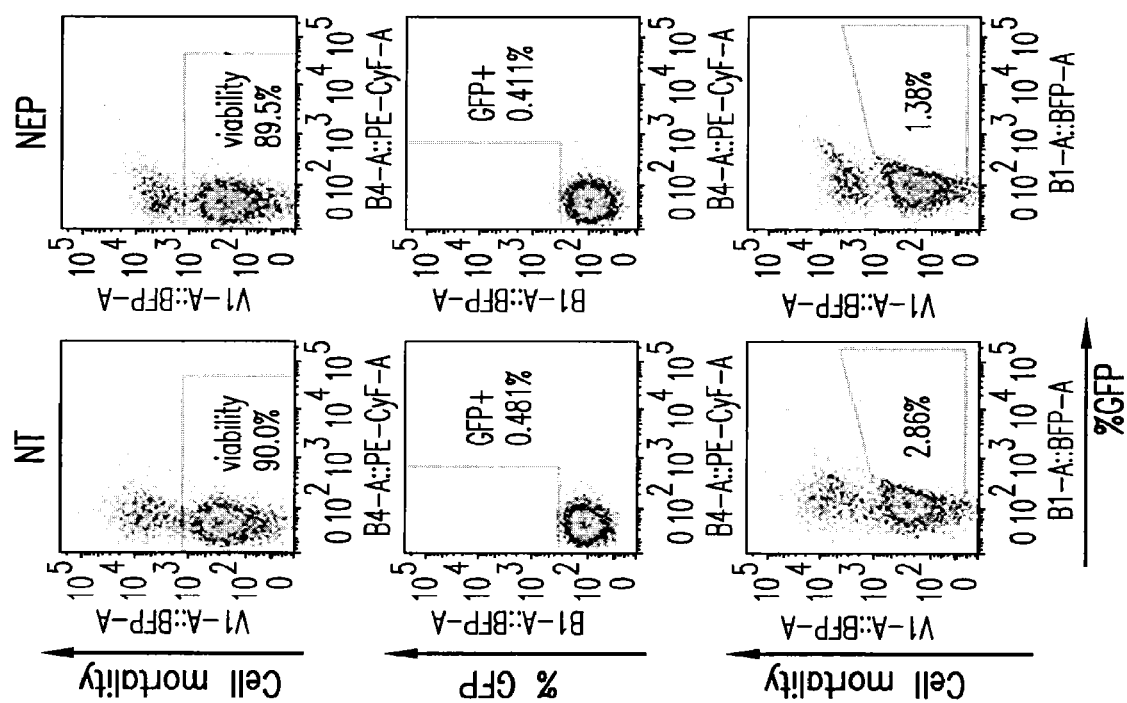
Figure 18B:
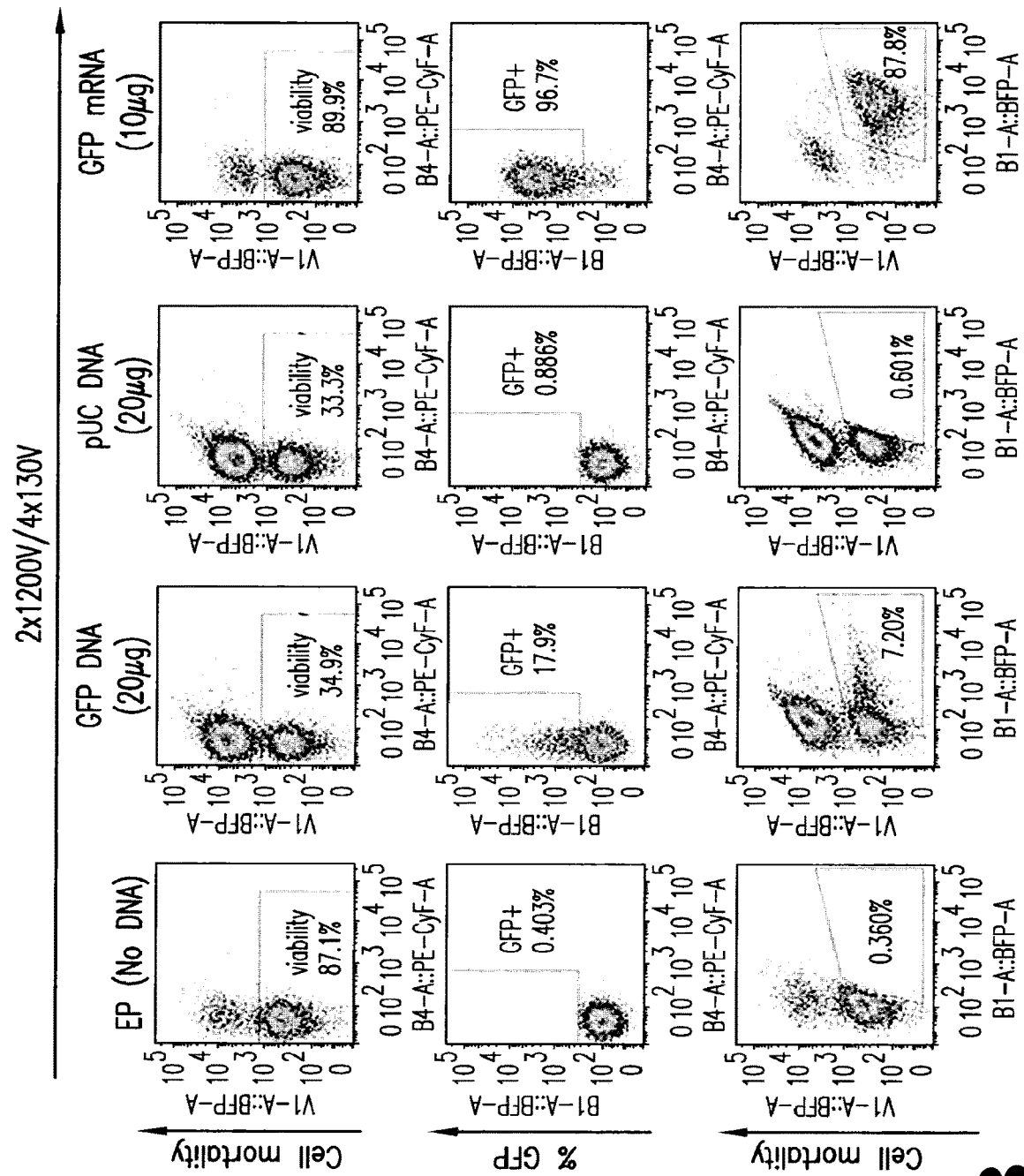

FIG. 18A-B: Flow cytometry analysis of purified T cell mortality using viability dye (eFluor-450) and of GFP positive cells among the viable population after electroporation with GFP mRNA, GFP DNA and control pUC DNA. NEP corresponds to cells that were maintained in electroporation buffer but were not electroporated and NT corresponds to non electroporated cells maintained in culture medium.

Figure 19:
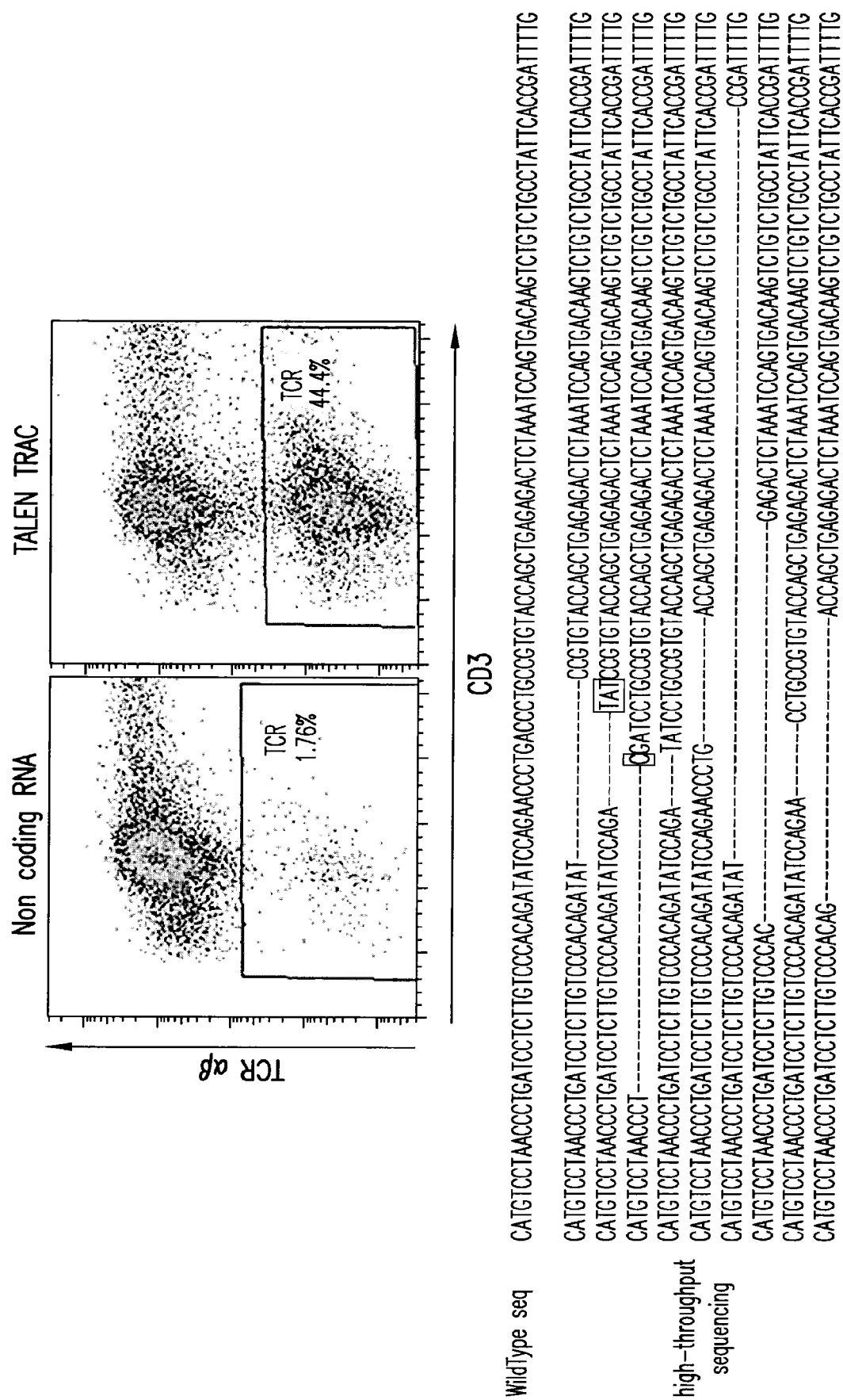

FIG. 19: Flow cytometry analysis of TCR alpha/beta and CD3 expression on human primary T cells following TRAC TALE-nuclease mRNA electroporation (top). Deep sequencing analysis (SEQ ID NO:130-139) of genomic DNA extracted from human primary T cells following TRAC TALE-nuclease mRNA electroporation (bottom).

Figure 20A:
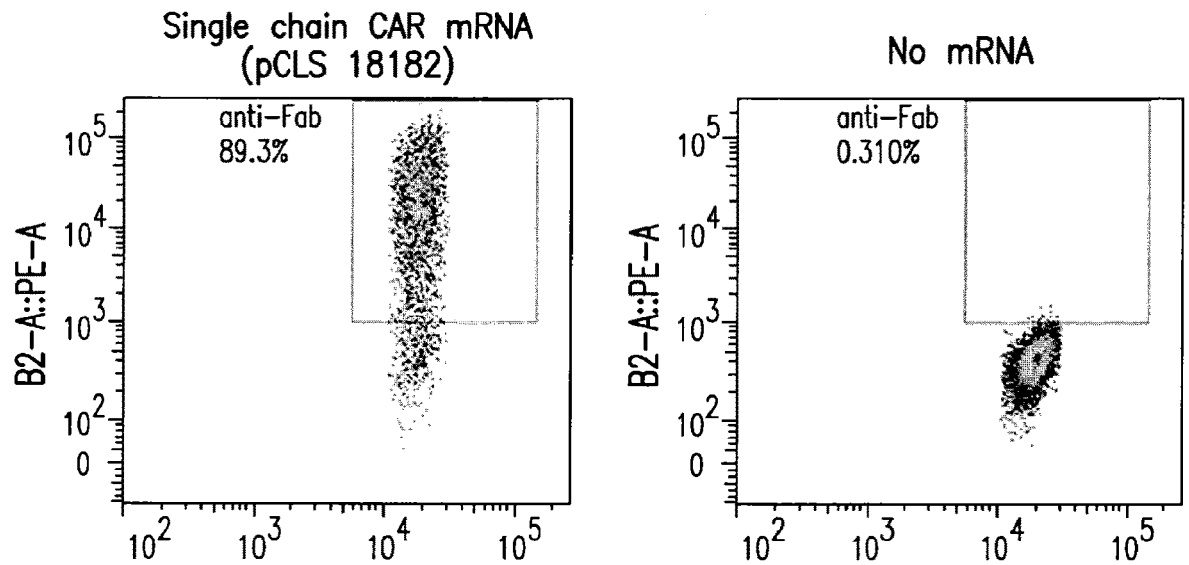
Figure 20B:
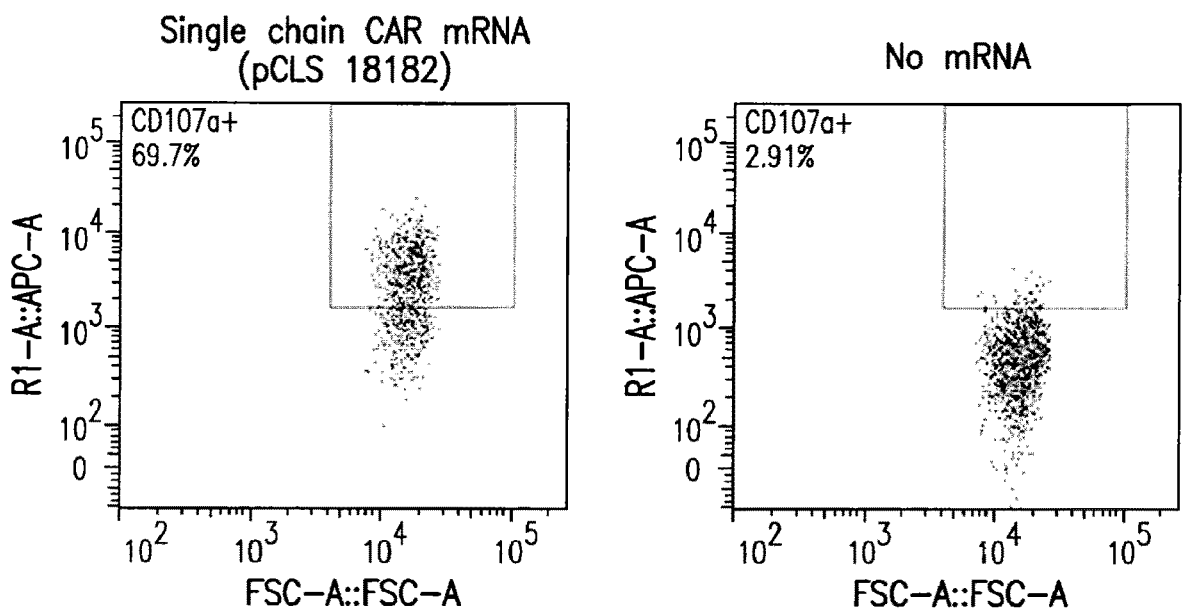

FIG. 20A-B: A. Flow cytometry analysis of CAR expression (anti F(ab')2) after electroporation of T cells with or without mRNA encoding a single chain CAR. B. Flow cytometry analysis of CD107a expression (marker of degranulation) on electroporated T cells cocultured with daudi cells.

Figure 21A:
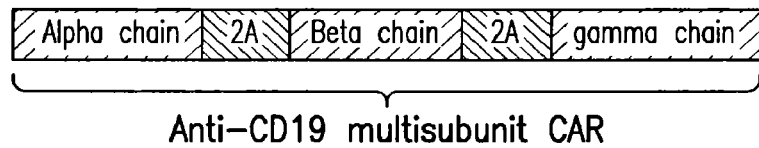
Figure 21B:
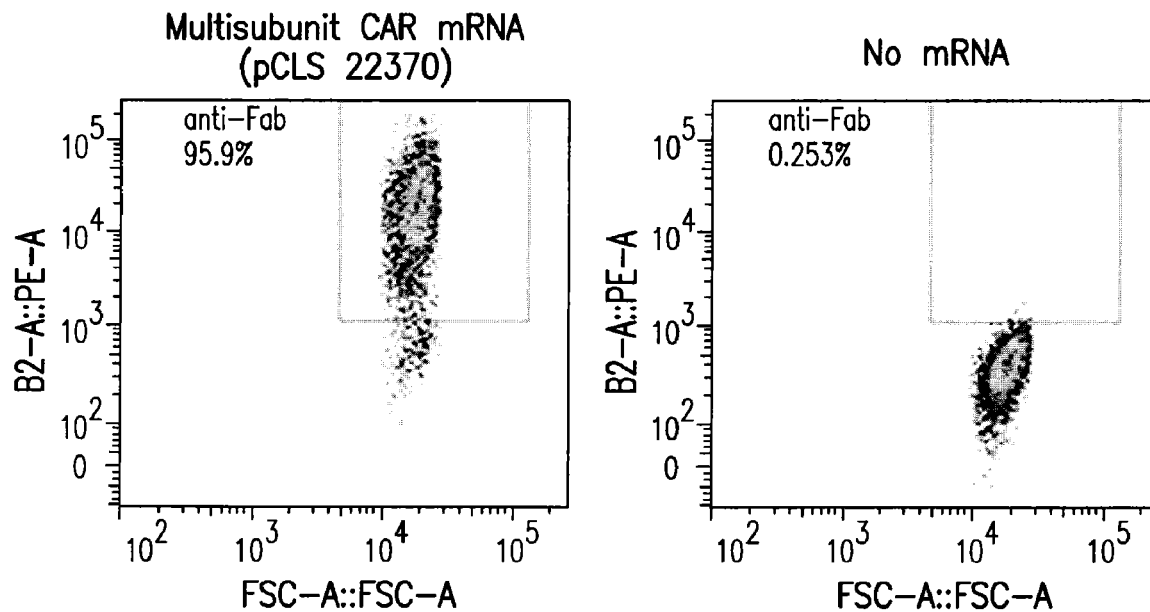
Figure 21C:
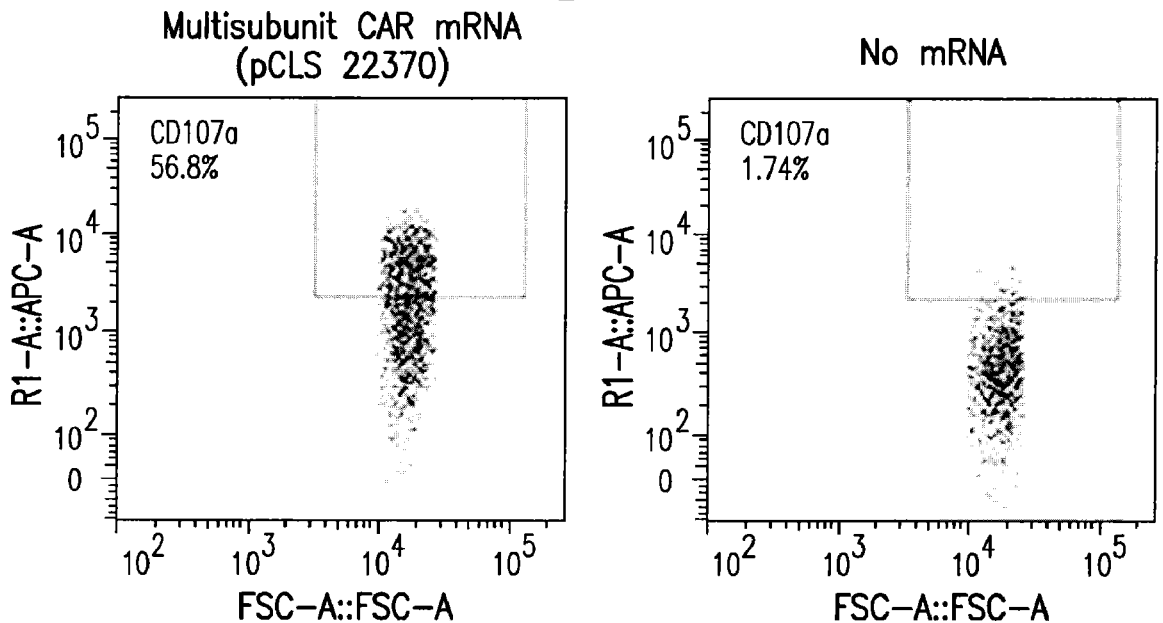

FIG. 21A-C: A. Representation of mRNA encoding a multi-chain CAR. B. Flow cytometry analysis of CAR expression (anti F(ab')2) on viable T cells electroporated with or without a polycistronic mRNA encoding a multi-chain CAR. C. Flow cytometry analysis of CD107a expression (marker of degranulation) on electroporated T cells cocultured with daudi cells.

Table 1: Description of the GR TALE-nucleases and sequences of the TALE-nucleases target sites in the human GR gene.

Table 2: Cleavage activity of the GR TALE-nucleases in yeast. Values are comprised between 0 and 1. Maximal value is 1.

Table 3: Percentage of targeted mutagenesis at endogenous TALE-nuclease target sites in 293 cells.

Table 4: Percentage of targeted mutagenesis at endogenous TALE-nuclease target sites in primary T lymphocytes.

Table 5: Description of the CD52, TRAC and TRBC TALE-nucleases and sequences of the TALE-nucleases target sites in the human corresponding genes.

Table 6: Additional target sequences for TRAC and CD52 TALE-nucleases.

Table 7: Percentage of indels for TALE-nuclease targeting CD52_T02, TRAC_T01, TRBC_T01 and TRBC_T02 targets.

Table 8: Percentages of CD52– negative, TCR-negative and CD52/TCR-double negative T lymphocytes after transfection of corresponding TALE-nuclease-expressing polynucleotides.

Table 9: Percentages of TCR-negative T lymphocytes after transfection of TRBC TALE-nuclease-expressing polynucleotides.

Table 10: Description of the CTLA4 and PDCD1 TALE-nucleases and sequences of the TALE-nucleases target sites in the human corresponding genes.

Table 11: Description of a subset of pTalpha constructs.

Table 12: Activity of the different pTalpha constructs in Jurkat TCR alpha inactivated cell. Activity was measured by flow cytometry analysis of CD3 expression on jurkat TCR alpha inactivated cell transfected with the different preTalpha constructs.

Table 13: Different cytopulse programs used to determine the minimal voltage required for electroporation in PBMC derived T-cells.

Table 14: Cytopulse program used to electroporate purified T-cells.

DETAILED DESCRIPTION OF THE INVENTION

Unless specifically defined herein, all technical and scientific terms used have the same meaning as commonly understood by a skilled artisan in the fields of gene therapy, biochemistry, genetics, and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail. Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, N.Y.: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

In a general aspect, the present invention relates to methods for new adoptive immunotherapy strategies in treating cancer and infections.

Non Alloreactive and Immunosuppressive Resistant T Cells:

In a particular aspect, the present invention relates to a method of engineering T-cells, especially for immunotherapy. In particular this method comprises:
 (a) modifying T-cells by inactivating at least:
  A first gene expressing a target for an immunosuppressive agent, and
  A second gene encoding a component of the T-cell receptor (TCR)
 (b) Expanding said cells, optionally in presence of said immunosuppressive agent.

An immunosuppressive agent is an agent that suppresses immune function by one of several mechanisms of action. In other words, an immunosuppressive agent is a role played by a compound which is exhibited by a capability to diminish the extent and/or voracity of an immune response. As non limiting example, an immunosuppressive agent can be a calcineurin inhibitor, a target of rapamycin, an interleukin-2 α-chain blocker, an inhibitor of inosine monophosphate dehydrogenase, an inhibitor of dihydrofolic acid reductase, a corticosteroid or an immunosuppressive antimetabolite. Classical cytotoxic immunosuppressants act by inhibiting DNA synthesis. Others may act through activation of T-cells or by inhibiting the activation of helper cells. The method according to the invention allows conferring immunosuppressive resistance to T cells for immunotherapy by inactivating the target of the immunosuppressive agent in T cells. As non limiting examples, targets for immunosuppressive agent can be a receptor for an immunosuppressive agent such as: CD52, glucocorticoid receptor (GR), a FKBP family gene member and a cyclophilin family gene member.

In a particular embodiment, the genetic modification step of the method relies on the inactivation of one gene selected from the group consisting of CD52, GR, TCR alpha and TCR beta. In another embodiment, the genetic modification step of the method relies on the inactivation of two genes selected from the group consisting of CD52 and GR, CD52 and TCR alpha, CDR52 and TCR beta, GR and TCR alpha, GR and TCR beta, TCR alpha and TCR beta. In another embodiment, the genetic modification step of the method relies on the inactivation of more than two genes. The genetic modification is preferably operated ex-vivo.

By inactivating a gene it is intended that the gene of interest is not expressed in a functional protein form. In particular embodiment, the genetic modification of the method relies on the expression, in provided cells to engineer, of one rare-cutting endonuclease such that said rare-cutting endonuclease specifically catalyzes cleavage in one targeted gene thereby inactivating said targeted gene. The nucleic acid strand breaks caused by the rare-cutting endonuclease are commonly repaired through the distinct mechanisms of homologous recombination or non-homologous end joining (NHEJ). However, NHEJ is an imperfect repair process that often results in changes to the DNA sequence at the site of the cleavage. Mechanisms involve rejoining of what remains of the two DNA ends through direct re-ligation (Critchlow and Jackson 1998) or via the so-called microhomology-mediated end joining (Ma, Kim et al. 2003). Repair via non-homologous end joining (NHEJ) often results in small insertions or deletions and can be used for the creation of specific gene knockouts. Said modification may be a substitution, deletion, or addition of at least one nucleotide. Cells in which a cleavage-induced mutagenesis event, i.e a mutagenesis event consecutive to an NHEJ event, has occurred can be identified and/or selected by well-known method in the art. In a particular embodiment, said method to engineer cells comprises at least one of the following steps:
(a) Providing a T-cell, preferably from a cell culture or from a blood sample;
(b) Selecting a gene in said T-cell expressing a target for an immunosuppressive agent;
(c) Introducing into said T-cell a rare-cutting endonuclease able to selectively inactivate by DNA cleavage, preferably by double-strand break respectively:
said gene encoding a target for said immunosuppressive agent, and
at least one gene encoding a component of the T-cell receptor (TCR).
(d) Expanding said cells, optionally in presence of said immunosuppressive agent.

In a more preferred embodiment, said method comprises:
(a) Providing a T-cell, preferably from a cell culture or from a blood sample;
(b) Selecting a gene in said T-cell expressing a target for an immunosuppressive agent;
(c) Transforming said T cell with nucleic acid encoding a rare-cutting endonuclease able to selectively inactivate by DNA cleavage, preferably by double-strand break respectively:
said gene encoding a target for said immunosuppressive agent, and
at least one gene encoding a component of the T-cell receptor (TCR);
(d) Expressing said rare-cutting endonucleases into said T-cells;
(e) Sorting the transformed T-cells, which do not express TCR on their cell surface;
(f) Expanding said cells, optionally in presence of said immunosuppressive agent.

In particular embodiment, said rare-cutting endonuclease specifically targets one gene selected from the group consisting of CD52, GR, TCR alpha and TCR beta. In another embodiment, the genetic modification of the method relies on the expression, in provided cells to engineer, of two rare-cutting endonucleases such that said each of the two rare-cutting endonucleases specifically and respectively catalyzes cleavage in each of the pairs of genes selected from the group consisting of CD52 and GR, CD52 and TCR alpha, CDR52 and TCR beta, GR and TCR alpha, GR and TCR beta, TCR alpha and TCR beta, thereby inactivating said targeted genes. In another embodiment, more than two rare-cutting endonucleases can be expressed in cells to engineer in order to target and/or inactivate more than two genes.

In another embodiment, said gene of step (b), specific for an immunosuppressive treatment, is CD52 and the immunosuppressive treatment of step (d) or (e) comprises a humanized antibody targeting CD52 antigen.

In another embodiment, said gene of step (b), specific for an immunosuppressive treatment, is a glucocorticoid receptor (GR) and the immunosuppressive treatment of step d) or (e) comprises a corticosteroid such as dexamethasone.

In another embodiment, said target gene of step (b), specific for an immunosuppressive treatment, is a FKBP family gene member or a variant thereof and the immunosuppressive treatment of step (d) or (e) comprises FK506 also known as Tacrolimus or fujimycin. In another embodiment, said FKBP family gene member is FKBP12 or a variant thereof.

In another embodiment, said gene of step (b), specific for an immunosuppressive treatment, is a cyclophilin family gene member or a variant thereof and the immunosuppressive treatment of step (d) or (e) comprises cyclosporine.

In another embodiment, said rare-cutting endonuclease can be a meganuclease, a Zinc finger nuclease or a TALE-nuclease. In a preferred embodiment, said rare-cutting endonuclease is a TALE-nuclease. By TALE-nuclease is intended a fusion protein consisting of a DNA-binding domain derived from a Transcription Activator Like Effector (TALE) and one nuclease catalytic domain to cleave a nucleic acid target sequence. (Boch, Scholze et al. 2009; Moscou and Bogdanove 2009)(Deng, Yan et al. 2012; Mak, Bradley et al. 2012)(Christian, Cermak et al. 2010; Cermak, Doyle et al. 2011; Geissler, Scholze et al. 2011; Huang, Xiao et al. 2011; Li, Huang et al. 2011; Mahfouz, Li et al. 2011; Miller, Tan et al. 2011; Morbitzer, Romer et al. 2011; Mussolino, Morbitzer et al. 2011; Sander, Cade et al. 2011; Tesson, Usal et al. 2011; Weber, Gruetzner et al. 2011; Zhang, Cong et al. 2011; Li, Piatek et al. 2012; Mahfouz, Li et al. 2012) In the present invention new TALE-nucleases have been designed for precisely targeting relevant genes for adoptive immunotherapy strategies.

Preferred TALE-nucleases according to the invention are those recognizing and cleaving the target sequence selected from the group consisting of:
SEQ ID NO: 1 to 6 (GR),
SEQ ID NO: 37, 57 to 60 (TCRalpha),
SEQ ID NO: 38 or 39 (TCRbeta), and
SEQ ID NO: 40, 61 to 65 (CD52)
Said TALE-nucleases preferably comprise a polypeptide sequence selected from SEQ ID NO: 7 to SEQ ID NO: 18 and SEQ ID NO: 41 to SEQ ID NO: 48, in order to cleave the respective target sequences SEQ ID NO: 1 to 6 and SEQ ID NO: 37 to 40.

In another embodiment, additional catalytic domain can be further introduced into the cell with said rare-cutting endonuclease to increase mutagenesis in order to enhance their capacity to inactivate targeted genes. In particular, said additional catalytic domain is a DNA end processing enzyme. Non limiting examples of DNA end-processing enzymes include 5-3' exonucleases, 3-5' exonucleases, 5-3' alkaline exonucleases, 5' flap endonucleases, helicases, hosphatase, hydrolases and template-independent DNA polymerases. Non limiting examples of such catalytic domain comprise of a protein domain or catalytically active derivate of the protein domain seleced from the group consisting of hExoI (EXO1_HUMAN), Yeast ExoI (EXO1_YEAST), E. coli ExoI, Human TREX2, Mouse TREX1, Human TREX1, Bovine TREX1, Rat TREX1, TdT (terminal deoxynucleotidyl transferase) Human DNA2, Yeast DNA2 (DNA2_YEAST). In a preferred embodiment, said additional catalytic domain has a 3'-5'-exonuclease activity, and in a more preferred embodiment, said additional catalytic domain is TREX, more preferably TREX2 catalytic domain (WO2012/058458). In another preferred embodiment, said catalytic domain is encoded by a single chain TREX polypeptide. Said additional catalytic domain may be fused to a nuclease fusion protein or chimeric protein according to the invention optionally by a peptide linker.

Endonucleolytic breaks are known to stimulate the rate of homologous recombination. Thus, in another embodiment, the genetic modification step of the method further comprises a step of introduction into cells an exogeneous nucleic acid comprising at least a sequence homologous to a portion of the target nucleic acid sequence, such that homologous recombination occurs between the target nucleic acid sequence and the exogeneous nucleic acid. In particular embodiments, said exogeneous nucleic acid comprises first and second portions which are homologous to region 5' and 3' of the target nucleic acid sequence, respectively. Said exogeneous nucleic acid in these embodiments also comprises a third portion positioned between the first and the second portion which comprises no homology with the regions 5' and 3' of the target nucleic acid sequence. Following cleavage of the target nucleic acid sequence, a homologous recombination event is stimulated between the target nucleic acid sequence and the exogeneous nucleic acid. Preferably, homologous sequences of at least 50 bp, preferably more than 100 bp and more preferably more than 200 bp are used within said donor matrix. Therefore, the exogenous nucleic acid is preferably from 200 bp to 6000 bp, more preferably from 1000 bp to 2000 bp. Indeed, shared nucleic acid homologies are located in regions flanking upstream and downstream the site of the break and the nucleic acid sequence to be introduced should be located between the two arms.

In particular, said exogeneous nucleic acid successively comprises a first region of homology to sequences upstream of said cleavage, a sequence to inactivate one targeted gene selected from the group consisting of CD52, GR, TCR alpha and TCR beta and a second region of homology to sequences downstream of the cleavage. Said polynucleotide introduction step can be simultaneous, before or after the introduction or expression of said rare-cutting endonuclease. Depending on the location of the target nucleic acid sequence wherein break event has occurred, such exogenous nucleic acid can be used to knock-out a gene, e.g. when exogeneous nucleic acid is located within the open reading frame of said gene, or to introduce new sequences or genes of interest. Sequence insertions by using such exogeneous nucleic acid can be used to modify a targeted existing gene, by correction or replacement of said gene (allele swap as a non-limiting example), or to up- or down-regulate the expression of the targeted gene (promoter swap as non-limiting example), said targeted gene correction or replacement. In preferred embodiment, inactivation of genes from the group consisting of CD52, GR, TCR alpha and TCR beta can be done at a precise genomic location targeted by a specific TALE-nuclease, wherein said specific TALE-nuclease catalyzes a cleavage and wherein said exogeneous nucleic acid successively comprising at least a region of homology and a sequence to inactivate one targeted gene selected from the group consisting of CD52, GR, TCR alpha and TCR beta which is integrated by homologous recombination. In another embodiment, several genes can be, successively or at the same time, inactivated by using several TALE-nucleases respectively and specifically targeting one defined gene and several specific polynucleotides for specific gene inactivation.

By additional genomic modification step, can be intended also the inactivation of another gene selected from the group consisting of CD52, GR, TCR alpha and TCR beta. As mentioned above, said additional genomic modification step can be an inactivation step comprising:
  (a) introducing into said cells at least one rare-cutting endonuclease such that said rare-cutting endonuclease specifically catalyzes cleavage in one targeted sequence of the genome of said cell.
  (b) Optionally introducing into said cells a exogenous nucleic acid successively comprising a first region of homology to sequences upstream of said cleavage, a sequence to be inserted in the genome of said cell and a second region of homology to sequences downstream of said cleavage,
wherein said introduced exogenous nucleic acid inactivates a gene and integrates at least one exogenous polynucleotide sequence encoding at least one recombinant protein of interest. In another embodiment, said exogenous polynucleotide sequence is integrated within a gene selected from the group consisting of CD52, GR, TCR alpha and TCR beta.

In particular embodiment said method to engineer cell further comprises an additional genomic modification step. By additional genomic modification step, can be intended the introduction into cells to engineer of one protein of interest. Said protein of interest can be, as non limiting examples, pTalpha or functional variant thereof, a Chimeric Antigen Receptor (CAR), a multi-chain CAR, a bispecific antibody or rare-cutting endonuclease targeting PDCD1 or CTLA-4 as described in the present disclosure.

The invention also relates to TALE-nucleases. Generally, the invention relates to TALE-nuclease comprising:
  (a) A Transcription Activator-Like Effector (TALE) DNA binding domain that has been engineered to bind a target sequence within genes selected from the group consisting of CD52, GR, TCR alpha and TCR beta;
  (b) A cleavage domain or a cleavage half-domain.

Preferred TALE-nucleases according to the invention are those recognizing and cleaving the target sequence selected from the group consisting of:
  SEQ ID NO: 1 to 6 (GR),
  SEQ ID NO: 37, 57 to 60 (TCRalpha),
  SEQ ID NO: 38 or 39 (TCRbeta), and
  SEQ ID NO: 40, 61 to 65 (CD52)

Said TALE-nucleases preferably comprise a polypeptide sequence selected from SEQ ID NO: 7 to SEQ ID NO: 18 and SEQ ID NO: 41 to SEQ ID NO: 48, in order to cleave the respective target sequences SEQ ID NO: 1 to 6 and SEQ ID NO: 37 to 40.

Because some variability may arise from the genomic data from which these polypeptides derive, and also to take into account the possibility to substitute some of the amino acids present in these polypeptides without significant loss of activity (functional variants), the invention encompasses polypeptides variants of the above polypeptides that share at least 70%, preferably at least 80%, more preferably at least 90% and even more preferably at least 95% identity with the sequences provided in this patent application.

The present invention is thus drawn to polypeptides comprising a polypeptide sequence that has at least 70%, preferably at least 80%, more preferably at least 90%, 95% 97% or 99% sequence identity with amino acid sequence selected from the group consisting of SEQ ID NO:7 to SEQ ID NO: 18 and SEQ ID NO: 41 to SEQ ID NO: 48.

Are also comprised in the scope of the present invention, polynucleotides, vectors encoding the above described rare-cutting endonucleases according to the invention.

In the scope of the present invention are also encompassed isolated cells or cell lines susceptible to be obtained by said method to engineer cells, in particular T cells, in which at least one gene selected from the group consisting of CD52, GR, TCR alpha and TCR beta has been inactivated. Preferably, two genes selected from the group consisting of CD52 and GR, CD52 and TCR alpha, CDR52 and TCR beta, GR and TCR alpha, GR and TCR beta, TCR alpha and TCR beta have been inactivated.

According to the invention, those genes are preferably inactivated by at least one rare-cutting endonuclease. It has been shown by the inventors that the use of TALE-nucleases was particularly advantageous to achieve double inactivation in T-cells. The invention encompasses an isolated T-cell comprising at least two polynucleotides, said polynucleotides encoding at least a first and second TALE-nucleases, preferably the first TALE-nuclease being directed against a gene encoding TCR and the second being directed against a gene encoding a receptor for an immunosuppressive agent, such as CD52 or GR.

In another embodiment, said isolated cell further comprises one additional genomic modification. In another embodiment, said additional genomic modification is the integration of at least one exogenous polynucleotide sequence. In another embodiment, said exogenous sequence is integrated into one gene selected from the group consisting of CD52, GR, TCR alpha and TCR beta.

PreTalpha

In another aspect, the invention relates to a method of expanding TCR alpha deficient T-cell comprising introducing into said T-cell pTalpha (also named preTCRα) or a functional variant thereof and expanding said cells, optionally through stimulation of the CD3 complex. In a preferred embodiment, the method comprises:
 a) Transforming said cells with nucleic acid encoding at least a fragment of pTalpha to support CD3 surface expression
 b) Expressing said pTalpha into said cells
 c) Expanding said cells optionally, optionally through stimulation of the CD3 complex.

The invention also relates to a method of preparing T-cells for immunotherapy comprising steps of the method for expansion for T-cell.

In particular embodiment, the pTalpha polynucleotide sequence can be introduced randomly or else through homologous recombination, in particular the insertion could be associated with the inactivation of the TCRalpha gene.

According to the invention, different functional variants of pTalpha are used. A "functional variant" of the peptide refers to a molecule substantially similar to either the entire peptide or a fragment thereof. A "fragment" of the pTalpha or functional variant thereof of the present Invention, refers to any subset of the molecule, that is, a shorter peptide. Preferred pTalpha or functional variants can be full length pTalpha or a C-terminal truncated pTalpha version. C-terminal truncated pTalpha lacks in C-terminal end one or more residues. As non limiting examples, C-terminal truncated pTalpha version lacks 18, 48, 62, 78, 92, 110 or 114 residues from the C-terminus of the protein (SEQ ID NO: 107 to SEQ ID NO: 114). Moreover, amino acid sequence variants of the peptide can be prepared by mutations in the DNA which encodes the peptide. Such functional variants include, for example, deletions from, or insertions or substitutions of, residues within the amino acid sequence. Any combination of deletion, insertion, and substitution may also be made to arrive at the final construct, provided that the final construct possesses the desired activity, in particular the restoration of a functional CD3 complex.

In preferred embodiment, at least one mutation is introduced in the different pTalpha versions as described above to affect dimerization. As non limiting example, mutated residue can be at least W46R, D22A, K24A, R102A or R117A of the human pTalpha protein or aligned positions using CLUSTALW method on pTalpha family or homologue member. Preferably pTalpha or variant thereof as described above comprise the mutated residue W46R (SEQ ID NO:123) or the mutated residues D22A, K24A, R102A and R117A (SEQ ID NO: 124). In particular embodiment, said pTalpha or variants are also fused to a signal-transducing domain such as CD28, OX40, ICOS, CD27, CD137 (4-1BB) and CD8 as non limiting examples (SEQ ID NO: 115 to SEQ ID NO: 120). The extracellular domain of pTalpha or variants as described above can be fused to a fragment of the TCRalpha protein, particularly the transmembrane and intracellular domain of TCRalpha (SEQ ID NO: 122). pTalpha variants can also be fused to the intracellular domain of TCRalpha (SEQ ID NO:121).

In another embodiment, said pTalpha versions are fused to an extracellular ligand-binding domain and more preferably pTalpha or functional variant thereof is fused to a single chain antibody fragment (scFV) comprising the light ($V_L$) and the heavy ($V_H$) variable fragment of a target antigen specific monoclonal antibody joined by a flexible linker. As a non limiting example, amino acid sequence of pTalpha or functional variant thereof is selected from the group consisting of SEQ ID NO: 107 to SEQ ID NO: 124.

Because some variability may arise from the genomic data from which these polypeptides derive, and also to take into account the possibility to substitute some of the amino acids present in these polypeptides without significant loss of activity (functional variants), the invention encompasses polypeptides variants of the above polypeptides that share at least 70%, preferably at least 80%, more preferably at least 90% and even more preferably at least 95% identity with the sequences provided in this patent application.

The present invention is thus drawn to polypeptides comprising a polypeptide sequence that has at least 70%, preferably at least 80%, more preferably at least 90%, 95% 97% or 99% sequence identity with amino acid sequence selected from the group consisting of SEQ ID NO:107 to SEQ ID NO: 124.

By TCR alpha deficient T cell is intended an isolated T cell that lacks expression of a functional TCR alpha chain. This may be accomplished by different means, as non limiting examples, by engineering a T cell such that it does not express any functional TCR alpha on its cell surface or by engineering a T cell such that it produces very little functional TCR alpha chain on its surface or by engineering a T cell to express mutated or truncated form of TCR alpha chain.

TCR alpha deficient cells can no longer be expanded through CD3 complex. Thus, to overcome this problem and to allow proliferation of TCR alpha deficient cells, pTalpha or functional variant thereof is introduced into said cells, thus restoring a functional CD3 complex. In a preferred embodiment, the method further comprises introducing into said T cells rare-cutting endonucleases able to selectively inactivate by DNA cleavage one gene encoding one component of the T-cell receptor (TCR). In particular embodiment, said rare-cutting endonuclease is a TALE-nucleases. As non limiting examples, TALE-nuclease is directed against one of the gene target sequences of TCRalpha selected from the group consisting of SEQ ID NO: 37 and SEQ ID NO: 57 to 60. Preferably, TALE-nucleases are selected from the group consisting of SEQ ID NO: 41 and SEQ ID NO: 42.

In particular embodiment said method for expansion of TCR alpha deficient T-cells comprises an additional genomic modification step. By additional genomic modification step, can be intended the introduction into cells to engineer of one protein of interest. Said protein of interest can be, as non limiting examples, a Chimeric Antigen Receptor (CAR), particularly CAR comprising amino acid sequence SEQ ID NO: 73, a multi-chain CAR, particularly multi-chain CAR comprising amino acid sequence SEQ ID NO: 125 a bispecific antibody, rare-cutting endonucleases targeting PDCD1 or CTLA-4, particularly targeting nucleic acid sequence SEQ ID NO: 74 to SEQ ID NO: 78 or a rare-cutting endonuclease targeting a target for immunosuppressive agent as described in the present disclosure.

Are also encompassed in the present invention polypeptides encoding pTalpha, particularly functional variants described above. In a preferred embodiment the invention relates to a pTalpha or functional variant thereof fused to a signal transducing domain such as CD28, OX40, ICOS, CD137 and CD8. More particularly, the invention relates to pTalpha functional variant comprising amino acid sequence selected form the group consisting of SEQ ID NO: 107 to SEQ ID NO: 124. Are also encompassed in the present invention polynucleotides, vectors encoding pTalpha or functional variants thereof described above.

In the scope of the present invention are also encompassed isolated cells or cell lines susceptible to be obtained by said method. In particular said isolated cells or cell lines are obtained by introducing into said cells a pTalpha or a functional variant thereof to support CD3 surface expression. In a preferred embodiment, said isolated cell or cell line are further genetically modified by inactivating TCRalpha gene. This gene is preferably inactivating by at least one rare-cutting endonuclease. In a preferred embodiment said rare-cutting endonuclease is TALE-nuclease.

Multi-Chain Chimeric Antigen Receptor (CAR)

In another embodiment, the invention relates to a multi-chain chimeric antigen receptor (CAR) particularly adapted to the production and expansion of engineered T-cells of the present invention. The multi-chain CAR comprising at least two of the following components:
a) one polypeptide comprising the transmembrembrane domain of FcεRI alpha chain and an extracellular ligand-binding domain,
b) one polypeptide comprising a part of N- and C-terminal cytoplasmic tail and the transmembrane domain of FcεRI beta chain and/or
c) two polypeptides comprising each a part of intracytoplasmic tail and the transmembrane domain of FcεRI gamma chain, whereby different polypeptides multimerize together spontaneously to form dimeric, trimeric or tetrameric CAR.

One example of tetrameric CAR is illustrated in FIG. 3. Different versions of multichain CARs are represented in FIG. 4. One example of multi-chain CAR comprises amino acid sequence SEQ ID NO: 125. The term "a part of" used herein refers to any subset of the molecule, that is a shorter peptide. Alternatively, amino acid sequence functional variants of the polypeptide can be prepared by mutations in the DNA which encodes the polypeptide. Such functional variants include, for example, deletions from, or insertions or substitutions of, residues within the amino acid sequence. Any combination of deletion, insertion, and substitution may also be made to arrive at the final construct, provided that the final construct possesses the desired activity, especially to exhibit a specific anti-target cellular immune activity.

In a preferred embodiment, said extracellular ligand-binding domain is a scFv. Other binding domain than scFv can also be used for predefined targeting of lymphocytes, such as camelid single-domain antibody fragments or receptor ligands like a vascular endothelial growth factor polypeptide, an integrin-binding peptide, heregulin or an IL-13 mutein, antibody binding domains, antibody hypervariable loops or CDRs as non limiting examples.

In a preferred embodiment said polypeptide of a) further comprises a stalk region between said extracellular ligand-binding domain and said transmembrane domain. The term "stalk region" used herein generally means any oligo- or polypeptide that functions to link the transmembrane domain to the extracellular ligand-binding domain. In particular, stalk region are used to provide more flexibility and accessibility for the extracellular ligand-binding domain. A stalk region may comprise up to 300 amino acids, preferably 10 to 100 amino acids and most preferably 25 to 50 amino acids. Stalk region may be derived from all or part of naturally occurring molecules, such as from all or part of the extracellular region of CD8, CD4 or CD28, or from all or part of an antibody constant region. Alternatively the stalk region may be a synthetic sequence that corresponds to a naturally occurring stalk sequence, or may be an entirely synthetic stalk sequence.

In a preferred embodiment, said polypeptide of a), b) and/or c) further comprises at least one signal-transducing domain. In a most preferred embodiment, said signal-transducing domain is selected from the group consisting of CD28, OX40, ICOS, CD137 and CD8.

In a preferred embodiment, said C-terminal cytoplasmic tail of FcεRI alpha, beta and/or gamma chain fragment further comprises TNFR-associated Factor 2 (TRAF2) binding motifs. In a most preferred embodiment, said C-terminal cytoplasmic tail of FcεRI alpha, beta and/or gamma chain is replaced by intracytoplasmic tail of costimulatory TNFR member family. Cytoplasmic tail of costimulatory TNFR family member contains TRAF2 binding motifs consisting of the major conserved motif (P/S/A)X(Q/E)E) or the minor motif (PXQXXD), wherein X is any amino acid. TRAF proteins are recruited to the intracellular tails of many TNFRs in response to receptor trimerization.

In another preferred embodiment said intracytoplasmic domain of FcεRI alpha, beta and/or gamma chain is replaced by intracytoplasmic domain of TCR zeta chain (also named CD3 zeta). In another preferred embodiment, said intracytoplasmic domain of FcεRI alpha, beta and/or gamma chain comprises at least one additional immunoreceptor tyrosine-based activation motif (ITAM). ITAMs are well defined signaling motifs found in the intracytoplasmic tail of a variety of receptors that serve as binding sites for syk/zap70 class tyrosine kinases. Examples of ITAM used in the invention include those derived from TCRzeta, FCRgamma, FCRbeta, CD3gamma, CD3delta, CD3epsilon, CD5, CD22, CD79a, CD79b, and CD66d.

As non limiting example, different versions of multi-chain CAR are illustrated in FIG. 4.

In a preferred embodiment the multi-chain CAR comprise the amino acid sequence SEQ ID NO: 125. The present invention relates to polypeptides comprising a polypeptide sequence that has at least 70%, preferably at least 80%, more preferably at least 90%, 95% 97% or 99% sequence identity with amino acid sequence selected from the group consisting of SEQ ID NO: 125.

Are also comprised in the scope of the present invention, polynucleotides, vectors encoding the above described multi-chain CAR according to the invention.

In encompassed particular embodiment, the invention relates to a method of preparing T-cells for immunotherapy comprising introducing into said T-cells the different polypeptides composing said multi-chain CAR and expanding said cells.

In another embodiment, said method further comprises a step of genetically modifying said cells by inactivating at least one gene expressing one component of the TCR and/or a target for an immunosuppressive agent. In a preferred embodiment, said gene is selected from the group consisting of TCRalpha, TCRbeta, CD52 and GR. In a preferred embodiment said method further comprises introducing into said T cells a rare-cutting endonuclease able to selectively inactivate by DNA cleavage said genes. In a more preferred embodiment said rare-cutting endonuclease is TALE-nuclease. Preferred TALE-nucleases according to the invention are those recognizing and cleaving the target sequence selected from the group consisting of: SEQ ID NO: 1 to 6 (GR), SEQ ID NO: 37, 57 to 60 (TCRalpha), SEQ ID NO: 38 or 39 (TCRbeta), and SEQ ID NO: 40, SEQ ID NO: 61 to SEQ ID NO: 65 (CD52).

In particular embodiment said method further comprises an additional genomic modification step. By additional genomic modification step, can be intended the introduction into cells to engineer of one protein of interest. Said protein of interest can be, as non limiting examples a bispecific antibody, rare-cutting endonuclease targeting PDCD1 or CTLA-4, a pTalpha or a functional variant thereof as described in the present disclosure.

The present invention also relates isolated cells or cell lines susceptible to be obtained by said method to engineer cells. In particular said isolated cell comprises exogenous polynucleotide sequences encoding polypeptides composing said multi-chain CAR.

Inactivated PDCD1 or CTLA4 T Cells

One another approach to activating therapeutic antitumor immunity is the blockade of immune checkpoints. Immunity response is regulated by the counterbalancing of stimulatory and inhibitory signal. The expression of immune-checkpoint proteins can be dysregulated by tumours and can be an important immune resistance mechanism. Negative regulators of T-cell function include molecules such as CTLA-4, a key negative regulatory molecule that down-regulates pathways of T-cell activation and programmed death-1 (PD1) also known as PDCD1, a transmembrane receptor up-regulated on activated T cells that when bound to its ligand (programmed death ligand-1, PD-L1) leads to decreased cytokine production and proliferation of T cells (Pardoll 2012). Thus, antagonists of inhibitory signal result in the amplification of antigen-specific T-cell response.

Thus the present invention relates to a method of engineering T-cells, especially for immunotherapy, comprising genetically modifying T-cells by inactivating at least one protein involved in the immune check-point, in particular PDCD1 and/or CTLA-4.

In a particular embodiment, the method comprises one of the following steps:

(a) providing a T cell,
(b) introducing into said T cell a rare-cutting endonuclease able to selectively inactivate by DNA cleavage PDCD1 gene or CTLA-4 gene; and
(c) expanding said cells.

In a preferred embodiment, said rare-cutting endonuclease is a TALE-nuclease. In the present invention new TALE-nucleases have been designed for precisely targeting relevant genes for adoptive immunotherapy strategies. Preferred TALE-nucleases according to the invention are those recognizing and cleaving the target sequence selected from the group consisting of SEQ ID NO: 77 and SEQ ID NO: 78 (PDCD-1), SEQ ID NO: 74 to SEQ ID NO: 76 (CTLA-4). The present invention also relates to TALE-nucleases polypeptides which comprise an amino acid sequence selected from the group consisting of SEQ ID NO: 79 to SEQ ID NO: 88.

The present invention also relates to polypeptides comprising an amino acid sequence that has at least 70%, preferably at least 80%, more preferably at least 90%, 95% 97% or 99% sequence identity with amino acid sequence selected from the group consisting of SEQ ID NO: 79 to SEQ ID NO: 88. Are also comprised in the scope of the present invention, polynucleotides, vectors encoding the above described rare-cutting endonucleases according to the invention. This method can be associated with any one of the different methods described in the present disclosure.

Bispecific Antibodies

According to a further embodiment, engineered T cells obtained by the different methods as previously described can be further exposed with bispecific antibodies. Said T-cells could be exposed to bispecific antibodies ex vivo prior to administration to a patient or in vivo following administration to a patient. Said bispecific antibodies comprise two variable regions with distinct antigen properties that allow bringing the engineered cells into proximity to a target antigen. As a non limiting example, said bispecific antibody is directed against a tumor marker and lymphocyte antigen such as CD3 and has the potential to redirect and activate any circulating T cells against tumors.

Delivery Methods

The different methods described above involve introducing pTalpha or functional variants thereof, rare cutting endonuclease, TALE-nuclease, CAR or multi-chain CAR optionally with DNA-end processing enzyme or exogenous nucleic acid into a cell.

As non-limiting example, said pTalpha or functional variant thereof, rare cutting endonucleases, TALE-nucleases, CAR or multi-chain CAR optionally with DNA-end processing enzyme or exogenous nucleic acid can be introduced as transgenes encoded by one or as different plasmidic vectors. Different transgenes can be included in one vector which comprises a nucleic acid sequence encoding ribosomal skip sequence such as a sequence encoding a 2A peptide. 2A peptides, which were identified in the Aphthovirus subgroup of picornaviruses, causes a ribosomal "skip" from one codon to the next without the formation of a peptide bond between the two amino acids encoded by the codons (see Donnelly et al., J. of General Virology 82: 1013-1025 (2001); Donnelly et al., J. of Gen. Virology 78: 13-21 (1997); Doronina et al., Mol. And. Cell. Biology 28(13): 4227-4239 (2008); Atkins et al., RNA 13: 803-810 (2007)). By "codon" is meant three nucleotides on an mRNA (or on the sense strand of a DNA molecule) that are translated by a ribosome into one amino acid residue. Thus, two polypeptides can be synthesized from a single, contiguous open reading frame within an mRNA when the polypeptides are separated by a 2A oligopeptide sequence that is in frame. Such ribosomal skip mechanisms are well known in the art and are known to be used by several vectors for the expression of several proteins encoded by a single messenger RNA. As non-limiting example, in the present invention, 2A peptides have been used to express into the cell the rare-cutting endonuclease and a DNA end-processing enzyme or the different polypeptides of the multi-chain CAR.

Said plasmid vector can contain a selection marker which provides for identification and/or selection of cells which received said vector.

Polypeptides may be synthesized in situ in the cell as a result of the introduction of polynucleotides encoding said polypeptides into the cell. Alternatively, said polypeptides could be produced outside the cell and then introduced thereto. Methods for introducing a polynucleotide construct into animal cells are known in the art and including as non limiting examples stable transformation methods wherein the polynucleotide construct is integrated into the genome of the cell, transient transformation methods wherein the polynucleotide construct is not integrated into the genome of the cell and virus mediated methods. Said polynucleotides may be introduced into a cell by for example, recombinant viral vectors (e.g. retroviruses, adenoviruses), liposome and the like. For example, transient transformation methods include for example microinjection, electroporation or particle bombardment. Said polynucleotides may be included in vectors, more particularly plasmids or virus, in view of being expressed in cells.

Electroporation

A more preferred embodiment of the invention, polynucleotides encoding polypeptides according to the present invention can be mRNA which is introduced directly into the cells, for example by electroporation. The inventors determined the optimal condition for mRNA electroporation in T-cell.

The inventor used the cytoPulse technology which allows, by the use of pulsed electric fields, to transiently permeabilize living cells for delivery of material into the cells. The technology, based on the use of PulseAgile (Cellectis property) electroporation waveforms grants the precise control of pulse duration, intensity as well as the interval between pulses (U.S. Pat. No. 6,010,613 and International PCT application WO2004083379). All these parameters can be modified in order to reach the best conditions for high transfection efficiency with minimal mortality. Basically, the first high electric field pulses allow pore formation, while subsequent lower electric field pulses allow to move the polynucleotide into the cell. In one aspect of the present invention, the inventor describe the steps that led to achievement of >95% transfection efficiency of mRNA in T cells, and the use of the electroporation protocol to transiently express different kind of proteins in T cells. In particular the invention relates to a method of transforming T cell comprising contacting said T cell with RNA and applying to T cell an agile pulse sequence consisting of:

(a) one electrical pulse with a voltage range from 2250 to 3000 V per centimeter, a pulse width of 0.1 ms and a pulse interval of 0.2 to 10 ms between the electrical pulses of step (a) and (b);
(b) one electrical pulse with a voltage range from 2250 to 3000 V with a pulse width of 100 ms and a pulse interval of 100 ms between the electrical pulse of step (b) and the first electrical pulse of step (c); and
(c) 4 electrical pulses with a voltage of 325 V with a pulse width of 0.2 ms and a pulse interval of 2 ms between each of 4 electrical pulses.

In particular embodiment, the method of transforming T cell comprising contacting said T cell with RNA and applying to T cell an agile pulse sequence consisting of:

(a) one electrical pulse with a voltage of 2250, 2300, 2350, 2400, 2450, 2500, 2550, 2400, 2450, 2500, 2600, 2700, 2800, 2900 or 3000V per centimeter, a pulse width of 0.1 ms and a pulse interval of 0.2, 0.5, 1, 2, 3, 4, 5, 6, 7, 8, 9 or 10 ms between the electrical pulses of step (a) and (b);
(b) one electrical pulse with a voltage range from 2250, of 2250, 2300, 2350, 2400, 2450, 2500, 2550, 2400, 2450, 2500, 2600, 2700, 2800, 2900 or 3000V with a pulse width of 100 ms and a pulse interval of 100 ms between the electrical pulse of step (b) and the first electrical pulse of step (c); and
(c) 4 electrical pulses with a voltage of 325 V with a pulse width of 0.2 ms and a pulse interval of 2 ms between each of 4 electrical pulses.

Any values included in the value range described above are disclosed in the present application. Electroporation medium can be any suitable medium known in the art. Preferably, the electroporation medium has conductivity in a range spanning 0.01 to 1.0 milliSiemens.

In particular embodiments, as non limiting examples, said RNA encodes a rare-cutting endonuclease, one monomer of the rare-cutting endonuclease such as Half-TALE-nuclease, a Chimeric Antigen Receptor, at least one component of the multi-chain chimeric antigen receptor, a pTalpha or functional variant thereof, an exogenous nucleic acid, one additional catalytic domain.

Activation and Expansion of T Cells

Whether prior to or after genetic modification of the T cells, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. T cells can be expanded in vitro or in vivo.

Generally, the T cells of the invention are expanded by contact with a surface having attached thereto an agent that stimulates a CD3 TCR complex associated signal and a ligand that stimulates a co-stimulatory molecule on the surface of the T cells.

In particular, T cell populations may be stimulated in vitro such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody. For example, the agents providing each signal may be in solution or coupled to a surface. As those of ordinary skill in the art can readily appreciate, the ratio of particles to cells may depend on particle size relative to the target cell. In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. Cell surface proteins may be ligated by allowing paramagnetic beads to which anti-CD3 and anti-CD28 are attached (3×28 beads) to contact the T cells. In one embodiment the cells (for example, 4 to 10 T cells) and beads (for example, DYNABEADS®

M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. The mixture may be cultured for several hours (about 3 hours) to about 14 days or any hourly integer value in between. In another embodiment, the mixture may be cultured for 21 days. Conditions appropriate for T cell culture include an appropriate media (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-g, 1L-4, 1L-7, GM-CSF, -10, -2, 1L-15, TGFp, and TNF- or any other additives for the growth of cells known to the skilled artisan. Other additives for the growth of cells include, but are not limited to, surfactant, plasmanate, and reducing agents such as N-acetyl-cysteine and 2-mercaptoethanoi. Media can include RPMI 1640, A1M-V, DMEM, MEM, a-MEM, F-12, X-Vivo 1, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% CO2). T cells that have been exposed to varied stimulation times may exhibit different characteristics In another particular embodiment, said cells can be expanded by co-culturing with tissue or cells. Said cells can also be expanded in vivo, for example in the subject's blood after administrating said cell into the subject.

Modified T-Cells

In the scope of the present invention is also encompassed an isolated T cell obtained according to any one of the methods previously described. Said T-cell according to the present invention can be derived from a stem cell. The stem cells can be adult stem cells, embryonic stem cells, more particularly non-human stem cells, cord blood stem cells, progenitor cells, bone marrow stem cells, induced pluripotent stem cells, totipotent stem cells or hematopoietic stem cells. Representative human cells are CD34+ cells. Said isolated cell can also be a dendritic cell, a NK-cell, a B-cell or a T-cell selected from the group consisting of inflammatory T-lymphocytes, cytotoxic T-lymphocytes, regulatory T-lymphocytes or helper T-lymphocytes. In another embodiment, said cell can be derived from the group consisting of CD4+ T-lymphocytes and CD8+ T-lymphocytes. Prior to expansion and genetic modification of the cells of the invention, a source of cells can be obtained from a subject through a variety of non-limiting methods. T cells can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available and known to those skilled in the art, may be used. In another embodiment, said cell can be derived from a healthy donor, from a patient diagnosed with cancer or from a patient diagnosed with an infection. In another embodiment, said cell is part of a mixed population of cells which present different phenotypic characteristics. In the scope of the present invention is also encompassed a cell line obtained from a transformed T-cell according to the method previously described. Modified cells resistant to an immunosuppressive treatment and susceptible to be obtained by the previous method are encompassed in the scope of the present invention.

In another embodiment, said isolated cell according to the present invention comprises one inactivated gene selected from the group consisting of CD52, GR, TCR alpha and TCR beta and/or expresses a CAR, a multi-chain CAR and/or a pTalpha transgene. In another embodiment, said isolated cell according to the present invention comprises two inactivated genes selected from the group consisting of CD52 and GR, CD52 and TCR alpha, CDR52 and TCR beta, GR and TCR alpha, GR and TCR beta, TCR alpha and TCR beta and/or expresses a CAR, a multi-chain CAR and/or a pTalpha transgene.

In another embodiment, TCR is rendered not functional in the cells according to the invention by inactivating TCR alpha gene and/or TCR beta gene(s). The above strategies are used more particularly to avoid GvHD. In a particular aspect of the present invention is a method to obtain modified cells derived from an individual, wherein said cells can proliferate independently of the Major Histocompatibility Complex signaling pathway. Said method comprises the following steps:
 (a) Recovering cells from said individual;
 (b) Genetically modifying said cells ex-vivo by inactivating TCR alpha or TCR beta genes;
 (c) Cultivating genetically modified T-cells in vitro in appropriate conditions to amplify said cells.

Modified cells, which can proliferate independently of the Major Histocompatibility Complex signaling pathway, susceptible to be obtained by this method are encompassed in the scope of the present invention. Said modified cells can be used in a particular aspect of the invention for treating patients in need thereof against Host versus Graft (HvG) rejection and Graft versus Host Disease (GvHD); therefore in the scope of the present invention is a method of treating patients in need thereof against Host versus Graft (HvG) rejection and Graft versus Host Disease (GvHD) comprising treating said patient by administering to said patient an effective amount of modified cells comprising inactivated TCR alpha and/or TCR beta genes.

Therapeutic Applications

In another embodiment, isolated cell obtained by the different methods or cell line derived from said isolated cell as previously described can be used as a medicament. In another embodiment, said medicament can be used for treating cancer or infections in a patient in need thereof. In another embodiment, said isolated cell according to the invention or cell line derived from said isolated cell can be used in the manufacture of a medicament for treatment of a cancer or a viral infection in a patient in need thereof.

In another aspect, the present invention relies on methods for treating patients in need thereof, said method comprising at least one of the following steps:
 (a) providing a T-cell obtainable by any one of the methods previously described;
 (b) Administrating said transformed T-cells to said patient, On one embodiment, said T cells of the invention can undergo robust in vivo T cell expansion and can persist for an extended amount of time.

Said treatment can be ameliorating, curative or prophylactic. It may be either part of an autologous immunotherapy or part of an allogenic immunotherapy treatment. By autologous, it is meant that cells, cell line or population of cells used for treating patients are originating from said patient or from a Human Leucocyte Antigen (HLA) compatible donor. By allogeneic is meant that the cells or population of cells used for treating patients are not originating from said patient but from a donor.

The invention is particularly suited for allogenic immunotherapy, insofar as it enables the transformation of T-cells, typically obtained from donors, into non-alloreactive cells. This may be done under standard protocols and reproduced as many times as needed. The resulted modified T cells may be pooled and administrated to one or several patients, being made available as an "off the shelf" therapeutic product.

Cells that can be used with the disclosed methods are described in the previous section. Said treatment can be used to treat patients diagnosed with cancer, viral infection, autoimmune disorders or Graft versus Host Disease (GvHD). Cancers that may be treated include tumors that are not vascularized, or not yet substantially vascularized, as well as vascularized tumors. The cancers may comprise nonsolid tumors (such as hematological tumors, for example, leukemias and lymphomas) or may comprise solid tumors. Types of cancers to be treated with the CARs of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

It can be a treatment in combination with one or more therapies against cancer selected from the group of antibodies therapy, chemotherapy, cytokines therapy, dendritic cell therapy, gene therapy, hormone therapy, laser light therapy and radiation therapy.

According to a preferred embodiment of the invention, said treatment can be administrated into patients undergoing an immunosuppressive treatment. Indeed, the present invention preferably relies on cells or population of cells, which have been made resistant to at least one immunosuppressive agent due to the inactivation of a gene encoding a receptor for such immunosuppressive agent. In this aspect, the immunosuppressive treatment should help the selection and expansion of the T-cells according to the invention within the patient.

The administration of the cells or population of cells according to the present invention may be carried out in any convenient manner, including by aerosol inhalation, injection, ingestion, transfusion, implantation or transplantation. The compositions described herein may be administered to a patient subcutaneously, intradermaliy, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. The cells or population of cells can be administrated in one or more doses. In another embodiment, said effective amount of cells are administered as a single dose. In another embodiment, said effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, said effective amount of cells or composition comprising those cells are administered parenterally. Said administration can be an intravenous administration. Said administration can be directly done by injection within a tumor.

In certain embodiments of the present invention, cells are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or nataliziimab treatment for MS patients or efaliztimab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycoplienolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 11; Henderson et al., Immun. 73:316-321, 1991; Bierer et al., Citrr. Opin. mm n. 5:763-773, 93). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH, In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgeiy. Said modified cells obtained by any one of the methods described here can be used in a particular aspect of the invention for treating patients in need thereof against Host versus Graft (HvG) rejection and Graft versus Host Disease (GvHD); therefore in the scope of the present invention is a method of treating patients in need thereof against Host versus Graft (HvG) rejection and Graft versus Host Disease (GvHD) comprising treating said patient by administering to said patient an effective amount of modified cells comprising inactivated TCR alpha and/or TCR beta genes.

Example of Method to Engineer Human Allogeneic Cells for Immunotherapy

For a better understanding of the invention, one example of method to engineer human allogenic cells for immunotherapy is illustrated in FIG. 5. The method comprising a combination of one or several of the following steps:

1. Providing T-cells from a cell culture or from a blood sample from one individual patient or from blood bank and activating said T cells using anti-CD3/C28 activator beads. The beads provide both the primary and co-stimulatory signals that are required for activation and expansion of T cells.

2. a) Transducing said cells with pTalpha or functional variant thereof transgene to support CD3 surface expression and allow cell expansion through stimulation of CD3 complex. TCR disruption is expected to the elimination of the TCR complex and removes alloreactivity (GvHD) but may alter allogenic cells expansion due to the loss of CD3 signaling component. Transduced cells are expected to express pTalpha chain or functional variant thereof. This pTalpha chain pairs with TCRbeta chain and CD3 signaling components to form the preTCR complex and, thus restore a functional CD3 complex and support activation or stimulation of inactivated TCRalpha cells. Transduction of T-cells with pTalpha lentiviral vector can be realized before or after TCRalpha inactivation.

b) Transducing said cells with multi-chain CARs allow redirecting T cells against antigens expressed at the surface of target cells from various malignancies including lymphomas and solid tumors. To improve the function of co-stimulatory domain, the inventors have designed a multi-chain CAR derived from FcɛRI as previously described. Transduction can be realized before or after the inactivation of TCRalpha and CD52 genes.

3. Engineering non alloreactive and immunosuppressive resistant T cells:

a) It is possible to Inactivate TCR alpha in said cells to eliminate the TCR from the surface of the cell and prevent recognition of host tissue as foreign by TCR of allogenic and thus to avoid GvHD.

b) It is also possible to inactive one gene encoding target for immunosuppressive agent to render said cells resistant to immunosuppressive treatment to prevent graft rejection without affecting transplanted T cells. In this example, target of immunosuppressive agents is CD52 and immunosuppressive agent is a humanized monoclonal anti-CD52 antibody.

It has been shown by the inventors that the use of TALE-nuclease by allowing higher rates of DSB events within T-cells was particularly advantageous to achieve the above double inactivation in T-cells. Preferably, TCRalpha and CD52 genes are inactivated by electoporating T cells with mRNA coding for TALE-nuclease targeting said genes. It has been found by the inventors that using mRNA resulted into high transformation rate was less harmful to T-cells and so, was critical in the process of engineering T-cells. Then, inactivated T cells are sorted using magnetic beads. For example, T cells expressing CD52 are removed by fixation on a solid surface, and inactivated cells are not exposed of the stress of being passed through a column. This gentle method increases the concentration of properly engineered T-cells.

4. Expansion in vitro of engineered T-cells prior to administration to a patient or in vivo following administration to a patient through stimulation of CD3 complex. Before administration step, patients are subjected to an immunosuppressive treatment such as CAMPATH1-H, a humanized monoclonal antibody anti-CD52.

5. Optionally exposed said cells with bispecific antibodies ex vivo prior to administration to a patient or in vivo following administration to a patient to bring the engineered cells into proximity to a target antigen.

Other Definitions

Amino acid residues in a polypeptide sequence are designated herein according to the one-letter code, in which, for example, Q means Gln or Glutamine residue, R means Arg or Arginine residue and D means Asp or Aspartic acid residue.

Amino acid substitution means the replacement of one amino acid residue with another, for instance the replacement of an Arginine residue with a Glutamine residue in a peptide sequence is an amino acid substitution.

Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

"As used herein, "nucleic acid" or "polynucleotides" refers to nucleotides and/or polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Nucleic acids can be either single stranded or double stranded.

by "polynucleotide successively comprising a first region of homology to sequences upstream of said double-stranded break, a sequence to be inserted in the genome of said cell and a second region of homology to sequences downstream of said double-stranded break" it is intended to mean a DNA construct or a matrix comprising a first and second portion that are homologous to regions 5' and 3' of a DNA target in situ. The DNA construct also comprises a third portion positioned between the first and second portion which comprise some homology with the corresponding DNA sequence in situ or alternatively comprise no homology with the regions 5' and 3' of the DNA target in situ. Following cleavage of the DNA target, a homologous recombination event is stimulated between the genome containing the targeted gene comprised in the locus of interest and this matrix, wherein the genomic sequence containing the DNA target is replaced by the third portion of the matrix and a variable part of the first and second portions of said matrix.

by "DNA target", "DNA target sequence", "target DNA sequence", "nucleic acid target sequence", "target sequence", or "processing site" is intended a polynucleotide sequence that can be targeted and processed by a rare-cutting endonuclease according to the present invention. These terms refer to a specific DNA location, preferably a genomic location in a cell, but also a portion of genetic material that can exist independently to the main body of genetic material such as plasmids, episomes, virus, transposons or in organelles such as mitochondria as non-limiting example. As non-limiting examples of TALE-nuclease targets, targeted genomic sequences generally consist of two 17-bp long sequences (called half targets) separated by a 15-bp spacer. Each half-target is recognized by repeats of TALE-nucleases listed in tables 1, 5, 6 and 10 as non-limiting examples, encoded in plasmids, under the control of EF1-alpha promoter or T7 promoter. The nucleic acid target sequence is defined by the 5' to 3' sequence of one strand of said target, as indicated in tables 1, 5, 6 and 10.

By chimeric antigen receptor (CAR) is intended molecules that combine a binding domain against a component present on the target cell, for example an antibody-based specificity for a desired antigen (e.g., tumor antigen) with a T cell receptor-activating intracellular domain to generate a chimeric protein that exhibits a specific anti-target cellular immune activity. Generally, CAR consists of an extracellular single chain antibody (scFvFc) fused to the intracellular signaling domain of the T cell antigen receptor complex zeta chain (scFvFc:ζ) and have the ability, when expressed in T cells, to redirect antigen recognition based on the monoclonal antibody's specificity. One example of CAR used in the present invention is a CAR directing against CD19 antigen and can comprise as non limiting example the amino acid sequence: SEQ ID NO: 73

By "delivery vector" or "delivery vectors" is intended any delivery vector which can be used in the present invention to put into cell contact (i.e "contacting") or deliver inside cells or subcellular compartments (i.e "introducing") agents/chemicals and molecules (proteins or nucleic acids) needed in the present invention. It includes, but is not limited to liposomal delivery vectors, viral delivery vectors, drug delivery vectors, chemical carriers, polymeric carriers, lipoplexes, polyplexes, dendrimers, microbubbles (ultrasound contrast agents), nanoparticles, emulsions or other appropriate transfer vectors. These delivery vectors allow delivery of molecules, chemicals, macromolecules (genes, proteins), or other vectors such as plasmids, peptides developed by Diatos. In these cases, delivery vectors are molecule carriers. By "delivery vector" or "delivery vectors" is also intended delivery methods to perform transfection.

The terms "vector" or "vectors" refer to a nucleic acid molecule capable of transporting another nucleic acid to which it has been linked. A "vector" in the present invention includes, but is not limited to, a viral vector, a plasmid, a RNA vector or a linear or circular DNA or RNA molecule which may consists of a chromosomal, non chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available.

Viral vectors include retrovirus, adenovirus, parvovirus (e. g. adenoassociated viruses), coronavirus, negative strand RNA viruses such as orthomyxovirus (e. g., influenza virus), rhabdovirus (e. g., rabies and vesicular stomatitis virus), paramyxovirus (e. g. measles and Sendai), positive strand RNA viruses such as picornavirus and alphavirus, and double-stranded DNA viruses including adenovirus, herpesvirus (e. g., Herpes Simplex virus types 1 and 2, Epstein-Barr virus, cytomegalovirus), and poxvirus (e. g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, Spumavirus (Coffin, J. M., Retroviridae: The viruses and their replication, In Fundamental Virology, Third Edition, B. N. Fields, et al., Eds., Lippincott-Raven Publishers, Philadelphia, 1996).

By "lentiviral vector" is meant HIV-Based lentiviral vectors that are very promising for gene delivery because of their relatively large packaging capacity, reduced immunogenicity and their ability to stably transduce with high efficiency a large range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration in the DNA of infected cells. By "integrative lentiviral vectors (or LV)", is meant such vectors as non limiting example, that are able to integrate the genome of a target cell. At the opposite by "non integrative lentiviral vectors (or NILV)" is meant efficient gene delivery vectors that do not integrate the genome of a target cell through the action of the virus integrate.

Delivery vectors and vectors can be associated or combined with any cellular permeabilization techniques such as sonoporation or electroporation or derivatives of these techniques.

By cell or cells is intended any eukaryotic living cells, primary cells and cell lines derived from these organisms for in vitro cultures.

By "primary cell" or "primary cells" are intended cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines.

As non limiting examples cell lines can be selected from the group consisting of CHO-K1 cells; HEK293 cells; Caco2 cells; U2-OS cells; NIH 3T3 cells; NSO cells; SP2 cells; CHO—S cells; DG44 cells; K-562 cells, U-937 cells; MRC5 cells; IMR90 cells; Jurkat cells; HepG2 cells; HeLa cells; HT-1080 cells; HCT-116 cells; Hu-h7 cells; Huvec cells; Molt 4 cells.

All these cell lines can be modified by the method of the present invention to provide cell line models to produce, express, quantify, detect, study a gene or a protein of interest; these models can also be used to screen biologically active molecules of interest in research and production and various fields such as chemical, biofuels, therapeutics and agronomy as non-limiting examples.

by "mutation" is intended the substitution, deletion, insertion of one or more nucleotides/amino acids in a polynucleotide (cDNA, gene) or a polypeptide sequence. Said mutation can affect the coding sequence of a gene or its regulatory sequence. It may also affect the structure of the genomic sequence or the structure/stability of the encoded mRNA.

by "variant(s)", it is intended a repeat variant, a variant, a DNA binding variant, a TALE-nuclease variant, a polypeptide variant obtained by mutation or replacement of at least one residue in the amino acid sequence of the parent molecule.

by "functional variant" is intended a catalytically active mutant of a protein or a protein domain; such mutant may have the same activity compared to its parent protein or protein domain or additional properties, higher or lower activity.

By "gene" is meant the basic unit of heredity, consisting of a segment of DNA arranged in a linear manner along a chromosome, which codes for a specific protein or segment of protein. A gene typically includes a promoter, a 5' untranslated region, one or more coding sequences (exons), optionally introns, a 3' untranslated region. The gene may further comprise a terminator, enhancers and/or silencers.

As used herein, the term "locus" is the specific physical location of a DNA sequence (e.g. of a gene) on a chromosome. The term "locus" can refer to the specific physical location of a rare-cutting endonuclease target sequence on a chromosome. Such a locus can comprise a target sequence that is recognized and/or cleaved by a rare-cutting endonuclease according to the invention. It is understood that the locus of interest of the present invention can not only qualify a nucleic acid sequence that exists in the main body of genetic material (i.e. in a chromosome) of a cell but also a portion of genetic material that can exist independently to said main body of genetic material such as plasmids, episomes, virus, transposons or in organelles such as mitochondria as non-limiting examples.

The term "endonuclease" refers to any wild-type or variant enzyme capable of catalyzing the hydrolysis (cleavage) of bonds between nucleic acids within a DNA or RNA molecule, preferably a DNA molecule. Endonucleases do not cleave the DNA or RNA molecule irrespective of its sequence, but recognize and cleave the DNA or RNA molecule at specific polynucleotide sequences, further referred to as "target sequences" or "target sites". Endonucleases can be classified as rare-cutting endonucleases when having typically a polynucleotide recognition site greater than 12 base pairs (bp) in length, more preferably of 14-55 bp. Rare-cutting endonucleases significantly increase HR by inducing DNA double-strand breaks (DSBs) at a defined locus (Rouet, Smih et al. 1994; Choulika, Perrin et al. 1995; Pingoud and Silva 2007). Rare-cutting endonucleases can for example be a homing endonuclease (Paques and Duchateau 2007), a chimeric Zinc-Finger nuclease (ZFN) resulting from the fusion of engineered zinc-finger domains with the catalytic domain of a restriction enzyme such as FokI (Porteus and Carroll 2005) or a chemical endonuclease (Eisenschmidt, Lanio et al. 2005; Arimondo, Thomas et al. 2006). In chemical endonucleases, a chemical or peptidic cleaver is conjugated either to a polymer of nucleic acids or to another DNA recognizing a specific target sequence, thereby targeting the cleavage activity to a specific sequence. Chemical endonucleases also encompass synthetic nucleases like conjugates of orthophenanthroline, a DNA cleaving molecule, and triplex-forming oligonucleotides (TFOs), known to bind specific DNA sequences (Kalish and Glazer 2005). Such chemical endonucleases are comprised in the term "endonuclease" according to the present invention.

Rare-cutting endonucleases can also be for example TALE-nucleases, a new class of chimeric nucleases using a FokI catalytic domain and a DNA binding domain derived from Transcription Activator Like Effector (TALE), a family of proteins used in the infection process by plant pathogens of the *Xanthomonas* genus (Boch, Scholze et al. 2009; Moscou and Bogdanove 2009; Christian, Cermak et al. 2010; Li, Huang et al.). The functional layout of a FokI-based TALE-nuclease (TALE-nuclease) is essentially that of a ZFN, with the Zinc-finger DNA binding domain being replaced by the TALE domain. As such, DNA cleavage by a TALE-nuclease requires two DNA recognition regions flanking an unspecific central region. Rare-cutting endonucleases encompassed in the present invention can also be derived from TALE-nucleases.

Rare-cutting endonuclease can be a homing endonuclease, also known under the name of meganuclease. Such homing endonucleases are well-known to the art (Stoddard 2005). Homing endonucleases recognize a DNA target sequence and generate a single- or double-strand break. Homing endonucleases are highly specific, recognizing DNA target sites ranging from 12 to 45 base pairs (bp) in length, usually ranging from 14 to 40 bp in length. The homing endonuclease according to the invention may for example correspond to a LAGLIDADG (SEQ ID NO:127) endonuclease, to a HNH endonuclease, or to a GIY-YIG endonuclease. Preferred homing endonuclease according to the present invention can be an I-CreI variant.

By a "TALE-nuclease" (TALEN) is intended a fusion protein consisting of a nucleic acid-binding domain typically derived from a Transcription Activator Like Effector (TALE) and one nuclease catalytic domain to cleave a nucleic acid target sequence. The catalytic domain is preferably a nuclease domain and more preferably a domain having endonuclease activity, like for instance I-TevI, ColE7, NucA and Fok-I. In a particular embodiment, the TALE domain can be fused to a meganuclease like for instance I-CreI and I-OnuI or functional variant thereof. In a more preferred embodiment, said nuclease is a monomeric TALE-Nuclease. A monomeric TALE-Nuclease is a TALE-Nuclease that does not require dimerization for specific recognition and cleavage, such as the fusions of engineered TAL repeats with the catalytic domain of I-TevI described in WO2012138927. Transcription Activator like Effector (TALE) are proteins from the bacterial species *Xanthomonas* comprise a plurality of repeated sequences, each repeat comprising di-residues in position 12 and 13 (RVD) that are specific to each nucleotide base of the nucleic acid targeted sequence. Binding domains with similar modular base-per-base nucleic acid binding properties (MBBBD) can also be derived from new modular proteins recently discovered by the applicant in a different bacterial species. The new modular proteins have the advantage of displaying more sequence variability than TAL repeats. Preferably, RVDs associated with recognition of the different nucleotides are HD for recognizing C, NG for recognizing T, NI for recognizing A, NN for recognizing G or A, NS for recognizing A, C, G or T, HG for recognizing T, IG for recognizing T, NK for recognizing G, HA for recognizing C, ND for recognizing C, HI for recognizing C, HN for recognizing G, NA for recognizing G, SN for recognizing G or A and YG for recognizing T, TL for recognizing A, VT for recognizing A or G and SW for recognizing A. In another embodiment, critical amino acids 12 and 13 can be mutated towards other amino acid residues in order to modulate their specificity towards nucleotides A, T, C and G and in particular to enhance this specificity. TALE-nuclease have been already described and used to stimulate gene targeting and gene modifications (Boch, Scholze et al. 2009; Moscou and Bogdanove 2009; Christian, Cermak et al. 2010; Li, Huang et al.). Engineered TAL-nucleases are commercially available under the trade name TALEN™ (Cellectis, 8 rue de la Croix Jarry, 75013 Paris, France).

The term "cleavage" refers to the breakage of the covalent backbone of a polynucleotide. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. Double stranded DNA, RNA, or DNA/RNA hybrid cleavage can result in the production of either blunt ends or staggered ends.

By "fusion protein" is intended the result of a well-known process in the art consisting in the joining of two or more genes which originally encode for separate proteins or part of them, the translation of said "fusion gene" resulting in a single polypeptide with functional properties derived from each of the original proteins.

"identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated.

"signal-transducing domain" or "co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory ligand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-IBB, OX40, CD30, CD40, PD-1, ICOS, lymphocyte function-associated antigen-1 (LFA-1), CD2, CD7, LTGHT, NKG2C, B7-H3, a ligand that specifically binds with CD83.

A "co-stimulatory molecule" refers to the cognate binding partner on a Tcell that specifically binds with a co-stimulatory ligand, thereby mediating a co-stimulatory response by the cell, such as, but not limited to proliferation. Co-stimulatory molecules include, but are not limited to an MHC class I molecule, BTLA and Toll ligand receptor.

A "co-stimulatory signal" as used herein refers to a signal, which in combination with primary signal, such as TCR/CD3 ligation, leads to T cell proliferation and/or upregulation or downregulation of key molecules.

"bispecific antibody" refers to an antibody that has binding sites for two different antigens within a single antibody molecule. It will be appreciated by those skilled in the art that other molecules in addition to the canonical antibody structure may be constructed with two binding specificities. It will further be appreciated that antigen binding by bispecific antibodies may be simultaneous or sequential. Bispecific antibodies can be produced by chemical techniques (see e.g., Kranz et al. (1981) Proc. Natl. Acad. Sci. USA 78, 5807), by "polydoma" techniques (See U.S. Pat. No. 4,474,893) or by recombinant DNA techniques, which all are known per se. As a non limiting example, each binding domain comprises at least one variable region from an antibody heavy chain ("VH or H region"), wherein the VH region of the first binding domain specifically binds to the lymphocyte marker such as CD3, and the VH region of the second binding domain specifically binds to tumor antigen.

The term "extracellular ligand-binding domain" as used herein is defined as an oligo- or polypeptide that is capable of binding a ligand. Preferably, the domain will be capable of interacting with a cell surface molecule. For example, the extracellular ligand-binding domain may be chosen to recognize a ligand that acts as a cell surface marker on target cells associated with a particular disease state. Thus examples of cell surface markers that may act as ligands include those associated with viral, bacterial and parasitic infections, autoimmune disease and cancer cells.

The term "subject" or "patient" as used herein includes all members of the animal kingdom including non-human primates and humans.

The above written description of the invention provides a manner and process of making and using it such that any person skilled in this art is enabled to make and use the same, this enablement being provided in particular for the subject matter of the appended claims, which make up a part of the original description.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Having generally described this invention, a further understanding can be obtained by reference to certain specific examples, which are provided herein for purposes of illustration only, and are not intended to be limiting unless otherwise specified.

EXAMPLES

Example 1: TALE-Nucleases Cleaving the Human GR Gene 6 heterodimeric TALE-nucleases targeting exons of the human GR gene were designed and produced. Table 1 below indicates the target sequences cleaved by each TALE-nuclease. GR TALE-nuclease was composed of two independent entities (called half TALE-nucleases) each containing a repeat sequence engineered to bind and cleave GR target sequences consisting of two 17-bp long sequences (called half targets) separated by a 15-bp spacer.

The amino acid sequences of the N-terminal, C-terminal domains and repeat are based on the AvrBs3 TALE (ref: GenBank: X16130.1). The C-terminal and the N-terminal domains are separated by two BsmBI restriction sites. The repeat arrays (SEQ ID NO: 7 to 18), targeting the desired sequences (SEQ ID NO: 1 to 6) were synthesized using a solid support method composed of consecutive restriction/ligation/washing steps (International PCT application WO2013/017950). In brief, the first block (coding for a di-repeat) was immobilized on a solid support through biotin/streptavidin interaction, the second block (tri-repeat) was then ligated to the first and after SfaNI digestion a third bloc (tri-repeat) was coupled. The process was repeated using tri- or di-repeat blocks upon obtaining the desired repeat array. The product was then cloned in a classical pAPG10 cloning plasmid for amplification in *E. coli* and sequenced. The repeat array sequences thus obtained were subcloned in a yeast expression TALE vector using type IIS restriction enzymes BsmBI for the receiving plasmid and BbvI and SfaNI for the inserted repeat sequence. DNA coding for the half TALE-nuclease, containing a TALE derived DNA binding domain fused to the catalytic domain of the FokI restriction enzyme, was amplified in *E. coli*, recovered by standard miniprep techniques and sequenced to assess the integrity of the insert.

Activity of GR TALE-Nucleases in Yeast:

Nuclease activity of the six GR-TALE-nucleases were tested at 37° C. and 30° C. in our yeast SSA assay previously described (International PCT Applications WO 2004/067736 and in (Epinat, Arnould et al. 2003; Chames, Epinat et al. 2005; Arnould, Chames et al. 2006; Smith, Grizot et al. 2006) on targets containing the two TALE target sequences facing each other on the DNA strand separated by a spacer

TABLE 1

Description of the GR TALE-nucleases and sequences of the TALE-nucleases target sites in the human GR gene.

| Target name | Target sequence | Repeat sequence | Half TALE-nuclease sequence |
|---|---|---|---|
| GRex2 | TATTCACTGATGGACTC caaagaatcattaac TCCTGGTAGAGAAGAAA (SEQ ID NO: 1) | Repeat GRex2-LPT9-L1 (SEQ ID NO: 7) Repeat-GRex2-LPT9-R1 (SEQ ID NO: 8) | GRex2-L TALEN (SEQ ID NO: 19) GRex2-R TALEN (SEQ ID NO: 20) |
| GRex3T2 | TGCCTGGTGTGCTCTGA tgaagcttcaggatg TCATTATGGAGTCTTAA (SEQ ID NO: 2) | Repeat-GRex3T2-L1 (SEQ ID NO: 9) Repeat-GRex3T2-R1 (SEQ ID NO: 10) | GRex3T2-L TALEN (SEQ ID NO: 21) GRex3T2-R TALEN (SEQ ID NO: 22) |
| GRex3T4 | TGCTCTGATGAAGCTTC aggatgtcattatgg AGTCTTAACTTGTGGAA (SEQ ID NO: 3) | Repeat-GRex3T4-L1 (SEQ ID NO: 11) Repeat-GRex3T4-R1 (SEQ ID NO: 12) | GRex3T4-L TALEN (SEQ ID NO: 23) GRex3T4-R TALEN (SEQ ID NO: 24) |
| GRex5T1 | TGGTGTCACTGTTGGAG gttattgaacctgaa GTGTTATATGCAGGATA (SEQ ID NO: 4) | Repeat-GRex5T1-LPT8-L1 (SEQ ID NO: 13) Repeat-GRex5T1-LPT8-R1 (SEQ ID NO: 14) | GRex5T1-L TALEN (SEQ ID NO: 25) GRex5T1-R TALEN (SEQ ID NO: 26) |
| GRex5T2 | TATGATAGCTCTGTTCC agactcaacttggag GATCATGACTACGCTCA (SEQ ID NO: 5) | Repeat-GRex5T2-L1 (SEQ ID NO: 15) Repeat GRex5T2-R1 (SEQ ID NO: 16) | GRex5T2-L TALEN (SEQ ID NO: 27) GRex5T2-R TALEN (SEQ ID NO: 28) |
| GRex5T3 | TTTATATGCAGGATATGA tagctctgttccaga CTCAACTTGGAGGATCA (SEQ ID NO: 6) | Repeat-GRex5T3-L1 (SEQ ID NO: 17) Repeat-GRex5T3-R1 (SEQ ID NO: 18) | GRex5T3-L TALEN (SEQ ID NO: 29) GRex5T3-R TALEN (SEQ ID NO: 30) | of 15 bps resulting in SEQ ID NO: 1 to 6. All the yeast target reporter plasmids containing the TALE-nuclease DNA target sequences were constructed as previously described (International PCT Applications WO 2004/067736 and in (Epinat, Arnould et al. 2003; Chames, Epinat et al. 2005; Arnould, Chames et al. 2006; Smith, Grizot et al. 2006). TALE-nuclease cleavage activity levels, in yeast, of individual clones on the targets are presented in table 2.

TABLE 2

Cleavage activity of the GR TALE-nucleases in yeast.

| Target | Half TALE-nuclease transfected | yeast gal 37° C. | yeast gal 30° C. |
|---|---|---|---|
| GRex2 | Grex2-L TALEN | 1 | 1 |
|  | Grex2-R TALEN |  |  |
| GRex3T2 | GRex3T2-L TALEN | 0.92 | 0.87 |
|  | GRex3T2-R TALEN |  |  |
| GRex3T4 | GRex3T4-L TALEN | 0.94 | 0.87 |
|  | GRex3T4-R TALEN |  |  |
| GRex5T1 | GRex5T1-L TALEN | 0.48 | 0.36 |
|  | GRex5T1-R TALEN |  |  |
| GRex5T2 | GRex5T2-L TALEN | 0.97 | 0.91 |
|  | GRex5T2-R TALEN |  |  |
| GRex5T3 | GRex5T3-L TALEN | 1 | 0.98 |
|  | GRex5T3-R TALEN |  |  |

Values are comprised between 0 and 1. Maximal value is 1.

Activity of GR TALE-Nucleases in HEK293 Cells:

Each TALE-nuclease construct was subcloned using restriction enzyme digestion in a mammalian expression vector under the control of a pEF1alpha long promoter.

One million HEK293cells were seeded one day prior to transfection. Cells were co-transfected with 2.5 µg of each of two plasmids encoding left and right half of GRex2, GRex3T2, GRex3T4, GRex5T1, GRex5T2 or GRex5T3 TALE-nuclease recognizing the two half targets genomic sequences of interest in the GR gene under the control of EF1alpha promoter using 25 µL of lipofectamine (Invitrogen) according to the manufacturer's instructions. As a control, cells were co-transfected with 2.5 µg of each of the two plasmids encoding the left and the right half of TALE-nucleases targeting the T-cell receptor alpha constant chain region (TRAC_T01) target site ((TRAC_T01-L and -R TALE-nuclease (SEQ ID NO: 41 and SEQ ID NO: 42), TRAC_T01 target site (SEQ ID NO: 37)) under the control of EF1alpha promoter. The double strand break generated by TALE-nucleases in GR coding sequence induces non homologous end joining (NHEJ), which is an error-prone mechanism. Activity of TALE-nucleases is measured by the frequency of insertions or deletions at the genomic locus targeted.

2 or 7 days post transfection cells were harvested and locus specific PCRs were performed on genomic DNA extracted using the following primers: 5'-CCATCT-CATCCCTGCGTGTCTCCGACTCAG-3' (forward adaptator sequence; SEQ ID NO:128)—10N (TAG)-locus specific forward sequence for GR exon 2: 5'-GGTTCATT-TAACAAGCTGCC-3' (SEQ ID NO: 31), for GR exon 3: 5'-GCATTCTGACTATGAAGTGA-3' (SEQ ID NO: 32) and for GR exon 5: 5'-TCAGCAGGCCACTACAG-GAGTCTCACAAG-3' (SEQ ID NO: 33) and the reverse primer 5'-CC-TATCCCCTGTGTGCCTTGGCAGTCTCAG-3' (reverse adaptor sequence; SEQ ID NO:129)—locus specific reverse sequence for GR exon 2:5'-AGCCAGTGAGGGTGAA-GACG-3' (SEQ ID NO: 34), for GR exon 3:5'-GGGCTTTGCATATAATGGAA-3' (SEQ ID NO: 35) and for GR exon 5:5'-CTGACTCTCCCCTTCAT-AGTCCCCAGAAC-3' (SEQ ID NO: 36).

PCR products were sequenced by a 454 sequencing system (454 Life Sciences). Approximately 10,000 sequences were obtained per PCR product and then analyzed for the presence of site-specific insertion or deletion events. Table 3 indicates the percentage of the sequences showing insertions or deletions at the TALE-nuclease target site among the total number of sequences in the sample. In table 3 are listed for GRex2, GRex3T2 and GRex3T4 the results of a representative experiment.

In all cases tested, the % of mutagenesis was similar at day 7 compared to the one of the sample at day 2 post transfection. The nature of the mutagenic events was also analyzed, revealing a majority of deletions in all cases compared to insertions.

TABLE 3

Percentage of targeted mutagenesis at endogenous TALE-nuclease Target sites in HEK293 cells.

| Target | % Indels at 2 days with GR TALE-nuclease transfection | % Indels at 7 days with GR TALE-nuclease transfection | % Indels at 2 days with TRAC_T01_TALE-nuclease control transfection |
|---|---|---|---|
| GRex2 | 20.3 | 24.9 | 0.5 |
| GRex3T2 | 9.3 | 9.8 | 0 |
| GRex3T4 | 19 | 18.3 | 0.0 |
| GRex5T1 | 11.2 | NA | 0.7 |
| GRex5T2 | 3.4 | NA | 0 |
| GRex5T3 | 8.3 | NA | 0 |

Activity of GR TALE-Nucleases in Primary T Lymphocytes:

Each TALE-nuclease construct was subcloned using restriction enzyme digestion in an expression vector under the control of a T7 promoter.

mRNA encoding TALE-nucleases cleaving GR genomic sequences were synthesized from each plasmid carrying the coding sequences downstream from the T7 promoter. T lymphocytes isolated from peripheral blood were activated for 5 days using anti-CD3/CD28 activator beads (Life technologies) and 5 million cells were transfected by electroporation with 10 µg of each of 2 mRNAs encoding both half TALE-nucleases using a CytoLVT-P instrument (BTX-Harvard apparatus). T cells transfected with 10 µg of each of the 2 mRNAs encoding both half TALE-nucleases targeting the CD52 gene (CD52_T02-L and -R TALEN (SEQ ID NO: 55 and 56), target sequence CD52_T02 SEQ ID NO: 40) are used as a control.

3 and 7 days after transfection, genomic DNA was isolated from transfected cells and locus specific PCRs were performed using the primers described previously. PCR products were sequenced by a 454 sequencing system (454 Life Sciences). Approximately 10,000 sequences were obtained per PCR product and then analyzed for the presence of site-specific insertion or deletion events; results are in Table 4.

TABLE 4

Percentage of targeted mutagenesis at endogenous TALE-nuclease target sites in primary T lymphocytes.

| Target | % Indels at day 3 with GR TALE-nuclease transfection | % Indels at day 7 with GR TALE-nuclease transfection | % Indels at day 3 with CD52 TALE-nuclease control transfection |
|---|---|---|---|
| GRex2 | 26.2 | 30.7 | 0.7 |
| GRex3T2 | 1.09 | 0.86 | 0.02 |
| GRex3T4 | 6.3 | 6.93 | 0 |
| GRex5T1 | 0.04 | 0.035 | 0.05 |
| GRex5T2 | 1.3 | 1.0 | 0.22 |
| GRex5T3 | 17.4 | NA | 0.41 |

Example 2: TALE-Nucleases Cleaving the Human CD52 Gene, the Human T-Cell Receptor Alpha Constant Chain (TRAC) and the Human T-Cell Receptor Beta Constant Chains 1 and 2 (TRBC)

As described in example 1, heterodimeric TALE-nucleases targeting respectively CD52, TRAC and TRBC genes were designed and produced. The targeted genomic sequences consist of two 17-bp long sequences (called half targets) separated by an 11 or 15-bp spacer. Each half-target is recognized by repeats of half TALE-nucleases listed in table 5. The human genome contains two functional T-cell receptor beta chains (TRBC1 and TRBC2). During the development of alpha/beta T lymphocytes, one of these two constant chains is selected in each cell to be spliced to the variable region of TCR-beta and form a functional full length beta chain. The 2 TRBC targets were chosen in sequences conserved between TRBC1 and TRBC2 so that the corresponding TALE-nuclease would cleave both TRBC1 and TRBC2 at the same time.

Other target sequences in TRAC and CD52 genes have been designed, which are displayed in Table 6.

TABLE 6

Additional target sequences for TRAC and CD52 TALE-nucleases.

| Target | Target sequence |
|---|---|
| TRAC_T02 | TTTAGAAAGTTCCTGTG atgtcaagctggtcg AGAAAAGCTTTGAAACA (SEQ ID NO: 57) |
| TRAC_T03 | TCCAGTGACAAGTCTGT ctgcctattcaccga TTTTGATTCTCAAACAA (SEQ ID NO: 58) |
| TRAC_T04 | TATATCACAGACAAAAC tgtgctagacatgag GTCTATGGACTTCAAGA (SEQ ID NO: 59) |
| TRAC_T05 | TGAGGTCTATGGACTTC aagagcaacagtgct GTGGCCTGGAGCAACAA (SEQ ID NO: 60) |
| CD52_T01 | TTCCTCTTCCTCCTAC caccatcagcctcct TTACCTGTACCATAAC (SEQ ID NO: 61) |
| CD52_T04 | TTCCTCCTACTCACCA cagcctcctgg TCTTACCTGTACCATA (SEQ ID NO: 62) |
| CD52_T05 | TCCTACTCACCATCAG ctcctggttat TTGCTCTTACCTGTAC (SEQ ID NO: 63) |
| CD52_T06 | TTATCCCACTTCTCCT ctacagatacaaact TTTTGTCCTGAGAGTC (SEQ ID NO: 64) |

TABLE 5

Description of the CD52, TRAC and TRBC TALE-nucleases and sequences of the TALE nucleases target sites in the human corresponding genes.

| Target | Target sequence | Repeat sequence | Half TALE-nuclease |
|---|---|---|---|
| TRAC_T01 | TTGTCCCACAGATATCC Agaaccctgaccctg CCGTGTACCAGCTGAGA (SEQ ID NO: 37) | Repeat TRAC_T01-L (SEQ ID NO: 41) Repeat TRAC_T01-R (SEQ ID NO: 42) | TRAC_T01-L TALEN (SEQ ID NO: 49) TRAC_T01-R TALEN (SEQ ID NO: 50) |
| TRBC_T01 | TGTGTTTGAGCCATCAG aagcagagatctccc ACACCCAAAAGGCCACA (SEQ ID NO: 38) | Repeat TRBC_T01-L (SEQ ID NO: 43) Repeat TRBC_T01-R (SEQ ID NO: 44) | TRBC_T01-L TALEN (SEQ ID NO: 51) TRBC_T01-R TALEN (SEQ ID NO: 52) |
| TRBC_T02 | TTCCCACCCGAGGTCGC tgtgtttgagccatca GAAGCAGAGATCTCCCA (SEQ ID NO: 39) | Repeat TRBC_T02-L (SEQ ID NO: 45) Repeat TRBC_T02-R (SEQ ID NO: 46) | TRBC_T02-L TALEN (SEQ ID NO: 53) TRBC_T02-R TALEN (SEQ ID NO: 54) |
| CD52_T02 | TTCCTCCTACTCACCAT cagcctcctggttat GGTACAGGTAAGAGCAA (SEQ ID NO: 40) | Repeat CD52_T02-L (SEQ ID NO: 47) Repeat CD52_T02-R (SEQ ID NO: 48) | CD52_T02-L TALEN (SEQ ID NO: 55) CD52_T02-R TALEN (SEQ ID NO: 56) |

TABLE 6-continued

Additional target sequences for TRAC and CD52 TALE-nucleases.

| Target | Target sequence |
| --- | --- |
| CD52_T07 | TGGACTCTCAGGACAA<br>acgacaccagccaaa<br>TGCTGAGGGGCTGCTG<br>(SEQ ID NO: 65) |

Activity of CD52-TALE-Nuclease, TRAC-TALE-Nuclease and TRBC-TALE-Nuclease in HEK293 Cells Each TALE-nuclease construct was subcloned using restriction enzyme digestion in a mammalian expression vector under the control of pEF1alpha long promoter. One million HEK293 cells were seeded one day prior to transfection. Cells were co-transfected with 2.5 µg of each of the two plasmids encoding the TALE-nucleases recognizing the two half targets in the genomic sequence of interest in the CD52 gene, T-cell receptor alpha constant chain region (TRAC) or T-cell receptor beta constant chain region (TRBC) under the control of the EF1-alpha promoter or 5 µg of a control pUC vector (pCLS0003) using 25 µl of lipofectamine (Invitrogen) according to the manufacturer's instructions. The double stranded cleavage generated by TALE-nucleases in CD52 or TRAC coding sequences is repaired in live cells by non homologous end joining (NHEJ), which is an error-prone mechanism. Activity of TALE-nucleases in live cells is measured by the frequency of insertions or deletions at the genomic locus targeted. 48 hours after transfection, genomic DNA was isolated from transfected cells and locus specific PCRs were performed using the following primers: 5'-CCATCT-CATCCCTGCGTGTCTCCGACTCAG (forward adaptor sequence; SEQ ID NO:128)—10N (TAG)-locus specific forward sequence for CD52: 5'-CA-GATCTGCAGAAAGGAAGC-3' (SEQ ID NO: 66), for TRAC: 5'-ATCACTGGCATCTGGACTCCA-3' (SEQ ID NO: 67), for TRBC1: 5'-AGAGCCCCTACCAGAACCA-GAC-3' (SEQ ID NO: 68), or for TRBC2: 5'-GGACCTAGTAACATAATTGTGC-3' (SEQ ID NO: 69), and the reverse primer 5'-CC-TATCCCCTGTGTGCCTTGGCAGTCTCAG (reverse adaptor sequence; SEQ ID NO:129)—endogenous locus specific reverse sequence for CD52: 5'-CCTGTTGGAGTC-CATCTGCTG-3' (SEQ ID NO: 70), for TRAC: 5'-CCT-CATGTCTAGCACAGTTT-3' (SEQ ID NO: 71), for TRBC1 and TRBC2: 5'-ACCAGCTCAGCTC-CACGTGGT-3' (SEQ ID NO: 72). PCR products were sequenced by a 454 sequencing system (454 Life Sciences). Approximately 10,000 sequences were obtained per PCR product and then analyzed for the presence of site-specific insertion or deletion events; results are in Table 7.

TABLE 7

Percentages of indels for TALE-nuclease targeting CD52_T02, TRAC_T01, TRBC_T01 and TRBC_T02 targets.

| Target | % Indels with TALE-nuclease transfection | % Indels with pUC control transfection |
| --- | --- | --- |
| CD52_T02 | 28.0 | 0.9 |
| TRAC_T01 | 41.9 | 0.3 |
| TRBC_T01 in constant chain 1 | 3.81 | 0 |
| TRBC_T01 in constant chain 2 | 2.59 | 0 |
| TRBC_T02 in constant chain 1 | 14.7 | 0 |
| TRBC_T02 in constant chain 1 | 5.99 | 0 |

Activity of CD52-TALE-Nuclease, TRBC-TALE-Nuclease and TRAC-TALE-Nuclease in Primary T Lymphocytes Each TALE-nuclease construct was subcloned using restriction enzyme digestion in a mammalian expression vector under the control of the T7 promoter.

mRNA encoding TALE-nuclease cleaving CD52 TRAC and TRBC genomic sequence were synthesized from plasmid carrying the coding sequences downstream from the T7 promoter. T lymphocytes isolated from peripheral blood were activated for 5 days using anti-CD3/CD28 activator beads (Life technologies) and 5 million cells were then transfected by electroporation with 10 µg of each of 2 mRNAs encoding both half TALE-nuclease (or non coding RNA as controls) using a CytoLVT-P instrument. As a consequence of the insertions and deletions induced by NHEJ, the coding sequence for CD52 and/or TRAC will be out of frame in a fraction of the cells resulting in non-functional genes. 5 days after electroporation, cells were labeled with fluorochrome-conjugated anti-CD52 or anti-TCR antibody by flow cytometry for the presence of CD52 or TCR at their cell surface. Since all T lymphocytes expanded from peripheral blood normally express CD52 and TCR, the proportion of CD52-negative or TCR-negative cells is a direct measure of TALE-nuclease activity. In table 8 are listed the results of a representative experiment. The table 9 shows the results of a representative experiment testing the efficiency of TRBC TALE-nucleases.

TABLE 8

Percentages of CD52-negative, TCR-negative and CD52/TCR-double negative T lymphocytes after transfection of corresponding TALE-nuclease-expressing polynucleotides.

| ARN transfected | % CD52-negative cells | % TCR-negative cells | % CD52/TCR double negative cells |
| --- | --- | --- | --- |
| non coding RNA | 1.21 | 1.531 | 0.111 |
| TALEN CD52_T02 | 49.2 | 1.6 | 0.78 |
| TALEN TRAC_T01 | 2.16 | 44.8 | 0.97 |
| TALEN CD52_T02 + TALEN TRAC_T01 | 29.3 | 39.6 | 15.5 |

TABLE 9

Percentages of TCR-negative T lymphocytes after transfection of TRBC TALE-nuclease-expressing polynucleotides.

| ARN transfected | % TCR-negative cells |
| --- | --- |
| no RNA | 1.22 |
| TALEN TRBC_T01 | 6.52 |
| TALEN TRBC_T02 | 23.5 |

Functional Analysis of T Cells with Targeted CD52 Gene

Figure 6:
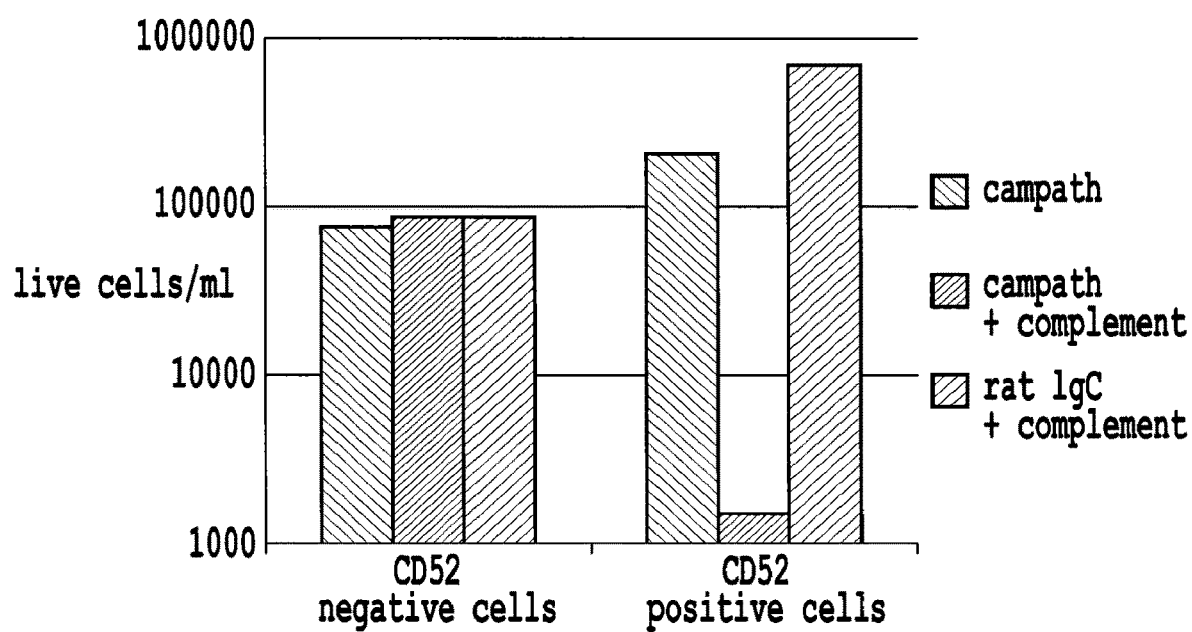

The goal of CD52 gene inactivation is to render T lymphocytes resistant to anti-CD52 antibody mediated immunosuppression. As described in the previous paragraph, T lymphocytes were transfected with mRNA encoding TALE-nuclease cleaving CD52. 7 days after transfection, cells were treated with 50 µg/ml anti-CD52 monoclonal antibody (or rat IgG as control) with or without 30% rabbit complement (Cedarlane). After 2 hours of incubation at 37° C., the cells were labeled with a fluorochrome-conjugated anti-CD52 antibody together with a fluorescent viability dye (eBioscience) and analyzed by flow cytometry to measure the frequency of CD52-positive and CD52-negative cells among live cells. FIG. 6 shows the result of a representative experiment, demonstrating that CD52-negative cells are completely resistant to complement-mediated anti-CD52 antibody toxicity.

Functional Analysis of T Cells with Targeted TRAC Gene

The goal of TRAC gene inactivation is to render T lymphocytes unresponsive to T-cell receptor stimulation. As described in the previous paragraph, T lymphocytes were transfected with mRNA encoding TALE-nuclease cleaving TRAC or CD52. 16 days after transfection, cells were treated with up to 5 µg/ml of phytohemagglutinin (PHA, Sigma-Aldrich), a T-cell mitogen acting through the T cell receptor. Cells with a functional T-cell receptor should increase in size following PHA treatment. After three days of incubation, cells were labeled with a fluorochrome-conjugated anti-CD52 or anti-TCR antibody and analyzed by flow cytometry to compare the cell size distribution between TCR-positive and TCR-negative cells, or between CD52-positive and CD52-negative cells. FIG. 7 shows that TCR-positive cells significantly increase in size after PHA treatment whereas TCR-negative cells have the same size as untreated cells indicating that TRAC inactivation rendered them unresponsive to TCR-signaling. By contrast, CD52-positive and CD52-negative increase in size to same extent.

Functional Analysis of T Cells with Targeted CD52 and TRAC Genes

To verify that genome engineering did not affect the ability of T cells to present anti-tumor activity when provided with a chimeric antigen receptor (CAR), we transfected T cells that had been targeted with CD52-TALE-nuclease and TRAC-TALE-nuclease with 10 µg of RNA encoding an anti-CD19 CAR (SEQ ID NO: 73). 24 hours later, T cells were incubated for 4 hours with CD19 expressing Daudi cells. The cell surface upregulation of CD107a, a marker of cytotoxic granule release by T lymphocytes (called degranulation) was measured by flow cytometry analysis (Betts, Brenchley et al. 2003). The results are included in FIG. 8 and show that CD52-negative/TCRαβ-negative cells and CD52-positive/TCRαβ-positive have the same ability to degranulate in response to PMA/ionomycin (positive control) or CD19+ Daudi cells. CD107 upregulation is dependent on the presence of a CD19+. These data suggest that genome engineering has no negative impact on the ability of T cells to mount a controlled anti-tumor response.

Genomic Safety of CD52-TALE-Nuclease and TRAC-TALE-Nuclease in Primary T Lymphocytes As our constructs include nuclease subunits, an important question is whether multiple TALE-nuclease transfection can lead to genotoxicity and off-target cleavage at 'close match' target sequences or by mispairing of half-TALE-nucleases. To estimate the impact of TRAC-TALE-nuclease and CD52-TALE-nuclease on the integrity of the cellular genomes, we listed sequences in the human genome that presented the potential for off-site cleavage. To generate this list, we identified all the sequences in the genome with up to 4 substitutions compared to the original half targets and then identified the pairs of potential half targets in a head to head orientation with a spacer of 9 to 30 bp from each other. This analysis included sites potentially targeted by homodimers of one half-TALE-nuclease molecule or heterodimers formed by one CD52 half TALE-nuclease and one TRAC half-TALE-nuclease. We scored the potential off-site targets based on the specificity data taking into account the cost of individual substitutions and the position of the substitutions (where mismatches are better tolerated for bases at the 3' end of the half target). We obtained 173 unique sequences with a score reflecting an estimation of the likelihood of cleavage. We selected the 15 top scores and analyzed by deep sequencing the frequency of mutations found at these loci in T cells simultaneously transfected with CD52 and TRAC TALE-nuclease and purified by magnetic separation as CD52-negative, TCRαβ-negative. Results are in FIG. 9. The highest frequency of insertion/deletion is $7 \times 10^{-4}$. These results make the putative offsite target at least 600 times less likely to be mutated than the intended targets. The TALE-nuclease reagents used in this study therefore appear extremely specific.

Example 3: TALE-Nucleases Cleaving the Human CTLA4 Gene and the Human PDCD1 Gene As described in example 1, heterodimeric TALE-nucleases targeting respectively PDCD1 and CTLA4 genes were designed and produced. The targeted genomic sequences consist of two 17-bp long sequences (called half targets) separated by an 11 or 15-bp spacer. Each half-target is recognized by repeats of half TALE-nucleases listed in table 10.

TABLE 10

Description of the CTLA4 and PDCD1 TALE-nucleases and sequences of the TALE-nucleases target sites in the human corresponding genes.

| Target | Target sequence | Repeat sequence | Half TALE-nuclease |
|---|---|---|---|
| CTLA4_T01 | TGGCCCTGCACTCTCCT gtttttcttctctt (SEQ ID NO: 74) | Repeat CTLA4_T01-L (SEQ ID NO: 79 ) | CTLA4_T01-L TALEN (SEQ ID NO: 89) |
|  | CATCCCTGTCTTCTGCA | Repeat CTLA4_T01-R (SEQ ID NO: 80) | CTLA4_T01-R TALEN (SEQ ID NO: 90) |
| CTLA4_T03 | TTTTCCATGCTAGCAAT gcacgtggcccagcc (SEQ ID NO : 75) | Repeat CTLA4_T03-L (SEQ ID NO: 81) | CTLA4_T03-L TALEN (SEQ ID NO: 91) |
|  | TGCTGTGGTACTGGCCA | Repeat CTLA4_T03-R (SEQ ID NO: 82) | CTLA4_T03-R TALEN (SEQ ID NO: 92) |
| CTLA4_T04 | TCCATGCTAGCAATGCA cgtggcccagcctgc | Repeat CTLA4_T04-L (SEQ ID NO: 84) | CTLA4_T04-L TALEN (SEQ ID NO: 93) |

TABLE 10 -continued

Description of the CTLA4 and PDCD1 TALE-nucleases and sequences of the TALE-nucleases target sites in the human corresponding genes.

| Target | Target sequence | Repeat sequence | Half TALE-nuclease |
|---|---|---|---|
| | TGTGGTACTGGCCAGCA (SEQ ID NO: 76) | Repeat CTLA4_T04-R (SEQ ID NO: 85) | CTLA4_T04-R TALEN (SEQ ID NO: 94) |
| PDCD1_T01 | TTCTCCCCAGCCCTGCT cgtggtgaccgaagg GGACAACGCCACCTTCA (SEQ ID NO : 77) | Repeat PDCD1_T01-L (SEQ ID NO: 86) Repeat PDCD1_T01-R (SEQ ID NO: 87) | PDCD1_T01-L TALEN (SEQ ID NO: 95) PDCD1_T01-R TALEN (SEQ ID NO: 96) |
| PDCD1_T03 | TACCTCTGTGGGGCCAT ctccctggcccccaa GGCGCAGATCAAAGAGA (SEQ ID NO : 78) | Repeat PDCD1_T03-L (SEQ ID NO: 88) Repeat PDCD1_T03-R (SEQ ID NO: 89) | PDCD1_T03-L TALEN (SEQ ID NO: 97) PDCD1_T03-R TALEN (SEQ ID NO: 98) |

Activity of CTLA4-TALE-Nuclease and PDCD1-TALE-Nuclease in HEK293 Cells

Each TALE-nuclease construct was subcloned using restriction enzyme digestion in a mammalian expression vector under the control of the pEF1alpha long promoter. One million HEK293 cells were seeded one day prior to transfection. Cells were co-transfected with 2.5 µg of each of two plasmids encoding the TALE-nucleases recognizing the two half targets in the genomic sequence of interest in the PDCD1 and CTLA-4 gene under the control of the EF1-alpha promoter or 5 µg of a control pUC vector (pCLS0003) using 25 µl of lipofectamine (Invitrogen) according to the manufacturer's instructions. The double stranded cleavage generated by TALE-nucleases in PDCD1 or CTLA-4 coding sequences is repaired in live cells by non homologous end joining (NHEJ), which is an error-prone mechanism. Activity of TALE-nucleases in live cells is measured by the frequency of insertions or deletions at the genomic locus targeted. 48 hours after transfection, genomic DNA was isolated from transfected cells and locus specific PCRs were performed using the following primers: 5'-CCATCT-CATCCCTGCGTGTCTCCGACTCAG (forward adaptor sequence; SEQ ID NO:128)—10N (TAG)-locus specific forward sequence for CTLA4_T01: 5'-CTCTACTTCCT-GAAGACCTG-3' (SEQ ID NO: 99), for CTLA4_T03/T04: 5'-ACAGTTGAGAGATGGAGGGG-3' (SEQ ID NO: 100), for PDCD1_T01: 5'-CCACAGAGGTAGGTGCCGC-3' (SEQ ID NO: 101) or for PDCD1_T03: 5'-GACAGAGATGCCGGTCACCA-3' (SEQ ID NO: 102) and the reverse primer 5'-CC-TATCCCCTGTGTGCCTTGGCAGTCTCAG (reverse adaptor sequence; SEQ ID NO:129)—endogenous locus specific reverse sequence for CTLA4_T01: 5'-TGGAATA-CAGAGCCAGCCAA-3' (SEQ ID NO: 103), for CTLA4_T03/T04: 5'-GGTGCCCGTGCAGATGGAAT-3' (SEQ ID NO: 104), for PDCD1_T01: 5'-GGCTCTGCAGTGGAGGCCAG-3' (SEQ ID NO: 105) or for PDCD1_T03: 5'-GGACAACGCCACCTTCACCT-3' (SEQ ID NO: 106).

PCR products were analyzed by T7-endonuclease assay: briefly, after denaturation and reannealing of the PCR product, T7 endonuclease will specifically digest mismatched DNA composed of wild type and mutated strands. The digestion product is then resolved by polyacrylamide gel electrophoresis. The presence of a digested product is indicative of mutated sequences induced by TALE-nuclease activity. Results are displayed in FIG. 10 where arrows point to the digested PCR products. They demonstrate that PDCD1_T1, PDCD1_T3, CTLA4_T1, CTLA4_T3 and CTLA4_T4 TALE-nucleases all exhibit mutagenic nuclease activity at their target sites.

Example 4: pTalpha Permits CD3 Surface Expression in Inactivated TCR Alpha T Lymphocytes Description of the Different preTalpha Versions:

The human pTalpha gene encodes a transmembrane glycoprotein comprising an extracellular Ig-like domain, a hydrophobic transmembrane domain and a large C-terminal intracytoplasmic tail. Different versions derived from human pTalpha glycoprotein have been designed and are described in Table 11 and represented in FIG. 11.

TABLE 11

Description of a subset of pTalpha constructs

| PTalpha versions | Description | SEQ ID |
|---|---|---|
| pTalpha-FL | Full-length of human pTalpha glycoprotein | 107 |
| pTalpha-Δ18 | Truncated Human pTalpha glycoprotein lacking 18 residues from the C-terminus. | 108 |
| pTalpha-Δ48 | Truncated Human pTalpha glycoprotein lacking 48 residues from the C-terminus. | 109 |
| pTalpha-Δ62 | Truncated Human pTalpha glycoprotein lacking 62 residues from the C-terminus. | 110 |
| pTalpha-Δ78 | Truncated Human pTalpha glycoprotein lacking 78 residues from the C-terminus. | 111 |
| pTalpha-Δ92 | Truncated Human pTalpha glycoprotein lacking 92 residues from the C-terminus. | 112 |
| pTalpha-Δ110 | Truncated Human pTalpha glycoprotein lacking 110 residues from the C-terminus. | 113 |
| pTalpha-Δ114 | Truncated Human pTalpha glycoprotein lacking 114 residues from the C-terminus. | 114 |

TABLE 11-continued

Description of a subset of pTalpha constructs

| PTalpha versions | Description | SEQ ID |
|---|---|---|
| pTalpha-FL-CD28 | Full-length of human pTalpha glycoprotein fused in C-terminus with CD28 activation domain | 115 |
| pTalpha-FL-CD8 | Full-length of human pTalpha glycoprotein fused in C-terminus with CD8 activation domain. | 116 |
| pTalpha-FL-4-1BB | Full-length of human pTalpha glycoprotein fused in C-terminus with 4-1BB activation domain.. | 117 |
| pTalpha-Δ48-CD28 | pTalpha-Δ48 glycoprotein fused in C-terminus with CD28 activation domain. | 118 |
| pTalpha-Δ48-CD8 | pTalpha-Δ48 glycoprotein fused in C-terminus with CD8 activation domain. | 119 |
| pTalpha -Δ48-41BB | pTalpha-Δ48 glycoprotein fused in C-terminus with 4-1BB activation domain. | 120 |
| pTalpha-Δ114/TCRα.IC | pTalpha-Δ114 glycoprotein fused in C-terminus with the intracellular domain of TCRalpha | 121 |
| pTalpha-EC/TCRα.TM.IC | pTalpha extracellular domain fused in C-terminus with the transmembrane and intracellular domain of TCRalpha. | 122 |
| pTalpha-Δ48-1xMUT | pTalpha-Δ48 glycoprotein with mutated residue W46R. | 123 |
| preTalpha-Δ48-4xMUT | pTalpha-Δ48 glycoprotein with mutated residues D22A, K24A, R102A, R117A | 124 |

The different preTalpha constructs tested include:
1) pTalpha deletion mutants: Different deletions were generated in the intracellular cytoplasmic tail of the human pTalpha protein (which comprises 114 amino acids) (SEQ ID NO: 107). The constructs tested include the full length version of the protein (FL) and mutants in which 18, 48, 62, 78, 92, 110 and 114 amino acids were deleted from the C-terminus of the protein (SEQ ID NO: 108 to SEQ ID NO: 114).
2) pTalpha mutants containing intracellular activation domains: The FL and Δ48 variants where fused to the CD8, CD28 or 4166 intracellular activation domains at their C-terminus (SEQ ID NO: 115 to SEQ ID NO: 120).
3) pTalpha/TCRα chimeric mutants: In one of the constructs, the TCRα intracellular domain (IC) was fused to a tail-less version (4114) of pTalpha (SEQ ID NO: 121). A second construct was also generated in which the pTalpha extracellular domain was fused to the transmembrane (TM) and the IC domains from TCRα (SEQ ID NO: 122).
4) pTalpha dimerization mutants: Some mutations have been described in the literature as being capable to alter the oligomerisation/dimerisation ability of the preTCR complex. These mutants are proposed to allow preTCR expression at the cell surface, without inducing the constitutive signaling (supposed to be induced upon preTCR oligomerization). The mutations have been introduced in the pTalphaΔ48 variant and are:
1xMUT: W46R (SEQ ID NO: 123)
4xMUT: D22A, K24A, R102A, R117A (SEQ ID NO: 124)

Activity of Different preTalpha Constructs in TRAC Inactivated Jurkat Cells:

In order to screen different pTalpha variants for their ability to restore CD3 surface expression in TCRalpha inactivated cells, a cell line was generated in which the TCRalpha gene was disrupted using TALEN targeting TRAC. Jurkat cells (a T-cell leukemia cell line) were transfected with plasmids coding for the TALEN cleaving TRAC using CytoPulse electroporation, and the KO cells (TCR$_{α/}$β$^{NEG}$; CD3$^{NEG}$) where then purified by negative selection using CD3 magnetic beads. The KO population (JKT_KOx3 cells) was amplified and used for screening of the different pTalpha variants. Screening was performed by transfection of one million of JKT_KOx3 cells with 15 μg of plasmid coding the different pTalpha variants under control of the EF1α promoter, followed by analysis by flow cytometry of CD3 cell surface expression 48 h after transfection. FIG. 12 is a representative example of the transfection efficiencies (% of BFP+ cells) and activity of the FL, 418 and Δ48 pTalpha constructs in JKT_KOx3 cells, based on the % of CD3+ cells, determined by flow cytometry. The results from the different constructs are grouped in Table 12.

TABLE 12

Activity of the different pTalpha constructs in Jurkat TCR alpha inactivated cells. Activity was measured by flow cytometry analysis of CD3 expression in jurkat TCR alpha inactivated cells transfected with the different preTalpha constructs.

| Mutant | ID | %CD3$_{LOW}$ | SD |
|---|---|---|---|
| 0 | NEG | 4.69 | 1.53 |
| 1 | preTCRα-FL | 31.18 | 4.15 |
| 2 | preTCRα-Δ18 | 20.13 | 4.56 |
| 3 | preTCRα-Δ48 | 44.86 | 3.90 |
| 4 | preTCRα-Δ62 | 32.42 | 2.95 |
| 5 | preTCRα-Δ78 | 24.75 | 3.87 |
| 6 | preTCRα-Δ92 | 20.63 | 3.70 |
| 7 | preTCRα-Δ110 | 18.18 | 3.49 |
| 8 | preTCRα-Δ114 | 4.29 | 2.74 |
| 9 | preTCRα-FL-CD8 | 18.16 | 5.30 |
| 10 | preTCRα-FL-CD28 | 5.67 | 2.77 |
| 11 | preTCRα-FL-41BB | 27.27 | 3.66 |
| 12 | preTCRα-Δ48-CD8 | 11.56 | 6.01 |
| 13 | preTCRα-Δ48-CD28 | 12.22 | 4.72 |
| 14 | preTCRα-Δ48-41BB | 35.93 | 4.55 |
| 15 | preTCRα-Δl14/TCRα.IC | 3.94 | 1.95 |
| 16 | preTCRα-EC/TCRα.TM.IC | 17.80 | 4.47 |
| 17 | preTCRα-Δ48-1x MUT | 26.88 | 4.37 |
| 18 | preTCRα-Δ48-4xMUT | 7.59 | 1.06 |

Activity of pTalpha-FL and pTalpha-Δ48 in TCR Alpha Inactivated Primary T Lymphocytes:

In order to test the ability of pTalpha-FL and pTalpha-Δ48 versions to induce CD3 surface expression in TCR alpha inactivated T lymphocytes, pTalpha-FL and pTalpha-Δ48 coding sequences were cloned into a self-inactivating pLV-SFFV-BFP-2A-PCTRA lentiviral vector that codes for Blue Fluorescent protein (BFP) under the SFFV promoter followed by the self-cleaving T2A peptide (FIG. 13).

T lymphocytes isolated from peripheral blood were activated for 72 hours using anti-CD3/CD28 activator beads (Life technologies) and 4.5 million cells were transfected by electroporation with 10 μg mRNA encoding the TALE-nuclease targeting TCR alpha constant chain region (TRAC) using a CytoLVT-S instrument (BTX-Harvard Harbour). Two days after electroporation, T cells were transduced with either the LV-SFFV-BFP-2A-pTalpha-Δ48 or LV-SFFV-BFP-2A-control lentiviral vectors. CD3 negative and CD3low T cells were then purified using anti-CD3 magnetic beads (Miltenyi Biotech). This experimental protocol is represented in FIG. 14A.

FIG. 14B represents flow cytometry analysis of TCRalpha/beta, CD3 cell surface expression, and BFP expression on TCRalpha inactivated T cells (KO) transduced with either BFP-2A-pTalphaΔ48 (KO/Δ48) or control BFP lentiviral vector (KO/BFP) before and after purification with CD3 beads. TCRalpha inactivated cells transduced with the BFP-T2A-pTalpha-Δ48 vector (BFP+ cells) show higher levels of CD3 compared to non transduced cells (BFP− cells). No differences are observed among cells transduced with the control BFP vector. These results indicate that pTalpha mediates restoration of CD3 expression at the cell surface of TCRalpha inactivated cells. In contrast, TCRalpha/beta staining remains, as expected, unchanged in cells transduced or not with the pTalpha-Δ48 expressing vector.

pTalpha-Mediated CD3 Expression Supports Activation of TCR-Deficient T-Cells:

To determine the capacity of pTalpha to transduce cell activation signals, expression of early and later activation markers was analyzed on TCR alpha inactivated T cells transduced with pTalpha-Δ48 and pTalpha-Δ48.41BB. TCR alpha inactivated T cells transduced with pTalpha-Δ48 and pTalpha-Δ48.41BB were generated from primary human T-cells as described in previous section and in FIG. 14A.

To detect signaling via CD3, cells were re-activated using anti-CD3/CD28-coated beads 3 days after purification of TCR alpha inactivated T cells with CD3 beads (FIG. 14A). Cells were stained with fluorochrome-conjugated anti-CD69 (early activation marker) and anti-CD25 (late activation marker), 24 and 48 hours after re-activation respectively and analyzed by flow cytometry (FIG. 15A-B). As represented in FIG. 15A-B, TCR alpha inactivated cells expressing pTalpha-Δ48 (KO/pTα-Δ48) or pTalpha-Δ48.41BB (KO/pTα-Δ48.BB) show upregulation of the activation markers, to levels similar to those observed in TCRalpha/beta expressing cells (NEP: non electroporated cells).

Another indicator of T cell activation is an increase in cell size which is sometimes referred to as "blasting". The capacity of the preTCR complexes to induce "blasting" was measured by flow cytometry analysis of the cell size 72 hours after re-activation using anti-CD3/CD28-beads (FIG. 15C). Stimulation with anti-CD3/CD28 beads induced comparable increases in cell size in cells expressing TCRalpha/beta complexes vs. cells expressing pTalpha-Δ48 or pTalpha-Δ48.41BB. Taken together, these results suggest that preTCR complexes are competent to transduce signals that efficiently couple to the mechanisms mediating activation marker upregulation.

pTalpha Mediated CD3 Expression Supports Expansion of TCR-Deficient Primary T-Cells Using Stimulatory Anti-CD3/CD28 Antibodies To evaluate the capacity of preTCR complexes to support long term cell proliferation, proliferation of cells generated as previously described was measured. Ten days after the initial activation, cells were maintained in IL2 (non-Re-act) or in IL2 with anti-CD3/CD28 beads (Re-act). For each condition, cells were counted and analyzed by flow cytometry at the different time points to estimate the number of BFP+ cells. The growth of TCRalpha inactivated cells (KO) transduced with BFP or BFP-T2A-preTCRα-Δ48 vectors was compared, and the fold induction of these cells was estimated with respect to the value obtained at day 2 post re-activation. FIG. 16 shows the results obtained with two independent donors. In both cases, TCRalpha inactivated cells expressing pTalpha-Δ48 displayed greater expansion than TCR alpha inactivated cells expressing only the BFP control vector. For the second donor, TCRalpha inactivated cells expressing pTalpha-Δ48.41BB or full-length pTalpha were also included, displaying also greater expansion than TCRalpha inactivated cells expressing only the BFP control vector.

Example 5: Optimization of mRNA Transfection in T Cells Using Cytopulse Technology Determination of the Optimized Cytopulse Program A first set of experiments were performed on non activated PBMCs in order to determine a voltage range in which cells could be transfected. Five different programs were tested as described in Table 13.

TABLE 13

Different cytopulse programs used to determine the minimal voltage required for electroporation in PBMC derived T-cells.

| Cyto-pulse program | Group 1 | | | | Group 2 | | | | Group 3 | | | |
|---|---|---|---|---|---|---|---|---|---|---|---|---|
| | Pulses | V | duration (ms) | Interval (ms) | Pulses | V | duration (ms) | Interval (ms) | Pulses | V | duration (ms) | Interval (ms) |
| 1 | 1 | 600 | 0.1 | 0.2 | 1 | 600 | 0.1 | 100 | 4 | 130 | 0.2 | 2 |
| 2 | 1 | 900 | 0.1 | 0.2 | 1 | 900 | 0.1 | 100 | 4 | 130 | 0.2 | 2 |
| 3 | 1 | 1200 | 0.1 | 0.2 | 1 | 1200 | 0.1 | 100 | 4 | 130 | 0.2 | 2 |
| 4 | 1 | 1200 | 0.1 | 10 | 1 | 900 | 0.1 | 100 | 4 | 130 | 0.2 | 2 |
| 5 | 1 | 900 | 0.1 | 20 | 1 | 600 | 0.1 | 100 | 4 | 130 | 0.2 | 2 |

3 or 6 million of cells were electroporated in 0.4 cm gap cuvette (30 or $15 \times 10^6$ cells/ml) with 20 μg of plasmids encoding GFP and control plasmids pUC using the different Cytopulse programs. 24 hours post electroporation, GFP expression was analyzed in electroporated cells by flow cytometry to determine the efficiency of transfection. The data shown in FIG. 17 indicates the minimal voltage required for plasmid electroporation in PBMC derived T cells. These results demonstrate that the cytopulse program 3 and 4 allow an efficient transformation of T cells (EP #3 and #4).

Electroporation of mRNA of Purified Tcells Activated

After determining the best cytopulse program that allows an efficient DNA electroporation of T cells, we tested whether this method was applicable to the mRNA electroporation.

$5\times10^6$ purified T cells preactivated 6 days with PHA/IL2 were resuspended in cytoporation buffer T (BTX-Harvard apparatus) and electroporated in 0.4 cm cuvettes with 10 µg of mRNA encoding GFP or 20 µg of plasmids encoding GFP or pUC using the preferred cytopulse program as determined in the previous section (table 14).

TABLE 14

Cytopulse program used to electroporate purified T-cells.

| Cyto- pulse program | Group 1 | | | | Group 2 | | | | Group 3 | | | |
|---|---|---|---|---|---|---|---|---|---|---|---|---|
| | Pulse | V | duration (ms) | Interval (ms) | Pulse | V | duration (ms) | Interval (ms) | Pulse | V | duration (ms) | Interval (ms) |
| 3 | 1 | 1200 | 0.1 | 0.2 | 1 | 1200 | 0.1 | 100 | 4 | 130 | 0.2 | 2 |

48 h after transfection cells were stained with viability dye (eFluor-450) and the cellular viability and % of viable GFP+ cells was determined by flow cytometry analysis (FIG. 18).

The data shown in FIG. 18 indicates that the electroporation of RNA with the optimal condition determined here is no toxic and allows transfection of more than 95% of the viable cells.

In synthesis, the whole dataset shows that T-cells can be efficiently transfected either with DNA or RNA. In particular, RNA transfection has no impact on cellular viability and allows uniform expression levels of the transfected gene of interest in the cellular population.

Efficient transfection can be achieved early after cellular activation, independently of the activation method used (PHA/IL-2 or CD3/CD28-coated-beads). The inventors have succeeded in transfecting cells from 72 h after activation with efficiencies of >95%. In addition, efficient transfection of T cells after thawing and activation can also be obtained using the same electroporation protocol.

mRNA Electroporation in Primary Human T Cells for TALE-Nuclease Functional Expression After demonstrating that mRNA electroporation allow efficient expression of GFP in primary human T cells, we tested whether this method was applicable to the expression of other proteins of interest. Transcription activator-like effector nucleases (TALE-nuclease) are site-specific nucleases generated by the fusion of a TAL DNA binding domain to a DNA cleavage domain. They are powerful genome editing tools as they induce double-strand breaks at practically any desired DNA sequence. These double-strand breaks activate Non-homologous end-joining (NHEJ), an error-prone DNA repair mechanism, potentially leading to inactivation of any desired gene of interest. Alternatively, if an adequate repair template is introduced into the cells at the same time, TALE-nuclease-induced DNA breaks can be repaired by homologous recombination, therefore offering the possibility of modifying at will the gene sequence.

We have used mRNA electroporation to express a TALE-nuclease designed to specifically cleave a sequence in the human gene coding for the alpha chain of the T cell antigen receptor (TRAC). Mutations induced in this sequence are expected to result in gene inactivation and loss of TCRαβ complex from the cell surface. TRAC TALE-nuclease RNA or non coding RNA as control are transfected into activated primary human T lymphocytes using Cytopulse technology. The electroporation sequence consisted in 2 pulses of 1200 V followed by four pulses of 130 V as described in Table 14.

By flow cytometry analysis of TCR surface expression 7 days post electroporation (FIG. 19, top panel), we observed that 44% of T cells lost the expression of TCRαβ. We analyzed the genomic DNA of the transfected cells by PCR amplification of the TRAC locus followed by 454 high throughput sequencing. 33% of alleles sequenced (727 out of 2153) contained insertion or deletion at the site of TALE-nuclease cleavage. FIG. 19 (bottom panel) shows examples of the mutated alleles.

These data indicate that electroporation of mRNA using cytopulse technology results in functional expression of TRAC TALE-nuclease.

Electroporation of T Cells with a Monocistronic mRNA Encoding for an Anti-CD19 Single Chain Chimeric Antigen Receptor (CAR):

$5\times10^6$ T cells preactivated several days (3-5) with anti-CD3/CD28 coated beads and IL2 were resuspended in cytoporation buffer T, and electroporated in 0.4 cm cuvettes without mRNA or with 10 µg of mRNA encoding a single chain CAR (SEQ ID NO: 73) using the program described in Table 14.

24 hours post electroporation, cells were stained with a fixable viability dye eFluor-780 and a PE-conjugated goat anti mouse IgG F(ab')2 fragment specific to assess the cell surface expression of the CAR on the live cells. The data is shown in the FIG. 20. A indicates that the vast majority of the live T cells electroporated with the monocitronic mRNA described previously express the CAR at their surface. 24 hours post electroporation, T cells were cocultured with Daudi (CD19+) cells for 6 hours and analyzed by flow cytometry to detect the expression of the degranulation marker CD107a at their surface (Betts, Brenchley et al. 2003).

The data shown in FIG. 20 indicates that the majority of the cells electroporated with the monocistronic mRNA described previously degranulate in the presence of target cells expressing CD19. These results clearly demonstrate that the CAR expressed at the surface of electroporated T cells is active.

Electroporation of T Cells with a Polycistronic mRNA Encoding for an Anti-CD19 Multisubunit Chimeric Antigen Receptor (CAR):

$5\times10^6$ T cells preactivated several days (3-5) with anti CD3/CD28 coated beads and IL2 were electroporated in cytoporation buffer T, and electroporated in 0.4 cm cuvettes without mRNA or with 45 µg of mRNA encoding a multi-chain CAR (SEQ ID NO: 125, encoded by SEQ ID NO: 126, FIG. 21A and FIG. 4B (csm4)) using the program as described in Table 14.

24 hours post electroporation, cells were stained with a fixable viability dye eFluor-780 and a PE-conjugated goat anti mouse IgG F(ab')2 fragment specific to assess the cell surface expression of the CAR on the live cells. The data shown in FIG. 21 indicates that the vast majority of the live T cells electroporated with the polycistronic mRNA described previously express the CAR at their surface.

24 hours post electroporation, T cells were cocultured with Daudi (CD19+) for 6 hours and analyzed by flow cytometry to detect the expression of the degranulation marker CD107a at their surface. The data shown in FIG. 21 indicates that the majority of the cells electroporated with the polycistronic mRNA described previously degranulate in the presence of target cells expressing CD19. These results clearly demonstrate that the CAR expressed at the surface of electroporated T cells is active.

LIST OF REFERENCES CITED IN THE DESCRIPTION

Arimondo, P. B., C. J. Thomas, et al. (2006). "Exploring the cellular activity of camptothecin-triple-helix-forming oligonucleotide conjugates." *Mol Cell Biol* 26(1): 324-33.

Arnould, S., P. Chames, et al. (2006). "Engineering of large numbers of highly specific homing endonucleases that induce recombination on novel DNA targets." *J Mol Biol* 355(3): 443-58.

Ashwell, J. D. and R. D. Klusner (1990). "Genetic and mutational analysis of the T-cell antigen receptor." *Annu Rev Immunol* 8: 139-67.

Betts, M. R., J. M. Brenchley, et al. (2003). "Sensitive and viable identification of antigen-specific CD8+ T cells by a flow cytometry assay for degranulation." *J Immunol Methods* 281(1-2): 65-78.

Boch, J., H. Scholze, et al. (2009). "Breaking the code of DNA binding specificity of TAL-type III effectors." *Science* 326(5959): 1509-12.

Boni, A., P. Muranski, et al. (2008). "Adoptive transfer of allogeneic tumor-specific T cells mediates effective regression of large tumors across major histocompatibility barriers." *Blood* 112(12): 4746-54.

Cambier, J. C. (1995). "Antigen and Fc receptor signaling. The awesome power of the immunoreceptor tyrosine-based activation motif (ITAM)." *J Immunol* 155(7): 3281-5.

Carrasco, Y. R., A. R. Ramiro, et al. (2001). "An endoplasmic reticulum retention function for the cytoplasmic tail of the human pre-T cell receptor (TCR) alpha chain: potential role in the regulation of cell surface pre-TCR expression levels." *J Exp Med* 193(9): 1045-58.

Cermak, T., E. L. Doyle, et al. (2011). "Efficient design and assembly of custom TALEN and other TAL effector-based constructs for DNA targeting." *Nucleic Acids Res* 39(12): e82.

Chames, P., J. C. Epinat, et al. (2005). "In vivo selection of engineered homing endonucleases using double-strand break induced homologous recombination." *Nucleic Acids Res* 33(20): e178.

Choulika, A., A. Perrin, et al. (1995). "Induction of homologous recombination in mammalian chromosomes by using the I-SceI system of *Saccharomyces cerevisiae*." *Mol Cell Biol* 15(4): 1968-73.

Christian, M., T. Cermak, et al. (2010). "Targeting DNA double-strand breaks with TAL effector nucleases." *Genetics* 186(2): 757-61.

Coutinho, A. E. and K. E. Chapman (2011). "The anti-inflammatory and immunosuppressive effects of glucocorticoids, recent developments and mechanistic insights." *Mol Cell Endocrinol* 335(1): 2-13.

Critchlow, S. E. and S. P. Jackson (1998). "DNA end-joining: from yeast to man." *Trends Biochem Sci* 23(10): 394-8.

Deng, D., C. Yan, et al. (2012). "Structural basis for sequence-specific recognition of DNA by TAL effectors." *Science* 335(6069): 720-3.

Eisenschmidt, K., T. Lanio, et al. (2005). "Developing a programmed restriction endonuclease for highly specific DNA cleavage." *Nucleic Acids Res* 33(22): 7039-47.

Epinat, J. C., S. Arnould, et al. (2003). "A novel engineered meganuclease induces homologous recombination in yeast and mammalian cells." *Nucleic Acids Res* 31(11): 2952-62.

Geissler, R., H. Scholze, et al. (2011). "Transcriptional activators of human genes with programmable DNA-specificity." *PLoS One* 6(5): e19509.

Howard, F. D., H. R. Rodewald, et al. (1990). "CD3 zeta subunit can substitute for the gamma subunit of Fc epsilon receptor type I in assembly and functional expression of the high-affinity IgE receptor: evidence for interreceptor complementation." *Proc Natl Acad Sci USA* 87(18): 7015-9.

Huang, P., A. Xiao, et al. (2011). "Heritable gene targeting in zebrafish using customized TALENs." *Nat Biotechnol* 29(8): 699-700.

Jena, B., G. Dotti, et al. (2010). "Redirecting T-cell specificity by introducing a tumor-specific chimeric antigen receptor." *Blood* 116(7): 1035-44.

Kalish, J. M. and P. M. Glazer (2005). "Targeted genome modification via triple helix formation." *Ann N Y Acad Sci* 1058: 151-61.

Li, L., M. J. Piatek, et al. (2012). "Rapid and highly efficient construction of TALE-based transcriptional regulators and nucleases for genome modification." *Plant Mol Biol* 78(4-5): 407-16.

Li, T., S. Huang, et al. (2011). "TAL nucleases (TALNs): hybrid proteins composed of TAL effectors and FokI DNA-cleavage domain." *Nucleic Acids Res* 39(1): 359-72.

Li, T., S. Huang, et al. (2011). "Modularly assembled designer TAL effector nucleases for targeted gene knock-out and gene replacement in eukaryotes." *Nucleic Acids Res* 39(14): 6315-25.

Ma, J. L., E. M. Kim, et al. (2003). "Yeast Mre11 and Rad1 proteins define a Ku-independent mechanism to repair double-strand breaks lacking overlapping end sequences." *Mol Cell Biol* 23(23): 8820-8.

Mahfouz, M. M., L. Li, et al. (2012). "Targeted transcriptional repression using a chimeric TALE-SRDX repressor protein." *Plant Mol Biol* 78(3): 311-21.

Mahfouz, M. M., L. Li, et al. (2011). "De novo-engineered transcription activator-like effector (TALE) hybrid nuclease with novel DNA binding specificity creates double-strand breaks." *Proc Natl Acad Sci USA* 108(6): 2623-8.

Mak, A. N., P. Bradley, et al. (2012). "The crystal structure of TAL effector PthXo1 bound to its DNA target." *Science* 335(6069): 716-9.

Metzger, H., G. Alcaraz, et al. (1986). "The receptor with high affinity for immunoglobulin E." *Annu Rev Immunol* 4: 419-70.

Miller, J. C., S. Tan, et al. (2011). "A TALE nuclease architecture for efficient genome editing." *Nat Biotechnol* 29(2): 143-8.

Morbitzer, R., P. Romer, et al. (2011). "Regulation of selected genome loci using de novo-engineered transcription activator-like effector (TALE)-type transcription factors." *Proc Natl Acad Sci USA* 107(50): 21617-22.

Moscou, M. J. and A. J. Bogdanove (2009). "A simple cipher governs DNA recognition by TAL effectors." *Science* 326(5959): 1501.

Mussolino, C., R. Morbitzer, et al. (2011). "A novel TALE nuclease scaffold enables high genome editing activity in combination with low toxicity." *Nucleic Acids Res* 39(21): 9283-93.

Pang, S. S., R. Berry, et al. (2010). "The structural basis for autonomous dimerization of the pre-T-cell antigen receptor." *Nature* 467(7317): 844-8.

Paques, F. and P. Duchateau (2007). "Meganucleases and DNA double-strand break-induced recombination: perspectives for gene therapy." *Curr Gene Ther* 7(1): 49-66.

Pardoll, D. M. (2012). "Immunology beats cancer: a blueprint for successful translation." *Nat Immunol* 13(12): 1129-32.

Park, T. S., S. A. Rosenberg, et al. (2011). "Treating cancer with genetically engineered T cells." *Trends Biotechnol* 29(11): 550-7.

Pingoud, A. and G. H. Silva (2007). "Precision genome surgery." *Nat Biotechnol* 25(7): 743-4.

Porteus, M. H. and D. Carroll (2005). "Gene targeting using zinc finger nucleases." *Nat Biotechnol* 23(8): 967-73.

Rouet, P., F. Smih, et al. (1994). "Introduction of double-strand breaks into the genome of mouse cells by expression of a rare-cutting endonuclease." *Mol Cell Biol* 14(12): 8096-106.

Saint-Ruf, C., O. Lechner, et al. (1998). "Genomic structure of the human pre-T cell receptor alpha chain and expression of two mRNA isoforms." *Eur J Immunol* 28(11): 3824-31.

Sander, J. D., L. Cade, et al. (2011). "Targeted gene disruption in somatic zebrafish cells using engineered TALENs." *Nat Biotechnol* 29(8): 697-8.

Smith, J., S. Grizot, et al. (2006). "A combinatorial approach to create artificial homing endonucleases cleaving chosen sequences." *Nucleic Acids Res* 34(22): e149.

Stoddard, B. L. (2005). "Homing endonuclease structure and function." *Q Rev Biophys* 38(1): 49-95.

Tesson, L., C. Usal, et al. (2011). "Knockout rats generated by embryo microinjection of TALENs." *Nat Biotechnol* 29(8): 695-6.

von Boehmer, H. (2005). "Unique features of the pre-T-cell receptor alpha-chain: not just a surrogate." *Nat Rev Immunol* 5(7): 571-7.

Waldmann, H. and G. Hale (2005). "CAMPATH: from concept to clinic." *Philos Trans R Soc Lond B Biol Sci* 360(1461): 1707-11.

Weber, E., R. Gruetzner, et al. (2011). "Assembly of designer TAL effectors by Golden Gate cloning." *PLoS One* 6(5): e19722.

Yamasaki, S., E. Ishikawa, et al. (2006). "Mechanistic basis of pre-T cell receptor-mediated autonomous signaling critical for thymocyte development." *Nat Immunol* 7(1): 67-75.

Zhang, F., L. Cong, et al. (2011). "Efficient construction of sequence-specific TAL effectors for modulating mammalian transcription." *Nat Biotechnol* 29(2): 149-53.

---

The invention claimed is:

1. A method for genetic modification of a cell comprising:
 providing human primary T cells comprising a target DNA gene sequence;
 culturing the T cells;
 electroporating mRNAs encoding two half-TALE-nucleases that together target said target DNA gene sequence into the T cells;
 wherein one of said mRNAs encodes a half-TALE-nuclease targeting said target DNA gene sequence,
 wherein another of said mRNAs encodes the other half-TALE-nuclease targeting said target DNA gene sequence; and
 transiently expressing the half-TALE-nucleases in the cells to generate a double-strand break at the DNA target gene sequence thereby inactivating the target gene to generate a sufficient number of T cells comprising the inactivated target gene for immunotherapy.

2. The method of claim 1, wherein the mRNAs are capped and polyadenylated mRNAs.

3. The method of claim 2, wherein the mRNAs are synthesized from a plasmid.

4. The method of claim 1, comprising generating $10^5$ T cells comprising the inactivated target gene.

5. The method of claim 4, comprising generating $10^6$ T cells comprising the inactivated target gene.

* * * * *

SEQUENCE LISTING

```
<160> NUMBER OF SEQ ID NOS: 139

<210> SEQ ID NO 1
<211> LENGTH: 49
<212> TYPE: DNA
<213> ORGANISM: Artificial sequence
<220> FEATURE:
<223> OTHER INFORMATION: GRex2

<400> SEQUENCE: 1
tattcactga tggactccaa agaatcatta actcctggta gagaagaaa          49

<210> SEQ ID NO 2
<211> LENGTH: 49
<212> TYPE: DNA
<213> ORGANISM: Artificialsequence
<220> FEATURE:
<223> OTHER INFORMATION: GRex3T2

<400> SEQUENCE: 2
tgcctggtgt gctctgatga agcttcagga tgtcattatg gagtcttaa          49

<210> SEQ ID NO 3
<211> LENGTH: 49
<212> TYPE: DNA
<213> ORGANISM: Artificialsequence
<220> FEATURE:
<223> OTHER INFORMATION: GRex3T4

<400> SEQUENCE: 3
tgctctgatg aagcttcagg atgtcattat ggagtcttaa cttgtggaa          49

<210> SEQ ID NO 4
<211> LENGTH: 49
<212> TYPE: DNA
<213> ORGANISM: Artificialsequence
```

<220> FEATURE:
<223> OTHER INFORMATION: GRex5T1

<400> SEQUENCE: 4
tggtgtcact gttggaggtt attgaacctg aagtgttata tgcaggata        49

<210> SEQ ID NO 5
<211> LENGTH: 49
<212> TYPE: DNA
<213> ORGANISM: Artificialsequence
<220> FEATURE:
<223> OTHER INFORMATION: GRex5T2

<400> SEQUENCE: 5
tatgatagct ctgttccaga ctcaacttgg aggatcatga ctacgctca        49

<210> SEQ ID NO 6
<211> LENGTH: 49
<212> TYPE: DNA
<213> ORGANISM: Artificialsequence
<220> FEATURE:
<223> OTHER INFORMATION: GRex5T3

<400> SEQUENCE: 6
ttatatgcag gatatgatag ctctgttcca gactcaactt ggaggatca        49

<210> SEQ ID NO 7
<211> LENGTH: 530
<212> TYPE: PRT
<213> ORGANISM: Artificialsequence
<220> FEATURE:
<223> OTHER INFORMATION: Repeat-GRex2-LPT9-L1

<400> SEQUENCE: 7

Leu Thr Pro Glu Gln Val Val Ala Ile Ala Ser Asn Ile Gly Gly Lys
1               5                   10                  15

Gln Ala Leu Glu Thr Val Gln Ala Leu Leu Pro Val Leu Cys Gln Ala
            20                  25                  30

His Gly Leu Thr Pro Gln Gln Val Val Ala Ile Ala Ser Asn Gly Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser Asn Ile Gly Gly Lys Gln Ala Leu Glu Thr Val Gln Ala
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Gly Lys Gln Ala Leu Glu
        210                 215                 220

Thr Val Gln Arg Leu Leu Pro Val Leu Cys Gln Ala His Gly Leu Thr
225                 230                 235                 240

Pro Gln Gln Val Val Ala Ile Ala Ser Asn Asn Gly Gly Lys Gln Ala
            245                 250                 255

Leu Glu Thr Val Gln Arg Leu Leu Pro Val Leu Cys Gln Ala His Gly
        260                 265                 270

Leu Thr Pro Glu Gln Val Val Ala Ile Ala Ser Asn Ile Gly Gly Lys
    275                 280                 285

Gln Ala Leu Glu Thr Val Gln Ala Leu Leu Pro Val Leu Cys Gln Ala
290                 295                 300

His Gly Leu Thr Pro Gln Gln Val Val Ala Ile Ala Ser Asn Gly Gly
305                 310                 315                 320

Gly Lys Gln Ala Leu Glu Thr Val Gln Arg Leu Leu Pro Val Leu Cys
            325                 330                 335

Gln Ala His Gly Leu Thr Pro Gln Gln Val Val Ala Ile Ala Ser Asn
        340                 345                 350

Asn Gly Gly Lys Gln Ala Leu Glu Thr Val Gln Arg Leu Leu Pro Val
    355                 360                 365

Leu Cys Gln Ala His Gly Leu Thr Pro Gln Gln Val Val Ala Ile Ala
370                 375                 380

Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
            405                 410                 415

Ile Ala Ser Asn Ile Gly Gly Lys Gln Ala Leu Glu Thr Val Gln Ala
        420                 425                 430

Leu Leu Pro Val Leu Cys Gln Ala His Gly Leu Thr Pro Glu Gln Val
    435                 440                 445

Val Ala Ile Ala Ser His Asp Gly Gly Lys Gln Ala Leu Glu Thr Val
450                 455                 460

Gln Arg Leu Leu Pro Val Leu Cys Gln Ala His Gly Leu Thr Pro Gln
465                 470                 475                 480

Gln Val Val Ala Ile Ala Ser Asn Gly Gly Gly Lys Gln Ala Leu Glu
            485                 490                 495

Thr Val Gln Arg Leu Leu Pro Val Leu Cys Gln Ala His Gly Leu Thr
        500                 505                 510

Pro Gln Gln Val Val Ala Ile Ala Ser Asn Gly Gly Gly Arg Pro Ala
    515                 520                 525

Leu Glu
    530

<210> SEQ ID NO 8
<211> LENGTH: 530
<212> TYPE: PRT
<213> ORGANISM: Artificialsequence
<220> FEATURE:
<223> OTHER INFORMATION: Repeat-GRex2-LPT9-R1

<400> SEQUENCE: 8

Leu Thr Pro Gln Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

```
His Gly Leu Thr Pro Gln Gln Val Ala Ile Ala Ser Asn Gly Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
            100                 105                 110

Ser Asn Gly Gly Gly Lys Gln Ala Leu Glu Thr Val Gln Arg Leu Leu
            115                 120                 125

Pro Val Leu Cys Gln Ala His Gly Leu Thr Pro Gln Gln Val Val Ala
            130                 135                 140

Ile Ala Ser Asn Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Gln
            195                 200                 205

Gln Val Val Ala Ile Ala Ser Asn Gly Gly Gly Lys Gln Ala Leu Glu
            210                 215                 220

Thr Val Gln Arg Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
            260                 265                 270

Leu Thr Pro Gln Gln Val Val Ala Ile Ala Ser Asn Gly Gly Gly Lys
            275                 280                 285

Gln Ala Leu Glu Thr Val Gln Arg Leu Leu Pro Val Leu Cys Gln Ala
            290                 295                 300

His Gly Leu Thr Pro Glu Gln Val Val Ala Ile Ala Ser Asn Ile Gly
305                 310                 315                 320

Gly Lys Gln Ala Leu Glu Thr Val Gln Ala Leu Leu Pro Val Leu Cys
                325                 330                 335

Gln Ala His Gly Leu Thr Pro Glu Gln Val Val Ala Ile Ala Ser His
            340                 345                 350

Asp Gly Gly Lys Gln Ala Leu Glu Thr Val Gln Arg Leu Leu Pro Val
            355                 360                 365

Leu Cys Gln Ala His Gly Leu Thr Pro Glu Gln Val Val Ala Ile Ala
            370                 375                 380

Ser His Asp Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser Asn Ile Gly Gly Lys Gln Ala Leu Glu Thr Val Gln Ala
            420                 425                 430

Leu Leu Pro Val Leu Cys Gln Ala His Gly Leu Thr Pro Gln Gln Val
            435                 440                 445
```

Val Ala Ile Ala Ser Asn Asn Gly Gly Lys Gln Ala Leu Glu Thr Val
450                 455                 460

Gln Arg Leu Leu Pro Val Leu Cys Gln Ala His Gly Leu Thr Pro Gln
465                 470                 475                 480

Gln Val Val Ala Ile Ala Ser Asn Asn Gly Gly Lys Gln Ala Leu Glu
            485                 490                 495

Thr Val Gln Arg Leu Leu Pro Val Leu Cys Gln Ala His Gly Leu Thr
        500                 505                 510

Pro Gln Gln Val Val Ala Ile Ala Ser Asn Gly Gly Gly Arg Pro Ala
            515                 520                 525

Leu Glu
    530

<210> SEQ ID NO 9
<211> LENGTH: 530
<212> TYPE: PRT
<213> ORGANISM: Artificialsequence
<220> FEATURE:
<223> OTHER INFORMATION: Repeat-GRex3T2-L1

<400> SEQUENCE: 9

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
            100                 105                 110

Ser Asn Gly Gly Gly Lys Gln Ala Leu Glu Thr Val Gln Arg Leu Leu
        115                 120                 125

Pro Val Leu Cys Gln Ala His Gly Leu Thr Pro Gln Gln Val Val Ala
130                 135                 140

Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Asn Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Gln Gln Val Val Ala Ile Ala Ser Asn Asn Gly Gly Lys Gln Ala
                245                 250                 255

Leu Glu Thr Val Gln Arg Leu Leu Pro Val Leu Cys Gln Ala His Gly
            260                 265                 270

```
Leu Thr Pro Gln Gln Val Val Ala Ile Ala Ser Asn Gly Gly Lys
            275                 280                 285

Gln Ala Leu Glu Thr Val Gln Arg Leu Leu Pro Val Leu Cys Gln Ala
        290                 295                 300

His Gly Leu Thr Pro Gln Gln Val Val Ala Ile Ala Ser Asn Asn Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser His
            340                 345                 350

Asp Gly Gly Lys Gln Ala Leu Glu Thr Val Gln Arg Leu Leu Pro Val
        355                 360                 365

Leu Cys Gln Ala His Gly Leu Thr Pro Gln Gln Val Val Ala Ile Ala
    370                 375                 380

Ser Asn Gly Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser His Asp Gly Gly Lys Gln Ala Leu Glu Thr Val Gln Arg
            420                 425                 430

Leu Leu Pro Val Leu Cys Gln Ala His Gly Leu Thr Pro Gln Gln Val
        435                 440                 445

Val Ala Ile Ala Ser Asn Gly Gly Lys Gln Ala Leu Glu Thr Val
    450                 455                 460

Gln Arg Leu Leu Pro Val Leu Cys Gln Ala His Gly Leu Thr Pro Gln
465                 470                 475                 480

Gln Val Val Ala Ile Ala Ser Asn Asn Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Arg Pro Ala
        515                 520                 525

Leu Glu
    530

<210> SEQ ID NO 10
<211> LENGTH: 530
<212> TYPE: PRT
<213> ORGANISM: Artificialsequence
<220> FEATURE:
<223> OTHER INFORMATION: Repeat-GRex3T2-R1

<400> SEQUENCE: 10

Leu Thr Pro Gln Gln Val Val Ala Ile Ala Ser Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser Asn Ile Gly
        35                  40                  45

Gly Lys Gln Ala Leu Glu Thr Val Gln Ala Leu Leu Pro Val Leu Cys
    50                  55                  60

Gln Ala His Gly Leu Thr Pro Glu Gln Val Val Ala Ile Ala Ser Asn
65                  70                  75                  80

Ile Gly Gly Lys Gln Ala Leu Glu Thr Val Gln Ala Leu Leu Pro Val
                85                  90                  95
```

```
Leu Cys Gln Ala His Gly Leu Thr Pro Gln Gln Val Val Ala Ile Ala
             100                 105                 110

Ser Asn Asn Gly Gly Lys Gln Ala Leu Glu Thr Val Gln Arg Leu Leu
         115                 120                 125

Pro Val Leu Cys Gln Ala His Gly Leu Thr Pro Glu Gln Val Val Ala
     130                 135                 140

Ile Ala Ser Asn Ile Gly Gly Lys Gln Ala Leu Glu Thr Val Gln Ala
145                 150                 155                 160

Leu Leu Pro Val Leu Cys Gln Ala His Gly Leu Thr Pro Glu Gln Val
                 165                 170                 175

Val Ala Ile Ala Ser His Asp Gly Gly Lys Gln Ala Leu Glu Thr Val
             180                 185                 190

Gln Arg Leu Leu Pro Val Leu Cys Gln Ala His Gly Leu Thr Pro Gln
         195                 200                 205

Gln Val Val Ala Ile Ala Ser Asn Gly Gly Gly Lys Gln Ala Leu Glu
     210                 215                 220

Thr Val Gln Arg Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                 245                 250                 255

Leu Glu Thr Val Gln Arg Leu Leu Pro Val Leu Cys Gln Ala His Gly
             260                 265                 270

Leu Thr Pro Glu Gln Val Val Ala Ile Ala Ser His Asp Gly Gly Lys
         275                 280                 285

Gln Ala Leu Glu Thr Val Gln Arg Leu Leu Pro Val Leu Cys Gln Ala
     290                 295                 300

His Gly Leu Thr Pro Glu Gln Val Val Ala Ile Ala Ser Asn Ile Gly
305                 310                 315                 320

Gly Lys Gln Ala Leu Glu Thr Val Gln Ala Leu Leu Pro Val Leu Cys
                 325                 330                 335

Gln Ala His Gly Leu Thr Pro Gln Gln Val Val Ala Ile Ala Ser Asn
             340                 345                 350

Gly Gly Gly Lys Gln Ala Leu Glu Thr Val Gln Arg Leu Leu Pro Val
         355                 360                 365

Leu Cys Gln Ala His Gly Leu Thr Pro Glu Gln Val Val Ala Ile Ala
     370                 375                 380

Ser Asn Ile Gly Gly Lys Gln Ala Leu Glu Thr Val Gln Ala Leu Leu
385                 390                 395                 400

Pro Val Leu Cys Gln Ala His Gly Leu Thr Pro Glu Gln Val Val Ala
                 405                 410                 415

Ile Ala Ser Asn Ile Gly Gly Lys Gln Ala Leu Glu Thr Val Gln Ala
             420                 425                 430

Leu Leu Pro Val Leu Cys Gln Ala His Gly Leu Thr Pro Gln Gln Val
         435                 440                 445

Val Ala Ile Ala Ser Asn Gly Gly Gly Lys Gln Ala Leu Glu Thr Val
     450                 455                 460

Gln Arg Leu Leu Pro Val Leu Cys Gln Ala His Gly Leu Thr Pro Gln
465                 470                 475                 480

Gln Val Val Ala Ile Ala Ser Asn Asn Gly Gly Lys Gln Ala Leu Glu
                 485                 490                 495

Thr Val Gln Arg Leu Leu Pro Val Leu Cys Gln Ala His Gly Leu Thr
             500                 505                 510

Pro Gln Gln Val Val Ala Ile Ala Ser Asn Gly Gly Gly Arg Pro Ala
```

Leu Glu
530

<210> SEQ ID NO 11
<211> LENGTH: 530
<212> TYPE: PRT
<213> ORGANISM: Artificialsequence
<220> FEATURE:
<223> OTHER INFORMATION: Repeat-GRex3T4-L1

<400> SEQUENCE: 11

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Gln Gln Val Val Ala
    130                 135                 140

Ile Ala Ser Asn Gly Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Asn Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser Asn Ile Gly Gly Lys Gln Ala Leu Glu
    210                 215                 220

Thr Val Gln Ala Leu Leu Pro Val Leu Cys Gln Ala His Gly Leu Thr
225                 230                 235                 240

Pro Gln Gln Val Val Ala Ile Ala Ser Asn Gly Gly Gly Lys Gln Ala
                245                 250                 255

Leu Glu Thr Val Gln Arg Leu Leu Pro Val Leu Cys Gln Ala His Gly
            260                 265                 270

Leu Thr Pro Gln Gln Val Val Ala Ile Ala Ser Asn Asn Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser Asn Ile Gly
305                 310                 315                 320

Gly Lys Gln Ala Leu Glu Thr Val Gln Ala Leu Leu Pro Val Leu Cys
                325                 330                 335

Gln Ala His Gly Leu Thr Pro Glu Gln Val Val Ala Ile Ala Ser Asn

```
                340                 345                 350
Ile Gly Gly Lys Gln Ala Leu Glu Thr Val Gln Ala Leu Leu Pro Val
            355                 360                 365
Leu Cys Gln Ala His Gly Leu Thr Pro Gln Gln Val Val Ala Ile Ala
            370                 375                 380
Ser Asn Asn Gly Gly Lys Gln Ala Leu Glu Thr Val Gln Arg Leu Leu
385                 390                 395                 400
Pro Val Leu Cys Gln Ala His Gly Leu Thr Pro Glu Gln Val Val Ala
                405                 410                 415
Ile Ala Ser His Asp Gly Gly Lys Gln Ala Leu Glu Thr Val Gln Arg
            420                 425                 430
Leu Leu Pro Val Leu Cys Gln Ala His Gly Leu Thr Pro Gln Gln Val
            435                 440                 445
Val Ala Ile Ala Ser Asn Gly Gly Gly Lys Gln Ala Leu Glu Thr Val
            450                 455                 460
Gln Arg Leu Leu Pro Val Leu Cys Gln Ala His Gly Leu Thr Pro Gln
465                 470                 475                 480
Gln Val Val Ala Ile Ala Ser Asn Gly Gly Gly Lys Gln Ala Leu Glu
                485                 490                 495
Thr Val Gln Arg Leu Leu Pro Val Leu Cys Gln Ala His Gly Leu Thr
            500                 505                 510
Pro Gln Gln Val Val Ala Ile Ala Ser Asn Gly Gly Gly Arg Pro Ala
            515                 520                 525
Leu Glu
    530

<210> SEQ ID NO 12
<211> LENGTH: 530
<212> TYPE: PRT
<213> ORGANISM: Artificialsequence
<220> FEATURE:
<223> OTHER INFORMATION: Repeat-GRex3T4-R1

<400> SEQUENCE: 12

Leu Thr Pro Gln Gln Val Val Ala Ile Ala Ser Asn Gly Gly Gly Lys
1               5                   10                  15
Gln Ala Leu Glu Thr Val Gln Arg Leu Leu Pro Val Leu Cys Gln Ala
                20                  25                  30
His Gly Leu Thr Pro Glu Gln Val Val Ala Ile Ala Ser His Asp Gly
            35                  40                  45
Gly Lys Gln Ala Leu Glu Thr Val Gln Arg Leu Leu Pro Val Leu Cys
        50                  55                  60
Gln Ala His Gly Leu Thr Pro Glu Gln Val Val Ala Ile Ala Ser His
65                  70                  75                  80
Asp Gly Gly Lys Gln Ala Leu Glu Thr Val Gln Arg Leu Leu Pro Val
                85                  90                  95
Leu Cys Gln Ala His Gly Leu Thr Pro Glu Gln Val Val Ala Ile Ala
                100                 105                 110
Ser Asn Ile Gly Gly Lys Gln Ala Leu Glu Thr Val Gln Ala Leu Leu
            115                 120                 125
Pro Val Leu Cys Gln Ala His Gly Leu Thr Pro Glu Gln Val Val Ala
        130                 135                 140
Ile Ala Ser His Asp Gly Gly Lys Gln Ala Leu Glu Thr Val Gln Arg
145                 150                 155                 160
Leu Leu Pro Val Leu Cys Gln Ala His Gly Leu Thr Pro Glu Gln Val
```

```
                    165                 170                 175
Val Ala Ile Ala Ser Asn Ile Gly Gly Lys Gln Ala Leu Glu Thr Val
                180                 185                 190

Gln Ala Leu Leu Pro Val Leu Cys Gln Ala His Gly Leu Thr Pro Glu
            195                 200                 205

Gln Val Val Ala Ile Ala Ser Asn Ile Gly Gly Lys Gln Ala Leu Glu
        210                 215                 220

Thr Val Gln Ala Leu Leu Pro Val Leu Cys Gln Ala His Gly Leu Thr
225                 230                 235                 240

Pro Gln Gln Val Val Ala Ile Ala Ser Asn Asn Gly Gly Lys Gln Ala
                245                 250                 255

Leu Glu Thr Val Gln Arg Leu Leu Pro Val Leu Cys Gln Ala His Gly
            260                 265                 270

Leu Thr Pro Gln Gln Val Val Ala Ile Ala Ser Asn Gly Gly Gly Lys
        275                 280                 285

Gln Ala Leu Glu Thr Val Gln Arg Leu Leu Pro Val Leu Cys Gln Ala
    290                 295                 300

His Gly Leu Thr Pro Gln Gln Val Val Ala Ile Ala Ser Asn Gly Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
            340                 345                 350

Ile Gly Gly Lys Gln Ala Leu Glu Thr Val Gln Ala Leu Leu Pro Val
        355                 360                 365

Leu Cys Gln Ala His Gly Leu Thr Pro Glu Gln Val Val Ala Ile Ala
    370                 375                 380

Ser Asn Ile Gly Gly Lys Gln Ala Leu Glu Thr Val Gln Ala Leu Leu
385                 390                 395                 400

Pro Val Leu Cys Gln Ala His Gly Leu Thr Pro Gln Gln Val Val Ala
                405                 410                 415

Ile Ala Ser Asn Asn Gly Gly Lys Gln Ala Leu Glu Thr Val Gln Arg
            420                 425                 430

Leu Leu Pro Val Leu Cys Gln Ala His Gly Leu Thr Pro Glu Gln Val
        435                 440                 445

Val Ala Ile Ala Ser Asn Ile Gly Gly Lys Gln Ala Leu Glu Thr Val
    450                 455                 460

Gln Ala Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
530

<210> SEQ ID NO 13
<211> LENGTH: 530
<212> TYPE: PRT
<213> ORGANISM: Artificialsequence
<220> FEATURE:
<223> OTHER INFORMATION: Repeat-GRex5T1-LPT8-L1
```

<400> SEQUENCE: 13

```
Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Asn Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
            100                 105                 110

Ser Asn Asn Gly Gly Lys Gln Ala Leu Glu Thr Val Gln Arg Leu Leu
        115                 120                 125

Pro Val Leu Cys Gln Ala His Gly Leu Thr Pro Gln Gln Val Val Ala
    130                 135                 140

Ile Ala Ser Asn Gly Gly Lys Gln Ala Leu Glu Thr Val Gln Arg
145                 150                 155                 160

Leu Leu Pro Val Leu Cys Gln Ala His Gly Leu Thr Pro Glu Gln Val
            165                 170                 175

Val Ala Ile Ala Ser His Asp Gly Gly Lys Gln Ala Leu Glu Thr Val
        180                 185                 190

Gln Arg Leu Leu Pro Val Leu Cys Gln Ala His Gly Leu Thr Pro Glu
    195                 200                 205

Gln Val Val Ala Ile Ala Ser Asn Ile Gly Gly Lys Gln Ala Leu Glu
210                 215                 220

Thr Val Gln Ala Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
            245                 250                 255

Leu Glu Thr Val Gln Arg Leu Leu Pro Val Leu Cys Gln Ala His Gly
        260                 265                 270

Leu Thr Pro Gln Gln Val Val Ala Ile Ala Ser Asn Gly Gly Gly Lys
    275                 280                 285

Gln Ala Leu Glu Thr Val Gln Arg Leu Leu Pro Val Leu Cys Gln Ala
290                 295                 300

His Gly Leu Thr Pro Gln Gln Val Val Ala Ile Ala Ser Asn Asn Gly
305                 310                 315                 320

Gly Lys Gln Ala Leu Glu Thr Val Gln Arg Leu Leu Pro Val Leu Cys
            325                 330                 335

Gln Ala His Gly Leu Thr Pro Gln Gln Val Val Ala Ile Ala Ser Asn
        340                 345                 350

Gly Gly Gly Lys Gln Ala Leu Glu Thr Val Gln Arg Leu Leu Pro Val
    355                 360                 365

Leu Cys Gln Ala His Gly Leu Thr Pro Gln Gln Val Val Ala Ile Ala
370                 375                 380

Ser Asn Gly Gly Gly Lys Gln Ala Leu Glu Thr Val Gln Arg Leu Leu
385                 390                 395                 400

Pro Val Leu Cys Gln Ala His Gly Leu Thr Pro Gln Gln Val Val Ala
            405                 410                 415
```

```
Ile Ala Ser Asn Asn Gly Gly Lys Gln Ala Leu Glu Thr Val Gln Arg
            420                 425                 430

Leu Leu Pro Val Leu Cys Gln Ala His Gly Leu Thr Pro Gln Gln Val
            435                 440                 445

Val Ala Ile Ala Ser Asn Asn Gly Gly Lys Gln Ala Leu Glu Thr Val
            450                 455                 460

Gln Arg Leu Leu Pro Val Leu Cys Gln Ala His Gly Leu Thr Pro Glu
465                 470                 475                 480

Gln Val Val Ala Ile Ala Ser Asn Ile Gly Gly Lys Gln Ala Leu Glu
                485                 490                 495

Thr Val Gln Ala Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
            515                 520                 525

Leu Glu
    530

<210> SEQ ID NO 14
<211> LENGTH: 530
<212> TYPE: PRT
<213> ORGANISM: Artificialsequence
<220> FEATURE:
<223> OTHER INFORMATION: Repeat-GRex5T1-LPT8-R1

<400> SEQUENCE: 14

Leu Thr Pro Glu Gln Val Val Ala Ile Ala Ser Asn Ile Gly Gly Lys
1               5                   10                  15

Gln Ala Leu Glu Thr Val Gln Ala Leu Leu Pro Val Leu Cys Gln Ala
            20                  25                  30

His Gly Leu Thr Pro Gln Gln Val Val Ala Ile Ala Ser Asn Gly Gly
            35                  40                  45

Gly Lys Gln Ala Leu Glu Thr Val Gln Arg Leu Leu Pro Val Leu Cys
        50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Gln Gln Val Val Ala
            130                 135                 140

Ile Ala Ser Asn Gly Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Asn Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser His Asp Gly Gly Lys Gln Ala Leu Glu
            210                 215                 220

Thr Val Gln Arg Leu Leu Pro Val Leu Cys Gln Ala His Gly Leu Thr
225                 230                 235                 240
```

```
Pro Glu Gln Val Val Ala Ile Ala Ser Asn Ile Gly Gly Lys Gln Ala
            245                 250                 255

Leu Glu Thr Val Gln Ala Leu Leu Pro Val Leu Cys Gln Ala His Gly
        260                 265                 270

Leu Thr Pro Gln Gln Val Val Ala Ile Ala Ser Asn Gly Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser Asn Ile Gly
305                 310                 315                 320

Gly Lys Gln Ala Leu Glu Thr Val Gln Ala Leu Leu Pro Val Leu Cys
            325                 330                 335

Gln Ala His Gly Leu Thr Pro Gln Gln Val Val Ala Ile Ala Ser Asn
        340                 345                 350

Gly Gly Gly Lys Gln Ala Leu Glu Thr Val Gln Arg Leu Leu Pro Val
        355                 360                 365

Leu Cys Gln Ala His Gly Leu Thr Pro Glu Gln Val Val Ala Ile Ala
    370                 375                 380

Ser Asn Ile Gly Gly Lys Gln Ala Leu Glu Thr Val Gln Ala Leu Leu
385                 390                 395                 400

Pro Val Leu Cys Gln Ala His Gly Leu Thr Pro Glu Gln Val Val Ala
            405                 410                 415

Ile Ala Ser Asn Ile Gly Gly Lys Gln Ala Leu Glu Thr Val Gln Ala
        420                 425                 430

Leu Leu Pro Val Leu Cys Gln Ala His Gly Leu Thr Pro Glu Gln Val
        435                 440                 445

Val Ala Ile Ala Ser His Asp Gly Gly Lys Gln Ala Leu Glu Thr Val
    450                 455                 460

Gln Arg Leu Leu Pro Val Leu Cys Gln Ala His Gly Leu Thr Pro Glu
465                 470                 475                 480

Gln Val Val Ala Ile Ala Ser Asn Ile Gly Gly Lys Gln Ala Leu Glu
            485                 490                 495

Thr Val Gln Ala Leu Leu Pro Val Leu Cys Gln Ala His Gly Leu Thr
        500                 505                 510

Pro Gln Gln Val Val Ala Ile Ala Ser Asn Gly Gly Gly Arg Pro Ala
        515                 520                 525

Leu Glu
    530

<210> SEQ ID NO 15
<211> LENGTH: 530
<212> TYPE: PRT
<213> ORGANISM: Artificialsequence
<220> FEATURE:
<223> OTHER INFORMATION: Repeat-GRex5T2-L1

<400> SEQUENCE: 15

Leu Thr Pro Glu Gln Val Val Ala Ile Ala Ser Asn Ile Gly Gly Lys
1               5                   10                  15

Gln Ala Leu Glu Thr Val Gln Ala Leu Leu Pro Val Leu Cys Gln Ala
            20                  25                  30

His Gly Leu Thr Pro Gln Gln Val Val Ala Ile Ala Ser Asn Gly Gly
        35                  40                  45

Gly Lys Gln Ala Leu Glu Thr Val Gln Arg Leu Leu Pro Val Leu Cys
    50                  55                  60
```

```
Gln Ala His Gly Leu Thr Pro Gln Gln Val Val Ala Ile Ala Ser Asn
65                  70                  75                  80

Asn Gly Gly Lys Gln Ala Leu Glu Thr Val Gln Arg Leu Leu Pro Val
            85                  90                  95

Leu Cys Gln Ala His Gly Leu Thr Pro Glu Gln Val Val Ala Ile Ala
        100                 105                 110

Ser Asn Ile Gly Gly Lys Gln Ala Leu Glu Thr Val Gln Ala Leu Leu
        115                 120                 125

Pro Val Leu Cys Gln Ala His Gly Leu Thr Pro Gln Gln Val Val Ala
        130                 135                 140

Ile Ala Ser Asn Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser Asn Ile Gly Gly Lys Gln Ala Leu Glu Thr Val
            180                 185                 190

Gln Ala Leu Leu Pro Val Leu Cys Gln Ala His Gly Leu Thr Pro Gln
        195                 200                 205

Gln Val Val Ala Ile Ala Ser Asn Asn Gly Gly Lys Gln Ala Leu Glu
210                 215                 220

Thr Val Gln Arg Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
                260                 265                 270

Leu Thr Pro Gln Gln Val Val Ala Ile Ala Ser Asn Gly Gly Gly Lys
            275                 280                 285

Gln Ala Leu Glu Thr Val Gln Arg Leu Leu Pro Val Leu Cys Gln Ala
290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Gln Gln Val Val Ala Ile Ala Ser Asn
            340                 345                 350

Gly Gly Gly Lys Gln Ala Leu Glu Thr Val Gln Arg Leu Leu Pro Val
        355                 360                 365

Leu Cys Gln Ala His Gly Leu Thr Pro Gln Gln Val Val Ala Ile Ala
        370                 375                 380

Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Gln Gln Val Val Ala
                405                 410                 415

Ile Ala Ser Asn Gly Gly Gly Lys Gln Ala Leu Glu Thr Val Gln Arg
            420                 425                 430

Leu Leu Pro Val Leu Cys Gln Ala His Gly Leu Thr Pro Gln Gln Val
        435                 440                 445

Val Ala Ile Ala Ser Asn Gly Gly Gly Lys Gln Ala Leu Glu Thr Val
        450                 455                 460

Gln Arg Leu Leu Pro Val Leu Cys Gln Ala His Gly Leu Thr Pro Glu
465                 470                 475                 480
```

```
Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530

<210> SEQ ID NO 16
<211> LENGTH: 530
<212> TYPE: PRT
<213> ORGANISM: Artificialsequence
<220> FEATURE:
<223> OTHER INFORMATION: Repeat-GRex5T2-R1

<400> SEQUENCE: 16

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser Asn Ile Gly
        35                  40                  45

Gly Lys Gln Ala Leu Glu Thr Val Gln Ala Leu Leu Pro Val Leu Cys
    50                  55                  60

Gln Ala His Gly Leu Thr Pro Gln Gln Val Val Ala Ile Ala Ser Asn
65                  70                  75                  80

Asn Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Gln Gln Val Val Ala
    130                 135                 140

Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Gly Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser Asn Ile Gly Gly Lys Gln Ala Leu Glu
    210                 215                 220

Thr Val Gln Ala Leu Leu Pro Val Leu Cys Gln Ala His Gly Leu Thr
225                 230                 235                 240

Pro Gln Gln Val Val Ala Ile Ala Ser Asn Asn Gly Gly Lys Gln Ala
                245                 250                 255

Leu Glu Thr Val Gln Arg Leu Leu Pro Val Leu Cys Gln Ala His Gly
            260                 265                 270

Leu Thr Pro Gln Gln Val Val Ala Ile Ala Ser Asn Gly Gly Gly Lys
        275                 280                 285

Gln Ala Leu Glu Thr Val Gln Arg Leu Leu Pro Val Leu Cys Gln Ala
    290                 295                 300
```

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
            325                 330                 335

Gln Ala His Gly Leu Thr Pro Glu Gln Val Val Ala Ile Ala Ser Asn
            340                 345                 350

Ile Gly Gly Lys Gln Ala Leu Glu Thr Val Gln Ala Leu Leu Pro Val
            355                 360                 365

Leu Cys Gln Ala His Gly Leu Thr Pro Gln Gln Val Ala Ile Ala
    370                 375                 380

Ser Asn Gly Gly Lys Gln Ala Leu Glu Thr Val Gln Arg Leu Leu
385                 390                 395                 400

Pro Val Leu Cys Gln Ala His Gly Leu Thr Pro Gln Gln Val Val Ala
            405                 410                 415

Ile Ala Ser Asn Asn Gly Gly Lys Gln Ala Leu Glu Thr Val Gln Arg
            420                 425                 430

Leu Leu Pro Val Leu Cys Gln Ala His Gly Leu Thr Pro Glu Gln Val
            435                 440                 445

Val Ala Ile Ala Ser Asn Ile Gly Gly Lys Gln Ala Leu Glu Thr Val
450                 455                 460

Gln Ala Leu Leu Pro Val Leu Cys Gln Ala His Gly Leu Thr Pro Gln
465                 470                 475                 480

Gln Val Val Ala Ile Ala Ser Asn Gly Gly Gly Lys Gln Ala Leu Glu
            485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
            515                 520                 525

Leu Glu
    530

<210> SEQ ID NO 17
<211> LENGTH: 530
<212> TYPE: PRT
<213> ORGANISM: Artificialsequence
<220> FEATURE:
<223> OTHER INFORMATION: Repeat-GRex5T3-L1

<400> SEQUENCE: 17

Leu Thr Pro Gln Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser Asn Ile Gly
            35                  40                  45

Gly Lys Gln Ala Leu Glu Thr Val Gln Ala Leu Leu Pro Val Leu Cys
    50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
            85                  90                  95

Leu Cys Gln Ala His Gly Leu Thr Pro Glu Gln Val Val Ala Ile Ala
            100                 105                 110

Ser Asn Ile Gly Gly Lys Gln Ala Leu Glu Thr Val Gln Ala Leu Leu
            115                 120                 125

```
Pro Val Leu Cys Gln Ala His Gly Leu Thr Pro Gln Gln Val Ala
130                 135                 140
Ile Ala Ser Asn Gly Gly Gly Lys Gln Ala Leu Glu Thr Val Gln Arg
145                 150                 155                 160
Leu Leu Pro Val Leu Cys Gln Ala His Gly Leu Thr Pro Gln Gln Val
                165                 170                 175
Val Ala Ile Ala Ser Asn Asn Gly Gly Lys Gln Ala Leu Glu Thr Val
                180                 185                 190
Gln Arg Leu Leu Pro Val Leu Cys Gln Ala His Gly Leu Thr Pro Glu
                195                 200                 205
Gln Val Val Ala Ile Ala Ser His Asp Gly Gly Lys Gln Ala Leu Glu
210                 215                 220
Thr Val Gln Arg Leu Leu Pro Val Leu Cys Gln Ala His Gly Leu Thr
225                 230                 235                 240
Pro Glu Gln Val Val Ala Ile Ala Ser Asn Ile Gly Gly Lys Gln Ala
                245                 250                 255
Leu Glu Thr Val Gln Ala Leu Leu Pro Val Leu Cys Gln Ala His Gly
                260                 265                 270
Leu Thr Pro Gln Gln Val Val Ala Ile Ala Ser Asn Asn Gly Gly Lys
                275                 280                 285
Gln Ala Leu Glu Thr Val Gln Arg Leu Leu Pro Val Leu Cys Gln Ala
290                 295                 300
His Gly Leu Thr Pro Gln Gln Val Val Ala Ile Ala Ser Asn Asn Gly
305                 310                 315                 320
Gly Lys Gln Ala Leu Glu Thr Val Gln Arg Leu Leu Pro Val Leu Cys
                325                 330                 335
Gln Ala His Gly Leu Thr Pro Glu Gln Val Val Ala Ile Ala Ser Asn
                340                 345                 350
Ile Gly Gly Lys Gln Ala Leu Glu Thr Val Gln Ala Leu Leu Pro Val
                355                 360                 365
Leu Cys Gln Ala His Gly Leu Thr Pro Gln Gln Val Val Ala Ile Ala
370                 375                 380
Ser Asn Gly Gly Gly Lys Gln Ala Leu Glu Thr Val Gln Arg Leu Leu
385                 390                 395                 400
Pro Val Leu Cys Gln Ala His Gly Leu Thr Pro Glu Gln Val Val Ala
                405                 410                 415
Ile Ala Ser Asn Ile Gly Gly Lys Gln Ala Leu Glu Thr Val Gln Ala
                420                 425                 430
Leu Leu Pro Val Leu Cys Gln Ala His Gly Leu Thr Pro Gln Gln Val
                435                 440                 445
Val Ala Ile Ala Ser Asn Gly Gly Gly Lys Gln Ala Leu Glu Thr Val
450                 455                 460
Gln Arg Leu Leu Pro Val Leu Cys Gln Ala His Gly Leu Thr Pro Gln
465                 470                 475                 480
Gln Val Val Ala Ile Ala Ser Asn Asn Gly Gly Lys Gln Ala Leu Glu
                485                 490                 495
Thr Val Gln Arg Leu Leu Pro Val Leu Cys Gln Ala His Gly Leu Thr
                500                 505                 510
Pro Gln Gln Val Val Ala Ile Ala Ser Asn Gly Gly Gly Arg Pro Ala
                515                 520                 525
Leu Glu
530
```

<210> SEQ ID NO 18
<211> LENGTH: 530
<212> TYPE: PRT
<213> ORGANISM: Artificialsequence
<220> FEATURE:
<223> OTHER INFORMATION: Repeat-GRex5T3-R1

<400> SEQUENCE: 18

```
Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser Asn Ile Gly
        35                  40                  45

Gly Lys Gln Ala Leu Glu Thr Val Gln Ala Leu Leu Pro Val Leu Cys
50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser His Asp Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser Asn Ile Gly Gly Lys
        275                 280                 285

Gln Ala Leu Glu Thr Val Gln Ala Leu Leu Pro Val Leu Cys Gln Ala
    290                 295                 300

His Gly Leu Thr Pro Glu Gln Val Val Ala Ile Ala Ser Asn Ile Gly
305                 310                 315                 320

Gly Lys Gln Ala Leu Glu Thr Val Gln Ala Leu Leu Pro Val Leu Cys
                325                 330                 335

Gln Ala His Gly Leu Thr Pro Gln Gln Val Val Ala Ile Ala Ser Asn
            340                 345                 350

Asn Gly Gly Lys Gln Ala Leu Glu Thr Val Gln Arg Leu Leu Pro Val
        355                 360                 365

Leu Cys Gln Ala His Gly Leu Thr Pro Gln Gln Val Val Ala Ile Ala
```

Ser Asn Gly Gly Gly Lys Gln Ala Leu Glu Thr Val Gln Arg Leu Leu
385                 390                 395                 400

Pro Val Leu Cys Gln Ala His Gly Leu Thr Pro Gln Gln Val Val Ala
            405                 410                 415

Ile Ala Ser Asn Gly Gly Lys Gln Ala Leu Glu Thr Val Gln Arg
                420                 425                 430

Leu Leu Pro Val Leu Cys Gln Ala His Gly Leu Thr Pro Gln Gln Val
            435                 440                 445

Val Ala Ile Ala Ser Asn Gly Gly Lys Gln Ala Leu Glu Thr Val
        450                 455                 460

Gln Arg Leu Leu Pro Val Leu Cys Gln Ala His Gly Leu Thr Pro Glu
465                 470                 475                 480

Gln Val Val Ala Ile Ala Ser Asn Ile Gly Gly Lys Gln Ala Leu Glu
                485                 490                 495

Thr Val Gln Ala Leu Leu Pro Val Leu Cys Gln Ala His Gly Leu Thr
            500                 505                 510

Pro Gln Gln Val Val Ala Ile Ala Ser Asn Gly Gly Arg Pro Ala
        515                 520                 525

Leu Glu
    530

<210> SEQ ID NO 19
<211> LENGTH: 2814
<212> TYPE: DNA
<213> ORGANISM: Artificialsequence
<220> FEATURE:
<223> OTHER INFORMATION: GRex2-L TALEN

<400> SEQUENCE: 19
atgggcgatc ctaaaaagaa acgtaaggtc atcgattacc catacgatgt tccagattac      60
gctatcgata tcgccgatct acgcacgctc ggctacagcc agcagcaaca ggagaagatc     120
aaaccgaagg ttcgttcgac agtggcgcag caccacgagg cactggtcgg ccacgggttt     180
acacacgcgc acatcgttgc gttaagccaa cacccggcag cgttagggac cgtcgctgtc     240
aagtatcagg acatgatcgc agcgttgcca gaggcgacac acgaagcgat cgttggcgtc     300
ggcaaacagt ggtccggcgc acgcgctctg gaggccttgc tcacggtggc gggagagttg     360
agaggtccac cgttacagtt ggacacaggc caacttctca gattgcaaa cgtggcggc      420
gtgaccgcag tggaggcagt gcatgcatgg cgcaatgcac tgacgggtgc cccgctcaac     480
ttgaccccgg agcaggtggt ggccatcgcc agcaatattg tggcaagca ggcgctggag      540
acggtgcagg cgctgttgcc ggtgctgtgc caggcccacg gcttgacccc ccagcaggtg     600
gtggccatcg ccagcaatgg cggtggcaag caggcgctgg agacggtcca gcggctgttg     660
ccggtgctgt gccaggccca cggcttgacc ccccagcagg tggtggccat cgccagcaat     720
ggcggtggca gcaggcgct ggagacggtc agcggctgt gccggtgct gtgccaggcc       780
cacggcttga ccccggagca ggtggtggcc atcgccagcc acgatggcgg caagcaggcg     840
ctggagacgg tccagcggct gttgccggtg ctgtgccagg cccacggctt gaccccggag     900
caggtggtgg ccatcgccag caatattggt ggcaagcagg cgctggagac ggtgcaggcg     960
ctgttgccgg tgctgtgcca ggcccacggc ttgaccccgg agcaggtggt ggccatcgcc    1020
agccacgatg cggcaagca ggcgctggag acgtccagc ggctgttgcc ggtgctgtgc     1080
caggcccacg gcttgacccc ccagcaggtg gtggccatcg ccagcaatgg cggtggcaag    1140

| | |
|---|---|
| caggcgctgg agacggtcca gcggctgttg ccggtgctgt gccaggccca cggcttgacc | 1200 |
| ccccagcagg tggtggccat cgccagcaat aatggtggca agcaggcgct ggagacggtc | 1260 |
| cagcggctgt tgccggtgct gtgccaggcc cacggcttga ccccggagca ggtggtggcc | 1320 |
| atcgccagca atattggtgg caagcaggcg ctggagacgg tgcaggcgct gttgccggtg | 1380 |
| ctgtgccagg cccacggctt gacccccag caggtggtgg ccatcgccag caatggcggt | 1440 |
| ggcaagcagg cgctggagac ggtccagcgg ctgttgccgg tgctgtgcca ggcccacggc | 1500 |
| ttgacccccc agcaggtggt ggccatcgcc agcaataatg gtggcaagca ggcgctggag | 1560 |
| acggtccagc ggctgttgcc ggtgctgtgc caggcccacg gcttgacccc ccagcaggtg | 1620 |
| gtggccatcg ccagcaataa tggtggcaag caggcgctgg agacggtcca gcggctgttg | 1680 |
| ccggtgctgt gccaggccca cggcttgacc ccggagcagg tggtggccat cgccagcaat | 1740 |
| attggtggca agcaggcgct ggagacggtg caggcgctgt tgccggtgct gtgccaggcc | 1800 |
| cacggcttga ccccggagca ggtggtggcc atcgccagcc acgatggcgg caagcaggcg | 1860 |
| ctggagacgg tccagcggct gttgccggtg ctgtgccagg cccacggctt gacccccag | 1920 |
| caggtggtgg ccatcgccag caatggcggt ggcaagcagg cgctggagac ggtccagcgg | 1980 |
| ctgttgccgg tgctgtgcca ggcccacggc ttgacccctc agcaggtggt ggccatcgcc | 2040 |
| agcaatggcg gcggcaggcc ggcgctggag agcattgttg cccagttatc tcgccctgat | 2100 |
| ccggcgttgg ccgcgttgac caacgaccac ctcgtcgcct tggcctgcct cggcgggcgt | 2160 |
| cctgcgctgg atgcagtgaa aaagggattg ggggatccta tcagccgttc ccagctggtg | 2220 |
| aagtccgagc tggaggagaa gaaatccgag ttgaggcaca agctgaagta cgtgccccac | 2280 |
| gagtacatcg agctgatcga gatcgcccgg aacagcaccc aggaccgtat cctggagatg | 2340 |
| aaggtgatgg agttcttcat gaaggtgtac ggctacaggg gcaagcacct gggcggctcc | 2400 |
| aggaagcccg acggcgccat ctacaccgtg ggctcccca tcgactacgg cgtgatcgtg | 2460 |
| gacaccaagg cctactccgg cggctacaac ctgcccatcg gccaggccga cgaaatgcag | 2520 |
| aggtacgtgg aggagaacca gaccaggaac aagcacatca ccccaacga gtggtggaag | 2580 |
| gtgtacccct ccagcgtgac cgagttcaag ttcctgttcg tgtccggcca cttcaagggc | 2640 |
| aactacaagg cccagctgac caggctgaac cacatcacca actgcaacgg cgccgtgctg | 2700 |
| tccgtggagg agctcctgat cggcggcgag atgatcaagg ccggcaccct gaccctggag | 2760 |
| gaggtgagga ggaagttcaa caacggcgag atcaacttcg cggccgactg ataa | 2814 |

<210> SEQ ID NO 20
<211> LENGTH: 2832
<212> TYPE: DNA
<213> ORGANISM: Artificialsequence
<220> FEATURE:
<223> OTHER INFORMATION: GRex2-R TALEN

<400> SEQUENCE: 20

| | |
|---|---|
| atgggcgatc ctaaaaagaa acgtaaggtc atcgataagg agaccgccgc tgccaagttc | 60 |
| gagagacagc acatggacag catcgatatc gccgatctac gcacgctcgg ctacagccag | 120 |
| cagcaacagg agaagatcaa accgaaggtt cgttcgacag tggcgcagca ccacgaggca | 180 |
| ctggtcggcc acgggtttac acacgcgcac atcgttgcgt taagccaaca cccggcagcg | 240 |
| ttagggaccg tcgctgtcaa gtatcaggac atgatcgcag cgttgccaga ggcgacacac | 300 |
| gaagcgatcg ttggcgtcgg caaacagtgg tccggcgcac gcgctctgga ggccttgctc | 360 |

-continued

```
acggtggcgg gagagttgag aggtccaccg ttacagttgg acacaggcca acttctcaag    420
attgcaaaac gtggcggcgt gaccgcagtg gaggcagtgc atgcatggcg caatgcactg    480
acgggtgccc cgctcaactt gaccccccag caggtggtgg ccatcgccag caatggcggt    540
ggcaagcagg cgctggagac ggtccagcgg ctgttgccgg tgctgtgcca ggcccacggc    600
ttgacccccc agcaggtggt ggccatcgcc agcaatggcg gtggcaagca ggcgctggag    660
acggtccagc ggctgttgcc ggtgctgtgc caggcccacg gcttgacccc ggagcaggtg    720
gtggccatcg ccagccacga tggcggcaag caggcgctgg agacggtcca gcggctgttg    780
ccggtgctgt gccaggccca cggcttgacc cccagcagg tggtggccat cgccagcaat    840
ggcggtggca agcaggcgct ggagacggtc cagcggctgt tgccggtgct gtgccaggcc    900
cacggcttga ccccccagca ggtggtggcc atcgccagca atggcggtgg caagcaggcg    960
ctggagacgg tccagcggct gttgccggtg ctgtgccagg cccacggctt gaccccggag   1020
caggtggtgg ccatcgccag ccacgatggc ggcaagcagg cgctggagac ggtccagcgg   1080
ctgttgccgg tgctgtgcca ggcccacggc ttgacccccc agcaggtggt ggccatcgcc   1140
agcaatggcg gtggcaagca ggcgctggag acggtccagc ggctgttgcc ggtgctgtgc   1200
caggcccacg gcttgacccc ggagcaggtg gtggccatcg ccagccacga tggcggcaag   1260
caggcgctgg agacggtcca gcggctgttg ccggtgctgt gccaggccca cggcttgacc   1320
ccccagcagg tggtggccat cgccagcaat ggcggtggca agcaggcgct ggagacggtc   1380
cagcggctgt tgccggtgct gtgccaggcc cacggcttga ccccggagca ggtggtggcc   1440
atcgccagca atattggtgg caagcaggcg ctggagacgg tgcaggcgct gttgccggtg   1500
ctgtgccagg cccacggctt gaccccggag caggtggtgg ccatcgccag ccacgatggc   1560
ggcaagcagg cgctggagac ggtccagcgg ctgttgccgg tgctgtgcca ggcccacggc   1620
ttgaccccgg agcaggtggt ggccatcgcc agccacgatg gcggcaagca ggcgctggag   1680
acggtccagc ggctgttgcc ggtgctgtgc caggcccacg gcttgacccc ggagcaggtg   1740
gtggccatcg ccagcaatat tggtggcaag caggcgctgg agacggtgca ggcgctgttg   1800
ccggtgctgt gccaggccca cggcttgacc ccccagcagg tggtggccat cgccagcaat   1860
aatggtggca agcaggcgct ggagacggtc cagcggctgt tgccggtgct gtgccaggcc   1920
cacggcttga ccccccagca ggtggtggcc atcgccagca ataatggtgg caagcaggcg   1980
ctggagacgg tccagcggct gttgccggtg ctgtgccagg cccacggctt gaccccctcag   2040 caggtggtgg ccatcgccag caatggcggc ggcaggccgg cgctggagag cattgttgcc   2100
cagttatctc gccctgatcc ggcgttggcc gcgttgacca acgaccacct cgtcgccttg   2160
gcctgcctcg gcgggcgtcc tgcgctggat gcagtgaaaa agggattggg ggatcctatc   2220
agccgttccc agctggtgaa gtccgagctg gaggagaaga atccgagtt gaggcacaag   2280 ctgaagtacg tgccccacga gtacatcgag ctgatcgaga tcgcccggaa cagcacccag   2340
gaccgtatcc tggagatgaa ggtgatggag ttcttcatga aggtgtacgg ctacaggggc   2400
aagcacctgg gcggctccag gaagcccgac ggcgccatct acaccgtggg ctcccccatc   2460
gactacggcg tgatcgtgga caccaaggcc tactccggcg gctacaacct gcccatcggc   2520
caggccgacg aaatgcagag gtacgtggag gagaaccaga ccaggaacaa gcacatcaac   2580
cccaacgagt ggtggaaggt gtaccctctc cagcgtgaccg agttcaagtt cctgttcgtg   2640 tccgccact tcaagggcaa ctacaaggcc cagctgacca ggctgaacca catcaccaac   2700
tgcaacggcg ccgtgctgtc cgtggaggag ctcctgatcg gcggcgagat gatcaaggcc   2760
```

| | |
|---|---|
| ggcaccctga ccctggagga ggtgaggagg aagttcaaca acggcgagat caacttcgcg | 2820 |
| gccgactgat aa | 2832 |

<210> SEQ ID NO 21
<211> LENGTH: 2814
<212> TYPE: DNA
<213> ORGANISM: Artificialsequence
<220> FEATURE:
<223> OTHER INFORMATION: GRex3T2-L TALEN

<400> SEQUENCE: 21

| | |
|---|---|
| atgggcgatc ctaaaaagaa acgtaaggtc atcgattacc catacgatgt tccagattac | 60 |
| gctatcgata tcgccgatct acgcacgctc ggctacagcc agcagcaaca ggagaagatc | 120 |
| aaaccgaagg ttcgttcgac agtggcgcag caccacgagg cactggtcgg ccacgggttt | 180 |
| acacacgcgc acatcgttgc gttaagccaa caccggcag cgttagggac cgtcgctgtc | 240 |
| aagtatcagg acatgatcgc agcgttgcca gaggcgacac acgaagcgat cgttggcgtc | 300 |
| ggcaaacagt ggtccggcgc acgcgctctg gaggccttgc tcacggtggc gggagagttg | 360 |
| agaggtccac cgttacagtt ggacacaggc caacttctca agattgcaaa acgtggcggc | 420 |
| gtgaccgcag tggaggcagt gcatgcatgg cgcaatgcac tgacgggtgc cccgctcaac | 480 |
| ttgaccccc agcaggtggt ggccatcgcc agcaataatg gtggcaagca ggcgctggag | 540 |
| acggtccagc ggctgttgcc ggtgctgtgc caggcccacg gcttgacccc ggagcaggtg | 600 |
| gtggccatcg ccagccacga tggcggcaag caggcgctgg agacggtcca gcggctgttg | 660 |
| ccggtgctgt gccaggccca cggcttgacc ccggagcagg tggtggccat cgccagccac | 720 |
| gatggcggca agcaggcgct ggagacggtc agcggctgt tgccggtgct gtgccaggcc | 780 |
| cacggcttga ccccccagca ggtggtggcc atcgccagca atggcggtgg caagcaggcg | 840 |
| ctggagacgg tccagcggct gttgccggtg ctgtgccagg cccacggctt gaccccccag | 900 |
| caggtggtgg ccatcgccag caataatggt ggcaagcagg cgctggagac ggtccagcgg | 960 |
| ctgttgccgg tgctgtgcca ggcccacggc ttgaccccc agcaggtggt ggccatcgcc | 1020 |
| agcaataatg gtggcaagca ggcgctggag acggtccagc ggctgttgcc ggtgctgtgc | 1080 |
| caggcccacg gcttgacccc ccagcaggtg gtggccatcg ccagcaatgg cggtggcaag | 1140 |
| caggcgctgg agacggtcca gcggctgttg ccggtgctgt gccaggccca cggcttgacc | 1200 |
| ccccagcagg tggtggccat cgccagcaat aatggtggca agcaggcgct ggagacggtc | 1260 |
| cagcggctgt tgccggtgct gtgccaggcc cacggcttga ccccccagca ggtggtggcc | 1320 |
| atcgccagca atggcggtgg caagcaggcg ctggagacgg tccagcggct gttgccggtg | 1380 |
| ctgtgccagg cccacggctt gacccccag caggtggtgg ccatcgccag caataatggt | 1440 |
| ggcaagcagg cgctggagac ggtccagcgg ctgttgccgg tgctgtgcca ggcccacggc | 1500 |
| ttgaccccgg agcaggtggt ggccatcgcc agccacgatg gcggcaagca ggcgctggag | 1560 |
| acggtccagc ggctgttgcc ggtgctgtgc caggcccacg gcttgacccc ccagcaggtg | 1620 |
| gtggccatcg ccagcaatgg cggtggcaag caggcgctgg agacggtcca gcggctgttg | 1680 |
| ccggtgctgt gccaggccca cggcttgacc ccggagcagg tggtggccat cgccagccac | 1740 |
| gatggcggca agcaggcgct ggagacggtc agcggctgt tgccggtgct gtgccaggcc | 1800 |
| cacggcttga ccccccagca ggtggtggcc atcgccagca atggcggtgg caagcaggcg | 1860 |
| ctggagacgg tccagcggct gttgccggtg ctgtgccagg cccacggctt gaccccccag | 1920 |

```
caggtggtgg ccatcgccag caataatggt ggcaagcagg cgctggagac ggtccagcgg     1980
ctgttgccgg tgctgtgcca ggcccacggc ttgacccctc agcaggtggt ggccatcgcc     2040
agcaatggcg gcggcaggcc ggcgctggag agcattgttg cccagttatc tcgccctgat     2100
ccggcgttgg ccgcgttgac caacgaccac ctcgtcgcct tggcctgcct cggcgggcgt     2160
cctgcgctgg atgcagtgaa aaagggattg ggggatccta tcagccgttc ccagctggtg     2220
aagtccgagc tggaggagaa gaaatccgag ttgaggcaca agctgaagta cgtgccccac     2280
gagtacatcg agctgatcga gatcgcccgg aacagcaccc aggaccgtat cctggagatg     2340
aaggtgatgg agttcttcat gaaggtgtac ggctacaggg gcaagcacct gggcggctcc     2400
aggaagcccg acggcgccat ctacaccgtg ggctccccca tcgactacgg cgtgatcgtg     2460
gacaccaagg cctactccgg cggctacaac ctgcccatcg gccaggccga cgaaatgcag     2520
aggtacgtgg aggagaacca gaccaggaac aagcacatca cccccaacga gtggtggaag     2580
gtgtacccct ccagcgtgac cgagttcaag ttcctgttcg tgtccggcca cttcaagggc     2640
aactacaagc cccagctgac caggctgaac cacatcacca ctgcaacggc gccgtgctg     2700 tccgtggagg agctcctgat cggcggcgag atgatcaagg ccggcaccct gaccctggag     2760
gaggtgagga ggaagttcaa caacggcgag atcaacttcg cggccgactg ataa           2814
```

<210> SEQ ID NO 22
<211> LENGTH: 2832
<212> TYPE: DNA
<213> ORGANISM: Artificialsequence
<220> FEATURE:
<223> OTHER INFORMATION: GRex3T2-R TALEN

<400> SEQUENCE: 22

```
atgggcgatc ctaaaaagaa acgtaaggtc atcgataagg agaccgccgc tgccaagttc       60
gagagacagc acatggacag catcgatatc gccgatctac gcacgctcgg ctacagccag      120
cagcaacagg agaagatcaa accgaaggtt cgttcgacag tggcgcagca ccacgaggca      180
ctggtcggcc acgggtttac acacgcgcac atcgttgcgt taagccaaca cccggcagcg      240
ttagggaccc tcgctgtcaa gtatcaggac atgatcgcag cgttgccaga ggcgacacac      300
gaagcgatcg ttggcgtcgg caaacagtgg tccggcgcac gcgctctgga ggccttgctc      360
acggtggcgg gagagttgag aggtccaccg ttacagttgg acacaggcca acttctcaag      420
attgcaaaac gtggcggcgt gaccgcagtg gaggcagtgc atgcatggcg caatgcactg      480
acgggtgccc cgctcaactt gacccccag caggtggtgg ccatcgccag caatggcggt      540
ggcaagcagg cgctggagac ggtccagcgg ctgttgccgg tgctgtgcca ggcccacggc      600 ttgacccccgg agcaggtggt ggccatcgcc agcaatattg gtggcaagca ggcgctggag      660
acggtgcagg cgctgttgcc ggtgctgtgc caggcccacg gcttgacccc ggagcaggtg      720
gtggccatcg ccagcaatat tggtggcaag caggcgctgg agacggtgca ggcgctgttg      780
ccggtgctgt gccaggccca cggcttgacc cccagcagg tggtggccat cgccagcaat      840
aatggtggca gcaggcgct ggagacggtc agcggctgt tgccggtgct gtgccaggcc      900
cacggcttga ccccggagca ggtggtggcc atcgccagca atattggtgg caagcaggcg      960
ctggagacgg tgcaggcgct gttgccggtg ctgtgccagg cccacggctt gaccccggag     1020
caggtggtgg ccatcgccag ccacgatggc ggcaagcagg cgctggagac ggtccagcgg     1080
ctgttgccgg tgctgtgcca ggcccacggc ttgacccccc agcaggtggt ggccatcgcc     1140
agcaatggcg gtggcaagca ggcgctggag acggtccagc ggctgttgcc ggtgctgtgc     1200
```

```
caggcccacg gcttgacccc ggagcaggtg gtggccatcg ccagccacga tggcggcaag   1260
caggcgctgg agacggtcca gcggctgttg ccggtgctgt gccaggccca cggcttgacc   1320
ccggagcagg tggtggccat cgccagccac gatgcggca agcaggcgct ggagacggtc    1380
cagcggctgt tgccggtgct gtgccaggcc cacggcttga ccccggagca ggtggtggcc   1440
atcgccagca atattggtgg caagcaggcg ctggagacgg tgcaggcgct gttgccggtg   1500
ctgtgccagg cccacggctt gaccccccag caggtggtgg ccatcgccag caatggcggt   1560
ggcaagcagg cgctggagac ggtccagcgg ctgttgccgg tgctgtgcca ggcccacggc   1620
ttgaccccgg agcaggtggt ggccatcgcc agcaatattg gtggcaagca ggcgctggag   1680
acggtgcagg cgctgttgcc ggtgctgtgc caggcccacg gcttgacccc ggagcaggtg   1740
gtggccatcg ccagcaatat tggtggcaag caggcgctgg agacggtgca ggcgctgttg   1800
ccggtgctgt gccaggccca cggcttgacc cccagcagg tggtggccat cgccagcaat    1860
ggcggtggca agcaggcgct ggagacggtc agcggctgt tgccggtgct gtgccaggcc    1920
cacggcttga ccccccagca ggtggtggcc atcgccagca ataatggtgg caagcaggcg   1980
ctggagacgg tccagcggct gttgccggtg ctgtgccagg cccacggctt gacccctcag   2040
caggtggtgg ccatcgccag caatggcggc ggcaggccgg cgctggagag cattgttgcc   2100
cagttatctc gccctgatcc ggcgttggcc gcgttgacca acgaccacct cgtcgccttg   2160
gcctgcctcg gcgggcgtcc tgcgctggat gcagtgaaaa agggattggg ggatcctatc   2220
agccgttccc agctggtgaa gtccgagctg gaggagaaga atccgagtt gaggcacaag    2280 ctgaagtacg tgccccacga gtacatcgag ctgatcgaga tcgcccggaa cagcacccag   2340
gaccgtatcc tggagatgaa ggtgatggag ttcttcatga aggtgtacgg ctacagggc    2400 aagcacctgg gcggctccag gaagcccgac ggcgccatct acaccgtggg ctcccccatc   2460
gactacggcg tgatcgtgga caccaaggcc tactccggcg gctacaacct gcccatcggc   2520
caggccgacg aaatgcagag gtacgtggag gagaaccaga ccaggaacaa gcacatcaac   2580
cccaacgagt ggtggaaggt gtaccctcc agcgtgaccg agttcaagtt cctgttcgtg    2640
tccggccact tcaagggcaa ctacaaggcc cagctgacca ggctgaacca catcaccaac   2700
tgcaacggcg ccgtgctgtc cgtggaggag ctcctgatcg gcggcgagat gatcaaggcc   2760
ggcacgctga ccctggagga ggtgaggagg aagttcaaca acggcgagat caacttcgcg   2820
gccgactgat aa                                                       2832

<210> SEQ ID NO 23
<211> LENGTH: 2814
<212> TYPE: DNA
<213> ORGANISM: Artificialsequence
<220> FEATURE:
<223> OTHER INFORMATION: GRex3T4-L TALEN

<400> SEQUENCE: 23
atgggcgatc ctaaaaagaa acgtaaggtc atcgattacc catacgatgt tccagattac    60
gctatcgata tcgccgatct acgcacgctc ggctacagcc agcagcaaca ggagaagatc   120
aaaccgaagg ttcgttcgac agtggcgcag caccacgagg cactggtcgg ccacgggttt   180
acacacgcgc acatcgttgc gttaagccaa cacccggcag cgttagggac cgtcgctgtc   240
aagtatcagg acatgatcgc agcgttgcca gaggcgacac acgaagcgat cgttggcgtc   300
ggcaaacagt ggtccggcgc acgcgctctg gaggccttgc tcacggtggc gggagagttg   360
```

```
agaggtccac cgttacagtt ggacacaggc caacttctca agattgcaaa acgtggcggc    420
gtgaccgcag tggaggcagt gcatgcatgg cgcaatgcac tgacgggtgc cccgctcaac    480
ttgaccsccc agcaggtggt ggccatcgcc agcaataatg gtggcaagca ggcgctggag    540
acggtccagc ggctgttgcc ggtgctgtgc caggcccacg gcttgacccc ggagcaggtg    600
gtggccatcg ccagccacga tggcggcaag caggcgctgg agacggtcca gcggctgttg    660
ccggtgctgt gccaggccca cggcttgacc ccccagcagg tggtggccat cgccagcaat    720
ggcggtggca agcaggcgct ggagacggtc agcggctgt tgccggtgct gtgccaggcc    780
cacggcttga ccccggagca ggtggtggcc atcgccagcc acgatggcgg caagcaggcg    840
ctggagacgg tccagcggct gttgccggtg ctgtgccagg cccacggctt gacccccag    900
caggtggtgg ccatcgccag caatggcggt ggcaagcagg cgctggagac ggtccagcgg    960
ctgttgccgg tgctgtgcca ggcccacggc ttgaccccc agcaggtggt ggccatcgcc    1020
agcaataatg gtggcaagca ggcgctggag acggtccagc ggctgttgcc ggtgctgtgc    1080
caggcccacg gcttgacccc ggagcaggtg gtggccatcg ccagcaatat tggtggcaag    1140
caggcgctgg agacggtgca ggcgctgttg ccggtgctgt gccaggccca cggcttgacc    1200
ccccagcagg tggtggccat cgccagcaat ggcggtggca agcaggcgct ggagacggtc    1260
cagcggctgt tgccggtgct gtgccaggcc cacggcttga ccccccagca ggtggtggcc    1320
atcgccagca ataatggtgg caagcaggcg ctggagacgg tccagcggct gttgccggtg    1380
ctgtgccagg cccacggctt gaccccggag caggtggtgg ccatcgccag caatattggt    1440
ggcaagcagg cgctggagac ggtgcaggcg ctgttgccgg tgctgtgcca ggcccacggc    1500
ttgaccccgg agcaggtggt ggccatcgcc agcaatattg gtggcaagca ggcgctggag    1560
acggtgcagg cgctgttgcc ggtgctgtgc caggcccacg gcttgacccc ccagcaggtg    1620
gtggccatcg ccagcaataa tggtggcaag caggcgctgg agacggtcca gcggctgttg    1680
ccggtgctgt gccaggccca cggcttgacc ccggagcagg tggtggccat cgccagccac    1740
gatggcggca agcaggcgct ggagacggtc agcggctgt tgccggtgct gtgccaggcc    1800
cacggcttga ccccccagca ggtggtggcc atcgccagca atggcggtgg caagcaggcg    1860
ctggagacgg tccagcggct gttgccggtg ctgtgccagg cccacggctt gacccccag    1920
caggtggtgg ccatcgccag caatggcggt ggcaagcagg cgctggagac ggtccagcgg    1980
ctgttgccgg tgctgtgcca ggcccacggc ttgacccctc agcaggtggt ggccatcgcc    2040
agcaatggcg gcggcaggcc ggcgctggag agcattgttg cccagttatc tcgccctgat    2100
ccggcgttgg ccgcgttgac caacgaccac ctcgtcgcct tggcctgcct cggcgggcgt    2160
cctgcgctgg atgcagtgaa aaagggattg ggggatccta tcagccgttc ccagctggtg    2220
aagtccgagc tggaggagaa gaaatccgag ttgaggcaca agctgaagta cgtgccccac    2280
gagtacatcg agctgatcga gatcgcccgg aacagcaccc aggaccgtat cctggagatg    2340
aaggtgatgg agttcttcat gaaggtgtac ggctacaggg gcaagcacct gggcggctcc    2400
aggaagcccg acggcgccat ctacaccgtg gcctccccca tcgactacgg cgtgatcgtg    2460
gacaccaagg cctactccgg cggctacaac ctgcccatcg ccaggcccga cgaaatgcag    2520
aggtacgtgg aggagaacca gaccaggaac aagcacatca ccccaacga gtggtggaag    2580
gtgtacccct ccagcgtgac cgagttcaag ttcctgttcg tgtccggcca cttcaagggc    2640
aactacaagg cccagctgac caggctgaac cacatcacca actgcaacgg cgccgtgctg    2700
tccgtggagg agctcctgat cggcggcgag atgatcaagg ccggcacact gacccctggag    2760
```
gaggtgagga ggaagttcaa caacggcgag atcaacttcg cggccgactg ataa      2814

<210> SEQ ID NO 24
<211> LENGTH: 2832
<212> TYPE: DNA
<213> ORGANISM: Artificialsequence
<220> FEATURE:
<223> OTHER INFORMATION: GRex3T4-R TALEN

<400> SEQUENCE: 24

| | |
|---|---|
| atgggcgatc ctaaaaagaa acgtaaggtc atcgataagg agaccgccgc tgccaagttc | 60 |
| gagagacagc acatggacag catcgatatc gccgatctac gcacgctcgg ctacagccag | 120 |
| cagcaacagg agaagatcaa accgaaggtt cgttcgacag tggcgcagca ccacgaggca | 180 |
| ctggtcggcc acgggtttac acacgcgcac atcgttgcgt taagccaaca cccggcagcg | 240 |
| ttagggaccg tcgctgtcaa gtatcaggac atgatcgcag cgttgccaga ggcgacacac | 300 |
| gaagcgatcc ttggcgtcgg caaacagtgg tccggcgcac gcgctctgga ggccttgctc | 360 |
| acggtggcgg gagagttgag aggtccaccg ttacagttgg acacaggcca acttctcaag | 420 |
| attgcaaaac gtggcggcgt gaccgcagtg gaggcagtgc atgcatggcg caatgcactg | 480 |
| acgggtgccc cgctcaactt gacccccag caggtggtgg ccatcgccag caatggcggt | 540 |
| ggcaagcagg cgctggagac ggtccagcgg ctgttgccgg tgctgtgcca ggcccacggc | 600 |
| ttgaccccgg agcaggtggt ggccatcgcc agccacgatg gcggcaagca ggcgctggag | 660 |
| acggtccagc ggctgttgcc ggtgctgtgc caggcccacg gcttgacccc ggagcaggtg | 720 |
| gtggccatcg ccagccacga tggcggcaag caggcgctgg agacggtcca gcggctgttg | 780 |
| ccggtgctgt gccaggccca cggcttgacc ccggagcagg tggtggccat cgccagcaat | 840 |
| attggtggca gcaggcgct ggagacggtg caggcgctgt gccggtgct gtgccaggcc | 900 |
| cacggcttga ccccggagca ggtggtggcc atcgccagcc acgatggcgg caagcaggcg | 960 |
| ctggagacgg tccagcggct gttgccggtg ctgtgccagg cccacggctt gaccccggag | 1020 |
| caggtggtgg ccatcgccag caatattggt ggcaagcagg cgctggagac ggtgcaggcg | 1080 |
| ctgttgccgg tgctgtgcca ggcccacggc ttgaccccgg agcaggtggt ggccatcgcc | 1140 |
| agcaatattg gtggcaagca ggcgctggag acggtgcagg cgctgttgcc ggtgctgtgc | 1200 |
| caggcccacg gcttgacccc ccagcaggtg gtggccatcg ccagcaataa tggtggcaag | 1260 |
| caggcgctgg agacggtcca gcggctgttg ccggtgctgt gccaggccca cggcttgacc | 1320 |
| ccccagcagg tggtggccat cgccagcaat ggcggtggca agcaggcgct ggagacggtc | 1380 |
| cagcggctgt tgccggtgct gtgccaggcc cacggcttga ccccagca ggtggtggcc | 1440 |
| atcgccagca atggcggtgg caagcaggcg ctggagacgg tccagcggct gttgccggtg | 1500 |
| ctgtgccagg cccacggctt gaccccggag caggtggtgg ccatcgccag caatattggt | 1560 |
| ggcaagcagg cgctggagac ggtgcaggcg ctgttgccgg tgctgtgcca ggcccacggc | 1620 |
| ttgaccccgg agcaggtggt ggccatcgcc agcaatattg gtggcaagca ggcgctggag | 1680 |
| acggtgcagg cgctgttgcc ggtgctgtgc caggcccacg gcttgacccc ccagcaggtg | 1740 |
| gtggccatcg ccagcaataa tggtggcaag caggcgctgg agacggtcca gcggctgttg | 1800 |
| ccggtgctgt gccaggccca cggcttgacc ccggagcagg tggtggccat cgccagcaat | 1860 |
| attggtggca gcaggcgct ggagacggtg caggcgctgt gccggtgct gtgccaggcc | 1920 |
| cacggcttga ccccggagca ggtggtggcc atcgccagcc acgatggcgg caagcaggcg | 1980 |

```
ctggagacgg tccagcggct gttgccggtg ctgtgccagg cccacggctt gacccctcag    2040
caggtggtgg ccatcgccag caatggcggc ggcaggccgg cgctggagag cattgttgcc    2100
cagttatctc gccctgatcc ggcgttggcc gcgttgacca acgaccacct cgtcgccttg    2160
gcctgcctcg gcgggcgtcc tgcgctggat gcagtgaaaa agggattggg ggatcctatc    2220
agccgttccc agctggtgaa gtccgagctg aggagaaga atccgagtt gaggcacaag     2280 ctgaagtacg tgccccacga gtacatcgag ctgatcgaga tcgcccggaa cagcacccag    2340
gaccgtatcc tggagatgaa ggtgatggag ttcttcatga aggtgtacgg ctacaggggc    2400
aagcacctgg gcggctccag gaagcccgac ggcgccatct acaccgtggg ctcccccatc    2460
gactacggcg tgatcgtgga caccaaggcc tactccggcg gctacaacct gcccatcggc    2520
caggccgacg aaatgcagag gtacgtggag gagaaccaga ccaggaacaa gcacatcaac    2580
cccaacgagt ggtggaaggt gtaccccctcc agcgtgaccg agttcaagtt cctgttcgtg    2640
tccggccact tcaagggcaa ctacaaggcc cagctgacca ggctgaacca catcaccaac    2700
tgcaacggcg ccgtgctgtc cgtggaggag ctcctgatcg gcggcgagat gatcaaggcc    2760 ggcacccctga ccctggagga ggtgaggagg aagttcaaca acggcgagat caacttcgcg    2820
gccgactgat aa                                                        2832

<210> SEQ ID NO 25
<211> LENGTH: 2814
<212> TYPE: DNA
<213> ORGANISM: Artificialsequence
<220> FEATURE:
<223> OTHER INFORMATION: GRex5T1-L TALEN

<400> SEQUENCE: 25
atgggcgatc ctaaaaagaa acgtaaggtc atcgattacc catacgatgt tccagattac      60
gctatcgata tcgccgatct acgcacgctc ggctacagcc agcagcaaca ggagaagatc     120
aaaccgaagg ttcgttcgac agtggcgcag caccacgagg cactggtcgg ccacgggttt     180
acacacgcgc acatcgttgc gttaagccaa cacccggcag cgttagggac cgtcgctgtc     240
aagtatcagg acatgatcgc agcgttgcca gaggcgacac acgaagcgat cgttggcgtc     300
ggcaaacagt ggtccggcgc acgcgctctg gaggccttgc tcacggtggc gggagagttg     360
agaggtccac cgttacagtt ggacacaggc caacttctca agattgcaaa acgtggcggc     420
gtgaccgcag tggaggcagt gcatgcatgg cgcaatgcac tgacgggtgc cccgctcaac     480
ttgacccccc agcaggtggt ggccatcgcc agcaataatg gtggcaagca ggcgctggag     540
acggtccagc ggctgttgcc ggtgctgtgc caggcccacg gcttgacccc ccagcaggtg     600
gtggccatcg ccagcaataa tggtggcaag caggcgctgg agacggtcca gcggctgttg     660
ccggtgctgt gccaggccca cggcttgacc cccagcagg tggtggccat cgccagcaat    720
ggcggtggca agcaggcgct ggagacggtc agcggctgt tgccggtgct gtgccaggcc     780
cacggcttga ccccccagca ggtggtggcc atcgccagca taatggtgg caagcaggcg    840 ctggagacgg tccagcggct gttgccggtg ctgtgccagg cccacggctt gacccccag     900 caggtggtgg ccatcgccag caatggcggt ggcaagcagg cgctggagac ggtccagcgg    960
ctgttgccgg tgctgtgcca ggcccacggc ttgaccccgg agcaggtggt ggccatcgcc    1020
agccacgatg gcggcaagca ggcgctggag acggtccagc ggctgttgcc ggtgctgtgc    1080
caggcccacg gcttgacccc ggagcaggtg gtggccatcg ccagcaatat tggtggcaag    1140
caggcgctgg agacggtgca ggcgctgttg ccggtgctgt gccaggccca cggcttgacc    1200
```

| | |
|---|---:|
| ccggagcagg tggtggccat cgccagccac gatggcggca agcaggcgct ggagacggtc | 1260 |
| cagcggctgt tgccggtgct gtgccaggcc cacggcttga cccccagca ggtggtggcc | 1320 |
| atcgccagca atggcggtgg caagcaggcg ctggagacgg tccagcggct gttgccggtg | 1380 |
| ctgtgccagg cccacggctt gacccccag caggtggtgg ccatcgccag caataatggt | 1440 |
| ggcaagcagg cgctggagac ggtccagcgg ctgttgccgg tgctgtgcca ggcccacggc | 1500 |
| ttgaccccc agcaggtggt ggccatcgcc agcaatggcg gtggcaagca ggcgctggag | 1560 |
| acggtccagc ggctgttgcc ggtgctgtgc caggcccacg gcttgacccc ccagcaggtg | 1620 |
| gtggccatcg ccagcaatgg cggtggcaag caggcgctgg agacggtcca gcggctgttg | 1680 |
| ccggtgctgt gccaggccca cggcttgacc cccagcagg tggtggccat cgccagcaat | 1740 |
| aatggtggca agcaggcgct ggagacggtc agcggctgt tgccggtgct gtgccaggcc | 1800 |
| cacggcttga ccccccagca ggtggtggcc atcgccagca ataatggtgg caagcaggcg | 1860 |
| ctggagacgg tccagcggct gttgccggtg ctgtgccagg cccacggctt gaccccggag | 1920 |
| caggtggtgg ccatcgccag caatattggt ggcaagcagg cgctggagac ggtgcaggcg | 1980 |
| ctgttgccgg tgctgtgcca ggcccacggc ttgaccccctc agcaggtggt ggccatcgcc | 2040 |
| agcaatggcg gcggcaggcc ggcgctggag agcattgttg cccagttatc tcgccctgat | 2100 |
| ccggcgttgg ccgcgttgac caacgaccac ctcgtcgcct ggcctgcct cggcgggcgt | 2160 |
| cctgcgctgg atgcagtgaa aaagggattg ggggatccta tcagccgttc ccagctggtg | 2220 |
| aagtccgagc tggaggagaa gaaatccgag ttgaggcaca agctgaagta cgtgccccac | 2280 |
| gagtacatcg agctgatcga gatcgcccgg aacagcaccc aggaccgtat cctggagatg | 2340 |
| aaggtgatga gttcttcat gaaggtgtac ggctacaggg gcaagcacct gggcggctcc | 2400 |
| aggaagcccg acggcgccat ctacaccgtg ggctcccca tcgactacgg cgtgatcgtg | 2460 |
| gacaccaagg cctactccgg cggctacaac ctgcccatcg ccaggccga cgaaatgcag | 2520 |
| aggtacgtgg aggagaacca gaccaggaac aagcacatca cccccaacga gtggtggaag | 2580 |
| gtgtacccct ccagcgtgac cgagttcaag ttcctgttcg tgtccggcca cttcaagggc | 2640 |
| aactacaagg cccagctgac caggctgaac cacatcacca ctgcaacgg cgccgtgctg | 2700 |
| tccgtggagg agctcctgat cggcggcgag atgatcaagg ccggcacct gaccctggag | 2760 |
| gaggtgagga ggaagttcaa caacggcgag atcaacttcg cggccgactg ataa | 2814 |

<210> SEQ ID NO 26
<211> LENGTH: 2832
<212> TYPE: DNA
<213> ORGANISM: Artificialsequence
<220> FEATURE:
<223> OTHER INFORMATION: GRex5T1-R TALEN

<400> SEQUENCE: 26

| | |
|---|---:|
| atgggcgatc ctaaaaagaa acgtaaggtc atcgataagg agaccgccgc tgccaagttc | 60 |
| gagagacagc acatggacag catcgatatc gccgatctac gcacgctcgg ctacagccag | 120 |
| cagcaacagg agaagatcaa accgaaggtt cgttcgacag tggcgcagca ccacgaggca | 180 |
| ctggtcggcc acgggtttac acacgcgcac atcgttgcgt taagccaaca cccggcagcg | 240 |
| ttagggaccg tcgctgtcaa gtatcaggac atgatcgcag cgttgccaga ggcgacacac | 300 |
| gaagcgatcg ttggcgtcgg caaacagtgg tccggcgcac gcgctctgga ggccttgctc | 360 |
| acggtggcgg gagagttgag aggtccaccg ttacagttgg acacaggcca acttctcaag | 420 |

```
attgcaaaac gtggcggcgt gaccgcagtg gaggcagtgc atgcatggcg caatgcactg    480
acgggtgccc cgctcaactt gaccccggag caggtggtgg ccatcgccag caatattggt    540
ggcaagcagg cgctggagac ggtgcaggcg ctgttgccgg tgctgtgcca ggcccacggc    600
ttgaccccc agcaggtggt ggccatcgcc agcaatggcg gtggcaagca ggcgctggag    660
acggtccagc ggctgttgcc ggtgctgtgc caggcccacg gcttgacccc ggagcaggtg    720
gtggccatcg ccagccacga tggcggcaag caggcgctgg agacggtcca gcggctgttg    780
ccggtgctgt gccaggccca cggcttgacc ccggagcagg tggtggccat cgccagccac    840
gatggcggca agcaggcgct ggagacggtc agcggctgt gccggtgct gtgccaggcc    900
cacggcttga ccccccagca ggtggtggcc atcgccagca atggcggtgg caagcaggcg    960
ctggagacgg tccagcggct gttgccggtg ctgtgccagg cccacggctt gaccccccag   1020
caggtggtgg ccatcgccag caataatggt ggcaagcagg cgctggagac ggtccagcgg   1080
ctgttgccgg tgctgtgcca ggcccacggc ttgaccccgg agcaggtggt ggccatcgcc   1140
agccacgatg gcggcaagca ggcgctggag acggtccagc ggctgttgcc ggtgctgtgc   1200
caggcccacg gcttgacccc ggagcaggtg gtggccatcg ccagcaatat tggtggcaag   1260
caggcgctgg agacggtgca ggcgctgttg ccggtgctgt gccaggccca cggcttgacc   1320
ccccagcagg tggtggccat cgccagcaat ggcggtggca agcaggcgct ggagacggtc   1380
cagcggctgt gccggtgct gtgccaggcc acggcttga ccccggagca ggtggtggcc   1440
atcgccagca atattggtgg caagcaggcg ctggagacgg tgcaggcgct gttgccggtg   1500
ctgtgccagg cccacggctt gaccccccag caggtggtgg ccatcgccag caatggcggt   1560
ggcaagcagg cgctggagac ggtccagcgg ctgttgccgg tgctgtgcca ggcccacggc   1620
ttgaccccgg agcaggtggt ggccatcgcc agcaatattg gtggcaagca ggcgctggag   1680
acggtgcagg cgctgttgcc ggtgctgtgc caggcccacg gcttgacccc ggagcaggtg   1740
gtggccatcg ccagcaatat tggtggcaag caggcgctgg agacggtgca ggcgctgttg   1800
ccggtgctgt gccaggccca cggcttgacc ccggagcagg tggtggccat cgccagccac   1860
gatggcggca agcaggcgct ggagacggtc agcggctgt gccggtgct gtgccaggcc   1920
cacggcttga ccccggagca ggtggtggcc atcgccagca atattggtgg caagcaggcg   1980
ctggagacgg tgcaggcgct gttgccggtg ctgtgccagg cccacggctt gaccccctag   2040
caggtggtgg ccatcgccag caatggcggc ggcaggccgg cgctggagag cattgttgcc   2100
cagttatctc gccctgatcc ggcgttggcc gcgttgacca acgaccacct cgtcgccttg   2160
gcctgcctcg gcgggcgtcc tgcgctggat gcagtgaaaa agggattggg ggatcctatc   2220
agccgttccc agctggtgaa gtccgagctg gaggagaaga atccgagtt gaggcacaag   2280
ctgaagtacg tgccccacga gtacatcgag ctgatcgaga tcgcccggaa cagcacccag   2340
gaccgtatcc tggagatgaa ggtgatggag ttcttcatga aggtgtacgg ctacaggggc   2400
aagcacctgg gcggctccag gaagccgac ggcgccatct acaccgtggg ctccccatc   2460
gactacggcg tgatcgtgga caccaaggcc tactccggcg gctacaacct gcccatcggc   2520
caggccgacg aaatgcagag gtacgtggag gagaaccaga ccaggaacaa gcacatcaac   2580
cccaacgagt ggtggaaggt gtaccctcc agcgtgaccg agttcaagtt cctgttcgtg   2640
tccggccact tcaagggcaa ctacaaggcc cagctgacca ggctgaacca catcaccaac   2700
tgcaacggcg ccgtgctgtc cgtggaggag ctcctgatcg gcggcgagat gatcaaggcc   2760
ggcacctga ccctggagga ggtgaggagg aagttcaaca cggcgagat caacttcgcg   2820
```

-continued gccgactgat aa    2832

<210> SEQ ID NO 27
<211> LENGTH: 2814
<212> TYPE: DNA
<213> ORGANISM: Artificialsequence
<220> FEATURE:
<223> OTHER INFORMATION: GRex5T2-L TALEN

<400> SEQUENCE: 27

| | |
|---|---|
| atgggcgatc ctaaaaagaa acgtaaggtc atcgattacc catacgatgt tccagattac | 60 |
| gctatcgata tcgccgatct acgcacgctc ggctacagcc agcagcaaca ggagaagatc | 120 |
| aaaccgaagg ttcgttcgac agtggcgcag caccacgagg cactggtcgg ccacgggttt | 180 |
| acacacgcgc acatcgttgc gttaagccaa cacccggcag cgttagggac cgtcgctgtc | 240 |
| aagtatcagg acatgatcgc agcgttgcca gaggcgacac acgaagcgat cgttggcgtc | 300 |
| ggcaaacagt ggtccggcgc acgcgctctg gaggccttgc tcacggtggc gggagagttg | 360 |
| agaggtccac cgttacagtt ggacacaggc caacttctca agattgcaaa cgtggcggc | 420 |
| gtgaccgcag tggaggcagt gcatgcatgg cgcaatgcac tgacgggtgc cccgctcaac | 480 |
| ttgacccccgg agcaggtggt ggccatcgcc agcaatattg gtggcaagca ggcgctggag | 540 |
| acggtgcagg cgctgttgcc ggtgctgtgc caggcccacg gcttgacccc ccagcaggtg | 600 |
| gtggccatcg ccagcaatgg cggtggcaag caggcgctgg agacggtcca gcggctgttg | 660 |
| ccggtgctgt gccaggccca cggcttgacc ccccagcagg tggtggccat cgccagcaat | 720 |
| aatggtggca agcaggcgct ggagacggtc cagcggctgt tgccggtgct gtgccaggcc | 780 |
| cacggcttga ccccgagca ggtggtggcc atcgccagca atattggtgg caagcaggcg | 840 |
| ctggagacgg tgcaggcgct gttgccggtg ctgtgccagg cccacggctt gaccccccag | 900 |
| caggtggtgg ccatcgccag caatggcggt ggcaagcagg cgctggagac ggtccagcgg | 960 |
| ctgttgccgg tgctgtgcca ggcccacggc ttgaccccgg agcaggtggt ggccatcgcc | 1020 |
| agcaatattg gtggcaagca ggcgctggag acggtgcagg cgctgttgcc ggtgctgtgc | 1080 |
| caggcccacg gcttgacccc ccagcaggtg gtggccatcg ccagcaataa tggtggcaag | 1140 |
| caggcgctgg agacggtcca gcggctgttg ccggtgctgt gccaggccca cggcttgacc | 1200 |
| ccggagcagg tggtggccat cgccagccac gatggcggca agcaggcgct ggagacggtc | 1260 |
| cagcggctgt tgccggtgct gtgccaggcc cacggcttga ccccccagca ggtggtggcc | 1320 |
| atcgccagca atggcggtgg caagcaggcg ctggagacgg tccagcggct gttgccggtg | 1380 |
| ctgtgccagg cccacggctt gaccccggag caggtggtgg ccatcgccag ccacgatggc | 1440 |
| ggcaagcagg cgctggagac ggtccagcgg ctgttgccgg tgctgtgcca ggcccacggc | 1500 |
| ttgaccccc agcaggtggt ggccatcgcc agcaatggcg gtggcaagca ggcgctggag | 1560 |
| acggtccagc ggctgttgcc ggtgctgtgc caggcccacg gcttgacccc ccagcaggtg | 1620 |
| gtggccatcg ccagcaataa tggtggcaag caggcgctgg agacggtcca gcggctgttg | 1680 |
| ccggtgctgt gccaggccca cggcttgacc ccccagcagg tggtggccat cgccagcaat | 1740 |
| ggcggtggca agcaggcgct ggagacggtc cagcggctgt tgccggtgct gtgccaggcc | 1800 |
| cacggcttga ccccccagca ggtggtggcc atcgccagca atggcggtgg caagcaggcg | 1860 |
| ctggagacgg tccagcggct gttgccggtg ctgtgccagg cccacggctt gaccccggag | 1920 |
| caggtggtgg ccatcgccag ccacgatggc ggcaagcagg cgctggagac ggtccagcgg | 1980 |

| | |
|---|---|
| ctgttgccgg tgctgtgcca ggcccacggc ttgacccctc agcaggtggt ggccatcgcc | 2040 |
| agcaatggcg gcggcaggcc ggcgctggag agcattgttg cccagttatc tcgccctgat | 2100 |
| ccggcgttgg ccgcgttgac caacgaccac ctcgtcgcct tggcctgcct cggcgggcgt | 2160 |
| cctgcgctat atgcagtgaa aaagggattg ggggatccta tcagccgttc ccagctggtg | 2220 |
| aagtccgagc tggaggagaa gaaatccgag ttgaggcaca agctgaagta cgtgcccac | 2280 |
| gagtacatcg agctgatcga gatcgcccgg aacagcaccc aggaccgtat cctggagatg | 2340 |
| aaggtgatgg agttcttcat gaaggtgtac ggctacaggg gcaagcacct gggcggctcc | 2400 |
| aggaagcccg acggcgccat ctacaccgtg ggctccccca tcgactacgg cgtgatcgtg | 2460 |
| gacaccaagg cctactccgg cggctacaac ctgcccatcg gccaggccga cgaaatgcag | 2520 |
| aggtacgtgg aggagaacca gaccaggaac aagcacatca accccaacga gtggtggaag | 2580 |
| gtgtacccct ccagcgtgac cgagttcaag ttcctgttcg tgtccggcca cttcaagggc | 2640 |
| aactacaagg cccagctgac caggctgaac cacatcacca actgcaacgg cgccgtgctg | 2700 |
| tccgtggagg agctcctgat cggcggcgag atgatcaagg ccggcaccct gacccctgag | 2760 |
| gaggtgagga ggaagttcaa caacggcgag atcaacttcg cggccgactg ataa | 2814 |

<210> SEQ ID NO 28
<211> LENGTH: 2832
<212> TYPE: DNA
<213> ORGANISM: Artificialsequence
<220> FEATURE:
<223> OTHER INFORMATION: GRex5T2-R TALEN

<400> SEQUENCE: 28

| | |
|---|---|
| atgggcgatc ctaaaaagaa acgtaaggtc atcgataagg agaccgccgc tgccaagttc | 60 |
| gagagacagc acatggacag catcgatatc gccgatctac gcacgctcgg ctacagccag | 120 |
| cagcaacagg agaagatcaa accgaaggtt cgttcgacag tggcgcagca ccacgaggca | 180 |
| ctggtcggcc acgggtttac acacgcgcac atcgttgcgt taagccaaca cccggcagcg | 240 |
| ttagggaccg tcgctgtcaa gtatcaggac atgatcgcag cgttgccaga ggcgacacac | 300 |
| gaagcgatcg ttggcgtcgg caaacagtgg tccggcgcac gcgctctgga ggccttgctc | 360 |
| acggtggcgg gagagttgag aggtccaccg ttacagttgg acacaggcca acttctcaag | 420 |
| attgcaaaac gtggcggcgt gaccgcagtg gaggcagtgc atgcatggcg caatgcactg | 480 |
| acgggtgccc cgctcaactt gacccccag caggtggtgg ccatcgccag caataatggt | 540 |
| ggcaagcagg cgctggagac ggtccagcgg ctgttgccgg tgctgtgcca ggcccacggc | 600 |
| ttgaccccgg agcaggtggt ggccatcgcc agcaatattg gtggcaagca ggcgctggag | 660 |
| acggtgcagg cgctgttgcc ggtgctgtgc caggcccacg gcttgacccc ccagcaggtg | 720 |
| gtggccatcg ccagcaataa tggtggcaag caggcgctgg agacggtcca gcggctgttg | 780 |
| ccggtgctgt gccaggccca cggcttgacc ccggagcagg tggtggccat cgccagccac | 840 |
| gatggcggca gcaggcgct ggagacggtc agcggctgt tgccggtgct gtgccaggcc | 900 |
| cacggcttga ccccccagca ggtggtggcc atcgccagca ataatggtgg caagcaggcg | 960 |
| ctggagacgt ccagcggct gttgccggtg ctgtgccagg cccacggctt gaccccccag | 1020 |
| caggtggtgg ccatcgccag caatggcggt ggcaagcagg cgctggagac ggtccagcgg | 1080 |
| ctgttgccgg tgctgtgcca ggcccacggc ttgaccccgg agcaggtggt ggccatcgcc | 1140 |
| agcaatattg gtggcaagca ggcgctggag acggtgcagg cgctgttgcc ggtgctgtgc | 1200 |
| caggcccacg gcttgacccc ccagcaggtg gtggccatcg ccagcaataa tggtggcaag | 1260 |

```
caggcgctgg agacggtcca gcggctgttg ccggtgctgt gccaggccca cggcttgacc    1320 cccagcagg tggtggccat cgccagcaat ggcggtggca agcaggcgct ggagacggtc     1380
cagcggctgt tgccggtgct gtgccaggcc cacggcttga ccccggagca ggtggtggcc    1440
atcgccagcc acgatggcgg caagcaggcg ctggagacgg tccagcggct gttgccggtg    1500
ctgtgccagg cccacggctt gaccccggag caggtggtgg ccatcgccag caatattggt    1560
ggcaagcagg cgctggagac ggtgcaggcg ctgttgccgg tgctgtgcca ggcccacggc    1620
ttgacccccc agcaggtggt ggccatcgcc agcaatggcg gtggcaagca ggcgctggag    1680
acggtccagc ggctgttgcc ggtgctgtgc caggcccacg gcttgacccc ccagcaggtg    1740
gtggccatcg ccagcaataa tggtggcaag caggcgctgg agacggtcca gcggctgttg    1800
ccggtgctgt gccaggccca cggcttgacc ccggagcagg tggtggccat cgccagcaat    1860
attggtggca agcaggcgct ggagacggtg caggcgctgt tgccggtgct gtgccaggcc    1920
cacggcttga ccccccagca ggtggtggcc atcgccagca atggcggtgg caagcaggcg    1980
ctggagacgg tccagcggct gttgccggtg ctgtgccagg cccacggctt gacccctcag    2040
caggtggtgg ccatcgccag caatggcggc ggcaggccgg cgctggagag cattgttgcc    2100
cagttatctc gccctgatcc ggcgttggcc gcgttgacca acgaccacct cgtcgccttg    2160
gcctgcctcg gcgggcgtcc tgcgctggat gcagtgaaaa agggattggg ggatcctatc    2220
agccgttccc agctggtgaa gtccgagctg gaggagaaga atccgagtt gaggcacaag     2280 ctgaagtacg tgccccacga gtacatcgag ctgatcgaga tcgcccggaa cagcacccag    2340
gaccgtatcc tggagatgaa ggtgatggag ttcttcatga aggtgtacgg ctacaggggc    2400
aagcacctgg gcggctccag gaagcccgac ggcgccatct acaccgtggg ctcccccatc    2460
gactacggcg tgatcgtgga caccaaggcc tactccggcg gctacaacct gcccatcggc    2520
caggccgacg aaatgcagag gtacgtggag gagaaccaga ccaggaacaa gcacatcaac    2580
cccaacgagt ggtggaaggt gtaccctcc agcgtgaccg agttcaagtt cctgttcgtg     2640
tccggccact tcaagggcaa ctacaaggcc cagctgacca ggctgaacca catcaccaac    2700
tgcaacggcg ccgtgctgtc cgtggaggag ctcctgatcg gcggcgagat gatcaaggcc    2760 ggcacccctga ccctggagga ggtgaggagg aagttcaaca cggcgagat caacttcgcg    2820 gccgactgat aa                                                        2832

<210> SEQ ID NO 29
<211> LENGTH: 2814
<212> TYPE: DNA
<213> ORGANISM: Artificialsequence
<220> FEATURE:
<223> OTHER INFORMATION: GRex5T3-L TALEN

<400> SEQUENCE: 29
atgggcgatc ctaaaaagaa acgtaaggtc atcgattacc catacgatgt tccagattac      60
gctatcgata tcgccgatct acgcacgctc ggctacagcc agcagcaaca ggagaagatc    120
aaaccgaagg ttcgttcgac agtggcgcag caccacgagg cactggtcgg ccacgggttt    180
acacacgcgc acatcgttgc gttaagccaa cacccggcag cgttagggac cgtcgctgtc    240
aagtatcagg acatgatcgc agcgttgcca gaggcgacac acgaagcgat cgttggcgtc    300
ggcaaacagt ggtccggcgc acgcgctctg gaggccttgc tcacggtggc gggagagttg    360
agaggtccac cgttacagtt ggacacaggc caacttctca gagattgcaa acgtggcggc    420
```

```
gtgaccgcag tggaggcagt gcatgcatgg cgcaatgcac tgacgggtgc ccgctcaac    480
ttgaccccc agcaggtggt ggccatcgcc agcaatggcg gtggcaagca ggcgctggag    540
acggtccagc ggctgttgcc ggtgctgtgc caggcccacg gcttgacccc ggagcaggtg    600
gtggccatcg ccagcaatat tggtggcaag caggcgctgg agacggtgca ggcgctgttg    660
ccggtgctgt gccaggccca cggcttgacc ccccagcagg tggtggccat cgccagcaat    720
ggcggtggca agcaggcgct ggagacggtc agcggctgt tgccggtgct gtgccaggcc    780
cacggcttga ccccggagca ggtggtggcc atcgccagca atattggtgg caagcaggcg    840
ctggagacgg tgcaggcgct gttgccggtg ctgtgccagg cccacggctt gaccccccag    900
caggtggtgg ccatcgccag caatggcggt ggcaagcagg cgctggagac ggtccagcgg    960
ctgttgccgg tgctgtgcca ggcccacggc ttgaccccc agcaggtggt ggccatcgcc    1020
agcaataatg gtggcaagca ggcgctggag acggtccagc ggctgttgcc ggtgctgtgc    1080
caggcccacg gcttgacccc ggagcaggtg gtggccatcg ccagccacga tggcggcaag    1140
caggcgctgg agacggtcca gcggctgttg ccggtgctgt gccaggccca cggcttgacc    1200
ccggagcagg tggtggccat cgccagcaat attggtggca agcaggcgct ggagacggtg    1260
caggcgctgt gccggtgct gtgccaggcc cacggcttga ccccccagca ggtggtggcc    1320
atcgccagca ataatggtgg caagcaggcg ctggagacgg tccagcggct gttgccggtg    1380
ctgtgccagg cccacggctt gaccccccag caggtggtgg ccatcgccag caataatggt    1440
ggcaagcagg cgctggagac ggtccagcgg ctgttgccgg tgctgtgcca ggcccacggc    1500
ttgaccccgg agcaggtggt ggccatcgcc agcaatattg gtggcaagca ggcgctggag    1560
acggtgcagg cgctgttgcc ggtgctgtgc caggcccacg gcttgacccc cagcaggtg    1620
gtggccatcg ccagcaatgg cggtggcaag caggcgctgg agacggtcca gcggctgttg    1680
ccggtgctgt gccaggccca cggcttgacc ccggagcagg tggtggccat cgccagcaat    1740
attggtggca agcaggcgct ggagacggtg caggcgctgt gccggtgct gtgccaggcc    1800
cacggcttga ccccccagca ggtggtggcc atcgccagca atggcggtgg caagcaggcg    1860
ctggagacgt ccagcggct gttgccggtg ctgtgccagg cccacggctt gaccccccag    1920
caggtggtgg ccatcgccag caataatggt ggcaagcagg cgctggagac ggtccagcgg    1980
ctgttgccgg tgctgtgcca ggcccacggc ttgacccctc agcaggtggt ggccatcgcc    2040
agcaatggcg gcggcaggcc ggcgctggag agcattgttg cccagttatc tcgccctgat    2100
ccggcgttgg ccgcgttgac caacgaccac ctcgtcgcct tggcctgcct cggcgggcgt    2160
cctgcgctgg atgcagtgaa aagggattg ggggatccta tcagccgttc ccagctggtg    2220
aagtccgagc tggaggagaa gaaatccgag ttgaggcaca agctgaagta cgtgccccac    2280
gagtacatcg agctgatcga gatcgcccgg aacagcaccc aggaccgtat cctggagatg    2340
aaggtgatga gttcttcat gaaggtgtac ggctacaggg gcaagcacct gggcggctcc    2400
aggaagcccg acgcgccat ctacaccgtg gctcccca tcgactacgg cgtgatcgtg    2460
gacaccaagg cctactccgg cggctacaac ctgcccatcg ccaggccga cgaaatgcag    2520
aggtacgtga aggagaacca gaccaggaac aagcacatca ccccaacga gtggtggaag    2580
gtgtacccct ccagcgtgac cgagttcaag ttcctgttcg tgtccggcca cttcaagggc    2640
aactacaagg cccagctgac caggctgaac cacatcacca actgcaacgg cgccgtgctg    2700
tccgtggagg agctcctgat cggcggcgag atgatcaagg ccggcaccct gaccctggag    2760
gaggtgagga ggaagttcaa caacggcgag atcaacttcg cggccgactg ataa    2814
```

<210> SEQ ID NO 30
<211> LENGTH: 2832
<212> TYPE: DNA
<213> ORGANISM: Artificialsequence
<220> FEATURE:
<223> OTHER INFORMATION: GRex5T3-R TALEN

<400> SEQUENCE: 30

| | |
|---|---|
| atgggcgatc ctaaaaagaa acgtaaggtc atcgataagg agaccgccgc tgccaagttc | 60 |
| gagagacagc acatggacag catcgatatc gccgatctac gcacgctcgg ctacagccag | 120 |
| cagcaacagg agaagatcaa accgaaggtt cgttcgacag tggcgcagca ccacgaggca | 180 |
| ctggtcggcc acgggtttac acacgcgcac atcgttgcgt taagccaaca cccggcagcg | 240 |
| ttagggaccg tcgctgtcaa gtatcaggac atgatcgcag cgttgccaga ggcgacacac | 300 |
| gaagcgatcg ttggcgtcgg caaacagtgg tccggcgcac gcgctctgga ggccttgctc | 360 |
| acggtggcgg agagttgag aggtccaccg ttacagttgg acacaggcca acttctcaag | 420 |
| attgcaaaac gtggcggcgt gaccgcagtg gaggcagtgc atgcatggcg caatgcactg | 480 |
| acgggtgccc cgctcaactt gacccccag caggtggtgg ccatcgccag caataatggt | 540 |
| ggcaagcagg cgctggagac ggtccagcgg ctgttgccgg tgctgtgcca ggcccacggc | 600 |
| ttgaccccgg agcaggtggt ggccatcgcc agcaatattg gtggcaagca ggcgctggag | 660 |
| acggtgcagg cgctgttgcc ggtgctgtgc caggcccacg gcttgacccc ccagcaggtg | 720 |
| gtggccatcg ccagcaatgg cggtggcaag caggcgctgg agacggtcca gcggctgttg | 780 |
| ccggtgctgt gccaggccca cggcttgacc ccggagcagg tggtggccat cgccagccac | 840 |
| gatggcggca gcaggcgct ggagacggtc agcggctgt gccggtgct gtgccaggcc | 900 |
| cacggcttga ccccggagca ggtggtggcc atcgccagcc acgatggcgg caagcaggcg | 960 |
| ctggagacgg tccagcggct gttgccggtg ctgtgccagg cccacggctt gaccccccag | 1020 |
| caggtggtgg ccatcgccag caatggcggt ggcaagcagg cgctggagac ggtccagcgg | 1080 |
| ctgttgccgg tgctgtgcca ggcccacggc ttgaccccgg agcaggtggt ggccatcgcc | 1140 |
| agccacgatg gcggcaagca ggcgctggag acggtccagc ggctgttgcc ggtgctgtgc | 1200 |
| caggcccacg gcttgacccc ggagcaggtg gtggccatcg ccagccacga tggcggcaag | 1260 |
| caggcgctgg agacggtcca gcggctgttg ccggtgctgt gccaggccca cggcttgacc | 1320 |
| ccggagcagg tggtggccat cgccagcaat attggtggca agcaggcgct ggagacggtg | 1380 |
| caggcgctgt tgccggtgct gtgccaggcc acggcttga ccccggagca ggtggtggcc | 1440 |
| atcgccagca atattggtgg caagcaggcg ctggagacgg tgcaggcgct gttgccggtg | 1500 |
| ctgtgccagg cccacggctt gaccccccag caggtggtgg ccatcgccag caataatggt | 1560 |
| ggcaagcagg cgctggagac ggtccagcgg ctgttgccgg tgctgtgcca ggcccacggc | 1620 |
| ttgaccccc agcaggtggt ggccatcgcc agcaatggcg gtggcaagca ggcgctggag | 1680 |
| acggtccagc ggctgttgcc ggtgctgtgc caggcccacg gcttgacccc ccagcaggtg | 1740 |
| gtggccatcg ccagcaatgg cggtggcaag caggcgctgg agacggtcca gcggctgttg | 1800 |
| ccggtgctgt gccaggccca cggcttgacc ccccagcagg tggtggccat cgccagcaat | 1860 |
| aatggtggca agcaggcgct ggagacggtc agcggctgt gccggtgct gtgccaggcc | 1920 |
| cacggcttga ccccggagca ggtggtggcc atcgccagca atattggtgg caagcaggcg | 1980 |
| ctggagacgg tgcaggcgct gttgccggtg ctgtgccagg cccacggctt gacccctcag | 2040 |

```
caggtggtgg ccatcgccag caatggcggc ggcaggccgg cgctggagag cattgttgcc    2100
cagttatctc gccctgatcc ggcgttggcc gcgttgacca acgaccacct cgtcgccttg    2160
gcctgcctcg gcgggcgtcc tgcgctggat gcagtgaaaa agggattggg ggatcctatc    2220
agccgttccc agctggtgaa gtccgagctg gaggagaaga atccgagtt gaggcacaag    2280 ctgaagtacg tgccccacga gtacatcgag ctgatcgaga tcgcccggaa cagcacccag    2340
gaccgtatcc tggagatgaa ggtgatggag ttcttcatga aggtgtacgg ctacaggggc    2400
aagcacctgg gcggctccag gaagcccgac ggcgccatct acaccgtggg ctcccccatc    2460
gactacggcg tgatcgtgga caccaaggcc tactccggcg gctacaacct gcccatcggc    2520
caggccgacg aaatgcagag gtacgtggag gagaaccaga ccaggaacaa gcacatcaac    2580
cccaacgagt ggtggaaggt gtaccccctcc agcgtgaccg agttcaagtt cctgttcgtg    2640
tccggccact tcaagggcaa ctacaaggcc cagctgacca ggctgaacca catcaccaac    2700
tgcaacggcg ccgtgctgtc cgtggaggag ctcctgatcg gcggcgagat gatcaaggcc    2760
ggcaccctga ccctggagga ggtgaggagg aagttcaaca cggcgagat caacttcgcg    2820 gccgactgat aa                                                        2832
```

<210> SEQ ID NO 31
<211> LENGTH: 60
<212> TYPE: DNA
<213> ORGANISM: Artificialsequence
<220> FEATURE:
<223> OTHER INFORMATION: Forward primer GR exon 2
<220> FEATURE:
<221> NAME/KEY: misc_feature
<222> LOCATION: (31); (32); (33); (34); (35); (36); (37); (38); (39);
      (40)
<223> OTHER INFORMATION: n is a or c or t or g

<400> SEQUENCE: 31

```
ccatctcatc cctgcgtgtc tccgactcag nnnnnnnnnn ggttcattta acaagctgcc    60
```

<210> SEQ ID NO 32
<211> LENGTH: 60
<212> TYPE: DNA
<213> ORGANISM: Artificialsequence
<220> FEATURE:
<223> OTHER INFORMATION: Forward primer GR exon 3
<220> FEATURE:
<221> NAME/KEY: misc_feature
<222> LOCATION: (31); (32); (33); (34); (35); (36); (37); (38); (39);
      (40)
<223> OTHER INFORMATION: n is a or c or t or g

<400> SEQUENCE: 32

```
ccatctcatc cctgcgtgtc tccgactcag nnnnnnnnnn gcattctgac tatgaagtga    60
```

<210> SEQ ID NO 33
<211> LENGTH: 69
<212> TYPE: DNA
<213> ORGANISM: Artificialsequence
<220> FEATURE:
<223> OTHER INFORMATION: Forward primer GR exon 5
<220> FEATURE:
<221> NAME/KEY: misc_feature
<222> LOCATION: (31); (32); (33); (34); (35); (36); (37); (38); (39);
      (40)
<223> OTHER INFORMATION: n is a or c or t or g

<400> SEQUENCE: 33

```
ccatctcatc cctgcgtgtc tccgactcag nnnnnnnnnn tcagcaggcc actacaggag    60
``` tctcacaag                                                            69

<210> SEQ ID NO 34
<211> LENGTH: 50
<212> TYPE: DNA
<213> ORGANISM: Artificialsequence
<220> FEATURE:
<223> OTHER INFORMATION: Reverse primer GR exon 2

<400> SEQUENCE: 34
cctatcccct gtgtgccttg gcagtctcag agccagtgag ggtgaagacg              50

<210> SEQ ID NO 35
<211> LENGTH: 50
<212> TYPE: DNA
<213> ORGANISM: Artificialsequence
<220> FEATURE:
<223> OTHER INFORMATION: Reverse primer GR exon 3

<400> SEQUENCE: 35
cctatcccct gtgtgccttg gcagtctcag gggctttgca tataatggaa              50

<210> SEQ ID NO 36
<211> LENGTH: 59
<212> TYPE: DNA
<213> ORGANISM: Artificialsequence
<220> FEATURE:
<223> OTHER INFORMATION: Reverse primer GR exon 5

<400> SEQUENCE: 36
cctatcccct gtgtgccttg gcagtctcag ctgactctcc ccttcatagt ccccagaac    59

<210> SEQ ID NO 37
<211> LENGTH: 49
<212> TYPE: DNA
<213> ORGANISM: Artificialsequence
<220> FEATURE:
<223> OTHER INFORMATION: TRAC_T01

<400> SEQUENCE: 37
ttgtcccaca gatatccaga accctgaccc tgccgtgtac cagctgaga               49

<210> SEQ ID NO 38
<211> LENGTH: 49
<212> TYPE: DNA
<213> ORGANISM: Artificialsequence
<220> FEATURE:
<223> OTHER INFORMATION: TRBC_T01

<400> SEQUENCE: 38
tgtgtttgag ccatcagaag cagagatctc ccacacccaa aaggccaca               49

<210> SEQ ID NO 39
<211> LENGTH: 50
<212> TYPE: DNA
<213> ORGANISM: Artificialsequence
<220> FEATURE:
<223> OTHER INFORMATION: TRBC_T02

<400> SEQUENCE: 39
ttcccacccg aggtcgctgt gtttgagcca tcagaagcag agatctccca              50

<210> SEQ ID NO 40
<211> LENGTH: 49
<212> TYPE: DNA
<213> ORGANISM: Artificialsequence

<220> FEATURE:
<223> OTHER INFORMATION: CD52_T02

<400> SEQUENCE: 40
ttcctcctac tcaccatcag cctcctggtt atggtacagg taagagcaa                49

<210> SEQ ID NO 41
<211> LENGTH: 530
<212> TYPE: PRT
<213> ORGANISM: Artificialsequence
<220> FEATURE:
<223> OTHER INFORMATION: Repeat TRAC_T01-L

<400> SEQUENCE: 41

```
Leu Thr Pro Gln Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Asn Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser Asn Ile Gly Gly Lys Gln Ala Leu Glu
    210                 215                 220

Thr Val Gln Ala Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser Asn Ile Gly Gly Lys
        275                 280                 285

Gln Ala Leu Glu Thr Val Gln Ala Leu Leu Pro Val Leu Cys Gln Ala
    290                 295                 300

His Gly Leu Thr Pro Gln Gln Val Val Ala Ile Ala Ser Asn Asn Gly
305                 310                 315                 320

Gly Lys Gln Ala Leu Glu Thr Val Gln Arg Leu Leu Pro Val Leu Cys
                325                 330                 335
```

```
Gln Ala His Gly Leu Thr Pro Glu Gln Val Ala Ile Ala Ser Asn
                340                 345                 350
Ile Gly Gly Lys Gln Ala Leu Glu Thr Val Gln Ala Leu Leu Pro Val
                355                 360                 365
Leu Cys Gln Ala His Gly Leu Thr Pro Gln Gln Val Ala Ile Ala
370                 375                 380
Ser Asn Gly Gly Lys Gln Ala Leu Glu Thr Val Gln Arg Leu Leu
385                 390                 395                 400
Pro Val Leu Cys Gln Ala His Gly Leu Thr Pro Glu Gln Val Val Ala
                405                 410                 415
Ile Ala Ser Asn Ile Gly Gly Lys Gln Ala Leu Glu Thr Val Gln Ala
                420                 425                 430
Leu Leu Pro Val Leu Cys Gln Ala His Gly Leu Thr Pro Gln Gln Val
                435                 440                 445
Val Ala Ile Ala Ser Asn Gly Gly Lys Gln Ala Leu Glu Thr Val
                450                 455                 460
Gln Arg Leu Leu Pro Val Leu Cys Gln Ala His Gly Leu Thr Pro Glu
465                 470                 475                 480
Gln Val Val Ala Ile Ala Ser His Asp Gly Gly Lys Gln Ala Leu Glu
                485                 490                 495
Thr Val Gln Arg Leu Leu Pro Val Leu Cys Gln Ala His Gly Leu Thr
                500                 505                 510
Pro Gln Gln Val Val Ala Ile Ala Ser Asn Gly Gly Arg Pro Ala
                515                 520                 525
Leu Glu
530

<210> SEQ ID NO 42
<211> LENGTH: 530
<212> TYPE: PRT
<213> ORGANISM: Artificialsequence
<220> FEATURE:
<223> OTHER INFORMATION: Repeat TRAC_T01-R

<400> SEQUENCE: 42

Leu Thr Pro Glu Gln Val Val Ala Ile Ala Ser His Asp Gly Gly Lys
1               5                   10                  15
Gln Ala Leu Glu Thr Val Gln Arg Leu Leu Pro Val Leu Cys Gln Ala
                20                  25                  30
His Gly Leu Thr Pro Gln Gln Val Val Ala Ile Ala Ser Asn Gly Gly
                35                  40                  45
Gly Lys Gln Ala Leu Glu Thr Val Gln Arg Leu Leu Pro Val Leu Cys
50                  55                  60
Gln Ala His Gly Leu Thr Pro Glu Gln Val Val Ala Ile Ala Ser His
65                  70                  75                  80
Asp Gly Gly Lys Gln Ala Leu Glu Thr Val Gln Arg Leu Leu Pro Val
                85                  90                  95
Leu Cys Gln Ala His Gly Leu Thr Pro Glu Gln Val Val Ala Ile Ala
                100                 105                 110
Ser Asn Ile Gly Gly Lys Gln Ala Leu Glu Thr Val Gln Ala Leu Leu
                115                 120                 125
Pro Val Leu Cys Gln Ala His Gly Leu Thr Pro Gln Gln Val Val Ala
                130                 135                 140
Ile Ala Ser Asn Asn Gly Gly Lys Gln Ala Leu Glu Thr Val Gln Arg
145                 150                 155                 160
```

```
Leu Leu Pro Val Leu Cys Gln Ala His Gly Leu Thr Pro Glu Gln Val
            165                 170                 175
Val Ala Ile Ala Ser His Asp Gly Gly Lys Gln Ala Leu Glu Thr Val
        180                 185                 190
Gln Arg Leu Leu Pro Val Leu Cys Gln Ala His Gly Leu Thr Pro Gln
    195                 200                 205
Gln Val Val Ala Ile Ala Ser Asn Gly Gly Lys Gln Ala Leu Glu
210                 215                 220
Thr Val Gln Arg Leu Leu Pro Val Leu Cys Gln Ala His Gly Leu Thr
225                 230                 235                 240
Pro Gln Gln Val Val Ala Ile Ala Ser Asn Asn Gly Gly Lys Gln Ala
                245                 250                 255
Leu Glu Thr Val Gln Arg Leu Leu Pro Val Leu Cys Gln Ala His Gly
            260                 265                 270
Leu Thr Pro Gln Gln Val Val Ala Ile Ala Ser Asn Asn Gly Gly Lys
        275                 280                 285
Gln Ala Leu Glu Thr Val Gln Arg Leu Leu Pro Val Leu Cys Gln Ala
    290                 295                 300
His Gly Leu Thr Pro Gln Gln Val Val Ala Ile Ala Ser Asn Gly Gly
305                 310                 315                 320
Gly Lys Gln Ala Leu Glu Thr Val Gln Arg Leu Leu Pro Val Leu Cys
                325                 330                 335
Gln Ala His Gly Leu Thr Pro Glu Gln Val Val Ala Ile Ala Ser Asn
            340                 345                 350
Ile Gly Gly Lys Gln Ala Leu Glu Thr Val Gln Ala Leu Leu Pro Val
        355                 360                 365
Leu Cys Gln Ala His Gly Leu Thr Pro Glu Gln Val Val Ala Ile Ala
    370                 375                 380
Ser His Asp Gly Gly Lys Gln Ala Leu Glu Thr Val Gln Arg Leu Leu
385                 390                 395                 400
Pro Val Leu Cys Gln Ala His Gly Leu Thr Pro Glu Gln Val Val Ala
                405                 410                 415
Ile Ala Ser Asn Ile Gly Gly Lys Gln Ala Leu Glu Thr Val Gln Ala
            420                 425                 430
Leu Leu Pro Val Leu Cys Gln Ala His Gly Leu Thr Pro Glu Gln Val
        435                 440                 445
Val Ala Ile Ala Ser His Asp Gly Gly Lys Gln Ala Leu Glu Thr Val
    450                 455                 460
Gln Arg Leu Leu Pro Val Leu Cys Gln Ala His Gly Leu Thr Pro Gln
465                 470                 475                 480
Gln Val Val Ala Ile Ala Ser Asn Asn Gly Gly Lys Gln Ala Leu Glu
                485                 490                 495
Thr Val Gln Arg Leu Leu Pro Val Leu Cys Gln Ala His Gly Leu Thr
            500                 505                 510
Pro Gln Gln Val Val Ala Ile Ala Ser Asn Gly Gly Gly Arg Pro Ala
        515                 520                 525
Leu Glu
    530

<210> SEQ ID NO 43
<211> LENGTH: 530
<212> TYPE: PRT
<213> ORGANISM: Artificialsequence
<220> FEATURE:
```

<223> OTHER INFORMATION: Repeat TRBC_T01-L

<400> SEQUENCE: 43

```
Leu Thr Pro Gln Gln Val Ala Ile Ala Ser Asn Asn Gly Gly Lys
 1               5                  10                  15

Gln Ala Leu Glu Thr Val Gln Arg Leu Leu Pro Val Leu Cys Gln Ala
            20                  25                  30

His Gly Leu Thr Pro Gln Gln Val Ala Ile Ala Ser Asn Gly Gly
         35                  40                  45

Gly Lys Gln Ala Leu Glu Thr Val Gln Arg Leu Leu Pro Val Leu Cys
     50                  55                  60

Gln Ala His Gly Leu Thr Pro Gln Gln Val Ala Ile Ala Ser Asn
 65                  70                  75                  80

Asn Gly Gly Lys Gln Ala Leu Glu Thr Val Gln Arg Leu Leu Pro Val
                 85                  90                  95

Leu Cys Gln Ala His Gly Leu Thr Pro Gln Gln Val Ala Ile Ala
                100                 105                 110

Ser Asn Gly Gly Gly Lys Gln Ala Leu Glu Thr Val Gln Arg Leu Leu
            115                 120                 125

Pro Val Leu Cys Gln Ala His Gly Leu Thr Pro Gln Gln Val Val Ala
            130                 135                 140

Ile Ala Ser Asn Gly Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Gly Gly Gly Lys Gln Ala Leu Glu Thr Val
            180                 185                 190

Gln Arg Leu Leu Pro Val Leu Cys Gln Ala His Gly Leu Thr Pro Gln
            195                 200                 205

Gln Val Val Ala Ile Ala Ser Asn Asn Gly Gly Lys Gln Ala Leu Glu
            210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
                260                 265                 270

Leu Thr Pro Gln Gln Val Val Ala Ile Ala Ser Asn Asn Gly Gly Lys
            275                 280                 285

Gln Ala Leu Glu Thr Val Gln Arg Leu Leu Pro Val Leu Cys Gln Ala
            290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser His
            340                 345                 350

Asp Gly Gly Lys Gln Ala Leu Glu Thr Val Gln Arg Leu Leu Pro Val
            355                 360                 365

Leu Cys Gln Ala His Gly Leu Thr Pro Glu Gln Val Val Ala Ile Ala
            370                 375                 380

Ser Asn Ile Gly Gly Lys Gln Ala Leu Glu Thr Val Gln Ala Leu Leu
385                 390                 395                 400
```

Pro Val Leu Cys Gln Ala His Gly Leu Thr Pro Gln Gln Val Val Ala
            405                 410                 415

Ile Ala Ser Asn Gly Gly Gly Lys Gln Ala Leu Glu Thr Val Gln Arg
            420                 425                 430

Leu Leu Pro Val Leu Cys Gln Ala His Gly Leu Thr Pro Glu Gln Val
        435                 440                 445

Val Ala Ile Ala Ser His Asp Gly Gly Lys Gln Ala Leu Glu Thr Val
    450                 455                 460

Gln Arg Leu Leu Pro Val Leu Cys Gln Ala His Gly Leu Thr Pro Glu
465                 470                 475                 480

Gln Val Val Ala Ile Ala Ser Asn Ile Gly Gly Lys Gln Ala Leu Glu
                485                 490                 495

Thr Val Gln Ala Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530

<210> SEQ ID NO 44
<211> LENGTH: 530
<212> TYPE: PRT
<213> ORGANISM: Artificialsequence
<220> FEATURE:
<223> OTHER INFORMATION: Repeat TRBC_T01-R

<400> SEQUENCE: 44

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Gly Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Asn Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
            100                 105                 110

Ser Asn Asn Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Gln Gln Val Val Ala Ile Ala Ser Asn Gly Gly Lys Gln Ala
            245                 250                 255

Leu Glu Thr Val Gln Arg Leu Leu Pro Val Leu Cys Gln Ala His Gly
        260                 265                 270

Leu Thr Pro Gln Gln Val Val Ala Ile Ala Ser Asn Gly Gly Lys
        275                 280                 285

Gln Ala Leu Glu Thr Val Gln Arg Leu Leu Pro Val Leu Cys Gln Ala
        290                 295                 300

His Gly Leu Thr Pro Gln Gln Val Val Ala Ile Ala Ser Asn Gly Gly
305                 310                 315                 320

Gly Lys Gln Ala Leu Glu Thr Val Gln Arg Leu Leu Pro Val Leu Cys
            325                 330                 335

Gln Ala His Gly Leu Thr Pro Gln Gln Val Val Ala Ile Ala Ser Asn
            340                 345                 350

Asn Gly Gly Lys Gln Ala Leu Glu Thr Val Gln Arg Leu Leu Pro Val
        355                 360                 365

Leu Cys Gln Ala His Gly Leu Thr Pro Gln Gln Val Val Ala Ile Ala
370                 375                 380

Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Gln Gln Val Val Ala
            405                 410                 415

Ile Ala Ser Asn Asn Gly Gly Lys Gln Ala Leu Glu Thr Val Gln Arg
            420                 425                 430

Leu Leu Pro Val Leu Cys Gln Ala His Gly Leu Thr Pro Gln Gln Val
        435                 440                 445

Val Ala Ile Ala Ser Asn Gly Gly Lys Gln Ala Leu Glu Thr Val
        450                 455                 460

Gln Arg Leu Leu Pro Val Leu Cys Gln Ala His Gly Leu Thr Pro Gln
465                 470                 475                 480

Gln Val Val Ala Ile Ala Ser Asn Asn Gly Gly Lys Gln Ala Leu Glu
            485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Arg Pro Ala
        515                 520                 525

Leu Glu
530

<210> SEQ ID NO 45
<211> LENGTH: 530
<212> TYPE: PRT
<213> ORGANISM: Artificialsequence
<220> FEATURE:
<223> OTHER INFORMATION: Repeat TRBC_T02-L

<400> SEQUENCE: 45

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser His Asp Gly
        35                  40                  45

```
Gly Lys Gln Ala Leu Glu Thr Val Gln Arg Leu Leu Pro Val Leu Cys
 50                  55                  60

Gln Ala His Gly Leu Thr Pro Glu Gln Val Val Ala Ile Ala Ser His
 65                  70                  75                  80

Asp Gly Gly Lys Gln Ala Leu Glu Thr Val Gln Arg Leu Leu Pro Val
                 85                  90                  95

Leu Cys Gln Ala His Gly Leu Thr Pro Glu Gln Val Val Ala Ile Ala
            100                 105                 110

Ser Asn Ile Gly Gly Lys Gln Ala Leu Glu Thr Val Gln Ala Leu Leu
        115                 120                 125

Pro Val Leu Cys Gln Ala His Gly Leu Thr Pro Glu Gln Val Val Ala
130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser His Asp Gly Gly Lys Gln Ala Leu Glu
210                 215                 220

Thr Val Gln Arg Leu Leu Pro Val Leu Cys Gln Ala His Gly Leu Thr
225                 230                 235                 240

Pro Gln Gln Val Val Ala Ile Ala Ser Asn Asn Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser Asn Ile Gly Gly Lys
        275                 280                 285

Gln Ala Leu Glu Thr Val Gln Ala Leu Leu Pro Val Leu Cys Gln Ala
290                 295                 300

His Gly Leu Thr Pro Gln Gln Val Val Ala Ile Ala Ser Asn Asn Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Gln Gln Val Val Ala Ile Ala Ser Asn
            340                 345                 350

Asn Gly Gly Lys Gln Ala Leu Glu Thr Val Gln Arg Leu Leu Pro Val
        355                 360                 365

Leu Cys Gln Ala His Gly Leu Thr Pro Gln Gln Val Val Ala Ile Ala
370                 375                 380

Ser Asn Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser His Asp Gly Gly Lys Gln Ala Leu Glu Thr Val Gln Arg
            420                 425                 430

Leu Leu Pro Val Leu Cys Gln Ala His Gly Leu Thr Pro Gln Gln Val
        435                 440                 445

Val Ala Ile Ala Ser Asn Asn Gly Gly Lys Gln Ala Leu Glu Thr Val
450                 455                 460

Gln Arg Leu Leu Pro Val Leu Cys Gln Ala His Gly Leu Thr Pro Glu
```

```
                465                 470                 475                 480
Gln Val Val Ala Ile Ala Ser His Asp Gly Gly Lys Gln Ala Leu Glu
                    485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Arg Pro Ala
        515                 520                 525

Leu Glu
    530

<210> SEQ ID NO 46
<211> LENGTH: 530
<212> TYPE: PRT
<213> ORGANISM: Artificialsequence
<220> FEATURE:
<223> OTHER INFORMATION: Repeat TRBC_T02-R

<400> SEQUENCE: 46

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Asn Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Asn Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser Asn Ile Gly Gly Lys Gln Ala Leu Glu Thr Val Gln Ala Leu Leu
        115                 120                 125

Pro Val Leu Cys Gln Ala His Gly Leu Thr Pro Gln Gln Val Val Ala
    130                 135                 140

Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser Asn Ile Gly Gly Lys Gln Ala Leu Glu Thr Val
            180                 185                 190

Gln Ala Leu Leu Pro Val Leu Cys Gln Ala His Gly Leu Thr Pro Gln
        195                 200                 205

Gln Val Val Ala Ile Ala Ser Asn Gly Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
            260                 265                 270

Leu Thr Pro Gln Gln Val Val Ala Ile Ala Ser Asn Gly Gly Gly Lys
        275                 280                 285

Gln Ala Leu Glu Thr Val Gln Arg Leu Leu Pro Val Leu Cys Gln Ala
```

```
                290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Gln Gln Val Val Ala Ile Ala Ser Asn
                340                 345                 350

Gly Gly Lys Gln Ala Leu Glu Thr Val Gln Arg Leu Leu Pro Val
            355                 360                 365

Leu Cys Gln Ala His Gly Leu Thr Pro Gln Gln Val Val Ala Ile Ala
    370                 375                 380

Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser His Asp Gly Gly Lys Gln Ala Leu Glu Thr Val Gln Arg
                420                 425                 430

Leu Leu Pro Val Leu Cys Gln Ala His Gly Leu Thr Pro Gln Gln Val
            435                 440                 445

Val Ala Ile Ala Ser Asn Gly Gly Gly Lys Gln Ala Leu Glu Thr Val
    450                 455                 460

Gln Arg Leu Leu Pro Val Leu Cys Gln Ala His Gly Leu Thr Pro Gln
465                 470                 475                 480

Gln Val Val Ala Ile Ala Ser Asn Gly Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Arg Pro Ala
    515                 520                 525

Leu Glu
    530

<210> SEQ ID NO 47
<211> LENGTH: 530
<212> TYPE: PRT
<213> ORGANISM: Artificialsequence
<220> FEATURE:
<223> OTHER INFORMATION: Repeat CD52_T02-L

<400> SEQUENCE: 47

Leu Thr Pro Gln Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
                20                  25                  30

His Gly Leu Thr Pro Glu Gln Val Val Ala Ile Ala Ser His Asp Gly
                35                  40                  45

Gly Lys Gln Ala Leu Glu Thr Val Gln Arg Leu Leu Pro Val Leu Cys
            50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
                100                 105                 110

Ser Asn Gly Gly Gly Lys Gln Ala Leu Glu Thr Val Gln Arg Leu Leu
```

```
            115                 120                 125
Pro Val Leu Cys Gln Ala His Gly Leu Thr Pro Glu Gln Val Val Ala
130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
            260                 265                 270

Leu Thr Pro Glu Gln Val Val Ala Ile Ala Ser His Asp Gly Gly Lys
        275                 280                 285

Gln Ala Leu Glu Thr Val Gln Arg Leu Leu Pro Val Leu Cys Gln Ala
290                 295                 300

His Gly Leu Thr Pro Gln Val Val Ala Ile Ala Ser Asn Gly Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser His
            340                 345                 350

Asp Gly Gly Lys Gln Ala Leu Glu Thr Val Gln Arg Leu Leu Pro Val
        355                 360                 365

Leu Cys Gln Ala His Gly Leu Thr Pro Glu Gln Val Val Ala Ile Ala
370                 375                 380

Ser Asn Ile Gly Gly Lys Gln Ala Leu Glu Thr Val Gln Ala Leu Leu
385                 390                 395                 400

Pro Val Leu Cys Gln Ala His Gly Leu Thr Pro Glu Gln Val Val Ala
                405                 410                 415

Ile Ala Ser His Asp Gly Gly Lys Gln Ala Leu Glu Thr Val Gln Arg
            420                 425                 430

Leu Leu Pro Val Leu Cys Gln Ala His Gly Leu Thr Pro Glu Gln Val
        435                 440                 445

Val Ala Ile Ala Ser His Asp Gly Gly Lys Gln Ala Leu Glu Thr Val
450                 455                 460

Gln Arg Leu Leu Pro Val Leu Cys Gln Ala His Gly Leu Thr Pro Glu
465                 470                 475                 480

Gln Val Val Ala Ile Ala Ser Asn Ile Gly Gly Lys Gln Ala Leu Glu
                485                 490                 495

Thr Val Gln Ala Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
530
```

<210> SEQ ID NO 48
<211> LENGTH: 530
<212> TYPE: PRT
<213> ORGANISM: Artificialsequence
<220> FEATURE:
<223> OTHER INFORMATION: Repeat CD52_T02-R

<400> SEQUENCE: 48

```
Leu Thr Pro Gln Gln Val Val Ala Ile Ala Ser Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Asn Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
            100                 105                 110

Ser Asn Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
        130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Lys Gln Ala Leu Glu
        210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
            260                 265                 270

Leu Thr Pro Glu Gln Val Val Ala Ile Ala Ser His Asp Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Gln Gln Val Val Ala Ile Ala Ser Asn
            340                 345                 350

Gly Gly Lys Gln Ala Leu Glu Thr Val Gln Arg Leu Leu Pro Val
        355                 360                 365
```

```
Leu Cys Gln Ala His Gly Leu Thr Pro Gln Gln Val Val Ala Ile Ala
        370                 375                 380

Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Gln Gln Val Val Ala
                405                 410                 415

Ile Ala Ser Asn Gly Gly Gly Lys Gln Ala Leu Glu Thr Val Gln Arg
            420                 425                 430

Leu Leu Pro Val Leu Cys Gln Ala His Gly Leu Thr Pro Glu Gln Val
        435                 440                 445

Val Ala Ile Ala Ser Asn Ile Gly Gly Lys Gln Ala Leu Glu Thr Val
    450                 455                 460

Gln Ala Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530

<210> SEQ ID NO 49
<211> LENGTH: 2814
<212> TYPE: DNA
<213> ORGANISM: Artificialsequence
<220> FEATURE:
<223> OTHER INFORMATION: TRAC_T01-L TALEN

<400> SEQUENCE: 49
atgggcgatc ctaaaaagaa acgtaaggtc atcgattacc catacgatgt tccagattac      60
gctatcgata tcgccgatct acgcacgctc ggctacagcc agcagcaaca ggagaagatc     120
aaaccgaagg ttcgttcgac agtggcgcag caccacgagg cactggtcgg ccacgggttt     180
acacacgcgc acatcgttgc gttaagccaa cacccggcag cgttagggac cgtcgctgtc     240
aagtatcagg acatgatcgc agcgttgcca gaggcgacac acgaagcgat cgttggcgtc     300
ggcaaacagt ggtccggcgc acgcgctctg gaggccttgc tcacggtggc gggagagttg     360
agaggtccac cgttacagtt ggacacaggc caacttctca agattgcaaa acgtggcggc     420
gtgaccgcag tggaggcagt gcatgcatgg cgcaatgcac tgacgggtgc cccgctcaac     480
ttgacccccc agcaggtggt ggccatcgcc agcaatggcg gtggcaagca ggcgctggag     540
acggtccagc ggctgttgcc ggtgctgtgc caggcccacg gcttgacccc ccagcaggtg     600
gtggccatcg ccagcaataa tggtggcaag caggcgctgg agacggtcca gcggctgttg     660
ccggtgctgt gccaggccca cggcttgacc ccccagcagg tggtggccat cgccagcaat     720
ggcggtggca agcaggcgct ggagacggtc agcggctgt tgccggtgct gtgccaggcc     780
cacggcttga ccccggagca ggtggtggcc atcgccagcc acgatggcgg caagcaggcg     840
ctggagacgg tccagcggct gttgccggtg ctgtgccagg cccacggctt gaccccggag     900
caggtggtgg ccatcgccag ccacgatggc ggcaagcagg cgctggagac ggtccagcgg    960
ctgttgccgt gctgtgcca ggcccacggc ttgaccccgg agcaggtggt ggccatcgcc    1020
agccacgatg gcggcaagca ggcgctggag acggtccagc ggctgttgcc ggtgctgtgc    1080
```

```
caggcccacg gcttgacccc ggagcaggtg gtggccatcg ccagcaatat tggtggcaag    1140
caggcgctgg agacggtgca ggcgctgttg ccggtgctgt gccaggccca cggcttgacc    1200
ccggagcagg tggtggccat cgccagccac gatggcggca agcaggcgct ggagacggtc    1260
cagcggctgt tgccggtgct gtgccaggcc cacggcttga ccccgagca ggtggtggcc     1320 atcgccagca atattggtgg caagcaggcg ctggagacgg tgcaggcgct gttgccggtg    1380
ctgtgccagg cccacggctt gaccccccag caggtggtgg ccatcgccag caataatggt    1440
ggcaagcagg cgctggagac ggtccagcgg ctgttgccgg tgctgtgcca ggcccacggc    1500
ttgaccccgg agcaggtggt ggccatcgcc agcaatattg gtggcaagca ggcgctggag    1560
acggtgcagg cgctgttgcc ggtgctgtgc caggcccacg gcttgacccc cagcaggtg    1620 gtggccatcg ccagcaatgg cggtggcaag caggcgctgg agacggtcca gcggctgttg    1680
ccggtgctgt gccaggccca cggcttgacc ccggagcagg tggtggccat cgccagcaat    1740
attggtggca agcaggcgct ggagacggtg caggcgctgt tgccggtgct gtgccaggcc    1800
cacggcttga ccccccagca ggtggtggcc atcgccagca atggcggtgg caagcaggcg    1860
ctggagacgg tccagcggct gttgccggtg ctgtgccagg cccacggctt gaccccggag    1920
caggtggtgg ccatcgccag ccacgatggc ggcaagcagg cgctggagac ggtccagcgg    1980
ctgttgccgg tgctgtgcca ggcccacggc ttgacccctc agcaggtggt ggccatcgcc    2040
agcaatggcg gcggcaggcc ggcgctggag agcattgttg cccagttatc tcgccctgat    2100
ccggcgttgg ccgcgttgac caacgaccac ctcgtcgcct tggcctgcct cggcgggcgt    2160
cctgcgctgg atgcagtgaa aaagggattg ggggatccta tcagccgttc ccagctggtg    2220
aagtccgagc tggaggagaa gaaatccgag ttgaggcaca agctgaagta cgtgccccac    2280
gagtacatcg agctgatcga gatcgcccgg aacagcaccc aggaccgtat cctggagatg    2340
aaggtgatgg agttcttcat gaaggtgtac ggctacaggg gcaagcacct gggcggctcc    2400
aggaagcccg acgcgccat ctacaccgtg gctccccca tcgactacgg cgtgatcgtg      2460
gacaccaagg cctactccgg cggctacaac ctgcccatcg ccaggccga cgaaatgcag     2520 aggtacgtgg aggagaacca gaccaggaac aagcacatca cccccaacga gtggtggaag    2580
gtgtacccct ccagcgtgac cgagttcaag ttcctgttcg tgtccggcca cttcaagggc    2640
aactacaagg cccagctgac caggctgaac cacatcacca ctgcaacgg cgccgtgctg     2700 tccgtggagg agctcctgat cggcggcgag atgatcaagg ccggcaccct gaccctggag    2760
gaggtgagga ggaagttcaa caacggcgag atcaacttcg cggccgactg ataa          2814
```

<210> SEQ ID NO 50
<211> LENGTH: 2832
<212> TYPE: DNA
<213> ORGANISM: Artificialsequence
<220> FEATURE:
<223> OTHER INFORMATION: TRAC_T01-R TALEN

<400> SEQUENCE: 50

```
atgggcgatc ctaaaaagaa acgtaaggtc atcgataagg agaccgccgc tgccaagttc     60
gagagacagc acatggacag catcgatatc gccgatctac gcacgctcgg ctacagccag    120
cagcaacagg agaagatcaa accgaaggtt cgttcgacag tggcgcagca ccacgaggca    180
ctggtcggcc acgggtttac acacgcgcac atcgttgcgt taagccaaca cccggcagcg    240
ttagggaccg tcgctgtcaa gtatcaggac atgatcgcag cgttgccaga ggcgacacac    300
```

```
gaagcgatcg ttggcgtcgg caaacagtgg tccggcgcac gcgctctgga ggccttgctc    360
acggtggcgg gagagttgag aggtccaccg ttacagttgg acacaggcca acttctcaag    420
attgcaaaac gtggcggcgt gaccgcagtg gaggcagtgc atgcatggcg caatgcactg    480
acgggtgccc cgctcaactt gaccccggag caggtggtgg ccatcgccag ccacgatggc    540
ggcaagcagg cgctggagac ggtccagcgg ctgttgccgg tgctgtgcca ggcccacggc    600
ttgacccccc agcaggtggt ggccatcgcc agcaatggcg gtggcaagca ggcgctggag    660
acggtccagc ggctgttgcc ggtgctgtgc caggcccacg gcttgacccc ggagcaggtg    720
gtggccatcg ccagccacga tggcggcaag caggcgctgg agacggtcca gcggctgttg    780
ccggtgctgt gccaggccca cggcttgacc ccggagcagg tggtggccat cgccagcaat    840
attggtggca agcaggcgct ggagacggtg caggcgctgt gccggtgctg tgccaggcc    900
cacggcttga ccccccagca ggtggtggcc atcgccagca ataatggtgg caagcaggcg    960
ctggagacgg tccagcggct gttgccggtg ctgtgccagg cccacggctt gaccccggag   1020
caggtggtgg ccatcgccag ccacgatggc ggcaagcagg cgctggagac ggtccagcgg   1080
ctgttgccgg tgctgtgcca ggcccacggc ttgacccccc agcaggtggt ggccatcgcc   1140
agcaatggcg gtggcaagca ggcgctggag acggtccagc ggctgttgcc ggtgctgtgc   1200
caggcccacg gcttgacccc cagcaggtg gtggccatcg ccagcaataa tggtggcaag   1260
caggcgctgg agacggtcca gcggctgttg ccggtgctgt gccaggccca cggcttgacc   1320
ccccagcagg tggtggccat cgccagcaat aatggtggca agcaggcgct ggagacggtc   1380
cagcggctgt gccggtgct gtgccaggcc cacggcttga ccccccagca ggtggtggcc   1440
atcgccagca atggcggtgg caagcaggcg ctggagacgg tccagcggct gttgccggtg   1500
ctgtgccagg cccacggctt gaccccggag caggtggtgg ccatcgccag caatattggt   1560
ggcaagcagg cgctggagac ggtgcaggcg ctgttgccgg tgctgtgcca ggcccacggc   1620
ttgacccccg gagcaggtgg tggccatcgc cagccacgatg gcggcaagca ggcgctggag   1680
acggtccagc ggctgttgcc ggtgctgtgc caggcccacg gcttgacccc ggagcaggtg   1740
gtggccatcg ccagcaatat tggtggcaag caggcgctgg agacggtgca ggcgctgttg   1800
ccggtgctgt gccaggccca cggcttgacc ccggagcagg tggtggccat cgccagccac   1860
gatgcggcag caggcgct ggagacggtc agcggctgt tgccggtgct gtgccaggcc   1920
cacggcttga ccccccagca ggtggtggcc atcgccagca ataatggtgg caagcaggcg   1980
ctggagacgg tccagcggct gttgccggtg ctgtgccagg cccacggctt gaccccctcag   2040
caggtggtgg ccatcgccag caatggcggc ggcaggccgg cgctggagag cattgttgcc   2100
cagttatctc gccctgatcc ggcgttggcc gcgttgacca acgaccacct cgtcgccttg   2160
gcctgcctcg gcgggcgtcc tgcgctggat gcagtgaaaa agggattggg ggatcctatc   2220
agccgttccc agctggtgaa gtccgagctg gaggagaaga atccgagtt gaggcacaag   2280
ctgaagtacg tgcccacga gtacatcgag ctgatcgaga tcgcccggaa cagcacccag   2340
gaccgtatcc tggagatgaa ggtgatggag ttcttcatga aggtgtacgg ctacaggggc   2400
aagcacctgg gcggctccag gaagcccgac ggcgccatct acaccgtggg ctcccccatc   2460
gactacggcg tgatcgtgga caccaaggcc tactccggcg gctacaacct gcccatcggc   2520
caggccgacg aaatgcagag gtacgtggag gagaaccaga ccaggaacaa gcacatcaac   2580
cccaacgagt ggtggaaggt gtaccccctcc agcgtgaccg agttcaagtt cctgttcgtg   2640
tccggccact tcaagggcaa ctacaaggcc cagctgacca ggctgaacca catcaccaac   2700
```

| tgcaacggcg ccgtgctgtc cgtggaggag ctcctgatcg gcggcgagat gatcaaggcc | 2760 |
| ggcaccctga ccctggagga ggtgaggagg aagttcaaca acggcgagat caacttcgcg | 2820 |
| gccgactgat aa | 2832 |

<210> SEQ ID NO 51
<211> LENGTH: 2814
<212> TYPE: DNA
<213> ORGANISM: Artificialsequence
<220> FEATURE:
<223> OTHER INFORMATION: TRBC_T01-L TALEN

<400> SEQUENCE: 51

| atgggcgatc ctaaaaagaa acgtaaggtc atcgattacc catacgatgt tccagattac | 60 |
| gctatcgata tcgccgatct acgcacgctc ggctacagcc agcagcaaca ggagaagatc | 120 |
| aaaccgaagg ttcgttcgac agtggcgcag caccacgagg cactggtcgg ccacgggttt | 180 |
| acacacgcgc acatcgttgc gttaagccaa caccccggcag cgttagggac cgtcgctgtc | 240 |
| aagtatcagg acatgatcgc agcgttgcca gaggcgacac acgaagcgat cgttggcgtc | 300 |
| ggcaaacagt ggtccggcgc acgcgctctg gaggccttgc tcacggtggc gggagagttg | 360 |
| agaggtccac cgttacagtt ggacacaggc caacttctca agattgcaaa acgtggcggc | 420 |
| gtgaccgcag tggaggcagt gcatgcatgg cgcaatgcac tgacgggtgc cccgctcaac | 480 |
| ttgaccccc agcaggtggt ggccatcgcc agcaataatg gtggcaagca ggcgctggag | 540 |
| acggtccagc ggctgttgcc ggtgctgtgc caggcccacg gcttgacccc ccagcaggtg | 600 |
| gtggccatcg ccagcaatgg cggtggcaag caggcgctgg agacggtcca gcggctgttg | 660 |
| ccggtgctgt gccaggccca cggcttgacc cccagcagg tggtggccat cgccagcaat | 720 |
| aatggtggca gcaggcgct ggagacggtc agcggctgt tgccggtgct gtgccaggcc | 780 |
| cacggcttga ccccccagca ggtggtggcc atcgccagca atggcggtgg caagcaggcg | 840 |
| ctggagacgg tccagcggct gttgccggtg ctgtgccagg cccacggctt gaccccccag | 900 |
| caggtggtgg ccatcgccag caatggcggt ggcaagcagg cgctggagac ggtccagcgg | 960 |
| ctgttgccgg tgctgtgcca ggcccacggc ttgaccccc agcaggtggt ggccatcgcc | 1020 |
| agcaatggcg gtggcaagca ggcgctggag acggtccagc ggctgttgcc ggtgctgtgc | 1080 |
| caggcccacg gcttgacccc ccagcaggtg gtggccatcg ccagcaataa tggtggcaag | 1140 |
| caggcgctgg agacggtcca gcggctgttg ccggtgctgt gccaggccca cggcttgacc | 1200 |
| ccggagcagg tggtggccat cgccagcaat attggtggca agcaggcgct ggagacggtg | 1260 |
| caggcgctgt tgccggtgct gtgccaggcc cacggcttga ccccccagca ggtggtggcc | 1320 |
| atcgccagca ataatggtgg caagcaggcg ctggagacgg tccagcggct gttgccggtg | 1380 |
| ctgtgccagg cccacggctt gaccccggag caggtggtgg ccatcgccag ccacgatggc | 1440 |
| ggcaagcagg cgctggagac ggtccagcgg ctgttgccgg tgctgtgcca ggcccacggc | 1500 |
| ttgaccccgg agcaggtggt ggccatcgcc agccacgatg gcggcaagca ggcgctggag | 1560 |
| acggtccagc ggctgttgcc ggtgctgtgc caggcccacg gcttgacccc ggagcaggtg | 1620 |
| gtggccatcg ccagcaatat tggtggcaag caggcgctgg agacggtgca ggcgctgttg | 1680 |
| ccggtgctgt gccaggccca cggcttgacc cccagcagg tggtggccat cgccagcaat | 1740 |
| ggcggtggca gcaggcgct ggagacggtc agcggctgt tgccggtgct gtgccaggcc | 1800 |
| cacggcttga ccccggagca ggtggtggcc atcgccagcc acgatggcgg caagcaggcg | 1860 |

| | |
|---|---|
| ctggagacgg tccagcggct gttgccggtg ctgtgccagg cccacggctt gaccccggag | 1920 |
| caggtggtgg ccatcgccag caatattggt ggcaagcagg cgctggagac ggtgcaggcg | 1980 |
| ctgttgccgg tgctgtgcca ggcccacggc ttgacccctc agcaggtggt ggccatcgcc | 2040 |
| agcaatggcg gcggcaggcc ggcgctggag agcattgttg cccagttatc tcgccctgat | 2100 |
| ccggcgttgg ccgcgttgac caacgaccac ctcgtcgcct tggcctgcct cggcgggcgt | 2160 |
| cctgcgctgg atgcagtgaa aaagggattg ggggatccta tcagccgttc ccagctggtg | 2220 |
| aagtccgagc tggaggagaa gaaatccgag ttgaggcaca agctgaagta cgtgccccac | 2280 |
| gagtacatcg agctgatcga gatcgcccgg aacagcaccc aggaccgtat cctggagatg | 2340 |
| aaggtgatgg agttcttcat gaaggtgtac ggctacaggg gcaagcacct gggcggctcc | 2400 |
| aggaagcccg acggcgccat ctacaccgtg ggctccccca tcgactacgg cgtgatcgtg | 2460 |
| gacaccaagg cctactccgg cggctacaac ctgcccatcg gccaggccga cgaaatgcag | 2520 |
| aggtacgtgg aggagaacca gaccaggaac aagcacatca accccaacga gtggtggaag | 2580 |
| gtgtacccct ccagcgtgac cgagttcaag ttcctgttcg tgtccggcca cttcaagggc | 2640 |
| aactacaagg cccagctgac caggctgaac cacatcacca actgcaacgg cgccgtgctg | 2700 |
| tccgtggagg agctcctgat cggcggcgag atgatcaagg ccggcaccct gaccctggag | 2760 |
| gaggtgagga ggaagttcaa caacggcgag atcaacttcg cggccgactg ataa | 2814 |

<210> SEQ ID NO 52
<211> LENGTH: 2832
<212> TYPE: DNA
<213> ORGANISM: Artificialsequence
<220> FEATURE:
<223> OTHER INFORMATION: TRBC_T01-R TALEN

<400> SEQUENCE: 52

| | |
|---|---|
| atgggcgatc ctaaaaagaa acgtaaggtc atcgataagg agaccgccgc tgccaagttc | 60 |
| gagagacagc acatggacag catcgatatc gccgatctac gcacgctcgg ctacagccag | 120 |
| cagcaacagg agaagatcaa accgaaggtt cgttcgacag tggcgcagca ccacgaggca | 180 |
| ctggtcggcc acgggtttac acacgcgcac atcgttgcgt taagccaaca cccggcagcg | 240 |
| ttagggaccg tcgctgtcaa gtatcaggac atgatcgcag cgttgccaga ggcgacacac | 300 |
| gaagcgatct tggcgtcgg caaacagtgg tccggcgcac gcgctctgga ggccttgctc | 360 |
| acggtggcgg gagagttgag aggtccaccg ttacagttgg acacaggcca acttctcaag | 420 |
| attgcaaaac gtggcggcgt gaccgcagtg gaggcagtgc atgcatggcg caatgcactg | 480 |
| acgggtgccc cgctcaactt gacccccag caggtggtgg ccatcgccag caataatggt | 540 |
| ggcaagcagg cgctggagac ggtccagcgg ctgttgccgg tgctgtgcca ggcccacggc | 600 |
| ttgaccccc agcaggtggt ggccatcgcc agcaatggcg gtggcaagca ggcgctggag | 660 |
| acggtccagc ggctgttgcc ggtgctgtgc caggcccacg gcttgacccc ccagcaggtg | 720 |
| gtggccatcg ccagcaataa tggtggcaag caggcgctgg agacggtcca gcggctgttg | 780 |
| ccggtgctgt gccaggccca cggcttgacc cccagcagg tggtggccat cgccagcaat | 840 |
| aatggtggca gcaggcgct ggagacggtc agcggctgt gccggtgct gtgccaggcc | 900 |
| cacggcttga ccccggagca ggtggtggcc atcgccagcc acgatggcgg caagcaggcg | 960 |
| ctggagacgg tccagcggct gttgccggtg ctgtgccagg cccacggctt gaccccggag | 1020 |
| caggtggtgg ccatcgccag ccacgatggc ggcaagcagg cgctggagac ggtccagcgg | 1080 |
| ctgttgccgg tgctgtgcca ggcccacggc ttgaccccc agcaggtggt ggccatcgcc | 1140 |

```
agcaatggcg gtggcaagca ggcgctggag acggtccagc ggctgttgcc ggtgctgtgc    1200
caggcccacg gcttgacccc ccagcaggtg gtggccatcg ccagcaatgg cggtggcaag    1260
caggcgctgg agacggtcca gcggctgttg ccggtgctgt gccaggccca cggcttgacc    1320
ccccagcagg tggtggccat cgccagcaat ggcggtggca agcaggcgct ggagacggtc    1380
cagcggctgt tgccggtgct gtgccaggcc cacggcttga ccccccagca ggtggtggcc    1440
atcgccagca atggcggtgg caagcaggcg ctggagacgg tccagcggct gttgccggtg    1500
ctgtgccagg cccacggctt gacccccag caggtggtgg ccatcgccag caataatggt    1560
ggcaagcagg cgctggagac ggtccagcgg ctgttgccgg tgctgtgcca ggcccacggc    1620
ttgacccccc agcaggtggt ggccatcgcc agcaataatg gtggcaagca ggcgctggag    1680
acggtccagc ggctgttgcc ggtgctgtgc caggcccacg gcttgacccc ccagcaggtg    1740
gtggccatcg ccagcaataa tggtggcaag caggcgctgg agacggtcca gcggctgttg    1800
ccggtgctgt gccaggccca cggcttgacc ccccagcagg tggtggccat cgccagcaat    1860
ggcggtggca agcaggcgct ggagacggtc cagcggctgt tgccggtgct gtgccaggcc    1920
cacggcttga ccccccagca ggtggtggcc atcgccagca ataatggtgg caagcaggcg    1980
ctggagacgg tccagcggct gttgccggtg ctgtgccagg cccacggctt gacccctcag    2040
caggtggtgg ccatcgccag caatggcggc ggcaggccgg cgctggagag cattgttgcc    2100
cagttatctc gccctgatcc ggcgttggcc gcgttgacca acgaccacct cgtcgccttg    2160
gcctgcctcg gcgggcgtcc tgcgctggat gcagtgaaaa agggattggg ggatcctatc    2220
agccgttccc agctggtgaa gtccgagctg gaggagaaga atccgagtt gaggcacaag    2280 ctgaagtacg tgccccacga gtacatcgag ctgatcgaga tcgcccggaa cagcacccag    2340
gaccgtatcc tggagatgaa ggtgatggag ttcttcatga aggtgtacgg ctacaggggc    2400
aagcacctgg gcggctccag gaagcccgac ggcgccatct acaccgtggg ctcccccatc    2460
gactacggcg tgatcgtgga caccaaggcc tactccggcg gctacaacct gcccatcggc    2520
caggccgacg aaatgcagag gtacgtggag gagaaccaga ccaggaacaa gcacatcaac    2580
cccaacgagt ggtggaaggt gtaccctcc agcgtgaccg agttcaagtt cctgttcgtg    2640
tccggccact tcaagggcaa ctacaaggcc cagctgacca ggctgaacca catcaccaac    2700
tgcaacggcg ccgtgctgtc cgtggaggag ctcctgatcg gcggcgagat gatcaaggcc    2760 ggcacctga ccctggagga ggtgaggagg aagttcaaca acggcgagat caacttcgcg    2820
gccgactgat aa                                                        2832
```

<210> SEQ ID NO 53
<211> LENGTH: 2814
<212> TYPE: DNA
<213> ORGANISM: Artificialsequence
<220> FEATURE:
<223> OTHER INFORMATION: TRBC_T02-L TALEN

<400> SEQUENCE: 53

```
atgggcgatc ctaaaaagaa acgtaaggtc atcgattacc catacgatgt tccagattac      60
gctatcgata tcgccgatct acgcacgctc ggctacagcc agcagcaaca ggagaagatc     120
aaaccgaagg ttcgttcgac agtggcgcag caccacgagg cactggtcgg ccacgggttt    180
acacacgcgc acatcgttgc gttaagccaa cacccggcag cgttagggac cgtcgctgtc    240
aagtatcagg acatgatcgc agcgttgcca gaggcgacac acgaagcgat cgttggcgtc    300
```

```
ggcaaacagt ggtccggcgc acgcgctctg gaggccttgc tcacggtggc gggagagttg    360
agaggtccac cgttacagtt ggacacaggc caacttctca agattgcaaa acgtggcggc    420
gtgaccgcag tggaggcagt gcatgcatgg cgcaatgcac tgacgggtgc cccgctcaac    480
ttgaccccgg agcaggtggt ggccatcgcc agccacgatg gcggcaagca ggcgctggag    540
acggtccagc ggctgttgcc ggtgctgtgc caggcccacg gcttgacccc ggagcaggtg    600
gtggccatcg ccagccacga tggcggcaag caggcgctgg agacggtcca gcggctgttg    660
ccggtgctgt gccaggccca cggcttgacc ccggagcagg tggtggccat cgccagccac    720
gatggcggca agcaggcgct ggagacggtc agcggctgt tgccggtgct gtgccaggcc    780
cacggcttga ccccggagca ggtggtggcc atcgccagca atattggtgg caagcaggcg    840
ctggagacgg tgcaggcgct gttgccggtg ctgtgccagg cccacggctt gaccccggag    900
caggtggtgg ccatcgccag ccacgatggc ggcaagcagg cgctggagac ggtccagcgg    960
ctgttgccgg tgctgtgcca ggcccacggc ttgaccccgg agcaggtggt ggccatcgcc   1020
agccacgatg gcggcaagca ggcgctggag acggtccagc ggctgttgcc ggtgctgtgc   1080
caggcccacg gcttgacccc ggagcaggtg gtggccatcg ccagccacga tggcggcaag   1140
caggcgctgg agacggtcca gcggctgttg ccggtgctgt gccaggccca cggcttgacc   1200
ccccagcagg tggtggccat cgccagcaat aatggtggca agcaggcgct ggagacggtc   1260
cagcggctgt tgccggtgct gtgccaggcc cacggcttga ccccggagca ggtggtggcc   1320
atcgccagca atattggtgg caagcaggcg ctggagacgg tgcaggcgct gttgccggtg   1380
ctgtgccagg cccacggctt gaccccccag caggtggtgg ccatcgccag caataatggt   1440
ggcaagcagg cgctggagac ggtccagcgg ctgttgccgg tgctgtgcca ggcccacggc   1500
ttgaccccc agcaggtggt ggccatcgcc agcaataatg gtggcaagca ggcgctggag   1560
acggtccagc ggctgttgcc ggtgctgtgc caggcccacg gcttgacccc ccagcaggtg   1620
gtggccatcg ccagcaatgg cggtggcaag caggcgctgg agacggtcca gcggctgttg   1680
ccggtgctgt gccaggccca cggcttgacc ccggagcagg tggtggccat cgccagccac   1740
gatggcggca agcaggcgct ggagacggtc agcggctgt tgccggtgct gtgccaggcc   1800
cacggcttga ccccccagca ggtggtggcc atcgccagca ataatggtgg caagcaggcg   1860
ctggagacgg tccagcggct gttgccggtg ctgtgccagg cccacggctt gaccccggag   1920
caggtggtgg ccatcgccag ccacgatggc ggcaagcagg cgctggagac ggtccagcgg   1980
ctgttgccgg tgctgtgcca ggcccacggc ttgaccccctc agcaggtggt ggccatcgcc   2040
agcaatggcg gcggcaggcc ggcgctggag agcattgttg cccagttatc tcgccctgat   2100
ccggcgttgg ccgcgttgac caacgaccac ctcgtcgcct tggcctgcct cggcgggcgt   2160
cctgcgctgg atgcagtgaa aaagggattg ggggatccta tcagccgttc ccagctggtg   2220
aagtccgagc tggaggagaa gaaatccgag ttgaggcaca agctgaagta cgtgccccac   2280
gagtacatcg agctgatcga gatcgcccgg aacagcaccc aggaccgtat cctggagatg   2340
aaggtgatgg agttcttcat gaaggtgtac ggctacaggg caagcacct gggcggctcc   2400
aggaagcccg acgcgccat ctacaccgtg gcctccccca tcgactacgg cgtgatcgtg   2460
gacaccaagg cctactccgg cggctacaac ctgcccatcg ccaggccga cgaaatgcag   2520
aggtacgtgg aggagaacca gaccaggaac aagcacatca ccccaacga gtggtggaag   2580
gtgtacccct ccagcgtgac cgagttcaag ttcctgttcg tgtccggcca cttcaagggc   2640
aactacaagg cccagctgac caggctgaac cacatcacca actgcaacgg cgccgtgctg   2700
```

| tccgtggagg agctcctgat cggcggcgag atgatcaagg ccggcaccct gaccctggag | 2760 |
| gaggtgagga ggaagttcaa caacggcgag atcaacttcg cggccgactg ataa | 2814 |

<210> SEQ ID NO 54
<211> LENGTH: 2832
<212> TYPE: DNA
<213> ORGANISM: Artificialsequence
<220> FEATURE:
<223> OTHER INFORMATION: TRBC_T02-R TALEN

<400> SEQUENCE: 54

| atgggcgatc ctaaaaagaa acgtaaggtc atcgataagg agaccgccgc tgccaagttc | 60 |
| gagagacagc acatggacag catcgatatc gccgatctac gcacgctcgg ctacagccag | 120 |
| cagcaacagg agaagatcaa accgaaggtt cgttcgacag tggcgcagca ccacgaggca | 180 |
| ctggtcggcc acgggtttac acacgcgcac atcgttgcgt taagccaaca cccggcagcg | 240 |
| ttagggaccg tcgctgtcaa gtatcaggac atgatcgcag cgttgccaga ggcgacacac | 300 |
| gaagcgatcg ttggcgtcgg caaacagtgg tccggcgcac gcgctctgga ggccttgctc | 360 |
| acggtggcgg gagagttgag aggtccaccg ttacagttgg acacaggcca acttctcaag | 420 |
| attgcaaaac gtggcggcgt gaccgcagtg gaggcagtgc atgcatggcg caatgcactg | 480 |
| acgggtgccc cgctcaactt gacccccag caggtggtgg ccatcgccag caataatggt | 540 |
| ggcaagcagg cgctggagac ggtccagcgg ctgttgccgg tgctgtgcca ggcccacggc | 600 |
| ttgacccccc agcaggtggt ggccatcgcc agcaataatg gtggcaagca ggcgctggag | 660 |
| acggtccagc ggctgttgcc ggtgctgtgc caggcccacg gcttgacccc ccagcaggtg | 720 |
| gtggccatcg ccagcaataa tggtggcaag caggcgctgg agacggtcca gcggctgttg | 780 |
| ccggtgctgt gccaggccca cggcttgacc ccggagcagg tggtggccat cgccagcaat | 840 |
| attggtggca agcaggcgct ggagacggtg caggcgctgt gccggtgct gtgccaggcc | 900 |
| cacggcttga cccccagca ggtggtggcc atcgccagca ataatggtgg caagcaggcg | 960 |
| ctggagacgg tccagcggct gttgccggtc tgtgccagg cccacggctt gaccccggag | 1020 |
| caggtggtgg ccatcgccag caatattggt ggcaagcagg cgctggagac ggtgcaggcg | 1080 |
| ctgttgccgg tgctgtgcca ggcccacggc ttgacccccc agcaggtggt ggccatcgcc | 1140 |
| agcaatggcg gtggcaagca ggcgctggag acggtccagc ggctgttgcc ggtgctgtgc | 1200 |
| caggcccacg gcttgacccc ggagcaggtg gtggccatcg ccagccacga tggcggcaag | 1260 |
| caggcgctgg agacggtcca gcggctgttg ccggtgctgt gccaggccca cggcttgacc | 1320 |
| ccccagcagg tggtggccat cgccagcaat ggcggtggca agcaggcgct ggagacggtc | 1380 |
| cagcggctgt tgccggtgct gtgccaggcc cacggcttga ccccggagca ggtggtggcc | 1440 |
| atcgccagcc acgatggcgg caagcaggcg ctggagacgg tccagcggct gttgccggtg | 1500 |
| ctgtgccagg cccacggctt gacccccag caggtggtgg ccatcgccag caatggcggt | 1560 |
| ggcaagcagg cgctggagac ggtccagcgg ctgttgccgg tgctgtgcca ggcccacggc | 1620 |
| ttgacccccc agcaggtggt ggccatcgcc agcaataatg gtggcaagca ggcgctggag | 1680 |
| acggtccagc ggctgttgcc ggtgctgtgc caggcccacg gcttgacccc ggagcaggtg | 1740 |
| gtggccatcg ccagccacga tggcggcaag caggcgctgg agacggtcca gcggctgttg | 1800 |
| ccggtgctgt gccaggccca cggcttgacc ccccagcagg tggtggccat cgccagcaat | 1860 |
| ggcggtggca agcaggcgct ggagacggtc cagcggctgt gccggtgct gtgccaggcc | 1920 |

| | |
|---|---|
| cacggcttga cccccagca ggtggtggcc atcgccagca atggcggtgg caagcaggcg | 1980 |
| ctggagacgg tccagcggct gttgccggtg ctgtgccagg cccacggctt gaccccctcag | 2040 |
| caggtggtgg ccatcgccag caatggcggc ggcaggccgg cgctggagag cattgttgcc | 2100 |
| cagttatctc gccctgatcc ggcgttggcc gcgttgacca acgaccacct cgtcgccttg | 2160 |
| gcctgcctcg gcgggcgtcc tgcgctggat gcagtgaaaa agggattggg ggatcctatc | 2220 |
| agccgttccc agctggtgaa gtccgagctg gaggagaaga atccgagtt gaggcacaag | 2280 |
| ctgaagtacg tgccccacga gtacatcgag ctgatcgaga tcgcccggaa cagcacccag | 2340 |
| gaccgtatcc tggagatgaa ggtgatgag ttcttcatga aggtgtacgg ctacaggggc | 2400 |
| aagcacctgg gcggctccag gaagcccgac ggcgccatct acaccgtggg ctcccccatc | 2460 |
| gactacggcg tgatcgtgga caccaaggcc tactccggcg gctacaacct gcccatcggc | 2520 |
| caggccgacg aaatgcagag gtacgtggag gagaaccaga ccaggaacaa gcacatcaac | 2580 |
| cccaacgagt ggtggaaggt gtaccctcc agcgtgaccg agttcaagtt cctgttcgtg | 2640 |
| tccggccact tcaagggcaa ctacaaggcc cagctgacca ggctgaacca catcaccaac | 2700 |
| tgcaacggcg ccgtgctgtc cgtggaggag ctcctgatcg gcggcgagat gatcaaggcc | 2760 |
| ggcacctga ccctggagga ggtgaggagg aagttcaaca acggcgagat caacttcgcg | 2820 |
| gccgactgat aa | 2832 |

<210> SEQ ID NO 55
<211> LENGTH: 2814
<212> TYPE: DNA
<213> ORGANISM: Artificialsequence
<220> FEATURE:
<223> OTHER INFORMATION: CD52_T02-L TALEN

<400> SEQUENCE: 55

| | |
|---|---|
| atgggcgatc ctaaaaagaa acgtaaggtc atcgattacc catacgatgt tccagattac | 60 |
| gctatcgata tcgccgatct acgcacgctc ggctacagcc agcagcaaca ggagaagatc | 120 |
| aaaccgaagg ttcgttcgac agtggcgcag caccacgagg cactggtcgg ccacgggttt | 180 |
| acacacgcgc acatcgttgc gttaagccaa caccccggcag cgttagggac gtcgctgtc | 240 |
| aagtatcagg acatgatcgc agcgttgcca gaggcgacac acgaagcgat cgttggcgtc | 300 |
| ggcaaacagt ggtccggcgc acgcgctctg gaggccttgc tcacggtggc gggagagttg | 360 |
| agaggtccac cgttacagtt ggacacaggc caacttctca gattgcaaa acgtggcggc | 420 |
| gtgaccgcag tggaggcagt gcatgcatgg cgcaatgcac tgacgggtgc cccgctcaac | 480 |
| ttgacccccc agcaggtggt ggccatcgcc agcaatggcg gtggcaagca ggcgctggag | 540 |
| acggtccagc ggctgttgcc ggtgctgtgc caggcccacg gcttgacccc ggagcaggtg | 600 |
| gtggccatcg ccagccacga tggcggcaag caggcgctgg agacggtcca gcggctgttg | 660 |
| ccggtgctgt gccaggccca cggcttgacc ccggagcagg tggtggccat cgccagccac | 720 |
| gatggcggca gcaggcgct ggagacgtc cagcggctgt tgccggtgct gtgccaggcc | 780 |
| cacggcttga cccccagca ggtggtggcc atcgccagca atggcggtgg caagcaggcg | 840 |
| ctggagacgg tccagcggct gttgccggtg ctgtgccagg cccacggctt gaccccggag | 900 |
| caggtggtgg ccatcgccag ccacgatggc ggcaagcagg cgctggagac ggtccagcgg | 960 |
| ctgttgccgg tgctgtgcca ggcccacggc ttgaccccgg agcaggtggt ggccatcgcc | 1020 |
| agccacgatg cggcaagca ggcgctggag acggtccagc ggctgttgcc ggtgctgtgc | 1080 |
| caggcccacg gcttgacccc cagcaggtg gtggccatcg ccagcaatgg cggtggcaag | 1140 |

-continued

```
caggcgctgg agacggtcca gcggctgttg ccggtgctgt gccaggccca cggcttgacc    1200
ccggagcagg tggtggccat cgccagcaat attggtggca agcaggcgct ggagacggtg    1260
caggcgctgt tgccggtgct gtgccaggcc cacggcttga ccccggagca ggtggtggcc    1320
atcgccagcc acgatggcgg caagcaggcg ctggagacgg tccagcggct gttgccggtg    1380
ctgtgccagg cccacggctt gacccccag caggtggtgg ccatcgccag caatggcggt     1440
ggcaagcagg cgctggagac ggtccagcgg ctgttgccgg tgctgtgcca ggcccacggc    1500
ttgaccccgg agcaggtggt ggccatcgcc agccacgatg gcggcaagca ggcgctggag    1560
acggtccagc ggctgttgcc ggtgctgtgc aggcccacg gcttgacccc ggagcaggtg    1620
gtggccatcg ccagcaatat tggtggcaag caggcgctgg agacggtgca ggcgctgttg    1680
ccggtgctgt gccaggccca cggcttgacc ccggagcagg tggtggccat cgccagccac    1740
gatggcggca agcaggcgct ggagacggtc agcggctgt tgccggtgct gtgccaggcc    1800
cacggcttga ccccggagca ggtggtggcc atcgccagcc acgatggcgg caagcaggcg    1860
ctggagacgg tccagcggct gttgccggtg ctgtgccagg cccacggctt gaccccggag    1920
caggtggtgg ccatcgccag caatattggt ggcaagcagg cgctggagac ggtgcaggcg    1980
ctgttgccgg tgctgtgcca ggcccacggc ttgacccctc agcaggtggt ggccatcgcc    2040
agcaatggcg gcggcaggcc ggcgctggag agcattgttg cccagttatc tcgccctgat    2100
ccggcgttgg ccgcgttgac caacgaccac ctcgtcgcct tggcctgcct cggcgggcgt    2160
cctgcgctgg atgcagtgaa aaagggattg ggggatccta tcagccgttc ccagctggtg    2220
aagtccgagc tggaggagaa gaaatccgag ttgaggcaca gctgaagta cgtgcccac     2280 gagtacatcg agctgatcga gatcgcccgg aacagcaccc aggaccgtat cctggagatg    2340
aaggtgatgg agttcttcat gaaggtgtac ggctacaggg gcaagcacct gggcggctcc    2400
aggaagcccg acggcgccat ctacaccgtg ggctccccca tcgactacgg cgtgatcgtg    2460
gacaccaagg cctactccgg cggctacaac ctgcccatcg ccaggccga cgaaatgcag    2520 aggtacgtgg aggagaacca gaccaggaac aagcacatca accccaacga gtggtggaag    2580
gtgtacccct ccagcgtgac cgagttcaag ttcctgttcg tgtccggcca cttcaagggc    2640
aactacaagg cccagctgac caggctgaac cacatcacca actgcaacgg cgccgtgctg    2700
tccgtggagg agctcctgat cggcggcgag atgatcaagg ccggcaccct gaccctggag    2760
gaggtgagga ggaagttcaa caacggcgag atcaacttcg cggccgactg ataa           2814
```

<210> SEQ ID NO 56
<211> LENGTH: 2832
<212> TYPE: DNA
<213> ORGANISM: Artificialsequence
<220> FEATURE:
<223> OTHER INFORMATION: CD52_T02-R TALEN

<400> SEQUENCE: 56

```
atgggcgatc ctaaaaagaa acgtaaggtc atcgataagg agaccgccgc tgccaagttc     60
gagagacagc acatggacag catcgatatc gccgatctac gcacgctcgg ctacagccag    120
cagcaacagg agaagatcaa accgaaggtt cgttcgacag tggcgcagca ccacgaggca    180
ctggtcggcc acgggtttac acacgcgcac atcgttgcgt taagccaaca cccggcagcg    240
ttagggaccg tcgctgtcaa gtatcaggac atgatcgcag cgttgccaga ggcgacacac    300
gaagcgatcg ttggcgtcgg caaacagtgg tccggcgcac gcgctctgga ggccttgctc    360
```

```
acggtggcgg gagagttgag aggtccaccg ttacagttgg acacaggcca acttctcaag      420
attgcaaaac gtggcggcgt gaccgcagtg gaggcagtgc atgcatggcg caatgcactg      480
acgggtgccc cgctcaactt gaccccccag caggtggtgg ccatcgccag caatggcggt      540
ggcaagcagg cgctggagac ggtccagcgg ctgttgccgg tgctgtgcca ggcccacggc      600 ttgaccccc agcaggtggt ggccatcgcc agcaataatg gtggcaagca ggcgctggag       660
acggtccagc ggctgttgcc ggtgctgtgc caggcccacg gcttgacccc ggagcaggtg      720
gtggccatcg ccagccacga tggcggcaag caggcgctgg agacggtcca gcggctgttg      780
ccggtgctgt gccaggccca cggcttgacc cccagcagg tggtggccat cgccagcaat       840
ggcggtggca agcaggcgct ggagacggtc cagcggctgt tgccggtgct gtgccaggcc      900
cacggcttga ccccggagca ggtggtggcc atcgccagcc acgatggcgg caagcaggcg      960
ctggagacgg tccagcggct gttgccggtg ctgtgccagg cccacggctt gacccccag     1020 caggtggtgg ccatcgccag caatggcggt ggcaagcagg cgctggagac ggtccagcgg     1080
ctgttgccgg tgctgtgcca ggcccacggc ttgaccccc agcaggtggt ggccatcgcc      1140
agcaatggcg gtggcaagca ggcgctggag acggtccagc ggctgttgcc ggtgctgtgc     1200
caggcccacg gcttgacccc ggagcaggtg gtggccatcg ccagcaatat tggtggcaag     1260
caggcgctgg agacggtgca ggcgctgttg ccggtgctgt gccaggccca cggcttgacc     1320
ccggagcagg tggtggccat cgccagccac gatggcggca agcaggcgct ggagacggtc     1380
cagcggctgt tgccggtgct gtgccaggcc cacggcttga ccccggagca ggtggtggcc     1440
atcgccagcc acgatggcgg caagcaggcg ctggagacgg tccagcggct gttgccggtg     1500
ctgtgccagg cccacggctt gacccccag caggtggtgg ccatcgccag caatggcggt      1560
ggcaagcagg cgctggagac ggtccagcgg ctgttgccgg tgctgtgcca ggcccacggc     1620 ttgaccccc agcaggtggt ggccatcgcc agcaataatg gtggcaagca ggcgctggag      1680
acggtccagc ggctgttgcc ggtgctgtgc caggcccacg gcttgacccc ccagcaggtg     1740
gtggccatcg ccagcaatgg cggtggcaag caggcgctgg agacggtcca gcggctgttg     1800
ccggtgctgt gccaggccca cggcttgacc ccggagcagg tggtggccat cgccagcaat     1860
attggtggca agcaggcgct ggagacggtg caggcgctgt gccggtgct gtgccaggcc      1920 cacggcttga ccccggagca ggtggtggcc atcgccagcc acgatggcgg caagcaggcg     1980
ctggagacgg tccagcggct gttgccggtg ctgtgccagg cccacggctt gaccctcag     2040 caggtggtgg ccatcgccag caatggcggc ggcaggccgg cgctggagag cattgttgcc     2100
cagttatctc gccctgatcc ggcgttggcc gcgttgacca acgaccacct cgtcgccttg     2160
gcctgcctcg gcgggcgtcc tgcgctggat gcagtgaaaa agggattggg ggatcctatc     2220
agccgttccc agctggtgaa gtccgagctg gaggagaaga atccgagtt gaggcacaag      2280 ctgaagtacg tgccccacga gtacatcgag ctgatcgaga tcgcccggaa cagcacccag     2340
gaccgtatcc tggagatgaa ggtgatggag ttcttcatga aggtgtacgg ctacaggggc     2400
aagcacctgg gcggctccag gaagcccgac ggcgccatct acaccgtggg ctcccccatc     2460
gactacggcg tgatcgtgga caccaaggcc tactccggcg gctacaacct gcccatcggc     2520
caggccgacg aaatgcagag gtacgtggag gagaaccaga ccaggaacaa gcacatcaac     2580
cccaacgagt ggtggaaggt gtaccctcc agcgtgaccg agttcaagtt cctgttcgtg      2640 tccgccact tcaagggcaa ctacaaggcc agctgacca ggctgaacca catcaccaac       2700
tgcaacggcg ccgtgctgtc cgtggaggag ctcctgatcg gcggcgagat gatcaaggcc     2760
```

```
ggcaccctga ccctggagga ggtgaggagg aagttcaaca acggcgagat caacttcgcg        2820
gccgactgat aa                                                           2832

<210> SEQ ID NO 57
<211> LENGTH: 49
<212> TYPE: DNA
<213> ORGANISM: Artificialsequence
<220> FEATURE:
<223> OTHER INFORMATION: TRAC_T02

<400> SEQUENCE: 57
tttagaaagt tcctgtgatg tcaagctggt cgagaaaagc tttgaaaca                    49

<210> SEQ ID NO 58
<211> LENGTH: 49
<212> TYPE: DNA
<213> ORGANISM: Artificialsequence
<220> FEATURE:
<223> OTHER INFORMATION: TRAC_T03

<400> SEQUENCE: 58
tccagtgaca agtctgtctg cctattcacc gattttgatt ctcaaacaa                    49

<210> SEQ ID NO 59
<211> LENGTH: 49
<212> TYPE: DNA
<213> ORGANISM: Artificialsequence
<220> FEATURE:
<223> OTHER INFORMATION: TRAC_T04

<400> SEQUENCE: 59
tatatcacag acaaaactgt gctagacatg aggtctatgg acttcaaga                    49

<210> SEQ ID NO 60
<211> LENGTH: 49
<212> TYPE: DNA
<213> ORGANISM: Artificialsequence
<220> FEATURE:
<223> OTHER INFORMATION: TRAC_T05

<400> SEQUENCE: 60
tgaggtctat ggacttcaag agcaacagtg ctgtggcctg gagcaacaa                    49

<210> SEQ ID NO 61
<211> LENGTH: 47
<212> TYPE: DNA
<213> ORGANISM: Artificial sequence
<220> FEATURE:
<223> OTHER INFORMATION: CD52_T01

<400> SEQUENCE: 61
ttcctcttcc tcctaccacc atcagcctcc tttacctgta ccataac                      47

<210> SEQ ID NO 62
<211> LENGTH: 43
<212> TYPE: DNA
<213> ORGANISM: Artificial sequence
<220> FEATURE:
<223> OTHER INFORMATION: CD52_T04

<400> SEQUENCE: 62
ttcctcctac tcaccacagc ctcctggtct tacctgtacc ata                          43

<210> SEQ ID NO 63
```

```
<211> LENGTH: 43
<212> TYPE: DNA
<213> ORGANISM: Artificial sequence
<220> FEATURE:
<223> OTHER INFORMATION: CD52_T05

<400> SEQUENCE: 63
tcctactcac catcagctcc tggttatttg ctcttacctg tac                 43

<210> SEQ ID NO 64
<211> LENGTH: 47
<212> TYPE: DNA
<213> ORGANISM: Artificial sequence
<220> FEATURE:
<223> OTHER INFORMATION: CD52_T06

<400> SEQUENCE: 64
ttatcccact tctcctctac agatacaaac tttttgtcct gagagtc             47

<210> SEQ ID NO 65
<211> LENGTH: 47
<212> TYPE: DNA
<213> ORGANISM: Artificial sequence
<220> FEATURE:
<223> OTHER INFORMATION: CD52_T07

<400> SEQUENCE: 65
tggactctca ggacaaacga caccagccaa atgctgaggg gctgctg             47

<210> SEQ ID NO 66
<211> LENGTH: 60
<212> TYPE: DNA
<213> ORGANISM: Artificial sequence
<220> FEATURE:
<223> OTHER INFORMATION: Forward primer CD52
<220> FEATURE:
<221> NAME/KEY: misc_feature
<222> LOCATION: (31); (32); (33); (34); (35); (36); (37); (38); (39);
      (40)
<223> OTHER INFORMATION: n is a or c or t or g

<400> SEQUENCE: 66
ccatctcatc cctgcgtgtc tccgactcag nnnnnnnnnn cagatctgca gaaaggaagc   60

<210> SEQ ID NO 67
<211> LENGTH: 61
<212> TYPE: DNA
<213> ORGANISM: Artificial sequence
<220> FEATURE:
<223> OTHER INFORMATION: Forward primer TRAC
<220> FEATURE:
<221> NAME/KEY: misc_feature
<222> LOCATION: (31); (32); (33); (34); (35); (36); (37); (38); (39);
      (40)
<223> OTHER INFORMATION: n is a or c or t or g

<400> SEQUENCE: 67
ccatctcatc cctgcgtgtc tccgactcag nnnnnnnnnn atcactggca tctggactcc   60
a                                                                  61

<210> SEQ ID NO 68
<211> LENGTH: 62
<212> TYPE: DNA
<213> ORGANISM: Artificial sequence
<220> FEATURE:
<223> OTHER INFORMATION: Forward primer TRBC1
<220> FEATURE:
<221> NAME/KEY: misc_feature
```

<222> LOCATION: (31); (32); (33); (34); (35); (36); (37); (38); (39); (40)
<223> OTHER INFORMATION: n is a or c or t or g

<400> SEQUENCE: 68
ccatctcatc cctgcgtgtc tccgactcag nnnnnnnnnn agagcccta ccagaaccag    60 ac    62

<210> SEQ ID NO 69
<211> LENGTH: 62
<212> TYPE: DNA
<213> ORGANISM: Artificial sequence
<220> FEATURE:
<223> OTHER INFORMATION: Forward primer TRBC2
<220> FEATURE:
<221> NAME/KEY: misc_feature
<222> LOCATION: (31); (32); (33); (34); (35); (36); (37); (38); (39); (40)
<223> OTHER INFORMATION: n is a or c or t or g

<400> SEQUENCE: 69
ccatctcatc cctgcgtgtc tccgactcag nnnnnnnnnn ggacctagta acataattgt    60
gc    62

<210> SEQ ID NO 70
<211> LENGTH: 51
<212> TYPE: DNA
<213> ORGANISM: Artificial sequence
<220> FEATURE:
<223> OTHER INFORMATION: Reverse primer GR CD52

<400> SEQUENCE: 70
cctatcccct gtgtgccttg gcagtctcag cctgttggag tccatctgct g    51

<210> SEQ ID NO 71
<211> LENGTH: 50
<212> TYPE: DNA
<213> ORGANISM: Artificial sequence
<220> FEATURE:
<223> OTHER INFORMATION: Reverse primer GR TRAC

<400> SEQUENCE: 71
cctatcccct gtgtgccttg gcagtctcag cctcatgtct agcacagttt    50

<210> SEQ ID NO 72
<211> LENGTH: 51
<212> TYPE: DNA
<213> ORGANISM: Artificial sequence
<220> FEATURE:
<223> OTHER INFORMATION: Reverse primer GR TRBC1-2

<400> SEQUENCE: 72
cctatcccct gtgtgccttg gcagtctcag accagctcag ctccacgtgg t    51

<210> SEQ ID NO 73
<211> LENGTH: 495
<212> TYPE: PRT
<213> ORGANISM: Artificial sequence
<220> FEATURE:
<223> OTHER INFORMATION: anti-CD19 CAR

<400> SEQUENCE: 73

Met Glu Thr Asp Thr Leu Leu Leu Trp Val Leu Leu Leu Trp Val Pro
1               5                   10                  15

Gly Ser Thr Gly Glu Val Gln Leu Gln Gln Ser Gly Pro Glu Leu Ile

```
            20                  25                  30
Lys Pro Gly Ala Ser Val Lys Met Ser Cys Lys Ala Ser Gly Tyr Thr
            35                  40                  45
Phe Thr Ser Tyr Val Met His Trp Val Lys Gln Lys Pro Gly Gln Gly
            50                  55                  60
Leu Glu Trp Ile Gly Tyr Ile Asn Pro Tyr Asn Asp Gly Thr Lys Tyr
 65                  70                  75                  80
Asn Glu Lys Phe Lys Gly Lys Ala Thr Leu Thr Ser Asp Lys Ser Ser
                85                  90                  95
Ser Thr Ala Tyr Met Glu Leu Ser Ser Leu Thr Ser Glu Asp Ser Ala
               100                 105                 110
Val Tyr Tyr Cys Ala Arg Gly Thr Tyr Tyr Gly Ser Arg Val Phe
               115                 120                 125
Asp Tyr Trp Gly Gln Gly Thr Thr Leu Thr Val Ser Ser Gly Gly Gly
               130                 135                 140
Gly Ser Gly Gly Gly Gly Ser Gly Gly Gly Gly Ser Asp Ile Val Met
145                 150                 155                 160
Thr Gln Ala Ala Pro Ser Ile Pro Val Thr Pro Gly Glu Ser Val Ser
               165                 170                 175
Ile Ser Cys Arg Ser Ser Lys Ser Leu Leu Asn Ser Asn Gly Asn Thr
               180                 185                 190
Tyr Leu Tyr Trp Phe Leu Gln Arg Pro Gly Gln Ser Pro Gln Leu Leu
               195                 200                 205
Ile Tyr Arg Met Ser Asn Leu Ala Ser Gly Val Pro Asp Arg Phe Ser
               210                 215                 220
Gly Ser Gly Ser Gly Thr Ala Phe Thr Leu Arg Ile Ser Arg Val Glu
225                 230                 235                 240
Ala Glu Asp Val Gly Val Tyr Tyr Cys Met Gln His Leu Glu Tyr Pro
               245                 250                 255
Phe Thr Phe Gly Ala Gly Thr Lys Leu Glu Leu Lys Arg Ser Asp Pro
               260                 265                 270
Thr Thr Thr Pro Ala Pro Arg Pro Pro Thr Pro Ala Pro Thr Ile Ala
               275                 280                 285
Ser Gln Pro Leu Ser Leu Arg Pro Glu Ala Cys Arg Pro Ala Ala Gly
               290                 295                 300
Gly Ala Val His Thr Arg Gly Leu Asp Phe Ala Cys Asp Ile Tyr Ile
305                 310                 315                 320
Trp Ala Pro Leu Ala Gly Thr Cys Gly Val Leu Leu Leu Ser Leu Val
               325                 330                 335
Ile Thr Leu Tyr Cys Lys Arg Gly Arg Lys Lys Leu Leu Tyr Ile Phe
               340                 345                 350
Lys Gln Pro Phe Met Arg Pro Val Gln Thr Thr Gln Glu Glu Asp Gly
               355                 360                 365
Cys Ser Cys Arg Phe Pro Glu Glu Glu Glu Gly Gly Cys Glu Leu Arg
               370                 375                 380
Val Lys Phe Ser Arg Ser Ala Asp Ala Pro Ala Tyr Gln Gln Gly Gln
385                 390                 395                 400
Asn Gln Leu Tyr Asn Glu Leu Asn Leu Gly Arg Arg Glu Glu Tyr Asp
               405                 410                 415
Val Leu Asp Lys Arg Arg Gly Arg Asp Pro Glu Met Gly Gly Lys Pro
               420                 425                 430
Arg Arg Lys Asn Pro Gln Glu Gly Leu Tyr Asn Glu Leu Gln Lys Asp
               435                 440                 445
```

```
Lys Met Ala Glu Ala Tyr Ser Glu Ile Gly Met Lys Gly Glu Arg Arg
        450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495

<210> SEQ ID NO 74
<211> LENGTH: 49
<212> TYPE: DNA
<213> ORGANISM: Artificial sequence
<220> FEATURE:
<223> OTHER INFORMATION: CTLA4_T01

<400> SEQUENCE: 74
tggccctgca ctctcctgtt ttttcttctc ttcatccctg tcttctgca                    49

<210> SEQ ID NO 75
<211> LENGTH: 49
<212> TYPE: DNA
<213> ORGANISM: Artificial sequence
<220> FEATURE:
<223> OTHER INFORMATION: CTLA4_T03

<400> SEQUENCE: 75
ttttccatgc tagcaatgca cgtggcccag cctgctgtgg tactggcca                    49

<210> SEQ ID NO 76
<211> LENGTH: 49
<212> TYPE: DNA
<213> ORGANISM: Artificial sequence
<220> FEATURE:
<223> OTHER INFORMATION: CTLA4_T04

<400> SEQUENCE: 76
tccatgctag caatgcacgt ggcccagcct gctgtggtac tggccagca                    49

<210> SEQ ID NO 77
<211> LENGTH: 49
<212> TYPE: DNA
<213> ORGANISM: Artificial sequence
<220> FEATURE:
<223> OTHER INFORMATION: PDCD1_T01

<400> SEQUENCE: 77
ttctccccag ccctgctcgt ggtgaccgaa ggggacaacg ccaccttca                    49

<210> SEQ ID NO 78
<211> LENGTH: 49
<212> TYPE: DNA
<213> ORGANISM: Artificial sequence
<220> FEATURE:
<223> OTHER INFORMATION: PDCD1_T03

<400> SEQUENCE: 78
tacctctgtg gggccatctc cctggccccc aaggcgcaga tcaaagaga                    49

<210> SEQ ID NO 79
<211> LENGTH: 530
<212> TYPE: PRT
<213> ORGANISM: Artificial sequence
<220> FEATURE:
<223> OTHER INFORMATION: Repeat CTLA4_T01-L

<400> SEQUENCE: 79
```

```
Leu Thr Pro Gln Gln Val Val Ala Ile Ala Ser Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Asn Gly
        35                  40                  45

Gly Lys Gln Ala Leu Glu Thr Val Gln Arg Leu Leu Pro Val Leu Cys
50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Gln Gln Val
            165                 170                 175

Val Ala Ile Ala Ser Asn Gly Gly Lys Gln Ala Leu Glu Thr Val
        180                 185                 190

Gln Arg Leu Leu Pro Val Leu Cys Gln Ala His Gly Leu Thr Pro Gln
            195                 200                 205

Gln Val Val Ala Ile Ala Ser Asn Asn Gly Gly Lys Gln Ala Leu Glu
        210                 215                 220

Thr Val Gln Arg Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
            245                 250                 255

Leu Glu Thr Val Gln Arg Leu Leu Pro Val Leu Cys Gln Ala His Gly
        260                 265                 270

Leu Thr Pro Glu Gln Val Val Ala Ile Ala Ser Asn Ile Gly Gly Lys
    275                 280                 285

Gln Ala Leu Glu Thr Val Gln Ala Leu Leu Pro Val Leu Cys Gln Ala
290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
            325                 330                 335

Gln Ala His Gly Leu Thr Pro Gln Gln Val Val Ala Ile Ala Ser Asn
        340                 345                 350

Gly Gly Gly Lys Gln Ala Leu Glu Thr Val Gln Arg Leu Leu Pro Val
    355                 360                 365

Leu Cys Gln Ala His Gly Leu Thr Pro Glu Gln Val Val Ala Ile Ala
370                 375                 380

Ser His Asp Gly Gly Lys Gln Ala Leu Glu Thr Val Gln Arg Leu Leu
385                 390                 395                 400

Pro Val Leu Cys Gln Ala His Gly Leu Thr Pro Gln Gln Val Val Ala
            405                 410                 415
```

```
Ile Ala Ser Asn Gly Gly Lys Gln Ala Leu Glu Thr Val Gln Arg
            420                 425                 430

Leu Leu Pro Val Leu Cys Gln Ala His Gly Leu Thr Pro Glu Gln Val
    435                 440                 445

Val Ala Ile Ala Ser His Asp Gly Gly Lys Gln Ala Leu Glu Thr Val
    450                 455                 460

Gln Arg Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Arg Pro Ala
        515                 520                 525

Leu Glu
    530

<210> SEQ ID NO 80
<211> LENGTH: 530
<212> TYPE: PRT
<213> ORGANISM: Artificial sequence
<220> FEATURE:
<223> OTHER INFORMATION: Repeat CTLA4_T01-R

<400> SEQUENCE: 80

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser Asn
65                  70                  75                  80

Ile Gly Gly Lys Gln Ala Leu Glu Thr Val Gln Ala Leu Leu Pro Val
                85                  90                  95

Leu Cys Gln Ala His Gly Leu Thr Pro Gln Gln Val Val Ala Ile Ala
            100                 105                 110

Ser Asn Asn Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser Asn Ile Gly Gly Lys Gln Ala Leu Glu Thr Val Gln Ala
145                 150                 155                 160

Leu Leu Pro Val Leu Cys Gln Ala His Gly Leu Thr Pro Glu Gln Val
                165                 170                 175

Val Ala Ile Ala Ser Asn Ile Gly Gly Lys Gln Ala Leu Glu Thr Val
            180                 185                 190

Gln Ala Leu Leu Pro Val Leu Cys Gln Ala His Gly Leu Thr Pro Gln
        195                 200                 205

Gln Val Val Ala Ile Ala Ser Asn Asn Gly Gly Lys Gln Ala Leu Glu
    210                 215                 220

Thr Val Gln Arg Leu Leu Pro Val Leu Cys Gln Ala His Gly Leu Thr
225                 230                 235                 240
```

```
Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
        260                 265                 270

Leu Thr Pro Glu Gln Val Val Ala Ile Ala Ser His Asp Gly Gly Lys
    275                 280                 285

Gln Ala Leu Glu Thr Val Gln Arg Leu Leu Pro Val Leu Cys Gln Ala
290                 295                 300

His Gly Leu Thr Pro Glu Gln Val Val Ala Ile Ala Ser Asn Ile Gly
305                 310                 315                 320

Gly Lys Gln Ala Leu Glu Thr Val Gln Ala Leu Leu Pro Val Leu Cys
                325                 330                 335

Gln Ala His Gly Leu Thr Pro Gln Gln Val Val Ala Ile Ala Ser Asn
            340                 345                 350

Asn Gly Gly Lys Gln Ala Leu Glu Thr Val Gln Arg Leu Leu Pro Val
        355                 360                 365

Leu Cys Gln Ala His Gly Leu Thr Pro Gln Gln Val Val Ala Ile Ala
    370                 375                 380

Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Gln Gln Val Val Ala
                405                 410                 415

Ile Ala Ser Asn Asn Gly Gly Lys Gln Ala Leu Glu Thr Val Gln Arg
            420                 425                 430

Leu Leu Pro Val Leu Cys Gln Ala His Gly Leu Thr Pro Glu Gln Val
        435                 440                 445

Val Ala Ile Ala Ser Asn Ile Gly Gly Lys Gln Ala Leu Glu Thr Val
    450                 455                 460

Gln Ala Leu Leu Pro Val Leu Cys Gln Ala His Gly Leu Thr Pro Gln
465                 470                 475                 480

Gln Val Val Ala Ile Ala Ser Asn Gly Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530

<210> SEQ ID NO 81
<211> LENGTH: 530
<212> TYPE: PRT
<213> ORGANISM: Artificial sequence
<220> FEATURE:
<223> OTHER INFORMATION: RepeatCTLA4_T03-L

<400> SEQUENCE: 81

Leu Thr Pro Gln Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Gly Gly
        35                  40                  45

Gly Lys Gln Ala Leu Glu Thr Val Gln Arg Leu Leu Pro Val Leu Cys
    50                  55                  60
```

```
Gln Ala His Gly Leu Thr Pro Gln Gln Val Val Ala Ile Ala Ser Asn
 65                  70                  75                  80

Gly Gly Gly Lys Gln Ala Leu Glu Thr Val Gln Arg Leu Leu Pro Val
             85                  90                  95

Leu Cys Gln Ala His Gly Leu Thr Pro Glu Gln Val Val Ala Ile Ala
        100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
        130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser Asn Ile Gly Gly Lys Gln Ala Leu Glu Thr Val
            180                 185                 190

Gln Ala Leu Leu Pro Val Leu Cys Gln Ala His Gly Leu Thr Pro Gln
        195                 200                 205

Gln Val Val Ala Ile Ala Ser Asn Gly Gly Gly Lys Gln Ala Leu Glu
        210                 215                 220

Thr Val Gln Arg Leu Leu Pro Val Leu Cys Gln Ala His Gly Leu Thr
225                 230                 235                 240

Pro Gln Gln Val Val Ala Ile Ala Ser Asn Gly Gly Lys Gln Ala
                245                 250                 255

Leu Glu Thr Val Gln Arg Leu Leu Pro Val Leu Cys Gln Ala His Gly
        260                 265                 270

Leu Thr Pro Glu Gln Val Val Ala Ile Ala Ser His Asp Gly Gly Lys
        275                 280                 285

Gln Ala Leu Glu Thr Val Gln Arg Leu Leu Pro Val Leu Cys Gln Ala
        290                 295                 300

His Gly Leu Thr Pro Gln Gln Val Val Ala Ile Ala Ser Asn Gly Gly
305                 310                 315                 320

Gly Lys Gln Ala Leu Glu Thr Val Gln Arg Leu Leu Pro Val Leu Cys
        325                 330                 335

Gln Ala His Gly Leu Thr Pro Glu Gln Val Val Ala Ile Ala Ser Asn
        340                 345                 350

Ile Gly Gly Lys Gln Ala Leu Glu Thr Val Gln Ala Leu Leu Pro Val
        355                 360                 365

Leu Cys Gln Ala His Gly Leu Thr Pro Gln Gln Val Val Ala Ile Ala
        370                 375                 380

Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
            405                 410                 415

Ile Ala Ser His Asp Gly Gly Lys Gln Ala Leu Glu Thr Val Gln Arg
            420                 425                 430

Leu Leu Pro Val Leu Cys Gln Ala His Gly Leu Thr Pro Glu Gln Val
            435                 440                 445

Val Ala Ile Ala Ser Asn Ile Gly Gly Lys Gln Ala Leu Glu Thr Val
            450                 455                 460

Gln Ala Leu Leu Pro Val Leu Cys Gln Ala His Gly Leu Thr Pro Glu
465                 470                 475                 480

Gln Val Val Ala Ile Ala Ser Asn Ile Gly Gly Lys Gln Ala Leu Glu
```

```
                            485                 490                 495
Thr Val Gln Ala Leu Leu Pro Val Leu Cys Gln Ala His Gly Leu Thr
                500                 505                 510

Pro Gln Gln Val Val Ala Ile Ala Ser Asn Gly Gly Arg Pro Ala
        515                 520                 525

Leu Glu
    530

<210> SEQ ID NO 82
<211> LENGTH: 530
<212> TYPE: PRT
<213> ORGANISM: Artificial sequence
<220> FEATURE:
<223> OTHER INFORMATION: Repeat CTLA4_T03-R

<400> SEQUENCE: 82

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Asn Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser Asn Ile Gly Gly Lys Gln Ala Leu Glu Thr Val Gln Ala
145                 150                 155                 160

Leu Leu Pro Val Leu Cys Gln Ala His Gly Leu Thr Pro Gln Gln Val
                165                 170                 175

Val Ala Ile Ala Ser Asn Asn Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
            260                 265                 270

Leu Thr Pro Glu Gln Val Val Ala Ile Ala Ser His Asp Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser His Asp Gly
```

```
              305                 310                 315                 320
Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
                340                 345                 350

Ile Gly Gly Lys Gln Ala Leu Glu Thr Val Gln Ala Leu Leu Pro Val
                355                 360                 365

Leu Cys Gln Ala His Gly Leu Thr Pro Glu Gln Val Val Ala Ile Ala
        370                 375                 380

Ser His Asp Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser Asn Ile Gly Gly Lys Gln Ala Leu Glu Thr Val Gln Ala
                420                 425                 430

Leu Leu Pro Val Leu Cys Gln Ala His Gly Leu Thr Pro Gln Gln Val
                435                 440                 445

Val Ala Ile Ala Ser Asn Asn Gly Gly Lys Gln Ala Leu Glu Thr Val
        450                 455                 460

Gln Arg Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
                500                 505                 510

Pro Gln Gln Val Val Ala Ile Ala Ser Asn Gly Gly Gly Arg Pro Ala
                515                 520                 525

Leu Glu
    530

<210> SEQ ID NO 83
<211> LENGTH: 530
<212> TYPE: PRT
<213> ORGANISM: Artificial sequence
<220> FEATURE:
<223> OTHER INFORMATION: Repeat CTLA4_T04-L

<400> SEQUENCE: 83

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
                20                  25                  30

His Gly Leu Thr Pro Glu Gln Val Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser Asn
65                  70                  75                  80

Ile Gly Gly Lys Gln Ala Leu Glu Thr Val Gln Ala Leu Leu Pro Val
                85                  90                  95

Leu Cys Gln Ala His Gly Leu Thr Pro Gln Gln Val Val Ala Ile Ala
                100                 105                 110

Ser Asn Gly Gly Gly Lys Gln Ala Leu Glu Thr Val Gln Arg Leu Leu
            115                 120                 125

Pro Val Leu Cys Gln Ala His Gly Leu Thr Pro Gln Gln Val Val Ala
```

```
            130                 135                 140
Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
            260                 265                 270

Leu Thr Pro Gln Gln Val Val Ala Ile Ala Ser Asn Asn Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
            340                 345                 350

Ile Gly Gly Lys Gln Ala Leu Glu Thr Val Gln Ala Leu Leu Pro Val
        355                 360                 365

Leu Cys Gln Ala His Gly Leu Thr Pro Glu Gln Val Val Ala Ile Ala
    370                 375                 380

Ser Asn Ile Gly Gly Lys Gln Ala Leu Glu Thr Val Gln Ala Leu Leu
385                 390                 395                 400

Pro Val Leu Cys Gln Ala His Gly Leu Thr Pro Gln Gln Val Val Ala
                405                 410                 415

Ile Ala Ser Asn Gly Gly Lys Gln Ala Leu Glu Thr Val Gln Arg
            420                 425                 430

Leu Leu Pro Val Leu Cys Gln Ala His Gly Leu Thr Pro Gln Gln Val
        435                 440                 445

Val Ala Ile Ala Ser Asn Asn Gly Gly Lys Gln Ala Leu Glu Thr Val
    450                 455                 460

Gln Arg Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530

<210> SEQ ID NO 84
```

<211> LENGTH: 530
<212> TYPE: PRT
<213> ORGANISM: Artificial sequence
<220> FEATURE:
<223> OTHER INFORMATION: Repeat CTLA4_T04-R

<400> SEQUENCE: 84

```
Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
            100                 105                 110

Ser Asn Asn Gly Gly Lys Gln Ala Leu Glu Thr Val Gln Arg Leu Leu
        115                 120                 125

Pro Val Leu Cys Gln Ala His Gly Leu Thr Pro Gln Gln Val Val Ala
    130                 135                 140

Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser His Asp Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
            260                 265                 270

Leu Thr Pro Gln Gln Val Val Ala Ile Ala Ser Asn Asn Gly Gly Lys
        275                 280                 285

Gln Ala Leu Glu Thr Val Gln Arg Leu Leu Pro Val Leu Cys Gln Ala
    290                 295                 300

His Gly Leu Thr Pro Gln Gln Val Val Ala Ile Ala Ser Asn Gly Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
            340                 345                 350

Ile Gly Gly Lys Gln Ala Leu Glu Thr Val Gln Ala Leu Leu Pro Val
        355                 360                 365

Leu Cys Gln Ala His Gly Leu Thr Pro Glu Gln Val Val Ala Ile Ala
    370                 375                 380
```

```
Ser His Asp Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
            405                 410                 415

Ile Ala Ser His Asp Gly Gly Lys Gln Ala Leu Glu Thr Val Gln Arg
        420                 425                 430

Leu Leu Pro Val Leu Cys Gln Ala His Gly Leu Thr Pro Glu Gln Val
            435                 440                 445

Val Ala Ile Ala Ser Asn Ile Gly Gly Lys Gln Ala Leu Glu Thr Val
        450                 455                 460

Gln Ala Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Arg Pro Ala
        515                 520                 525

Leu Glu
    530

<210> SEQ ID NO 85
<211> LENGTH: 530
<212> TYPE: PRT
<213> ORGANISM: Artificial sequence
<220> FEATURE:
<223> OTHER INFORMATION: Repeat PDCD1_T01-L

<400> SEQUENCE: 85

Leu Thr Pro Gln Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205
```

Gln Val Val Ala Ile Ala Ser His Asp Gly Gly Lys Gln Ala Leu Glu
                210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
                260                 265                 270

Leu Thr Pro Gln Gln Val Val Ala Ile Ala Ser Asn Gly Gly Lys
            275                 280                 285

Gln Ala Leu Glu Thr Val Gln Arg Leu Leu Pro Val Leu Cys Gln Ala
            290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser His
                340                 345                 350

Asp Gly Gly Lys Gln Ala Leu Glu Thr Val Gln Arg Leu Leu Pro Val
            355                 360                 365

Leu Cys Gln Ala His Gly Leu Thr Pro Glu Gln Val Val Ala Ile Ala
370                 375                 380

Ser His Asp Gly Gly Lys Gln Ala Leu Glu Thr Val Gln Arg Leu Leu
385                 390                 395                 400

Pro Val Leu Cys Gln Ala His Gly Leu Thr Pro Gln Gln Val Val Ala
                405                 410                 415

Ile Ala Ser Asn Gly Gly Gly Lys Gln Ala Leu Glu Thr Val Gln Arg
                420                 425                 430

Leu Leu Pro Val Leu Cys Gln Ala His Gly Leu Thr Pro Gln Gln Val
            435                 440                 445

Val Ala Ile Ala Ser Asn Asn Gly Gly Lys Gln Ala Leu Glu Thr Val
        450                 455                 460

Gln Arg Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Arg Pro Ala
            515                 520                 525

Leu Glu
    530

<210> SEQ ID NO 86
<211> LENGTH: 529
<212> TYPE: PRT
<213> ORGANISM: Artificial sequence
<220> FEATURE:
<223> OTHER INFORMATION: RepeatPDCD1_T01-R

<400> SEQUENCE: 86

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Ala Ile Ala Ser Asn Ile Gly
         35                  40                  45

Gly Lys Gln Ala Leu Glu Thr Val Gln Ala Leu Leu Pro Val Leu Cys
 50                  55                  60

Gln Ala His Gly Leu Thr Pro Glu Gln Val Val Ala Ile Ala Ser Asn
 65                  70                  75                  80

Ile Gly Gly Lys Gln Ala Leu Glu Thr Val Gln Ala Leu Leu Pro Val
                 85                  90                  95

Leu Cys Gln Ala His Gly Leu Thr Pro Gln Gln Val Val Ala Ile Ala
                100                 105                 110

Ser Asn Asn Gly Gly Lys Gln Ala Leu Glu Thr Val Gln Arg Leu Leu
            115                 120                 125

Pro Val Leu Cys Gln Ala His Gly Leu Thr Pro Gln Gln Val Val Ala
        130                 135                 140

Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Gly Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Asn Gly Gly Lys Gln Ala Leu Glu
210                 215                 220

Thr Val Gln Arg Leu Leu Pro Val Leu Cys Gln Ala His Gly Leu Thr
225                 230                 235                 240

Pro Gln Gln Val Val Ala Ile Ala Ser Asn Asn Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser Asn Gly Gly Lys Gln
        275                 280                 285

Ala Leu Glu Thr Val Gln Arg Leu Leu Pro Val Leu Cys Gln Ala His
        290                 295                 300

Gly Leu Thr Pro Gln Gln Val Val Ala Ile Ala Ser Asn Asn Gly Gly
305                 310                 315                 320

Lys Gln Ala Leu Glu Thr Val Gln Arg Leu Leu Pro Val Leu Cys Gln
                325                 330                 335

Ala His Gly Leu Thr Pro Gln Gln Val Val Ala Ile Ala Ser Asn Gly
            340                 345                 350

Gly Gly Lys Gln Ala Leu Glu Thr Val Gln Arg Leu Leu Pro Val Leu
        355                 360                 365

Cys Gln Ala His Gly Leu Thr Pro Gln Gln Val Val Ala Ile Ala Ser
370                 375                 380

Asn Gly Gly Gly Lys Gln Ala Leu Glu Thr Val Gln Arg Leu Leu Pro
385                 390                 395                 400

Val Leu Cys Gln Ala His Gly Leu Thr Pro Gln Gln Val Val Ala Ile
                405                 410                 415

Ala Ser Asn Asn Gly Gly Lys Gln Ala Leu Glu Thr Val Gln Arg Leu
            420                 425                 430

Leu Pro Val Leu Cys Gln Ala His Gly Leu Thr Pro Gln Gln Val Val
        435                 440                 445

```
Ala Ile Ala Ser Asn Gly Gly Gly Lys Gln Ala Leu Glu Thr Val Gln
    450                 455                 460

Arg Leu Leu Pro Val Leu Cys Gln Ala His Gly Leu Thr Pro Glu Gln
465                 470                 475                 480

Val Val Ala Ile Ala Ser His Asp Gly Lys Gln Ala Leu Glu Thr
                485                 490                 495

Val Gln Arg Leu Leu Pro Val Leu Cys Gln Ala His Gly Leu Thr Pro
            500                 505                 510

Gln Gln Val Val Ala Ile Ala Ser Asn Gly Gly Gly Arg Pro Ala Leu
            515                 520                 525

Glu

<210> SEQ ID NO 87
<211> LENGTH: 530
<212> TYPE: PRT
<213> ORGANISM: Artificial sequence
<220> FEATURE:
<223> OTHER INFORMATION: Repeat PDCD1_T03-L

<400> SEQUENCE: 87

Leu Thr Pro Glu Gln Val Val Ala Ile Ala Ser Asn Ile Gly Gly Lys
1               5                   10                  15

Gln Ala Leu Glu Thr Val Gln Ala Leu Leu Pro Val Leu Cys Gln Ala
            20                  25                  30

His Gly Leu Thr Pro Glu Gln Val Ala Ile Ala Ser His Asp Gly
            35                  40                  45

Gly Lys Gln Ala Leu Glu Thr Val Gln Arg Leu Leu Pro Val Leu Cys
50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
            100                 105                 110

Ser Asn Gly Gly Gly Lys Gln Ala Leu Glu Thr Val Gln Arg Leu Leu
            115                 120                 125

Pro Val Leu Cys Gln Ala His Gly Leu Thr Pro Glu Gln Val Val Ala
130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Gly Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Asn Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Gln Gln Val Val Ala Ile Ala Ser Asn Gly Gly Lys Gln Ala
                245                 250                 255

Leu Glu Thr Val Gln Arg Leu Leu Pro Val Leu Cys Gln Ala His Gly
            260                 265                 270

Leu Thr Pro Gln Gln Val Val Ala Ile Ala Ser Asn Asn Gly Gly Lys
```

```
                275                 280                 285
Gln Ala Leu Glu Thr Val Gln Arg Leu Leu Pro Val Leu Cys Gln Ala
    290                 295                 300
His Gly Leu Thr Pro Gln Gln Val Val Ala Ile Ala Ser Asn Asn Gly
305                 310                 315                 320
Gly Lys Gln Ala Leu Glu Thr Val Gln Arg Leu Leu Pro Val Leu Cys
                325                 330                 335
Gln Ala His Gly Leu Thr Pro Gln Gln Val Val Ala Ile Ala Ser Asn
            340                 345                 350
Asn Gly Gly Lys Gln Ala Leu Glu Thr Val Gln Arg Leu Leu Pro Val
        355                 360                 365
Leu Cys Gln Ala His Gly Leu Thr Pro Gln Gln Val Val Ala Ile Ala
    370                 375                 380
Ser Asn Asn Gly Gly Lys Gln Ala Leu Glu Thr Val Gln Arg Leu Leu
385                 390                 395                 400
Pro Val Leu Cys Gln Ala His Gly Leu Thr Pro Glu Gln Val Val Ala
                405                 410                 415
Ile Ala Ser His Asp Gly Gly Lys Gln Ala Leu Glu Thr Val Gln Arg
            420                 425                 430
Leu Leu Pro Val Leu Cys Gln Ala His Gly Leu Thr Pro Glu Gln Val
        435                 440                 445
Val Ala Ile Ala Ser His Asp Gly Gly Lys Gln Ala Leu Glu Thr Val
    450                 455                 460
Gln Arg Leu Leu Pro Val Leu Cys Gln Ala His Gly Leu Thr Pro Glu
465                 470                 475                 480
Gln Val Val Ala Ile Ala Ser Asn Ile Gly Gly Lys Gln Ala Leu Glu
                485                 490                 495
Thr Val Gln Ala Leu Leu Pro Val Leu Cys Gln Ala His Gly Leu Thr
            500                 505                 510
Pro Gln Gln Val Val Ala Ile Ala Ser Asn Gly Gly Gly Arg Pro Ala
        515                 520                 525
Leu Glu
    530

<210> SEQ ID NO 88
<211> LENGTH: 529
<212> TYPE: PRT
<213> ORGANISM: Artificial sequence
<220> FEATURE:
<223> OTHER INFORMATION: Repeat PDCD1_T03-R

<400> SEQUENCE: 88

Leu Thr Pro Glu Gln Val Val Ala Ile Ala Ser His Asp Gly Gly Lys
1               5                   10                  15
Gln Ala Leu Glu Thr Val Gln Arg Leu Leu Pro Val Leu Cys Gln Ala
                20                  25                  30
His Gly Leu Thr Pro Gln Gln Val Val Ala Ile Ala Ser Asn Gly Gly
            35                  40                  45
Gly Lys Gln Ala Leu Glu Thr Val Gln Arg Leu Leu Pro Val Leu Cys
        50                  55                  60
Gln Ala His Gly Leu Thr Pro Glu Gln Val Val Ala Ile Ala Ser His
65                  70                  75                  80
Asp Gly Gly Lys Gln Ala Leu Glu Thr Val Gln Arg Leu Leu Pro Val
                85                  90                  95
Leu Cys Gln Ala His Gly Leu Thr Pro Gln Gln Val Val Ala Ile Ala
```

```
            100                 105                 110
Ser Asn Gly Gly Gly Lys Gln Ala Leu Glu Thr Val Gln Arg Leu Leu
            115                 120                 125

Pro Val Leu Cys Gln Ala His Gly Leu Thr Pro Gln Gln Val Val Ala
            130                 135                 140

Ile Ala Ser Asn Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                    165                 170                 175

Val Ala Ile Ala Ser Asn Gly Gly Lys Gln Ala Leu Glu Thr Val
                180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
            260                 265                 270

Leu Thr Pro Gln Gln Val Val Ala Ile Ala Ser Asn Gly Gly Lys
            275                 280                 285

Gln Ala Leu Glu Thr Val Gln Arg Leu Leu Pro Val Leu Cys Gln Ala
        290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Gln Gln Val Val Ala Ile Ala Ser Asn
                340                 345                 350

Gly Gly Gly Lys Gln Ala Leu Glu Thr Val Gln Arg Leu Leu Pro Val
            355                 360                 365

Leu Cys Gln Ala His Gly Leu Thr Pro Gln Gln Val Val Ala Ile Ala
        370                 375                 380

Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser Asn Gly Gly Lys Gln Ala Leu Glu Thr Val Gln Arg Leu
                420                 425                 430

Leu Pro Val Leu Cys Gln Ala His Gly Leu Thr Pro Gln Gln Val Val
            435                 440                 445

Ala Ile Ala Ser Asn Asn Gly Gly Lys Gln Ala Leu Glu Thr Val Gln
        450                 455                 460

Arg Leu Leu Pro Val Leu Cys Gln Ala His Gly Leu Thr Pro Glu Gln
465                 470                 475                 480

Val Val Ala Ile Ala Ser His Asp Gly Gly Lys Gln Ala Leu Glu Thr
                485                 490                 495

Val Gln Arg Leu Leu Pro Val Leu Cys Gln Ala His Gly Leu Thr Pro
                500                 505                 510

Gln Gln Val Val Ala Ile Ala Ser Asn Gly Gly Gly Arg Pro Ala Leu
            515                 520                 525
```

Glu

<210> SEQ ID NO 89
<211> LENGTH: 2814
<212> TYPE: DNA
<213> ORGANISM: Artificial sequence
<220> FEATURE:
<223> OTHER INFORMATION: CTLA4_T01-L  TALEN

<400> SEQUENCE: 89

| | | | | | | |
|---|---|---|---|---|---|---|
| atgggcgatc | ctaaaaagaa | acgtaaggtc | atcgattacc | catacgatgt | tccagattac | 60 |
| gctatcgata | tcgccgatct | acgcacgctc | ggctacagcc | agcagcaaca | ggagaagatc | 120 |
| aaaccgaagg | ttcgttcgac | agtggcgcag | caccacgagg | cactggtcgg | ccacgggttt | 180 |
| acacacgcgc | acatcgttgc | gttaagccaa | cacccggcag | cgttagggac | cgtcgctgtc | 240 |
| aagtatcagg | acatgatcgc | agcgttgcca | gaggcgacac | acgaagcgat | cgttggcgtc | 300 |
| ggcaaacagt | ggtccggcgc | acgcgctctg | gaggccttgc | tcacggtggc | gggagagttg | 360 |
| agaggtccac | cgttacagtt | ggacacaggc | caacttctca | agattgcaaa | acgtggcggc | 420 |
| gtgaccgcag | tggaggcagt | gcatgcatgg | cgcaatgcac | tgacgggtgc | cccgctcaac | 480 |
| ttgacccccc | agcaggtggt | ggccatcgcc | agcaataatg | gtggcaagca | ggcgctggag | 540 |
| acggtccagc | ggctgttgcc | ggtgctgtgc | caggcccacg | gcttgacccc | ccagcaggtg | 600 |
| gtggccatcg | ccagcaataa | tggtggcaag | caggcgctgg | agacggtcca | gcggctgttg | 660 |
| ccggtgctgt | gccaggccca | cggcttgacc | ccggagcagg | tggtggccat | cgccagccac | 720 |
| gatggcggca | agcaggcgct | ggagacggtc | cagcggctgt | tgccggtgct | gtgccaggcc | 780 |
| cacggcttga | ccccggagca | ggtggtggcc | atcgccagcc | acgatggcgg | caagcaggcg | 840 |
| ctggagacgg | tccagcggct | gttgccggtg | ctgtgccagg | cccacggctt | gaccccggag | 900 |
| caggtggtgg | ccatcgccag | ccacgatggc | ggcaagcagg | cgctggagac | ggtccagcgg | 960 |
| ctgttgccgg | tgctgtgcca | ggcccacggc | ttgaccccc | agcaggtggt | ggccatcgcc | 1020 |
| agcaatggcg | gtggcaagca | ggcgctggag | acggtccagc | ggctgttgcc | ggtgctgtgc | 1080 |
| caggcccacg | gcttgacccc | ccagcaggtg | gtggccatcg | ccagcaataa | tggtggcaag | 1140 |
| caggcgctgg | agacggtcca | gcggctgttg | ccggtgctgt | gccaggccca | cggcttgacc | 1200 |
| ccggagcagg | tggtggccat | cgccagccac | gatggcggca | agcaggcgct | ggagacggtc | 1260 |
| cagcggctgt | tgccggtgct | gtgccaggcc | cacggcttga | ccccggagca | ggtggtggcc | 1320 |
| atcgccagca | atattggtgg | caagcaggcg | ctggagacgg | tgcaggcgct | gttgccggtg | 1380 |
| ctgtgccagg | cccacggctt | gaccccggag | caggtggtgg | ccatcgccag | ccacgatggc | 1440 |
| ggcaagcagg | cgctggagac | ggtccagcgg | ctgttgccgg | tgctgtgcca | ggcccacggc | 1500 |
| ttgaccccc | agcaggtggt | ggccatcgcc | agcaatggcg | gtggcaagca | ggcgctggag | 1560 |
| acggtccagc | ggctgttgcc | ggtgctgtgc | caggcccacg | gcttgacccc | ggagcaggtg | 1620 |
| gtggccatcg | ccagccacga | tggcggcaag | caggcgctgg | agacggtcca | gcggctgttg | 1680 |
| ccggtgctgt | gccaggccca | cggcttgacc | ccccagcagg | tggtggccat | cgccagcaat | 1740 |
| ggcggtggca | agcaggcgct | ggagacggtc | cagcggctgt | tgccggtgct | gtgccaggcc | 1800 |
| cacggcttga | ccccggagca | ggtggtggcc | atcgccagcc | acgatggcgg | caagcaggcg | 1860 |
| ctggagacgg | tccagcggct | gttgccggtg | ctgtgccagg | cccacggctt | gaccccggag | 1920 |
| caggtggtgg | ccatcgccag | ccacgatggc | ggcaagcagg | cgctggagac | ggtccagcgg | 1980 |

| | |
|---|---|
| ctgttgccgg tgctgtgcca ggcccacggc ttgacccctc agcaggtggt ggccatcgcc | 2040 |
| agcaatggcg gcggcaggcc ggcgctggag agcattgttg cccagttatc tcgccctgat | 2100 |
| ccggcgttgg ccgcgttgac caacgaccac ctcgtcgcct tggcctgcct cggcgggcgt | 2160 |
| cctgcgctat atgcagtgaa aaagggattg ggggatccta tcagccgttc ccagctggtg | 2220 |
| aagtccgagc tggaggagaa gaaatccgag ttgaggcaca agctgaagta cgtgccccac | 2280 |
| gagtacatcg agctgatcga gatcgcccgg aacagcaccc aggaccgtat cctggagatg | 2340 |
| aaggtgatgg agttcttcat gaaggtgtac ggctacaggg gcaagcacct gggcggctcc | 2400 |
| aggaagcccg acggcgccat ctacaccgtg gctcccccca tcgactacgg cgtgatcgtg | 2460 |
| gacaccaagg cctactccgg cggctacaac ctgcccatcg gccaggccga cgaaatgcag | 2520 |
| aggtacgtgg aggagaacca gaccaggaac aagcacatca accccaacga gtggtggaag | 2580 |
| gtgtacccct ccagcgtgac cgagttcaag ttcctgttcg tgtccggcca cttcaagggc | 2640 |
| aactacaagg cccagctgac caggctgaac cacatcacca actgcaacgg cgccgtgctg | 2700 |
| tccgtggagg agctcctgat cggcggcgag atgatcaagg ccggcaccct gaccctggag | 2760 |
| gaggtgagga ggaagttcaa caacggcgag atcaacttcg cggccgactg ataa | 2814 |

<210> SEQ ID NO 90
<211> LENGTH: 2832
<212> TYPE: DNA
<213> ORGANISM: Artificial sequence
<220> FEATURE:
<223> OTHER INFORMATION: CTLA4_T01-R TALEN

<400> SEQUENCE: 90

| | |
|---|---|
| atgggcgatc ctaaaaagaa acgtaaggtc atcgataagg agaccgccgc tgccaagttc | 60 |
| gagagacagc acatggacag catcgatatc gccgatctac gcacgctcgg ctacagccag | 120 |
| cagcaacagg agaagatcaa accgaaggtt cgttcgacag tggcgcagca ccacgaggca | 180 |
| ctggtcggcc acgggtttac acacgcgcac atcgttgcgt taagccaaca cccggcagcg | 240 |
| ttagggaccg tcgctgtcaa gtatcaggac atgatcgcag cgttgccaga ggcgacacac | 300 |
| gaagcgatct tggcgtcggc caaacagtgg tccggcgcac gcgctctgga ggccttgctc | 360 |
| acggtggcgg gagagttgag aggtccaccg ttacagttgg acacaggcca acttctcaag | 420 |
| attgcaaaac gtggcggcgt gaccgcagtg gaggcagtgc atgcatggcg caatgcactg | 480 |
| acgggtgccc cgctcaactt gacccccag caggtggtgg ccatcgccag caataatggt | 540 |
| ggcaagcagg cgctggagac ggtccagcgg ctgttgccgg tgctgtgcca ggcccacggc | 600 |
| ttgacccccgg agcaggtggt ggccatcgcc agccacgatg gcggcaagca ggcgctggag | 660 |
| acggtccagc ggctgttgcc ggtgctgtgc caggcccacg gcttgacccc ggagcaggtg | 720 |
| gtggccatcg ccagcaatat tggtggcaag caggcgctgg agacggtgca ggcgctgttg | 780 |
| ccggtgctgt gccaggccca cggcttgacc cccagcagg tggtggccat cgccagcaat | 840 |
| aatggtggca gcaggcgct ggagacggtc agcggctgt tgccggtgct gtgccaggcc | 900 |
| cacggcttga ccccggagca ggtggtggcc atcgccagca atattggtgg caagcaggcg | 960 |
| ctggagacgt gcaggcgct gttgccgtg ctgtgccagg cccacggctt gaccccggag | 1020 |
| caggtggtgg ccatcgccag caatattggt ggcaagcagg cgctggagac ggtgcaggcg | 1080 |
| ctgttgccgg tgctgtgcca ggcccacggc ttgaccccc agcaggtggt ggccatcgcc | 1140 |
| agcaataatg gtggcaagca ggcgctggag acggtccagc ggctgttgcc ggtgctgtgc | 1200 |
| caggcccacg gcttgacccc ggagcaggtg gtggccatcg ccagcaatat tggtggcaag | 1260 |

```
caggcgctgg agacggtgca ggcgctgttg ccggtgctgt gccaggccca cggcttgacc      1320
ccggagcagg tggtggccat cgccagccac gatggcggca agcaggcgct ggagacggtc      1380
cagcggctgt tgccggtgct gtgccaggcc cacggcttga ccccggagca ggtggtggcc      1440
atcgccagca atattggtgg caagcaggcg ctggagacgg tgcaggcgct gttgccggtg      1500
ctgtgccagg cccacggctt gaccccccag caggtggtgg ccatcgccag caataatggt      1560
ggcaagcagg cgctggagac ggtccagcgg ctgttgccgg tgctgtgcca ggcccacggc      1620 ttgaccccc agcaggtggt ggccatcgcc agcaataatg tggcaagca ggcgctggag      1680 acggtccagc ggctgttgcc ggtgctgtgc caggcccacg gcttgacccc ccagcaggtg      1740
gtggccatcg ccagcaataa tggtggcaag caggcgctgg agacggtcca gcggctgttg      1800
ccggtgctgt gccaggccca cggcttgacc ccggagcagg tggtggccat cgccagcaat      1860
attggtggca agcaggcgct ggagacggtg caggcgctgt gccggtgct gtgccaggcc      1920 cacggcttga ccccccagca ggtggtggcc atcgccagca atggcggtgg caagcaggcg      1980
ctggagacgg tccagcggct gttgccggtg ctgtgccagg cccacggctt gacccctcag      2040
caggtggtgg ccatcgccag caatggcggc ggcaggccgg cgctggagag cattgttgcc      2100
cagttatctc gccctgatcc ggcgttggcc gcgttgacca acgaccacct cgtcgccttg      2160
gcctgcctcg gcgggcgtcc tgcgctggat gcagtgaaaa agggattggg ggatcctatc      2220
agccgttccc agctggtgaa gtccgagctg gaggagaaga atccgagtt gaggcacaag      2280 ctgaagtacg tgccccacga gtacatcgag ctgatcgaga tcgcccggaa cagcaccccag      2340 gaccgtatcc tggagatgaa ggtgatggag ttcttcatga aggtgtacgg ctacaggggc      2400
aagcacctgg gcggctccag gaagcccgac ggcgccatct acaccgtggg ctcccccatc      2460
gactacggcg tgatcgtgga caccaaggcc tactccggcg gctacaacct gcccatcggc      2520
caggccgacg aaatgcagag gtacgtggag gagaaccaga ccaggaacaa gcacatcaac      2580
cccaacgagt ggtggaaggt gtacccctcc agcgtgaccg agttcaagtt cctgttcgtg      2640
tccggccact tcaagggcaa ctacaaggcc cagctgacca ggctgaacca catcaccaac      2700
tgcaacggcg ccgtgctgtc cgtggaggag ctcctgatcg gcggcgagat gatcaaggcc      2760
ggcaccctga ccctggagga ggtgaggagg aagttcaaca acggcgagat caacttcgcg      2820
gccgactgat aa                                                         2832

<210> SEQ ID NO 91
<211> LENGTH: 2814
<212> TYPE: DNA
<213> ORGANISM: Artificial sequence
<220> FEATURE:
<223> OTHER INFORMATION: CTLA4_T03-L TALEN

<400> SEQUENCE: 91
atgggcgatc ctaaaaagaa acgtaaggtc atcgattacc catacgatgt tccagattac       60
gctatcgata tcgccgatct acgcacgctc ggctacagcc agcagcaaca ggagaagatc      120
aaaccgaagg ttcgttcgac agtggcgcag caccacgagg cactggtcgg ccacgggttt      180
acacacgcgc acatcgttgc gttaagccaa cacccggcag cgttagggac cgtcgctgtc      240
aagtatcagg acatgatcgc agcgttgcca gaggcgacac acgaagcgat cgttggcgtc      300
ggcaaacagt ggtccggcgc acgcgctctg gaggccttgc tcacggtggc gggagagttg      360
agaggtccac cgttacagtt ggacacaggc caacttctca gagattgcaaa acgtggcggc      420
```

```
gtgaccgcag tggaggcagt gcatgcatgg cgcaatgcac tgacgggtgc ccgctcaac      480
ttgacccccc agcaggtggt ggccatcgcc agcaatggcg gtggcaagca ggcgctggag     540
acggtccagc ggctgttgcc ggtgctgtgc caggcccacg gcttgacccc ccagcaggtg     600
gtggccatcg ccagcaatgg cggtggcaag caggcgctgg agacggtcca gcggctgttg     660
ccggtgctgt gccaggccca cggcttgacc ccccagcagg tggtggccat cgccagcaat     720
ggcggtggca agcaggcgct ggagacggtc agcggctgt tgccggtgct gtgccaggcc      780
cacggcttga ccccggagca ggtggtggcc atcgccagcc acgatggcgg caagcaggcg     840
ctggagacgg tccagcggct gttgccggtg ctgtgccagg cccacggctt gaccccggag     900
caggtggtgg ccatcgccag ccacgatggc ggcaagcagg cgctggagac ggtccagcgg     960
ctgttgccgg tgctgtgcca ggcccacggc ttgaccccgg agcaggtggt ggccatcgcc    1020
agcaatattg gtggcaagca ggcgctggag acggtgcagg cgctgttgcc ggtgctgtgc    1080
caggcccacg gcttgacccc ccagcaggtg gtggccatcg ccagcaatgg cggtggcaag    1140
caggcgctgg agacggtcca gcggctgttg ccggtgctgt gccaggccca cggcttgacc    1200
ccccagcagg tggtggccat cgccagcaat aatggtggca agcaggcgct ggagacggtc    1260
cagcggctgt tgccggtgct gtgccaggcc cacggcttga ccccggagca ggtggtggcc    1320
atcgccagcc acgatggcgg caagcaggcg ctggagacgg tccagcggct gttgccggtg    1380
ctgtgccagg cccacggctt gaccccccag caggtggtgg ccatcgccag caatggcggt    1440
ggcaagcagg cgctggagac ggtccagcgg ctgttgccgg tgctgtgcca ggcccacggc    1500
ttgaccccgg agcaggtggt ggccatcgcc agcaatattg gtggcaagca ggcgctggag    1560
acggtgcagg cgctgttgcc ggtgctgtgc caggcccacg gcttgacccc ccagcaggtg    1620
gtggccatcg ccagcaataa tgtggcaag caggcgctgg agacggtcca gcggctgttg    1680
ccggtgctgt gccaggccca cggcttgacc ccggagcagg tggtggccat cgccagccac    1740
gatggcggca agcaggcgct ggagacggtc agcggctgt tgccggtgct gtgccaggcc    1800
cacggcttga ccccggagca ggtggtggcc atcgccagca atattggtgg caagcaggcg    1860
ctggagacgg tgcaggcgct gttgccggtg ctgtgccagg cccacggctt gaccccggag    1920
caggtggtgg ccatcgccag caatattggt ggcaagcagg cgctggagac ggtgcaggcg    1980
ctgttgccgg tgctgtgcca ggcccacggc ttgaccccc agcaggtggt ggccatcgcc    2040
agcaatggcg gcggcaggcc ggcgctggag agcattgttg cccagttatc tcgccctgat    2100
ccggcgttgg ccgcgttgac caacgaccac ctcgtcgcct tggcctgcct cggcgggcgt    2160
cctgcgctgg atgcagtgaa aaagggattg ggggatccta tcagccgttc ccagctggtg    2220
aagtccgagc tggaggagaa gaaatccgag ttgaggcaca agctgaagta cgtgccccac    2280
gagtacatcg agctgatcga gatcgcccgg aacagcaccc aggaccgtat cctggagatg    2340
aaggtgatgg agttcttcat gaaggtgtac ggctacaggg gcaagcacct gggcggctcc    2400
aggaagcccg acgcgccat ctacaccgtg gctcccccca tcgactacgg cgtgatcgtg    2460
gacaccaagg cctactccgg cggctacaac ctgcccatcg ccaggccga cgaaatgcag    2520
aggtacgtga ggagaaccga ccaggaacaa gcacatca accccaacga gtggtggaag    2580
gtgtaccccct ccagcgtgac cgagttcaag ttcctgttcg tgtccggcca cttcaagggc    2640
aactacaagg cccagctgac caggctgaac cacatcacca actgcaacgg cgccgtgctg    2700
tccgtggagg agctcctgat cggcggcgag atgatcaagg ccggcacccct gaccctggag    2760
gaggtgagga ggaagttcaa caacggcgag atcaacttcg cggccgactg ataa             2814
```

<210> SEQ ID NO 92
<211> LENGTH: 2832
<212> TYPE: DNA
<213> ORGANISM: Artificial sequence
<220> FEATURE:
<223> OTHER INFORMATION: CTLA4_T03-RTALEN

<400> SEQUENCE: 92

```
atgggcgatc ctaaaaagaa acgtaaggtc atcgataagg agaccgccgc tgccaagttc      60
gagagacagc acatggacag catcgatatc gccgatctac gcacgctcgg ctacagccag     120
cagcaacagg agaagatcaa accgaaggtt cgttcgacag tggcgcagca ccacgaggca     180
ctggtcggcc acgggtttac acacgcgcac atcgttgcgt taagccaaca cccggcagcg     240
ttagggaccg tcgctgtcaa gtatcaggac atgatcgcag cgttgccaga ggcgacacac     300
gaagcgatcg ttggcgtcgg caaacagtgg tccggcgcac gcgctctgga ggccttgctc     360
acggtggcgg agagttgag aggtccaccg ttacagttgg acacaggcca acttctcaag     420
attgcaaaac gtggcggcgt gaccgcagtg gaggcagtgc atgcatggcg caatgcactg     480
acgggtgccc cgctcaactt gacccccag caggtggtgg ccatcgccag caataatggt     540
ggcaagcagg cgctggagac ggtccagcgg ctgttgccgg tgctgtgcca ggcccacggc     600
ttgacccccc agcaggtggt ggccatcgcc agcaataatg gtggcaagca ggcgctggag     660
acggtccagc ggctgttgcc ggtgctgtgc caggcccacg gcttgacccc ggagcaggtg     720
gtggccatcg ccagccacga tggcggcaag caggcgctgg agacggtcca gcggctgttg     780
ccggtgctgt gccaggccca cggcttgacc ccggagcagg tggtggccat cgccagccac     840
gatggcggca agcaggcgct ggagacggtc agcggctgt tgccggtgct gtgccaggcc     900
cacggcttga ccccggagca ggtggtggcc atcgccagca atattggtgg caagcaggcg     960
ctggagacgg tgcaggcgct gttgccggtg ctgtgccagg cccacggctt gacccccag    1020
caggtggtgg ccatcgccag caataatggt ggcaagcagg cgctggagac ggtccagcgg    1080
ctgttgccgg tgctgtgcca ggcccacggc ttgacccccc agcaggtggt ggccatcgcc    1140
agcaatggcg gtggcaagca ggcgctggag acggtccagc ggctgttgcc ggtgctgtgc    1200
caggcccacg gcttgacccc ggagcaggtg gtggccatcg ccagcaatat tggtggcaag    1260
caggcgctgg agacggtgca ggcgctgttg ccggtgctgt gccaggccca cggcttgacc    1320
ccggagcagg tggtggccat cgccagccac gatggcggca agcaggcgct ggagacggtc    1380
cagcggctgt tgccggtgct gtgccaggcc acggcttga ccccggagca ggtggtggcc    1440
atcgccagcc acgatggcgg caagcaggcg ctggagacgg tccagcggct gttgccggtg    1500
ctgtgccagg cccacggctt gacccggag caggtggtgg ccatcgccag caatattggt    1560
ggcaagcagg cgctggagac ggtgcaggcg ctgttgccgg tgctgtgcca ggcccacggc    1620
ttgacccccgg agcaggtggt ggccatcgcc agccacgatg cggcaagca ggcgctggag    1680
acggtccagc ggctgttgcc ggtgctgtgc caggcccacg gcttgacccc ggagcaggtg    1740
gtggccatcg ccagcaatat tggtggcaag caggcgctgg agacggtgca ggcgctgttg    1800
ccggtgctgt gccaggccca cggcttgacc ccccagcagg tggtggccat cgccagcaat    1860
aatggtggca agcaggcgct ggagacggtc agcggctgt tgccggtgct gtgccaggcc    1920
cacggcttga ccccggagca ggtggtggcc atcgccagcc acgatggcgg caagcaggcg    1980
ctggagacgg tccagcggct gttgccggtg ctgtgccagg cccacggctt gacccctcag    2040
```

| | |
|---|---|
| caggtggtgg ccatcgccag caatggcggc ggcaggccgg cgctggagag cattgttgcc | 2100 |
| cagttatctc gccctgatcc ggcgttggcc gcgttgacca acgaccacct cgtcgccttg | 2160 |
| gcctgcctcg gcgggcgtcc tgcgctggat gcagtgaaaa agggattggg ggatcctatc | 2220 |
| agccgttccc agctggtgaa gtccgagctg gaggagaaga atccgagtt gaggcacaag | 2280 |
| ctgaagtacg tgccccacga gtacatcgag ctgatcgaga tcgcccggaa cagcacccag | 2340 |
| gaccgtatcc tggagatgaa ggtgatggag ttcttcatga aggtgtacgg ctacaggggc | 2400 |
| aagcacctgg gcggctccag gaagcccgac ggcgccatct acaccgtggg ctcccccatc | 2460 |
| gactacggcg tgatcgtgga caccaaggcc tactccggcg gctacaacct gcccatcggc | 2520 |
| caggccgacg aaatgcagag gtacgtggag gagaaccaga ccaggaacaa gcacatcaac | 2580 |
| cccaacgagt ggtggaaggt gtacccctcc agcgtgaccg agttcaagtt cctgttcgtg | 2640 |
| tccggccact tcaagggcaa ctacaaggcc cagctgacca ggctgaacca catcaccaac | 2700 |
| tgcaacggcg ccgtgctgtc cgtggaggag ctcctgatcg gcggcgagat gatcaaggcc | 2760 |
| ggcaccctga ccctggagga ggtgaggagg aagttcaaca cggcgagat caacttcgcg | 2820 |
| gccgactgat aa | 2832 |

<210> SEQ ID NO 93
<211> LENGTH: 2814
<212> TYPE: DNA
<213> ORGANISM: Artificial sequence
<220> FEATURE:
<223> OTHER INFORMATION: CTLA4_T04-L TALEN

<400> SEQUENCE: 93

| | |
|---|---|
| atgggcgatc ctaaaaagaa acgtaaggtc atcgattacc catacgatgt tccagattac | 60 |
| gctatcgata tcgccgatct acgcacgctc ggctacagcc agcagcaaca ggagaagatc | 120 |
| aaaccgaagg ttcgttcgac agtggcgcag caccacgagg cactggtcgg ccacgggttt | 180 |
| acacacgcgc acatcgttgc gttaagccaa cacccggcag cgttagggac cgtcgctgtc | 240 |
| aagtatcagg acatgatcgc agcgttgcca gaggcgacac acgaagcgat cgttggcgtc | 300 |
| ggcaaacagt ggtccggcgc acgcgctctg gaggccttgc tcacggtggc gggagagttg | 360 |
| agaggtccac cgttacagtt ggacacaggc caacttctca agattgcaaa cgtggcggc | 420 |
| gtgaccgcag tggaggcagt gcatgcatgg cgcaatgcac tgacgggtgc cccgctcaac | 480 |
| ttgaccccgg agcaggtggt ggccatcgcc agccacgatg gcggcaagca ggcgctggag | 540 |
| acggtccagc ggctgttgcc ggtgctgtgc caggcccacg gcttgacccc ggagcaggtg | 600 |
| gtggccatcg ccagccacga tggcggcaag caggcgctgg agacggtcca gcggctgttg | 660 |
| ccggtgctgt gccaggccca cggcttgacc ccggagcagg tggtggccat cgccagcaat | 720 |
| attggtggca agcaggcgct ggagacggtg caggcgctgt gccggtgct gtgccaggcc | 780 |
| cacggcttga ccccccagca ggtggtggcc atcgccagca atggcggtgg caagcaggcg | 840 |
| ctggagacgg tccagcggct gttgccgtg ctgtgccagg cccacggctt gaccccccag | 900 |
| caggtggtgg ccatcgccag caataatggt ggcaagcagg cgctggagac ggtccagcgg | 960 |
| ctgttgccgg tgctgtgcca ggcccacggc ttgaccccgg agcaggtggt ggccatcgcc | 1020 |
| agccacgatg gcggcaagca ggcgctggag acggtccagc ggctgttgcc ggtgctgtgc | 1080 |
| caggcccacg gcttgacccc ccagcaggtg gtggccatcg ccagcaatgg cggtggcaag | 1140 |
| caggcgctgg agacggtcca gcggctgttg ccggtgctgt gccaggccca cggcttgacc | 1200 |
| ccggagcagg tggtggccat cgccagcaat attggtggca agcaggcgct ggagacggtg | 1260 |

```
caggcgctgt tgccggtgct gtgccaggcc cacggcttga ccccccagca ggtggtggcc    1320
atcgccagca ataatggtgg caagcaggcg ctggagacgg tccagcggct gttgccggtg    1380
ctgtgccagg cccacggctt gaccccggag caggtggtgg ccatcgccag ccacgatggc    1440
ggcaagcagg cgctggagac ggtccagcgg ctgttgccgg tgctgtgcca ggcccacggc    1500
ttgaccccgg agcaggtggt ggccatcgcc agcaatattg gtggcaagca ggcgctggag    1560
acggtgcagg cgctgttgcc ggtgctgtgc caggcccacg gcttgacccc ggagcaggtg    1620
gtggccatcg ccagcaatat tggtggcaag caggcgctgg agacggtgca ggcgctgttg    1680
ccggtgctgt gccaggccca cggcttgacc cccagcagg tggtggccat cgccagcaat    1740
ggcggtggca agcaggcgct ggagacggtc cagcggctgt gccggtgct gtgccaggcc    1800 cacggcttga ccccccagca ggtggtggcc atcgccagca ataatggtgg caagcaggcg    1860
ctggagacgg tccagcggct gttgccggtg ctgtgccagg cccacggctt gaccccggag    1920
caggtggtgg ccatcgccag ccacgatggc ggcaagcagg cgctggagac ggtccagcgg    1980
ctgttgccgg tgctgtgcca ggcccacggc ttgacccctc agcaggtggt ggccatcgcc    2040
agcaatggcg gcggcaggcc ggcgctggag agcattgttg cccagttatc tcgccctgat    2100
ccggcgttgg ccgcgttgac caacgaccac ctcgtcgcct tggcctgcct cggcgggcgt    2160
cctgcgctgg atgcagtgaa aaagggattg ggggatccta tcagccgttc ccagctggtg    2220
aagtccgagc tggaggagaa gaaatccgag ttgaggcaca agctgaagta cgtgcccac    2280 gagtacatcg agctgatcga gatcgcccgg aacagcaccc aggaccgtat cctggagatg    2340
aaggtgatgg agttcttcat gaaggtgtac ggctacaggg gcaagcacct gggcggctcc    2400
aggaagcccg acggcgccat ctacaccgtg ggctccccca tcgactacgg cgtgatcgtg    2460
gacaccaagg cctactccgg cggctacaac ctgcccatcg ccaggccga cgaaatgcag    2520 aggtacgtgg aggagaacca gaccaggaac aagcacatca ccccaacga gtggtggaag    2580 gtgtacccct ccagcgtgac cgagttcaag ttcctgttcg tgtccggcca cttcaagggc    2640
aactacaagg cccagctgac caggctgaac cacatcacca actgcaacgg cgccgtgctg    2700
tccgtggagg agctcctgat cggcggcgag atgatcaagg ccggcaccct gaccctggag    2760
gaggtgagga ggaagttcaa caacggcgag atcaacttcg cggccgactg ataa          2814
```

<210> SEQ ID NO 94
<211> LENGTH: 2832
<212> TYPE: DNA
<213> ORGANISM: Artificial sequence
<220> FEATURE:
<223> OTHER INFORMATION: CTLA4_T04-R TALEN

<400> SEQUENCE: 94

```
atgggcgatc ctaaaaagaa acgtaaggtc atcgataagg agaccgccgc tgccaagttc      60
gagagacagc acatggacag catcgatatc gccgatctac gcacgctcgg ctacagccag     120
cagcaacagg agaagatcaa accgaaggtt cgttcgacag tggcgcagca ccacgaggca     180
ctggtcggcc acgggtttac acacgcgcac atcgttgcgt taagccaaca cccggcagcg     240
ttagggaccg tcgctgtcaa gtatcaggac atgatcgcac cgttgccaga ggcgacacac     300
gaagcgatcg ttggcgtcgg caaacagtgg tccggcgcac gcgctctgga ggccttgctc     360
acggtggcgg gagagttgag aggtccaccg ttacagttgg acacaggcca acttctcaag     420
attgcaaaac gtggcggcgt gaccgcagtg gaggcagtgc atgcatggcg caatgcactg     480
```

-continued

```
acgggtgccc cgctcaactt gaccccccag caggtggtgg ccatcgccag caataatggt    540
ggcaagcagg cgctggagac ggtccagcgg ctgttgccgg tgctgtgcca ggcccacggc    600
ttgaccccgg agcaggtggt ggccatcgcc agccacgatg gcggcaagca ggcgctggag    660
acggtccagc ggctgttgcc ggtgctgtgc caggcccacg gcttgacccc ccagcaggtg    720
gtggccatcg ccagcaatgg cggtggcaag caggcgctgg agacggtcca gcggctgttg    780
ccggtgctgt gccaggccca cggcttgacc ccccagcagg tggtggccat cgccagcaat    840
aatggtggca agcaggcgct ggagacggtc cagcggctgt tgccggtgct gtgccaggcc    900
cacggcttga ccccccagca ggtggtggcc atcgccagca ataatggtgg caagcaggcg    960
ctggagacgg tccagcggct gttgccggtg ctgtgccagg cccacggctt gaccccggag   1020
caggtggtgg ccatcgccag ccacgatggc ggcaagcagg cgctggagac ggtccagcgg   1080
ctgttgccgg tgctgtgcca ggcccacggc ttgaccccgg agcaggtggt ggccatcgcc   1140
agccacgatg gcggcaagca ggcgctggag acggtccagc ggctgttgcc ggtgctgtgc   1200
caggcccacg gcttgacccc ggagcaggtg gtggccatcg ccagcaatat tggtggcaag   1260
caggcgctgg agacggtgca ggcgctgttg ccggtgctgt gccaggccca cggcttgacc   1320
ccccagcagg tggtggccat cgccagcaat aatggtggca agcaggcgct ggagacggtc   1380
cagcggctgt tgccggtgct gtgccaggcc cacggcttga ccccccagca ggtggtggcc   1440
atcgccagca atggcggtgg caagcaggcg ctggagacgg tccagcggct gttgccggtg   1500
ctgtgccagg cccacggctt gaccccggag caggtggtgg ccatcgccag caatattggt   1560
ggcaagcagg cgctggagac ggtgcaggcg ctgttgccgg tgctgtgcca ggcccacggc   1620
ttgaccccgg agcaggtggt ggccatcgcc agccacgatg gcggcaagca ggcgctggag   1680
acggtccagc ggctgttgcc ggtgctgtgc caggcccacg gcttgacccc ggagcaggtg   1740
gtggccatcg ccagccacga tggcggcaag caggcgctgg agacggtcca gcggctgttg   1800
ccggtgctgt gccaggccca cggcttgacc ccggagcagg tggtggccat cgccagcaat   1860
attggtggca agcaggcgct ggagacggtg caggcgctgt tgccggtgct gtgccaggcc   1920
cacggcttga ccccggagca ggtggtggcc atcgccagcc acgatggcgg caagcaggcg   1980
ctggagacgg tccagcggct gttgccggtg ctgtgccagg cccacggctt gaccccctcag   2040
caggtggtgg ccatcgccag caatggcggc ggcaggccgg cgctggagag cattgttgcc   2100
cagttatctc gccctgatcc ggcgttggcc gcgttgacca acgaccacct cgtcgccttg   2160
gcctgcctcg gcgggcgtcc tgcgctggat gcagtgaaaa agggattggg ggatcctatc   2220
agccgttccc agctggtgaa gtccgagctg gaggagaaga atccgagtt gaggcacaag   2280
ctgaagtacg tgccccacga gtacatcgag ctgatcgaga tcgccggaaa cagcacccag   2340
gaccgtatcc tggagatgaa ggtgatggag ttcttcatga aggtgtacgg ctacaggggc   2400
aagcacctgg gcggctccag gaagcccgac ggcgccatct acaccgtggg ctcccccatc   2460
gactacggcg tgatcgtgga caccaaggcc tactccggcg gctacaacct gcccatcggc   2520
caggccgacg aaatgcagag gtacgtggag gagaaccaga ccaggaacaa gcacatcaac   2580
cccaacgagt ggtggaaggt gtaccccctcc agcgtgaccg agttcaagtt cctgttcgtg   2640
tccggccact tcaagggcaa ctacaaggcc cagctgacca ggctgaacca catcaccaac   2700
tgcaacggcg ccgtgctgtc cgtggaggag ctcctgatcg gcggcgagat gatcaaggcc   2760
ggcacctga ccctggagga ggtgaggagg aagttcaaca acggcgagat caacttcgcg   2820
gccgactgat aa                                                        2832
```

<210> SEQ ID NO 95
<211> LENGTH: 2814
<212> TYPE: DNA
<213> ORGANISM: Artificial sequence
<220> FEATURE:
<223> OTHER INFORMATION: PDCD1_T01-L TALEN

<400> SEQUENCE: 95

| | | | | | | |
|---|---|---|---|---|---|---|
| atgggcgatc | ctaaaaagaa | acgtaaggtc | atcgattacc | catacgatgt | tccagattac | 60 |
| gctatcgata | tcgccgatct | acgcacgctc | ggctacagcc | agcagcaaca | ggagaagatc | 120 |
| aaaccgaagg | ttcgttcgac | agtggcgcag | caccacgagg | cactggtcgg | ccacgggttt | 180 |
| acacacgcgc | acatcgttgc | gttaagccaa | cacccggcag | cgttagggac | cgtcgctgtc | 240 |
| aagtatcagg | acatgatcgc | agcgttgcca | gaggcgacac | acgaagcgat | cgttggcgtc | 300 |
| ggcaaacagt | ggtccggcgc | acgcgctctg | gaggccttgc | tcacggtggc | gggagagttg | 360 |
| agaggtccac | cgttacagtt | ggacacaggc | caacttctca | agattgcaaa | acgtggcggc | 420 |
| gtgaccgcag | tggaggcagt | gcatgcatgg | cgcaatgcac | tgacgggtgc | cccgctcaac | 480 |
| ttgaccccc | agcaggtggt | ggccatcgcc | agcaatggcg | gtggcaagca | ggcgctggag | 540 |
| acggtccagc | ggctgttgcc | ggtgctgtgc | caggcccacg | gcttgacccc | ggagcaggtg | 600 |
| gtggccatcg | ccagccacga | tggcggcaag | caggcgctgg | agacggtcca | gcggctgttg | 660 |
| ccggtgctgt | gccaggccca | cggcttgacc | cccagcagg | tggtggccat | cgccagcaat | 720 |
| ggcggtggca | agcaggcgct | ggagacggtc | agcggctgt | tgccggtgct | gtgccaggcc | 780 |
| cacggcttga | ccccggagca | ggtggtggcc | atcgccagcc | acgatggcgg | caagcaggcg | 840 |
| ctggagacgg | tccagcggct | gttgccggtg | ctgtgccagg | cccacggctt | gaccccggag | 900 |
| caggtggtgg | ccatcgccag | ccacgatggc | ggcaagcagg | cgctggagac | ggtccagcgg | 960 |
| ctgttgccgg | tgctgtgcca | ggcccacggc | ttgaccccgg | agcaggtggt | ggccatcgcc | 1020 |
| agccacgatg | cggcaagca | ggcgctggag | acggtccagc | ggctgttgcc | ggtgctgtgc | 1080 |
| caggcccacg | gcttgacccc | ggagcaggtg | gtggccatcg | ccagccacga | tggcggcaag | 1140 |
| caggcgctgg | agacggtcca | gcggctgttg | ccggtgctgt | gccaggccca | cggcttgacc | 1200 |
| ccggagcagg | tggtggccat | cgccagcaat | attggtggca | agcaggcgct | ggagacggtg | 1260 |
| caggcgctgt | tgccggtgct | gtgccaggcc | cacggcttga | ccccccagca | ggtggtggcc | 1320 |
| atcgccagca | ataatggtgg | caagcaggcg | ctggagacgg | tccagcggct | gttgccggtg | 1380 |
| ctgtgccagg | cccacggctt | gaccccggag | caggtggtgg | ccatcgccag | ccacgatggc | 1440 |
| ggcaagcagg | cgctggagac | ggtccagcgg | ctgttgccgg | tgctgtgcca | gcccacggc | 1500 |
| ttgaccccgg | agcaggtggt | ggccatcgcc | agccacgatg | cggcaagca | ggcgctggag | 1560 |
| acggtccagc | ggctgttgcc | ggtgctgtgc | caggcccacg | gcttgacccc | ggagcaggtg | 1620 |
| gtggccatcg | ccagccacga | tggcggcaag | caggcgctgg | agacggtcca | gcggctgttg | 1680 |
| ccggtgctgt | gccaggccca | cggcttgacc | cccagcagg | tggtggccat | cgccagcaat | 1740 |
| ggcggtggca | agcaggcgct | ggagacggtc | agcggctgt | tgccggtgct | gtgccaggcc | 1800 |
| cacggcttga | ccccccagca | ggtggtggcc | atcgccagca | ataatggtgg | caagcaggcg | 1860 |
| ctggagacgg | tccagcggct | gttgccggtg | ctgtgccagg | cccacggctt | gaccccggag | 1920 |
| caggtggtgg | ccatcgccag | ccacgatggc | ggcaagcagg | cgctggagac | ggtccagcgg | 1980 |
| ctgttgccgg | tgctgtgcca | ggcccacggc | ttgacccctc | agcaggtggt | ggccatcgcc | 2040 |

```
agcaatggcg gcggcaggcc ggcgctggag agcattgttg cccagttatc tcgccctgat    2100
ccggcgttgg ccgcgttgac caacgaccac ctcgtcgcct tggcctgcct cggcgggcgt    2160
cctgcgctgg atgcagtgaa aaagggattg ggggatccta tcagccgttc ccagctggtg    2220
aagtccgagc tggaggagaa gaaatccgag ttgaggcaca agctgaagta cgtgccccac    2280
gagtacatcg agctgatcga gatcgcccgg aacagcaccc aggaccgtat cctggagatg    2340
aaggtgatgg agttcttcat gaaggtgtac ggctacaggg gcaagcacct gggcggctcc    2400
aggaagcccg acggcgccat ctacaccgtg ggctccccca tcgactacgg cgtgatcgtg    2460
gacaccaagg cctactccgg cggctacaac ctgcccatcg ccaggccgga cgaaatgcag    2520
aggtacgtgg aggagaacca gaccaggaac aagcacatca cccccaacga gtggtggaag    2580
gtgtaccccc tccagcgtga ccgagttcaag ttcctgttcg tgtccggcca cttcaagggc    2640
aactacaagc ccagctgac caggctgaac cacatcacca ctgcaacgg cgccgtgctg       2700 tccgtggagg agctcctgat cggcggcgag atgatcaagg ccggcaccct gaccctggag    2760
gaggtgagga ggaagttcaa caacggcgag atcaacttcg cggccgactg ataa           2814
```

<210> SEQ ID NO 96
<211> LENGTH: 2829
<212> TYPE: DNA
<213> ORGANISM: Artificial sequence
<220> FEATURE:
<223> OTHER INFORMATION: PDCD1_T01-R TALEN

<400> SEQUENCE: 96

```
atgggcgatc ctaaaaagaa acgtaaggtc atcgataagg agaccgccgc tgccaagttc      60
gagagacagc acatggacag catcgatatc gccgatctac gcacgctcgg ctacagccag    120
cagcaacagg agaagatcaa accgaaggtt cgttcgacag tggcgcagca ccacgaggca    180
ctggtcggcc acgggtttac acacgcgcac atcgttgcgt taagccaaca cccggcagcg    240
ttagggaccc tcgctgtcaa gtatcaggac atgatcgcac cgttgccaga ggcgacacac    300
gaagcgatcg ttggcgtcgg caaacagtgg tccggcgcac gcgctctgga ggccttgctc    360
acggtggcgg gagagttgag aggtccaccg ttacagttgg acacaggcca acttctcaag    420
attgcaaaac gtggcggcgt gaccgcagtg gaggcagtgc atgcatggcg caatgcactg    480
acgggtgccc cgctcaactt gacccccag caagtcgtcg caatcgccag caataacgga    540
gggaagcaag ccctcgaaac cgtgcagcgg ttgcttcctg tgctctgcca ggcccacggc    600 cttaccctg agcaggtggt ggccatcgca agtaacattg aggaaagca agccttggag     660 acagtgcagg ccctgttgcc cgtgctgtgc caggcacacg gcctcacacc agagcaggtc    720
gtggccattg cctccaacat cggggggaaa caggctctgg agaccgtcca ggccctgctg    780
cccgtcctct gtcaagctca cggcctgact ccccaacaag tggtcgccat cgcctctaat    840
aacggcggga gcaggcact ggaaacagtg cagagactgc tccctgtgct ttgccaagct      900
catgggttga ccccccaaca ggtcgtcgct attgcctcaa caacggggg caagcaggcc     960 cttgagactg tgcagaggct gttgccagtg ctgtgtcagg ctcacgggct cactccacaa    1020
caggtggtcg caattgccag caacggcggc ggaaagcaag ctcttgaaac cgtgcaacgc    1080
ctcctgcccg tgctctgtca ggctcatggc ctgacaccac aacaagtcgt ggccatcgcc    1140
agtaataatg gcgggaaaca ggctcttgag accgtccaga ggctgctccc agtgctctgc    1200
caggcacacg gctgaccccc ccagcaggtg gtggctatcg ccagcaataa tggggggcaag   1260 caggccctgg aaacagtcca gcgcctgctg ccagtgcttt gccaggctca cggctcact     1320
```

-continued

```
cccgaacagg tcgtggcaat cgcctccaac ggagggaagc aggctctgga gaccgtgcag    1380
agactgctgc ccgtcttgtg ccaggcccac ggactcacac ctcagcaggt cgtcgccatt    1440
gcctctaaca acgggggcaa acaagccctg gagacagtgc agcggctgtt gcctgtgttg    1500
tgccaagccc acggcttgac tcctcaacaa gtggtcgcca tcgcctcaaa tggcggcgga    1560
aaacaagctc tggagacagt gcagaggttg ctgcccgtcc tctgccaagc ccacggcctg    1620
actccccaac aggtcgtcgc cattgccagc aacggcggag aaagcaggc tctcgaaact     1680 gtgcagcggc tgcttcctgt gctgtgtcag gctcatgggc tgaccccca gcaagtggtg     1740 gctattgcct ctaacaatgg aggcaagcaa gcccttgaga cagtccagag gctgttgcca    1800
gtgctgtgcc aggcccacgg gctcacaccc cagcaggtgg tcgccatcgc cagtaacggc    1860
gggggcaaac aggcattgga aaccgtccag cgcctgcttc cagtgctctg ccaggcacac    1920
ggactgacac ccgaacaggt ggtggccatt gcatcccatg atggggcaa gcaggccctg    1980 gagaccgtgc agagactcct gccagtgttg tgccaagctc acggcctcac ccctcagcaa    2040
gtcgtggcca tcgcctcaaa cggggggggc cggcctgcac tggagagcat tgttgcccag    2100
ttatctcgcc ctgatccggc gttggccgcg ttgaccaacg accacctcgt cgccttggcc    2160
tgcctcggcg gcgtcctgc gctggatgca gtgaaaaagg gattggggga tcctatcagc    2220
cgttcccagc tggtgaagtc cgagctggag gagaagaaat ccgagttgag gcacaagctg    2280
aagtacgtgc cccacgagta catcgagctg atcgagatcg cccggaacag cacccaggac    2340
cgtatcctgg agatgaaggt gatggagttc ttcatgaagg tgtacggcta caggggcaag    2400
cacctgggcg gctccaggaa gcccgacggc gccatctaca ccgtgggctc ccccatcgac    2460
tacggcgtga tcgtggacac caaggcctac tccggcggct acaacctgcc catcggccag    2520
gccgacgaaa tgcagaggta cgtggaggag aaccagacca ggaacaagca catcaacccc    2580
aacgagtggt ggaaggtgta ccctccagc gtgaccgagt tcaagttcct gttcgtgtcc     2640
ggccacttca agggcaacta caaggcccag ctgaccaggc tgaaccacat caccaactgc    2700
aacggcgccg tgctgtccgt ggaggagctc ctgatcggcg gcgagatgat caaggccggc    2760
accctgaccc tggaggaggt gaggaggaag ttcaacaacg gcgagatcaa cttcgcggcc    2820
gactgataa                                                             2829
```

<210> SEQ ID NO 97
<211> LENGTH: 2814
<212> TYPE: DNA
<213> ORGANISM: Artificial sequence
<220> FEATURE:
<223> OTHER INFORMATION: PDCD1_T03-L TALEN

<400> SEQUENCE: 97

```
atgggcgatc ctaaaaagaa acgtaaggtc atcgattacc catacgatgt tccagattac     60
gctatcgata tcgccgatct acgcacgctc ggctacagcc agcagcaaca ggagaagatc    120
aaaccgaagg ttcgttcgac agtggcgcag caccacgagg cactggtcgg ccacgggttt    180
acacacgcgc acatcgttgc gttaagccaa caccggcag cgttagggac cgtcgctgtc     240
aagtatcagg acatgatcgc agcgttgcca gaggcgacac acgaagcgat cgttggcgtc    300
ggcaaacagt ggtccggcgc acgcgctctg gaggccttgc tcacggtggc gggagagttg    360
agaggtccac cgttacagtt ggacacaggc caacttctca gattgcaaa acgtggcggc    420 gtgaccgcag tggaggcagt gcatgcatgg cgcaatgcac tgacgggtgc cccgctcaac    480
```

```
ttgaccccgg agcaggtggt ggccatcgcc agcaatattg gtggcaagca ggcgctggag    540
acggtgcagg cgctgttgcc ggtgctgtgc caggcccacg gcttgacccc ggagcaggtg    600
gtggccatcg ccagccacga tggcggcaag caggcgctgg agacggtcca gcggctgttg    660
ccggtgctgt gccaggccca cggcttgacc ccggagcagg tggtggccat cgccagccac    720
gatggcggca agcaggcgct ggagacggtc agcggctgt tgccggtgct gtgccaggcc    780
cacggcttga ccccccagca ggtggtggcc atcgccagca atggcggtgg caagcaggcg    840
ctggagacgg tccagcggct gttgccggtg ctgtgccagg cccacggctt gaccccggag    900
caggtggtgg ccatcgccag ccacgatggc ggcaagcagg cgctggagac ggtccagcgg    960
ctgttgccgg tgctgtgcca ggcccacggc ttgaccccc agcaggtggt ggccatcgcc   1020
agcaatggcg gtggcaagca ggcgctggag acggtccagc ggctgttgcc ggtgctgtgc   1080
caggcccacg gcttgacccc ccagcaggtg gtggccatcg ccagcaataa tggtggcaag   1140
caggcgctgg agacggtcca gcggctgttg ccggtgctgt gccaggccca cggcttgacc   1200
ccccagcagg tggtggccat cgccagcaat ggcggtggca agcaggcgct ggagacggtc   1260
cagcggctgt tgccggtgct gtgccaggcc cacggcttga ccccccagca ggtggtggcc   1320
atcgccagca ataatggtgg caagcaggcg ctggagacgg tccagcggct gttgccggtg   1380
ctgtgccagg cccacggctt gaccccccag caggtggtgg ccatcgccag caataatggt   1440
ggcaagcagg cgctggagac ggtccagcgg ctgttgccgg tgctgtgcca ggcccacggc   1500
ttgaccccc agcaggtggt ggccatcgcc agcaataatg gtggcaagca ggcgctggag   1560
acggtccagc ggctgttgcc ggtgctgtgc caggcccacg gcttgacccc ccagcaggtg   1620
gtggccatcg ccagcaataa tggtggcaag caggcgctgg agacggtcca gcggctgttg   1680
ccggtgctgt gccaggccca cggcttgacc ccggagcagg tggtggccat cgccagccac   1740
gatggcggca agcaggcgct ggagacggtc agcggctgt tgccggtgct gtgccaggcc   1800
cacggcttga ccccggagca ggtggtggcc atcgccagcc acgatggcgg caagcaggcg   1860
ctggagacgg tccagcggct gttgccggtg ctgtgccagg cccacggctt gaccccggag   1920
caggtggtgg ccatcgccag caatattggt ggcaagcagg cgctggagac ggtgcaggcg   1980
ctgttgccgg tgctgtgcca ggcccacggc ttgacccctc agcaggtggt ggccatcgcc   2040
agcaatggcg gcggcaggcc ggcgctggag agcattgttg cccagttatc tcgccctgat   2100
ccggcgttgg ccgcgttgac caacgaccac ctcgtcgcct tggcctgcct cggcgggcgt   2160
cctgcgctga tgcagtgaa aagggattg ggggatccta tcagccgttc ccagctggtg   2220
aagtccgagc tggaggagaa gaaatccgag ttgaggcaca agctgaagta cgtgcccac   2280
gagtacatcg agctgatcga gatcgcccgg aacagcaccc aggaccgtat cctggagatg   2340
aaggtgatgg agttcttcat gaaggtgtac ggctacaggg gcaagcacct gggcggctcc   2400
aggaagcccg acggcgccat ctacaccgtg ggctccccca tcgactacgg cgtgatcgtg   2460
gacaccaagg cctactccgg cggctacaac ctgcccatcg ccaggccga cgaaatgcag   2520
aggtacgtgg aggagaacca gaccaggaac aagcacatca ccccaacga gtggtggaag   2580
gtgtaccccct ccagcgtgac cgagttcaag ttcctgttcg tgtccggcca cttcaagggc   2640
aactacaagg cccagctgac caggctgaac cacatcacca ctgcaacgg cgccgtgctg   2700
tccgtggagg agctcctgat cggcggcgag atgatcaagg ccgcaccct gaccctggag   2760
gaggtgagga ggaagttcaa caacggcgag atcaacttcg cggccgactg ataa        2814
```

<210> SEQ ID NO 98
<211> LENGTH: 2829
<212> TYPE: DNA
<213> ORGANISM: Artificial sequence
<220> FEATURE:
<223> OTHER INFORMATION: PDCD1_T03-R TALEN

<400> SEQUENCE: 98

| | |
|---|---|
| atgggcgatc ctaaaaagaa acgtaaggtc atcgataagg agaccgccgc tgccaagttc | 60 |
| gagagacagc acatggacag catcgatatc gccgatctac gcacgctcgg ctacagccag | 120 |
| cagcaacagg agaagatcaa accgaaggtt cgttcgacag tggcgcagca ccacgaggca | 180 |
| ctggtcggcc acgggtttac acacgcgcac atcgttgcgt taagccaaca cccggcagcg | 240 |
| ttagggaccg tcgctgtcaa gtatcaggac atgatcgcag cgttgccaga ggcgacacac | 300 |
| gaagcgatcg ttggcgtcgg caaacagtgg tccggcgcac gcgctctgga ggccttgctc | 360 |
| acggtggcgg gagagttgag aggtccaccg ttacagttgg acacaggcca acttctcaag | 420 |
| attgcaaaac gtggcggcgt gaccgcagtg gaggcagtgc atgcatggcg caatgcactg | 480 |
| acgggtgccc cgctcaactt gaccccgag caagtcgtcg caatcgccag ccatgatgga | 540 |
| gggaagcaag ccctcgaaac cgtgcagcgg ttgcttcctg tgctctgcca ggcccacggc | 600 |
| cttacccctc agcaggtggt ggccatcgca agtaacggag gaggaaagca agccttggag | 660 |
| acagtgcagc gcctgttgcc cgtgctgtgc caggcacacg gcctcacacc agagcaggtc | 720 |
| gtggccattg cctcccatga cggggggaaa caggctctgg agaccgtcca gaggctgctg | 780 |
| cccgtcctct gtcaagctca cggcctgact ccccaacaag tggtcgccat cgcctctaat | 840 |
| ggcggcggga agcaggcact ggaaacagtg cagagactgc tccctgtgct ttgccaagct | 900 |
| catgggttga cccccaaca ggtcgtcgct attgcctcaa acgggggggg caagcaggcc | 960 |
| cttgagactg tgcagaggct gttgccagtg ctgtgtcagg ctcacgggct cactccacaa | 1020 |
| caggtggtcg caattgccag caacggcggc ggaaagcaag ctcttgaaac cgtgcaacgc | 1080 |
| ctcctgcccg tgctctgtca ggctcatggc ctgacaccac aacaagtcgt ggccatcgcc | 1140 |
| agtaataatg gcgggaaaca ggctcttgag accgtccaga ggctgctccc agtgctctgc | 1200 |
| caggcacacg gctgaccccc cgagcaggtg gtggctatcg ccagcaatat tgggggcaag | 1260 |
| caggccctgg aaacagtcca ggccctgctg ccagtgcttt gccaggctca cgggctcact | 1320 |
| ccccagcagg tcgtggcaat cgcctccaac ggcggaggga agcaggctct ggagaccgtg | 1380 |
| cagagactgc tgcccgtctt gtgccaggcc acggactca cacctgaaca ggtcgtcgcc | 1440 |
| attgcctctc acgatggggg caacaagcc ctggagacag tgcagcggct gttgcctgtg | 1500 |
| ttgtgccaag cccacggctt gactcctcaa caagtggtcg ccatcgcctc aaatggcggc | 1560 |
| ggaaaacaag ctctggagac agtgcagagg ttgctgcccg tcctctgcca agcccacggc | 1620 |
| ctgactcccc aacaggtcgt cgccattgcc agcaacaacg gaggaaagca ggctctcgaa | 1680 |
| actgtgcagc ggctgcttcc tgtgctgtgt caggctcatg gctgaccccc cgagcaagtg | 1740 |
| gtggctattg cctctaatgg aggcaagcaa gcccttgaga cagtccagag gctgttgcca | 1800 |
| gtgctgtgcc aggcccacgg ctcacaccc cagcaggtgg tcgccatcgc cagtaacaac | 1860 |
| gggggcaaac aggcattgga aaccgtccag cgcctgcttc agtgctctg ccaggcacac | 1920 |
| ggactgacac ccgaacaggt ggtggccatt gcatcccatg atggggcaa gcaggccctg | 1980 |
| gagaccgtgc agagactcct gccagtgttg tgccaagctc acggcctcac ccctcagcaa | 2040 |
| gtcgtggcca tcgcctcaaa cggggggggc cggcctgcac tggagagcat tgttgcccag | 2100 |

```
ttatctcgcc ctgatccggc gttggccgcg ttgaccaacg accacctcgt cgccttggcc    2160
tgcctcggcg gcgtcctgc gctggatgca gtgaaaaagg gattggggga tcctatcagc     2220
cgttcccagc tggtgaagtc cgagctggag gagaagaaat ccgagttgag gcacaagctg    2280
aagtacgtgc cccacgagta catcgagctg atcgagatcg cccggaacag cacccaggac    2340
cgtatcctgg agatgaaggt gatggagttc ttcatgaagg tgtacggcta caggggcaag    2400
cacctgggcg gctccaggaa gcccgacggc gccatctaca ccgtgggctc ccccatcgac    2460
tacggcgtga tcgtggacac caaggcctac tccggcggct acaacctgcc catcggccag    2520
gccgacgaaa tgcagaggta cgtggaggag aaccagacca ggaacaagca catcaacccc    2580
aacgagtggt ggaaggtgta cccctccagc gtgaccgagt tcaagttcct gttcgtgtcc    2640
ggccacttca agggcaacta caaggcccag ctgaccaggc tgaaccacat caccaactgc    2700
aacggcgccg tgctgtccgt ggaggagctc ctgatcggcg gcgagatgat caaggccggc    2760
accctgaccc tggaggaggt gaggaggaag ttcaacaacg gcgagatcaa cttcgcggcc    2820
gactgataa                                                            2829

<210> SEQ ID NO 99
<211> LENGTH: 60
<212> TYPE: DNA
<213> ORGANISM: Artificial sequence
<220> FEATURE:
<223> OTHER INFORMATION: Forward primer CTLA4_T01
<220> FEATURE:
<221> NAME/KEY: misc_feature
<222> LOCATION: (31); (32); (33); (34); (35); (36); (37); (38); (39);
      (40)
<223> OTHER INFORMATION: n is a or c or t or g

<400> SEQUENCE: 99
ccatctcatc cctgcgtgtc tccgactcag nnnnnnnnnn ctctacttcc tgaagacctg    60

<210> SEQ ID NO 100
<211> LENGTH: 60
<212> TYPE: DNA
<213> ORGANISM: Artificial sequence
<220> FEATURE:
<223> OTHER INFORMATION: Forward primer CTLA4_T03/T04
<220> FEATURE:
<221> NAME/KEY: misc_feature
<222> LOCATION: (31); (32); (33); (34); (35); (36); (37); (38); (39);
      (40)
<223> OTHER INFORMATION: n is a or c or t or g

<400> SEQUENCE: 100
ccatctcatc cctgcgtgtc tccgactcag nnnnnnnnnn acagttgaga gatggagggg    60

<210> SEQ ID NO 101
<211> LENGTH: 59
<212> TYPE: DNA
<213> ORGANISM: Artificial sequence
<220> FEATURE:
<223> OTHER INFORMATION: Forward primer PDCD1_T01
<220> FEATURE:
<221> NAME/KEY: misc_feature
<222> LOCATION: (31); (32); (33); (34); (35); (36); (37); (38); (39);
      (40)
<223> OTHER INFORMATION: n is a or c or t or g

<400> SEQUENCE: 101
ccatctcatc cctgcgtgtc tccgactcag nnnnnnnnnn ccacagaggt aggtgccgc     59

<210> SEQ ID NO 102
```

```
<211> LENGTH: 60
<212> TYPE: DNA
<213> ORGANISM: Artificial sequence
<220> FEATURE:
<223> OTHER INFORMATION: Forward primer PDCD1_T03
<220> FEATURE:
<221> NAME/KEY: misc_feature
<222> LOCATION: (31); (32); (33); (34); (35); (36); (37); (38); (39);
      (40)
<223> OTHER INFORMATION: n is a or c or t or g

<400> SEQUENCE: 102
ccatctcatc cctgcgtgtc tccgactcag nnnnnnnnnn gacagagatg ccggtcacca      60

<210> SEQ ID NO 103
<211> LENGTH: 50
<212> TYPE: DNA
<213> ORGANISM: Artificial sequence
<220> FEATURE:
<223> OTHER INFORMATION: Reverse primer CTLA4_T01

<400> SEQUENCE: 103
cctatcccct gtgtgccttg gcagtctcag tggaatacag agccagccaa                50

<210> SEQ ID NO 104
<211> LENGTH: 50
<212> TYPE: DNA
<213> ORGANISM: Artificial sequence
<220> FEATURE:
<223> OTHER INFORMATION: Reverse primer CTLA4_T03/04

<400> SEQUENCE: 104
cctatcccct gtgtgccttg gcagtctcag ggtgcccgtg cagatggaat                50

<210> SEQ ID NO 105
<211> LENGTH: 50
<212> TYPE: DNA
<213> ORGANISM: Artificial sequence
<220> FEATURE:
<223> OTHER INFORMATION: Reverse primer PDCD1_T01

<400> SEQUENCE: 105
cctatcccct gtgtgccttg gcagtctcag ggctctgcag tggaggccag                50

<210> SEQ ID NO 106
<211> LENGTH: 50
<212> TYPE: DNA
<213> ORGANISM: Artificial sequence
<220> FEATURE:
<223> OTHER INFORMATION: Reverse primer PDCD1_T03

<400> SEQUENCE: 106
cctatcccct gtgtgccttg gcagtctcag ggacaacgcc accttcacct                50

<210> SEQ ID NO 107
<211> LENGTH: 281
<212> TYPE: PRT
<213> ORGANISM: Artificialsequence
<220> FEATURE:
<223> OTHER INFORMATION: pTalpha-FL

<400> SEQUENCE: 107

Met Ala Gly Thr Trp Leu Leu Leu Leu Ala Leu Gly Cys Pro Ala
1               5                   10                  15

Leu Pro Thr Gly Val Gly Gly Thr Pro Phe Pro Ser Leu Ala Pro Pro
            20                  25                  30
```

```
Ile Met Leu Leu Val Asp Gly Lys Gln Gln Met Val Val Cys Leu
        35                  40                  45

Val Leu Asp Val Ala Pro Pro Gly Leu Asp Ser Pro Ile Trp Phe Ser
    50                  55                  60

Ala Gly Asn Gly Ser Ala Leu Asp Ala Phe Thr Tyr Gly Pro Ser Pro
65                  70                  75                  80

Ala Thr Asp Gly Thr Trp Thr Asn Leu Ala His Leu Ser Leu Pro Ser
                85                  90                  95

Glu Glu Leu Ala Ser Trp Glu Pro Leu Val Cys His Thr Gly Pro Gly
                100                 105                 110

Ala Glu Gly His Ser Arg Ser Thr Gln Pro Met His Leu Ser Gly Glu
                115                 120                 125

Ala Ser Thr Ala Arg Thr Cys Pro Gln Glu Pro Leu Arg Gly Thr Pro
    130                 135                 140

Gly Gly Ala Leu Trp Leu Gly Val Leu Arg Leu Leu Leu Phe Lys Leu
145                 150                 155                 160

Leu Leu Phe Asp Leu Leu Leu Thr Cys Ser Cys Leu Cys Asp Pro Ala
                165                 170                 175

Gly Pro Leu Pro Ser Pro Ala Thr Thr Thr Arg Leu Arg Ala Leu Gly
                180                 185                 190

Ser His Arg Leu His Pro Ala Thr Glu Thr Gly Gly Arg Glu Ala Thr
            195                 200                 205

Ser Ser Pro Arg Pro Gln Pro Arg Asp Arg Arg Trp Gly Asp Thr Pro
            210                 215                 220

Pro Gly Arg Lys Pro Gly Ser Pro Val Trp Gly Glu Gly Ser Tyr Leu
225                 230                 235                 240

Ser Ser Tyr Pro Thr Cys Pro Ala Gln Ala Trp Cys Ser Arg Ser Arg
                245                 250                 255

Leu Arg Ala Pro Ser Ser Ser Leu Gly Ala Phe Phe Arg Gly Asp Leu
                260                 265                 270

Pro Pro Pro Leu Gln Ala Gly Ala Ala
                275                 280

<210> SEQ ID NO 108
<211> LENGTH: 263
<212> TYPE: PRT
<213> ORGANISM: Artificialsequence
<220> FEATURE:
<223> OTHER INFORMATION: pTalpha-Delta18

<400> SEQUENCE: 108

Met Ala Gly Thr Trp Leu Leu Leu Leu Ala Leu Gly Cys Pro Ala
1               5                   10                  15

Leu Pro Thr Gly Val Gly Gly Thr Pro Phe Pro Ser Leu Ala Pro Pro
                20                  25                  30

Ile Met Leu Leu Val Asp Gly Lys Gln Gln Met Val Val Cys Leu
        35                  40                  45

Val Leu Asp Val Ala Pro Pro Gly Leu Asp Ser Pro Ile Trp Phe Ser
    50                  55                  60

Ala Gly Asn Gly Ser Ala Leu Asp Ala Phe Thr Tyr Gly Pro Ser Pro
65                  70                  75                  80

Ala Thr Asp Gly Thr Trp Thr Asn Leu Ala His Leu Ser Leu Pro Ser
                85                  90                  95

Glu Glu Leu Ala Ser Trp Glu Pro Leu Val Cys His Thr Gly Pro Gly
                100                 105                 110
```

```
Ala Glu Gly His Ser Arg Ser Thr Gln Pro Met His Leu Ser Gly Glu
            115                 120                 125

Ala Ser Thr Ala Arg Thr Cys Pro Gln Glu Pro Leu Arg Gly Thr Pro
130                 135                 140

Gly Gly Ala Leu Trp Leu Gly Val Leu Arg Leu Leu Leu Phe Lys Leu
145                 150                 155                 160

Leu Leu Phe Asp Leu Leu Leu Thr Cys Ser Cys Leu Cys Asp Pro Ala
                165                 170                 175

Gly Pro Leu Pro Ser Pro Ala Thr Thr Thr Arg Leu Arg Ala Leu Gly
            180                 185                 190

Ser His Arg Leu His Pro Ala Thr Glu Thr Gly Gly Arg Glu Ala Thr
        195                 200                 205

Ser Ser Pro Arg Pro Gln Pro Arg Asp Arg Arg Trp Gly Asp Thr Pro
210                 215                 220

Pro Gly Arg Lys Pro Gly Ser Pro Val Trp Gly Glu Gly Ser Tyr Leu
225                 230                 235                 240

Ser Ser Tyr Pro Thr Cys Pro Ala Gln Ala Trp Cys Ser Arg Ser Arg
                245                 250                 255

Leu Arg Ala Pro Ser Ser Ser
            260

<210> SEQ ID NO 109
<211> LENGTH: 233
<212> TYPE: PRT
<213> ORGANISM: Artificialsequence
<220> FEATURE:
<223> OTHER INFORMATION: pTalpha-Delta48

<400> SEQUENCE: 109

Met Ala Gly Thr Trp Leu Leu Leu Leu Ala Leu Gly Cys Pro Ala
1               5                   10                  15

Leu Pro Thr Gly Val Gly Gly Thr Pro Phe Pro Ser Leu Ala Pro Pro
            20                  25                  30

Ile Met Leu Leu Val Asp Gly Lys Gln Gln Met Val Val Val Cys Leu
                35                  40                  45

Val Leu Asp Val Ala Pro Pro Gly Leu Asp Ser Pro Ile Trp Phe Ser
50                  55                  60

Ala Gly Asn Gly Ser Ala Leu Asp Ala Phe Thr Tyr Gly Pro Ser Pro
65                  70                  75                  80

Ala Thr Asp Gly Thr Trp Thr Asn Leu Ala His Leu Ser Leu Pro Ser
                85                  90                  95

Glu Glu Leu Ala Ser Trp Glu Pro Leu Val Cys His Thr Gly Pro Gly
            100                 105                 110

Ala Glu Gly His Ser Arg Ser Thr Gln Pro Met His Leu Ser Gly Glu
            115                 120                 125

Ala Ser Thr Ala Arg Thr Cys Pro Gln Glu Pro Leu Arg Gly Thr Pro
130                 135                 140

Gly Gly Ala Leu Trp Leu Gly Val Leu Arg Leu Leu Leu Phe Lys Leu
145                 150                 155                 160

Leu Leu Phe Asp Leu Leu Leu Thr Cys Ser Cys Leu Cys Asp Pro Ala
                165                 170                 175

Gly Pro Leu Pro Ser Pro Ala Thr Thr Thr Arg Leu Arg Ala Leu Gly
            180                 185                 190

Ser His Arg Leu His Pro Ala Thr Glu Thr Gly Gly Arg Glu Ala Thr
        195                 200                 205
```

-continued

Ser Ser Pro Arg Pro Gln Pro Arg Asp Arg Arg Trp Gly Asp Thr Pro
    210                 215                 220

Pro Gly Arg Lys Pro Gly Ser Pro Val
225                 230

<210> SEQ ID NO 110
<211> LENGTH: 219
<212> TYPE: PRT
<213> ORGANISM: Artificialsequence
<220> FEATURE:
<223> OTHER INFORMATION: pTalpha-Delta62

<400> SEQUENCE: 110

Met Ala Gly Thr Trp Leu Leu Leu Leu Ala Leu Gly Cys Pro Ala
1               5                   10                  15

Leu Pro Thr Gly Val Gly Gly Thr Pro Phe Pro Ser Leu Ala Pro Pro
            20                  25                  30

Ile Met Leu Leu Val Asp Gly Lys Gln Gln Met Val Val Cys Leu
        35                  40                  45

Val Leu Asp Val Ala Pro Pro Gly Leu Asp Ser Pro Ile Trp Phe Ser
    50                  55                  60

Ala Gly Asn Gly Ser Ala Leu Asp Ala Phe Thr Tyr Gly Pro Ser Pro
65                  70                  75                  80

Ala Thr Asp Gly Thr Trp Thr Asn Leu Ala His Leu Ser Leu Pro Ser
                85                  90                  95

Glu Glu Leu Ala Ser Trp Glu Pro Leu Val Cys His Thr Gly Pro Gly
            100                 105                 110

Ala Glu Gly His Ser Arg Ser Thr Gln Pro Met His Leu Ser Gly Glu
        115                 120                 125

Ala Ser Thr Ala Arg Thr Cys Pro Gln Glu Pro Leu Arg Gly Thr Pro
    130                 135                 140

Gly Gly Ala Leu Trp Leu Gly Val Leu Arg Leu Leu Leu Phe Lys Leu
145                 150                 155                 160

Leu Leu Phe Asp Leu Leu Leu Thr Cys Ser Cys Leu Cys Asp Pro Ala
                165                 170                 175

Gly Pro Leu Pro Ser Pro Ala Thr Thr Thr Arg Leu Arg Ala Leu Gly
            180                 185                 190

Ser His Arg Leu His Pro Ala Thr Glu Thr Gly Gly Arg Glu Ala Thr
        195                 200                 205

Ser Ser Pro Arg Pro Gln Pro Arg Asp Arg Arg
    210                 215

<210> SEQ ID NO 111
<211> LENGTH: 203
<212> TYPE: PRT
<213> ORGANISM: Artificialsequence
<220> FEATURE:
<223> OTHER INFORMATION: pTalpha-Delta78

<400> SEQUENCE: 111

Met Ala Gly Thr Trp Leu Leu Leu Leu Ala Leu Gly Cys Pro Ala
1               5                   10                  15

Leu Pro Thr Gly Val Gly Gly Thr Pro Phe Pro Ser Leu Ala Pro Pro
            20                  25                  30

Ile Met Leu Leu Val Asp Gly Lys Gln Gln Met Val Val Cys Leu
        35                  40                  45

Val Leu Asp Val Ala Pro Pro Gly Leu Asp Ser Pro Ile Trp Phe Ser
    50                  55                  60

Ala Gly Asn Gly Ser Ala Leu Asp Ala Phe Thr Tyr Gly Pro Ser Pro
65                  70                  75                  80

Ala Thr Asp Gly Thr Trp Thr Asn Leu Ala His Leu Ser Leu Pro Ser
                85                  90                  95

Glu Glu Leu Ala Ser Trp Glu Pro Leu Val Cys His Thr Gly Pro Gly
            100                 105                 110

Ala Glu Gly His Ser Arg Ser Thr Gln Pro Met His Leu Ser Gly Glu
        115                 120                 125

Ala Ser Thr Ala Arg Thr Cys Pro Gln Glu Pro Leu Arg Gly Thr Pro
    130                 135                 140

Gly Gly Ala Leu Trp Leu Gly Val Leu Arg Leu Leu Phe Lys Leu
145                 150                 155                 160

Leu Leu Phe Asp Leu Leu Leu Thr Cys Ser Cys Leu Cys Asp Pro Ala
                165                 170                 175

Gly Pro Leu Pro Ser Pro Ala Thr Thr Thr Arg Leu Arg Ala Leu Gly
            180                 185                 190

Ser His Arg Leu His Pro Ala Thr Glu Thr Gly
        195                 200

<210> SEQ ID NO 112
<211> LENGTH: 189
<212> TYPE: PRT
<213> ORGANISM: Artificialsequence
<220> FEATURE:
<223> OTHER INFORMATION: pTalpha-Delta92

<400> SEQUENCE: 112

Met Ala Gly Thr Trp Leu Leu Leu Leu Ala Leu Gly Cys Pro Ala
1               5                   10                  15

Leu Pro Thr Gly Val Gly Gly Thr Pro Phe Pro Ser Leu Ala Pro Pro
                20                  25                  30

Ile Met Leu Leu Val Asp Gly Lys Gln Gln Met Val Val Val Cys Leu
            35                  40                  45

Val Leu Asp Val Ala Pro Pro Gly Leu Asp Ser Pro Ile Trp Phe Ser
    50                  55                  60

Ala Gly Asn Gly Ser Ala Leu Asp Ala Phe Thr Tyr Gly Pro Ser Pro
65                  70                  75                  80

Ala Thr Asp Gly Thr Trp Thr Asn Leu Ala His Leu Ser Leu Pro Ser
                85                  90                  95

Glu Glu Leu Ala Ser Trp Glu Pro Leu Val Cys His Thr Gly Pro Gly
            100                 105                 110

Ala Glu Gly His Ser Arg Ser Thr Gln Pro Met His Leu Ser Gly Glu
        115                 120                 125

Ala Ser Thr Ala Arg Thr Cys Pro Gln Glu Pro Leu Arg Gly Thr Pro
    130                 135                 140

Gly Gly Ala Leu Trp Leu Gly Val Leu Arg Leu Leu Phe Lys Leu
145                 150                 155                 160

Leu Leu Phe Asp Leu Leu Leu Thr Cys Ser Cys Leu Cys Asp Pro Ala
                165                 170                 175

Gly Pro Leu Pro Ser Pro Ala Thr Thr Thr Arg Leu Arg
            180                 185

<210> SEQ ID NO 113
<211> LENGTH: 171
<212> TYPE: PRT
<213> ORGANISM: Artificialsequence
<220> FEATURE:
<223> OTHER INFORMATION: pTalpha-Delta110

<400> SEQUENCE: 113

```
Met Ala Gly Thr Trp Leu Leu Leu Leu Ala Leu Gly Cys Pro Ala
1               5                   10                  15

Leu Pro Thr Gly Val Gly Gly Thr Pro Phe Pro Ser Leu Ala Pro Pro
            20                  25                  30

Ile Met Leu Leu Val Asp Gly Lys Gln Gln Met Val Val Cys Leu
                35                  40                  45

Val Leu Asp Val Ala Pro Pro Gly Leu Asp Ser Pro Ile Trp Phe Ser
    50                  55                  60

Ala Gly Asn Gly Ser Ala Leu Asp Ala Phe Thr Tyr Gly Pro Ser Pro
65                  70                  75                  80

Ala Thr Asp Gly Thr Trp Thr Asn Leu Ala His Leu Ser Leu Pro Ser
                85                  90                  95

Glu Glu Leu Ala Ser Trp Glu Pro Leu Val Cys His Thr Gly Pro Gly
            100                 105                 110

Ala Glu Gly His Ser Arg Ser Thr Gln Pro Met His Leu Ser Gly Glu
        115                 120                 125

Ala Ser Thr Ala Arg Thr Cys Pro Gln Glu Pro Leu Arg Gly Thr Pro
    130                 135                 140

Gly Gly Ala Leu Trp Leu Gly Val Leu Arg Leu Leu Leu Phe Lys Leu
145                 150                 155                 160

Leu Leu Phe Asp Leu Leu Leu Thr Cys Ser Cys
                165                 170
```

<210> SEQ ID NO 114
<211> LENGTH: 167
<212> TYPE: PRT
<213> ORGANISM: Artificialsequence
<220> FEATURE:
<223> OTHER INFORMATION: pTalpha-Delta114

<400> SEQUENCE: 114

```
Met Ala Gly Thr Trp Leu Leu Leu Leu Ala Leu Gly Cys Pro Ala
1               5                   10                  15

Leu Pro Thr Gly Val Gly Gly Thr Pro Phe Pro Ser Leu Ala Pro Pro
            20                  25                  30

Ile Met Leu Leu Val Asp Gly Lys Gln Gln Met Val Val Cys Leu
                35                  40                  45

Val Leu Asp Val Ala Pro Pro Gly Leu Asp Ser Pro Ile Trp Phe Ser
    50                  55                  60

Ala Gly Asn Gly Ser Ala Leu Asp Ala Phe Thr Tyr Gly Pro Ser Pro
65                  70                  75                  80

Ala Thr Asp Gly Thr Trp Thr Asn Leu Ala His Leu Ser Leu Pro Ser
                85                  90                  95

Glu Glu Leu Ala Ser Trp Glu Pro Leu Val Cys His Thr Gly Pro Gly
            100                 105                 110

Ala Glu Gly His Ser Arg Ser Thr Gln Pro Met His Leu Ser Gly Glu
        115                 120                 125

Ala Ser Thr Ala Arg Thr Cys Pro Gln Glu Pro Leu Arg Gly Thr Pro
    130                 135                 140

Gly Gly Ala Leu Trp Leu Gly Val Leu Arg Leu Leu Leu Phe Lys Leu
145                 150                 155                 160

Leu Leu Phe Asp Leu Leu Leu
```

<210> SEQ ID NO 115
<211> LENGTH: 344
<212> TYPE: PRT
<213> ORGANISM: Artificialsequence
<220> FEATURE:
<223> OTHER INFORMATION: pTalpha-FL-CD28

<400> SEQUENCE: 115

```
Met Ala Gly Thr Trp Leu Leu Leu Leu Ala Leu Gly Cys Pro Ala
1               5                   10                  15

Leu Pro Thr Gly Val Gly Gly Thr Pro Phe Pro Ser Leu Ala Pro Pro
            20                  25                  30

Ile Met Leu Leu Val Asp Gly Lys Gln Gln Met Val Val Cys Leu
        35                  40                  45

Val Leu Asp Val Ala Pro Pro Gly Leu Asp Ser Pro Ile Trp Phe Ser
    50                  55                  60

Ala Gly Asn Gly Ser Ala Leu Asp Ala Phe Thr Tyr Gly Pro Ser Pro
65                  70                  75                  80

Ala Thr Asp Gly Thr Trp Thr Asn Leu Ala His Leu Ser Leu Pro Ser
                85                  90                  95

Glu Glu Leu Ala Ser Trp Glu Pro Leu Val Cys His Thr Gly Pro Gly
                100                 105                 110

Ala Glu Gly His Ser Arg Ser Thr Gln Pro Met His Leu Ser Gly Glu
            115                 120                 125

Ala Ser Thr Ala Arg Thr Cys Pro Gln Glu Pro Leu Arg Gly Thr Pro
130                 135                 140

Gly Gly Ala Leu Trp Leu Gly Val Leu Arg Leu Leu Leu Phe Lys Leu
145                 150                 155                 160

Leu Leu Phe Asp Leu Leu Leu Thr Cys Ser Cys Leu Cys Asp Pro Ala
                165                 170                 175

Gly Pro Leu Pro Ser Pro Ala Thr Thr Thr Arg Leu Arg Ala Leu Gly
            180                 185                 190

Ser His Arg Leu His Pro Ala Thr Glu Thr Gly Gly Arg Glu Ala Thr
        195                 200                 205

Ser Ser Pro Arg Pro Gln Pro Arg Asp Arg Arg Trp Gly Asp Thr Pro
    210                 215                 220

Pro Gly Arg Lys Pro Gly Ser Pro Val Trp Gly Glu Gly Ser Tyr Leu
225                 230                 235                 240

Ser Ser Tyr Pro Thr Cys Pro Ala Gln Ala Trp Cys Ser Arg Ser Arg
                245                 250                 255

Leu Arg Ala Pro Ser Ser Leu Gly Ala Phe Phe Arg Gly Asp Leu
            260                 265                 270

Pro Pro Pro Leu Gln Ala Gly Ala Ala Ser Gly Gly Val Leu Ala
        275                 280                 285

Cys Tyr Ser Leu Leu Val Thr Val Ala Phe Ile Ile Phe Trp Val Arg
    290                 295                 300

Ser Lys Arg Ser Arg Gly Gly His Ser Asp Tyr Met Asn Met Thr Pro
305                 310                 315                 320

Arg Arg Pro Gly Pro Thr Arg Lys His Tyr Gln Pro Tyr Ala Pro Pro
                325                 330                 335

Arg Asp Phe Ala Ala Tyr Arg Ser
            340
```

<210> SEQ ID NO 116
<211> LENGTH: 311
<212> TYPE: PRT
<213> ORGANISM: Artificialsequence
<220> FEATURE:
<223> OTHER INFORMATION: pTalpha-FL-CD8

<400> SEQUENCE: 116

```
Met Ala Gly Thr Trp Leu Leu Leu Ala Leu Gly Cys Pro Ala
1               5                   10                  15

Leu Pro Thr Gly Val Gly Gly Thr Pro Phe Pro Ser Leu Ala Pro Pro
            20                  25                  30

Ile Met Leu Leu Val Asp Gly Lys Gln Gln Met Val Val Cys Leu
        35                  40                      45

Val Leu Asp Val Ala Pro Pro Gly Leu Asp Ser Pro Ile Trp Phe Ser
50                      55                      60

Ala Gly Asn Gly Ser Ala Leu Asp Ala Phe Thr Tyr Gly Pro Ser Pro
65                  70                  75                      80

Ala Thr Asp Gly Thr Trp Thr Asn Leu Ala His Leu Ser Leu Pro Ser
                85                  90                  95

Glu Glu Leu Ala Ser Trp Glu Pro Leu Val Cys His Thr Gly Pro Gly
            100                 105                 110

Ala Glu Gly His Ser Arg Ser Thr Gln Pro Met His Leu Ser Gly Glu
        115                 120                 125

Ala Ser Thr Ala Arg Thr Cys Pro Gln Glu Pro Leu Arg Gly Thr Pro
130                 135                 140

Gly Gly Ala Leu Trp Leu Gly Val Leu Arg Leu Leu Leu Phe Lys Leu
145                 150                 155                 160

Leu Leu Phe Asp Leu Leu Leu Thr Cys Ser Cys Leu Cys Asp Pro Ala
                165                 170                 175

Gly Pro Leu Pro Ser Pro Ala Thr Thr Thr Arg Leu Arg Ala Leu Gly
            180                 185                 190

Ser His Arg Leu His Pro Ala Thr Glu Thr Gly Gly Arg Glu Ala Thr
        195                 200                 205

Ser Ser Pro Arg Pro Gln Pro Arg Asp Arg Arg Trp Gly Asp Thr Pro
210                 215                 220

Pro Gly Arg Lys Pro Gly Ser Pro Val Trp Gly Glu Gly Ser Tyr Leu
225                 230                 235                 240

Ser Ser Tyr Pro Thr Cys Pro Ala Gln Ala Trp Cys Ser Arg Ser Arg
                245                 250                 255

Leu Arg Ala Pro Ser Ser Ser Leu Gly Ala Phe Phe Arg Gly Asp Leu
            260                 265                 270

Pro Pro Pro Leu Gln Ala Gly Ala Ala Ala Ser His Arg Asn Arg Arg
        275                 280                 285

Arg Val Cys Lys Cys Pro Arg Pro Val Val Lys Ser Gly Asp Lys Pro
290                 295                 300

Ser Leu Ser Ala Arg Tyr Val
305                 310
```

<210> SEQ ID NO 117
<211> LENGTH: 325
<212> TYPE: PRT
<213> ORGANISM: Artificialsequence
<220> FEATURE:
<223> OTHER INFORMATION: pTalpha-FL-41BB

<400> SEQUENCE: 117

Met Ala Gly Thr Trp Leu Leu Leu Leu Ala Leu Gly Cys Pro Ala
1               5                   10                  15

Leu Pro Thr Gly Val Gly Gly Thr Pro Phe Pro Ser Leu Ala Pro Pro
            20                  25                  30

Ile Met Leu Leu Val Asp Gly Lys Gln Gln Met Val Val Cys Leu
                35                  40                  45

Val Leu Asp Val Ala Pro Pro Gly Leu Asp Ser Pro Ile Trp Phe Ser
50                  55                  60

Ala Gly Asn Gly Ser Ala Leu Asp Ala Phe Thr Tyr Gly Pro Ser Pro
65                  70                  75                  80

Ala Thr Asp Gly Thr Trp Thr Asn Leu Ala His Leu Ser Leu Pro Ser
                85                  90                  95

Glu Glu Leu Ala Ser Trp Glu Pro Leu Val Cys His Thr Gly Pro Gly
            100                 105                 110

Ala Glu Gly His Ser Arg Ser Thr Gln Pro Met His Leu Ser Gly Glu
        115                 120                 125

Ala Ser Thr Ala Arg Thr Cys Pro Gln Glu Pro Leu Arg Gly Thr Pro
130                 135                 140

Gly Gly Ala Leu Trp Leu Gly Val Leu Arg Leu Leu Leu Phe Lys Leu
145                 150                 155                 160

Leu Leu Phe Asp Leu Leu Thr Cys Ser Cys Leu Cys Asp Pro Ala
                165                 170                 175

Gly Pro Leu Pro Ser Pro Ala Thr Thr Thr Arg Leu Arg Ala Leu Gly
            180                 185                 190

Ser His Arg Leu His Pro Ala Thr Glu Thr Gly Gly Arg Glu Ala Thr
        195                 200                 205

Ser Ser Pro Arg Pro Gln Pro Arg Asp Arg Arg Trp Gly Asp Thr Pro
210                 215                 220

Pro Gly Arg Lys Pro Gly Ser Pro Val Trp Gly Glu Gly Ser Tyr Leu
225                 230                 235                 240

Ser Ser Tyr Pro Thr Cys Pro Ala Gln Ala Trp Cys Ser Arg Ser Arg
                245                 250                 255

Leu Arg Ala Pro Ser Ser Ser Leu Gly Ala Phe Phe Arg Gly Asp Leu
            260                 265                 270

Pro Pro Pro Leu Gln Ala Gly Ala Ala Gly Ser Lys Arg Gly Arg Lys
        275                 280                 285

Lys Leu Leu Tyr Ile Phe Lys Gln Pro Phe Met Arg Pro Val Gln Thr
        290                 295                 300

Thr Gln Glu Glu Asp Gly Cys Ser Cys Arg Phe Pro Glu Glu Glu Glu
305                 310                 315                 320

Gly Gly Cys Glu Leu
            325

<210> SEQ ID NO 118
<211> LENGTH: 296
<212> TYPE: PRT
<213> ORGANISM: Artificialsequence
<220> FEATURE:
<223> OTHER INFORMATION: pTalpha-Delta48-CD28

<400> SEQUENCE: 118

Met Ala Gly Thr Trp Leu Leu Leu Leu Ala Leu Gly Cys Pro Ala
1               5                   10                  15

Leu Pro Thr Gly Val Gly Gly Thr Pro Phe Pro Ser Leu Ala Pro Pro
            20                  25                  30

Ile Met Leu Leu Val Asp Gly Lys Gln Gln Met Val Val Cys Leu
        35                  40                  45

Val Leu Asp Val Ala Pro Pro Gly Leu Asp Ser Pro Ile Trp Phe Ser
 50                  55                  60

Ala Gly Asn Gly Ser Ala Leu Asp Ala Phe Thr Tyr Gly Pro Ser Pro
 65                  70                  75                  80

Ala Thr Asp Gly Thr Trp Thr Asn Leu Ala His Leu Ser Leu Pro Ser
                 85                  90                  95

Glu Glu Leu Ala Ser Trp Glu Pro Leu Val Cys His Thr Gly Pro Gly
                100                 105                 110

Ala Glu Gly His Ser Arg Ser Thr Gln Pro Met His Leu Ser Gly Glu
            115                 120                 125

Ala Ser Thr Ala Arg Thr Cys Pro Gln Glu Pro Leu Arg Gly Thr Pro
    130                 135                 140

Gly Gly Ala Leu Trp Leu Gly Val Leu Arg Leu Leu Phe Lys Leu
145                 150                 155                 160

Leu Leu Phe Asp Leu Leu Leu Thr Cys Ser Cys Leu Cys Asp Pro Ala
                165                 170                 175

Gly Pro Leu Pro Ser Pro Ala Thr Thr Thr Arg Leu Arg Ala Leu Gly
            180                 185                 190

Ser His Arg Leu His Pro Ala Thr Glu Thr Gly Gly Arg Glu Ala Thr
    195                 200                 205

Ser Ser Pro Arg Pro Gln Pro Arg Asp Arg Arg Trp Gly Asp Thr Pro
210                 215                 220

Pro Gly Arg Lys Pro Gly Ser Pro Val Ala Ser Gly Val Leu Ala
225                 230                 235                 240

Cys Tyr Ser Leu Leu Val Thr Val Ala Phe Ile Ile Phe Trp Val Arg
                245                 250                 255

Ser Lys Arg Ser Arg Gly Gly His Ser Asp Tyr Met Asn Met Thr Pro
                260                 265                 270

Arg Arg Pro Gly Pro Thr Arg Lys His Tyr Gln Pro Tyr Ala Pro Pro
            275                 280                 285

Arg Asp Phe Ala Ala Tyr Arg Ser
    290                 295

<210> SEQ ID NO 119
<211> LENGTH: 263
<212> TYPE: PRT
<213> ORGANISM: Artificialsequence
<220> FEATURE:
<223> OTHER INFORMATION: pTalpha-Delta48-CD8

<400> SEQUENCE: 119

Met Ala Gly Thr Trp Leu Leu Leu Leu Ala Leu Gly Cys Pro Ala
 1               5                  10                  15

Leu Pro Thr Gly Val Gly Gly Thr Pro Phe Pro Ser Leu Ala Pro Pro
                 20                  25                  30

Ile Met Leu Leu Val Asp Gly Lys Gln Gln Met Val Val Cys Leu
        35                  40                  45

Val Leu Asp Val Ala Pro Pro Gly Leu Asp Ser Pro Ile Trp Phe Ser
 50                  55                  60

Ala Gly Asn Gly Ser Ala Leu Asp Ala Phe Thr Tyr Gly Pro Ser Pro
 65                  70                  75                  80

Ala Thr Asp Gly Thr Trp Thr Asn Leu Ala His Leu Ser Leu Pro Ser
                 85                  90                  95

```
Glu Glu Leu Ala Ser Trp Glu Pro Leu Val Cys His Thr Gly Pro Gly
            100                 105                 110

Ala Glu Gly His Ser Arg Ser Thr Gln Pro Met His Leu Ser Gly Glu
        115                 120                 125

Ala Ser Thr Ala Arg Thr Cys Pro Gln Glu Pro Leu Arg Gly Thr Pro
    130                 135                 140

Gly Gly Ala Leu Trp Leu Gly Val Leu Arg Leu Leu Phe Lys Leu
145                 150                 155                 160

Leu Leu Phe Asp Leu Leu Leu Thr Cys Ser Cys Leu Cys Asp Pro Ala
                165                 170                 175

Gly Pro Leu Pro Ser Pro Ala Thr Thr Thr Arg Leu Arg Ala Leu Gly
                180                 185                 190

Ser His Arg Leu His Pro Ala Thr Glu Thr Gly Gly Arg Glu Ala Thr
            195                 200                 205

Ser Ser Pro Arg Pro Gln Pro Arg Asp Arg Arg Trp Gly Asp Thr Pro
210                 215                 220

Pro Gly Arg Lys Pro Gly Ser Pro Val Ala Ser His Arg Asn Arg Arg
225                 230                 235                 240

Arg Val Cys Lys Cys Pro Arg Pro Val Val Lys Ser Gly Asp Lys Pro
                245                 250                 255

Ser Leu Ser Ala Arg Tyr Val
            260

<210> SEQ ID NO 120
<211> LENGTH: 277
<212> TYPE: PRT
<213> ORGANISM: Artificialsequence
<220> FEATURE:
<223> OTHER INFORMATION: pTalpha-Delta48-41BB

<400> SEQUENCE: 120

Met Ala Gly Thr Trp Leu Leu Leu Leu Ala Leu Gly Cys Pro Ala
1               5                   10                  15

Leu Pro Thr Gly Val Gly Gly Thr Pro Phe Pro Ser Leu Ala Pro Pro
                20                  25                  30

Ile Met Leu Leu Val Asp Gly Lys Gln Gln Met Val Val Cys Leu
            35                  40                  45

Val Leu Asp Val Ala Pro Pro Gly Leu Asp Ser Pro Ile Trp Phe Ser
    50                  55                  60

Ala Gly Asn Gly Ser Ala Leu Asp Ala Phe Thr Tyr Gly Pro Ser Pro
65                  70                  75                  80

Ala Thr Asp Gly Thr Trp Thr Asn Leu Ala His Leu Ser Leu Pro Ser
                85                  90                  95

Glu Glu Leu Ala Ser Trp Glu Pro Leu Val Cys His Thr Gly Pro Gly
            100                 105                 110

Ala Glu Gly His Ser Arg Ser Thr Gln Pro Met His Leu Ser Gly Glu
        115                 120                 125

Ala Ser Thr Ala Arg Thr Cys Pro Gln Glu Pro Leu Arg Gly Thr Pro
    130                 135                 140

Gly Gly Ala Leu Trp Leu Gly Val Leu Arg Leu Leu Phe Lys Leu
145                 150                 155                 160

Leu Leu Phe Asp Leu Leu Leu Thr Cys Ser Cys Leu Cys Asp Pro Ala
                165                 170                 175

Gly Pro Leu Pro Ser Pro Ala Thr Thr Thr Arg Leu Arg Ala Leu Gly
                180                 185                 190
```

```
Ser His Arg Leu His Pro Ala Thr Glu Thr Gly Gly Arg Glu Ala Thr
        195                 200                 205
Ser Ser Pro Arg Pro Gln Pro Arg Asp Arg Arg Trp Gly Asp Thr Pro
    210                 215                 220
Pro Gly Arg Lys Pro Gly Ser Pro Val Gly Ser Lys Arg Gly Arg Lys
225                 230                 235                 240
Lys Leu Leu Tyr Ile Phe Lys Gln Pro Phe Met Arg Pro Val Gln Thr
                245                 250                 255
Thr Gln Glu Glu Asp Gly Cys Ser Cys Arg Phe Pro Glu Glu Glu Glu
            260                 265                 270
Gly Gly Cys Glu Leu
        275

<210> SEQ ID NO 121
<211> LENGTH: 172
<212> TYPE: PRT
<213> ORGANISM: Artificialsequence
<220> FEATURE:
<223> OTHER INFORMATION: pTalpha-Delta114-TCRalpha.IC

<400> SEQUENCE: 121

Met Ala Gly Thr Trp Leu Leu Leu Leu Ala Leu Gly Cys Pro Ala
1               5                   10                  15
Leu Pro Thr Gly Val Gly Gly Thr Pro Phe Pro Ser Leu Ala Pro Pro
            20                  25                  30
Ile Met Leu Leu Val Asp Gly Lys Gln Gln Met Val Val Cys Leu
        35                  40                  45
Val Leu Asp Val Ala Pro Pro Gly Leu Asp Ser Pro Ile Trp Phe Ser
    50                  55                  60
Ala Gly Asn Gly Ser Ala Leu Asp Ala Phe Thr Tyr Gly Pro Ser Pro
65                  70                  75                  80
Ala Thr Asp Gly Thr Trp Thr Asn Leu Ala His Leu Ser Leu Pro Ser
                85                  90                  95
Glu Glu Leu Ala Ser Trp Glu Pro Leu Val Cys His Thr Gly Pro Gly
            100                 105                 110
Ala Glu Gly His Ser Arg Ser Thr Gln Pro Met His Leu Ser Gly Glu
        115                 120                 125
Ala Ser Thr Ala Arg Thr Cys Pro Gln Glu Pro Leu Arg Gly Thr Pro
    130                 135                 140
Gly Gly Ala Leu Trp Leu Gly Val Leu Arg Leu Leu Leu Phe Lys Leu
145                 150                 155                 160
Leu Leu Phe Asp Leu Leu Leu Arg Leu Trp Ser Ser
                165                 170

<210> SEQ ID NO 122
<211> LENGTH: 173
<212> TYPE: PRT
<213> ORGANISM: Artificialsequence
<220> FEATURE:
<223> OTHER INFORMATION: pTalpha.EC-TCRalpha.TM.IC

<400> SEQUENCE: 122

Met Ala Gly Thr Trp Leu Leu Leu Leu Ala Leu Gly Cys Pro Ala
1               5                   10                  15
Leu Pro Thr Gly Val Gly Gly Thr Pro Phe Pro Ser Leu Ala Pro Pro
            20                  25                  30
Ile Met Leu Leu Val Asp Gly Lys Gln Gln Met Val Val Cys Leu
        35                  40                  45
```

```
Val Leu Asp Val Ala Pro Pro Gly Leu Asp Ser Pro Ile Trp Phe Ser
     50                  55                  60

Ala Gly Asn Gly Ser Ala Leu Asp Ala Phe Thr Tyr Gly Pro Ser Pro
 65                  70                  75                  80

Ala Thr Asp Gly Thr Trp Thr Asn Leu Ala His Leu Ser Leu Pro Ser
                 85                  90                  95

Glu Glu Leu Ala Ser Trp Glu Pro Leu Val Cys His Thr Gly Pro Gly
             100                 105                 110

Ala Glu Gly His Ser Arg Ser Thr Gln Pro Met His Leu Ser Gly Glu
             115                 120                 125

Ala Ser Thr Ala Arg Thr Cys Pro Gln Glu Pro Leu Arg Gly Thr Pro
         130                 135                 140

Gly Gly Leu Ser Val Ile Gly Phe Arg Ile Leu Leu Leu Lys Val Ala
145                 150                 155                 160

Gly Phe Asn Leu Leu Met Thr Leu Arg Leu Trp Ser Ser
                 165                 170

<210> SEQ ID NO 123
<211> LENGTH: 233
<212> TYPE: PRT
<213> ORGANISM: Artificialsequence
<220> FEATURE:
<223> OTHER INFORMATION: pTalpha.EC-Delta48-1xMUT

<400> SEQUENCE: 123

Met Ala Gly Thr Trp Leu Leu Leu Leu Ala Leu Gly Cys Pro Ala
  1               5                  10                  15

Leu Pro Thr Gly Val Gly Gly Thr Pro Phe Pro Ser Leu Ala Pro Pro
                 20                  25                  30

Ile Met Leu Leu Val Asp Gly Lys Gln Gln Met Val Val Cys Leu
             35                  40                  45

Val Leu Asp Val Ala Pro Pro Gly Leu Asp Ser Pro Ile Arg Phe Ser
     50                  55                  60

Ala Gly Asn Gly Ser Ala Leu Asp Ala Phe Thr Tyr Gly Pro Ser Pro
 65                  70                  75                  80

Ala Thr Asp Gly Thr Trp Thr Asn Leu Ala His Leu Ser Leu Pro Ser
                 85                  90                  95

Glu Glu Leu Ala Ser Trp Glu Pro Leu Val Cys His Thr Gly Pro Gly
             100                 105                 110

Ala Glu Gly His Ser Arg Ser Thr Gln Pro Met His Leu Ser Gly Glu
             115                 120                 125

Ala Ser Thr Ala Arg Thr Cys Pro Gln Glu Pro Leu Arg Gly Thr Pro
         130                 135                 140

Gly Gly Ala Leu Trp Leu Gly Val Leu Arg Leu Leu Leu Phe Lys Leu
145                 150                 155                 160

Leu Leu Phe Asp Leu Leu Leu Thr Cys Ser Cys Leu Cys Asp Pro Ala
                 165                 170                 175

Gly Pro Leu Pro Ser Pro Ala Thr Thr Thr Arg Leu Arg Ala Leu Gly
             180                 185                 190

Ser His Arg Leu His Pro Ala Thr Glu Thr Gly Gly Arg Glu Ala Thr
             195                 200                 205

Ser Ser Pro Arg Pro Gln Pro Arg Asp Arg Trp Gly Asp Thr Pro
         210                 215                 220

Pro Gly Arg Lys Pro Gly Ser Pro Val
225                 230
```

<210> SEQ ID NO 124
<211> LENGTH: 233
<212> TYPE: PRT
<213> ORGANISM: Artificialsequence
<220> FEATURE:
<223> OTHER INFORMATION: pTalpha.EC-Delta48-4xMUT

<400> SEQUENCE: 124

Met Ala Gly Thr Trp Leu Leu Leu Leu Ala Leu Gly Cys Pro Ala
1               5                   10                  15

Leu Pro Thr Gly Val Gly Gly Thr Pro Phe Pro Ser Leu Ala Pro Pro
            20                  25                  30

Ile Met Leu Leu Val Ala Gly Gln Gln Met Val Val Val Cys Leu
            35                  40                  45

Val Leu Asp Val Ala Pro Pro Gly Leu Asp Ser Pro Ile Trp Phe Ser
50                  55                  60

Ala Gly Asn Gly Ser Ala Leu Asp Ala Phe Thr Tyr Gly Pro Ser Pro
65                  70                  75                  80

Ala Thr Asp Gly Thr Trp Thr Asn Leu Ala His Leu Ser Leu Pro Ser
                85                  90                  95

Glu Glu Leu Ala Ser Trp Glu Pro Leu Val Cys His Thr Gly Pro Gly
            100                 105                 110

Ala Glu Gly His Ser Ala Ser Thr Gln Pro Met His Leu Ser Gly Glu
        115                 120                 125

Ala Ser Thr Ala Ala Thr Cys Pro Gln Glu Pro Leu Arg Gly Thr Pro
130                 135                 140

Gly Gly Ala Leu Trp Leu Gly Val Leu Arg Leu Leu Leu Phe Lys Leu
145                 150                 155                 160

Leu Leu Phe Asp Leu Leu Leu Thr Cys Ser Cys Leu Cys Asp Pro Ala
                165                 170                 175

Gly Pro Leu Pro Ser Pro Ala Thr Thr Thr Arg Leu Arg Ala Leu Gly
            180                 185                 190

Ser His Arg Leu His Pro Ala Thr Glu Thr Gly Gly Arg Glu Ala Thr
        195                 200                 205

Ser Ser Pro Arg Pro Gln Pro Arg Asp Arg Arg Trp Gly Asp Thr Pro
210                 215                 220

Pro Gly Arg Lys Pro Gly Ser Pro Val
225                 230

<210> SEQ ID NO 125
<211> LENGTH: 848
<212> TYPE: PRT
<213> ORGANISM: Artificialsequence
<220> FEATURE:
<223> OTHER INFORMATION: Multi-chain CAR

<400> SEQUENCE: 125

Met Ala Pro Ala Met Glu Ser Pro Thr Leu Leu Cys Val Ala Leu Leu
1               5                   10                  15

Phe Phe Ala Pro Asp Gly Val Leu Ala Glu Val Gln Leu Gln Gln Ser
            20                  25                  30

Gly Pro Glu Leu Ile Lys Pro Gly Ala Ser Val Lys Met Ser Cys Lys
        35                  40                  45

Ala Ser Gly Tyr Thr Phe Thr Ser Tyr Val Met His Trp Val Lys Gln
    50                  55                  60

Lys Pro Gly Gln Gly Leu Glu Trp Ile Gly Tyr Ile Asn Pro Tyr Asn

```
                65                  70                  75                  80
           Asp Gly Thr Lys Tyr Asn Glu Lys Phe Lys Gly Lys Ala Thr Leu Thr
                                85                  90                  95
           Ser Asp Lys Ser Ser Thr Ala Tyr Met Glu Leu Ser Ser Leu Thr
                           100                 105                 110
           Ser Glu Asp Ser Ala Val Tyr Tyr Cys Ala Arg Gly Thr Tyr Tyr
                       115                 120                 125
           Gly Ser Arg Val Phe Asp Tyr Trp Gly Gln Gly Thr Thr Leu Thr Val
                   130                 135                 140
           Ser Ser Gly Gly Gly Gly Ser Gly Gly Gly Gly Ser Gly Gly Gly Gly
           145                 150                 155                 160
           Ser Asp Ile Val Met Thr Gln Ala Ala Pro Ser Ile Pro Val Thr Pro
                               165                 170                 175
           Gly Glu Ser Val Ser Ile Ser Cys Arg Ser Ser Lys Ser Leu Leu Asn
                           180                 185                 190
           Ser Asn Gly Asn Thr Tyr Leu Tyr Trp Phe Leu Gln Arg Pro Gly Gln
                       195                 200                 205
           Ser Pro Gln Leu Leu Ile Tyr Arg Met Ser Asn Leu Ala Ser Gly Val
                   210                 215                 220
           Pro Asp Arg Phe Ser Gly Ser Gly Ser Gly Thr Ala Phe Thr Leu Arg
           225                 230                 235                 240
           Ile Ser Arg Val Glu Ala Glu Asp Val Gly Val Tyr Tyr Cys Met Gln
                               245                 250                 255
           His Leu Glu Tyr Pro Phe Thr Phe Gly Ala Gly Thr Lys Leu Glu Leu
                           260                 265                 270
           Lys Arg Ala Asp Thr Thr Thr Pro Ala Pro Arg Pro Pro Thr Pro Ala
                       275                 280                 285
           Pro Thr Ile Ala Ser Gln Pro Leu Ser Leu Arg Pro Glu Ala Cys Arg
                   290                 295                 300
           Pro Ala Ala Gly Gly Ala Val His Thr Arg Gly Leu Asp Phe Ala Cys
           305                 310                 315                 320
           Asp Phe Phe Ile Pro Leu Leu Val Val Ile Leu Phe Ala Val Asp Thr
                               325                 330                 335
           Gly Leu Phe Ile Ser Thr Gln Gln Gln Val Thr Phe Leu Leu Lys Ile
                           340                 345                 350
           Lys Arg Thr Arg Lys Gly Phe Arg Leu Leu Asn Pro His Pro Lys Pro
                       355                 360                 365
           Asn Pro Lys Asn Asn Arg Ala Glu Gly Arg Gly Ser Leu Leu Thr Cys
                   370                 375                 380
           Gly Asp Val Glu Glu Asn Pro Gly Pro Met Asp Thr Glu Ser Asn Arg
           385                 390                 395                 400
           Arg Ala Asn Leu Ala Leu Pro Gln Glu Pro Ser Ser Val Pro Ala Phe
                               405                 410                 415
           Glu Val Leu Glu Ile Ser Pro Gln Glu Val Ser Ser Gly Arg Leu Leu
                           420                 425                 430
           Lys Ser Ala Ser Ser Pro Pro Leu His Thr Trp Leu Thr Val Leu Lys
                       435                 440                 445
           Lys Glu Gln Glu Phe Leu Gly Val Thr Gln Ile Leu Thr Ala Met Ile
                   450                 455                 460
           Cys Leu Cys Phe Gly Thr Val Val Cys Ser Val Leu Asp Ile Ser His
           465                 470                 475                 480
           Ile Glu Gly Asp Ile Phe Ser Ser Phe Lys Ala Gly Tyr Pro Phe Trp
                               485                 490                 495
```

Gly Ala Ile Phe Phe Ser Ile Ser Gly Met Leu Ser Ile Ile Ser Glu
             500                 505                 510

Arg Arg Asn Ala Thr Tyr Leu Val Arg Gly Ser Leu Gly Ala Asn Thr
             515                 520                 525

Ala Ser Ser Ile Ala Gly Gly Thr Gly Ile Thr Ile Leu Ile Ile Asn
        530                 535                 540

Leu Lys Lys Ser Leu Ala Tyr Ile His Ile His Ser Cys Gln Lys Phe
545                 550                 555                 560

Phe Glu Thr Lys Cys Phe Met Ala Ser Phe Ser Thr Glu Ile Val Val
                565                 570                 575

Met Met Leu Phe Leu Thr Ile Leu Gly Leu Gly Ser Ala Val Ser Leu
                580                 585                 590

Thr Ile Cys Gly Ala Glu Glu Leu Lys Gly Asn Lys Val Pro Glu
                595                 600                 605

Lys Arg Gly Arg Lys Lys Leu Leu Tyr Ile Phe Lys Gln Pro Phe Met
                610                 615                 620

Arg Pro Val Gln Thr Thr Gln Glu Glu Asp Gly Cys Ser Cys Arg Phe
625                 630                 635                 640

Pro Glu Glu Glu Glu Gly Gly Cys Glu Leu Gly Ser Gly Val Lys Gln
                645                 650                 655

Thr Leu Asn Phe Asp Leu Leu Lys Leu Ala Gly Asp Val Glu Ser Asn
                660                 665                 670

Pro Gly Pro Met Ile Pro Ala Val Val Leu Leu Leu Leu Leu Leu Val
            675                 680                 685

Glu Gln Ala Ala Ala Leu Gly Glu Pro Gln Leu Cys Tyr Ile Leu Asp
            690                 695                 700

Ala Ile Leu Phe Leu Tyr Gly Ile Val Leu Thr Leu Leu Tyr Cys Arg
705                 710                 715                 720

Leu Lys Ile Gln Val Arg Lys Ala Ala Ile Thr Ser Tyr Glu Lys Ser
                725                 730                 735

Arg Val Lys Phe Ser Arg Ser Ala Asp Ala Pro Ala Tyr Gln Gln Gly
                740                 745                 750

Gln Asn Gln Leu Tyr Asn Glu Leu Asn Leu Gly Arg Arg Glu Glu Tyr
            755                 760                 765

Asp Val Leu Asp Lys Arg Arg Gly Arg Asp Pro Glu Met Gly Gly Lys
            770                 775                 780

Pro Arg Arg Lys Asn Pro Gln Glu Gly Leu Tyr Asn Glu Leu Gln Lys
785                 790                 795                 800

Asp Lys Met Ala Glu Ala Tyr Ser Glu Ile Gly Met Lys Gly Glu Arg
                805                 810                 815

Arg Arg Gly Lys Gly His Asp Gly Leu Tyr Gln Gly Leu Ser Thr Ala
                820                 825                 830

Thr Lys Asp Thr Tyr Asp Ala Leu His Met Gln Ala Leu Pro Pro Arg
                835                 840                 845

<210> SEQ ID NO 126
<211> LENGTH: 2547
<212> TYPE: DNA
<213> ORGANISM: Artificialsequence
<220> FEATURE:
<223> OTHER INFORMATION: Multi-chain CAR

<400> SEQUENCE: 126
atggctcctg ccatggaatc ccctactcta ctgtgtgtag ccttactgtt cttcgctcca    60

```
gatggcgtgt tagcagaggt gcagttgcag cagtcagggc cagagttgat taagcccgga    120
gcctccgtca agatgtcctg caaggccagc gggtacactt tcaccagcta cgtcatgcat    180
tgggtgaagc agaagccagg ccaggggctt gagtggattg ggtacatcaa ccccctacaac   240 gacgggacca aatacaacga gaaattcaag ggcaaagcca cactcacctc cgataagtcc    300
tcctctaccg cctacatgga gctcagctcc ctgacctccg aggatagcgc tgtgtattac    360
tgcgcaaggg gcacatacta ctatggctct agggtgttcg actactgggg cagggcact    420 actctcacag tgagctcagg cggaggaggc agtggcggag ggggaagtgg gggcggcggc    480
agcgatattg tcatgaccca ggcagcccct agtatccctg tgactccagg cgagagcgtg    540
agcatcagct gccggtccag caagagcctg ctgaacagta acggaaacac ataccctac    600 tggtttctgc agaggcccgg ccagagccct cagctgctga tttaccgcat gtcaaatctt    660
gcctctgggg tgcccgatag atttagtggg agcggatccg gcacagcttt tacattgcgg    720
atctccagag tcgaggccga agacgtgggg gtctattact gtatgcaaca cctggaatac    780
ccctttacct tcggagccgg cacaaagctg gagctgaagc gggctgacac cacaaccccc    840
gctccaaggc cccctacccc cgcaccaact attgcctccc agccactctc actgcggcct    900
gaggcctgtc ggcccgctgc tggaggcgca gtgcatacaa ggggcctcga tttcgcctgc    960 gatttttta tcccattgtt ggtggtgatt ctgtttgctg tggacacagg attatttatc   1020
tcaactcagc agcaggtcac atttctcttg aagattaaga gaaccaggaa aggcttcaga   1080
cttctgaacc cacatcctaa gccaaacccc aaaaacaaca gagccgaggg cagaggcagc   1140
ctgctgacct gcgcgacgt ggaggagaac ccaggcccca tggacacaga aagtaatagg    1200
agagcaaatc ttgctctccc acaggagcct tccagtgtgc ctgcatttga agtcttggaa   1260
atatctcccc aggaagtatc ttcaggcaga ctattgaagt cggcctcatc cccaccactg   1320
catacatggc tgacagtttt gaaaaagag caggagttcc tgggggtaac acaaattctg    1380
actgctatga tatgcctttg ttttggaaca gttgtctgct ctgtacttga tatttcacac   1440
attgagggag acatttttc atcatttaaa gcaggttatc cattctgggg agccatattt   1500
ttttctattt ctggaatgtt gtcaattata tctgaaagga gaaatgcaac atatctggtg   1560
agaggaagcc tgggagcaaa cactgccagc agcatagctg ggggaacggg aattaccatc   1620
ctgatcatca acctgaagaa gagccttggcc tatatccaca tccacagttg ccagaaattt   1680
tttgagacca agtgctttat ggcttccttt tccactgaaa ttgtagtgat gatgctgttt   1740
ctcaccattc tgggacttgg tagtgctgtg tcactcacaa tctgtggagc tggggaagaa   1800
ctcaaaggaa acaaggttcc agagaaacgg ggccggaaga agctcctcta catttttaag   1860 cagccttca tgcggccagt gcagacaacc aagaggagg atgggtgttc ctgcagattc   1920
cctgaggaag aggaaggcgg gtgcgagctg ggttctggcg tgaaacagac tttgaatttt   1980
gaccttctca gttggcggg agacgtggag tccaacccag gcccatgat tccagcagtg    2040 gtcttgctct tactccttt ggttgaacaa gcagcggccc tgggagagcc tcagctctgc   2100
tatatcctgg atgccatcct gtttctgtat ggaattgtcc tcaccctcct ctactgtcga   2160
ctgaagatcc aagtgcgaaa ggcagctata accagctatg agaaatcaag agtgaagttc   2220
tccaggagcg cagatgcccc cgcctatcaa cagggccaga accagctcta caacgagctt   2280
aacctcggga gcgcgaaga atacgacgtg ttggataaga aaggggggcg ggaccccgag   2340
atgggaggaa agcccggag gaagaaccct caggagggcc tgtacaacga gctgcagaag   2400
gataagatgg ccgaggccta ctcagagatc gggatgaagg gggagcggcg ccgcgggaag   2460
```

-continued

```
gggcacgatg ggctctacca ggggctgagc acagccacaa aggacacata cgacgccttg    2520
cacatgcagg cccttccacc ccggtga                                        2547
```

<210> SEQ ID NO 127
<211> LENGTH: 9
<212> TYPE: PRT
<213> ORGANISM: Unknown
<220> FEATURE:
<223> OTHER INFORMATION: Description of Unknown: 'LAGLIDADG' family
      motif endonuclease sequence

<400> SEQUENCE: 127

Leu Ala Gly Leu Ile Asp Ala Asp Gly
1               5

<210> SEQ ID NO 128
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Forward adaptator sequence

<400> SEQUENCE: 128

```
ccatctcatc cctgcgtgtc tccgactcag                                       30
```

<210> SEQ ID NO 129
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Reverse adaptator sequence

<400> SEQUENCE: 129

```
cctatcccct gtgtgccttg gcagtctcag                                       30
```

<210> SEQ ID NO 130
<211> LENGTH: 116
<212> TYPE: DNA
<213> ORGANISM: Homo sapiens

<400> SEQUENCE: 130

```
catgtcctaa ccctgatcct cttgtcccac agatatccag aaccctgacc ctgccgtgta     60
ccagctgaga gactctaaat ccagtgacaa gtctgtctgc ctattcaccg attttg        116
```

<210> SEQ ID NO 131
<211> LENGTH: 99
<212> TYPE: DNA
<213> ORGANISM: Homo sapiens

<400> SEQUENCE: 131

```
catgtcctaa ccctgatcct cttgtcccac agatatccgt gtaccagctg agagactcta     60
aatccagtga caagtctgtc tgcctattca ccgattttg                            99
```

<210> SEQ ID NO 132
<211> LENGTH: 107
<212> TYPE: DNA
<213> ORGANISM: Homo sapiens

<400> SEQUENCE: 132
catgtcctaa ccctgatcct cttgtcccac agatatccag atatccgtgt accagctgag    60
agactctaaa tccagtgaca agtctgtctg cctattcacc gattttg                 107

<210> SEQ ID NO 133
<211> LENGTH: 85
<212> TYPE: DNA
<213> ORGANISM: Homo sapiens

<400> SEQUENCE: 133
catgtcctaa ccctcgatcc tgccgtgtac cagctgagag actctaaatc cagtgacaag    60
tctgtctgcc tattcaccga ttttg                                          85

<210> SEQ ID NO 134
<211> LENGTH: 111
<212> TYPE: DNA
<213> ORGANISM: Homo sapiens

<400> SEQUENCE: 134
catgtcctaa ccctgatcct cttgtcccac agatatccag atatcctgcc gtgtaccagc    60
tgagagactc taaatccagt gacaagtctg tctgcctatt caccgatttt g            111

<210> SEQ ID NO 135
<211> LENGTH: 104
<212> TYPE: DNA
<213> ORGANISM: Homo sapiens

<400> SEQUENCE: 135
catgtcctaa ccctgatcct cttgtcccac agatatccag aaccctgacc agctgagaga    60
ctctaaatcc agtgacaagt ctgtctgcct attcaccgat tttg                   104

<210> SEQ ID NO 136
<211> LENGTH: 45
<212> TYPE: DNA
<213> ORGANISM: Homo sapiens

<400> SEQUENCE: 136
catgtcctaa ccctgatcct cttgtcccac agatatccga ttttg                    45

<210> SEQ ID NO 137
<211> LENGTH: 78
<212> TYPE: DNA
<213> ORGANISM: Homo sapiens

<400> SEQUENCE: 137
catgtcctaa ccctgatcct cttgtcccac gagactctaa atccagtgac aagtctgtct    60
gcctattcac cgattttg                                                  78

<210> SEQ ID NO 138
<211> LENGTH: 109
<212> TYPE: DNA
<213> ORGANISM: Homo sapiens

<400> SEQUENCE: 138
catgtcctaa ccctgatcct cttgtcccac agatatccag aacctgccgt gtaccagctg    60
agagactcta atccagtga caagtctgtc tgcctattca ccgattttg                109

<210> SEQ ID NO 139
<211> LENGTH: 89

```
<212> TYPE: DNA
<213> ORGANISM: Homo sapiens

<400> SEQUENCE: 139
catgtcctaa ccctgatcct cttgtcccac agaccagctg agagactcta aatccagtga      60
caagtctgtc tgcctattca ccgattttg                                        89
```